United States Patent
Mangel et al.

(10) Patent No.: US 10,065,989 B2
(45) Date of Patent: Sep. 4, 2018

(54) MOLECULAR SLEDS AND USES THEREOF

(71) Applicants: The Broad Institute, Inc., Cambridge, MA (US); President And Fellows Of Harvard College, Cambridge, MA (US); Rijksuniversiteit Groningen, Groningen (NL)

(72) Inventors: Walter F. Mangel, Shoreham, NY (US); Paul Blainey, Cambridge, MA (US); Vito Graziano, West Babylon, NY (US); Andreas Herrmann, Groningen (NL); William J. McGrath, Wadding River, NY (US); Antonius Martinus Van Oijen, Groningen (NL); Xiaoliang Sunney Xie, Lexington, MA (US)

(73) Assignees: The Broad Institute Inc., Cambridge, MA (US); President and Fellows of Harvard College, Cambridge, MA (US); Rijksuniversiteit Groningen, CP Groningen (NL)

( * ) Notice: Subject to any disclaimer, the term of this patent is extended or adjusted under 35 U.S.C. 154(b) by 183 days.

(21) Appl. No.: 14/595,941

(22) Filed: Jan. 13, 2015

(65) Prior Publication Data
US 2015/0210738 A1 Jul. 30, 2015

Related U.S. Application Data

(63) Continuation-in-part of application No. PCT/US2013/050451, filed on Jul. 15, 2013.

(60) Provisional application No. 61/671,615, filed on Jul. 13, 2012.

(51) Int. Cl.
| | |
|---|---|
| A61K 47/48 | (2006.01) |
| A61K 31/4375 | (2006.01) |
| A61K 31/4709 | (2006.01) |
| A61K 38/48 | (2006.01) |
| A61K 38/16 | (2006.01) |
| A61K 38/52 | (2006.01) |
| A61K 31/7105 | (2006.01) |
| A61K 31/711 | (2006.01) |
| A61K 39/395 | (2006.01) |
| C12N 15/11 | (2006.01) |
| A61P 31/04 | (2006.01) |
| C07K 4/00 | (2006.01) |
| A61K 31/713 | (2006.01) |
| C12Q 1/6806 | (2018.01) |
| A61K 47/65 | (2017.01) |
| A61K 47/64 | (2017.01) |

(52) U.S. Cl.
CPC ............ *C07K 4/00* (2013.01); *A61K 31/4375* (2013.01); *A61K 31/4709* (2013.01); *A61K 31/711* (2013.01); *A61K 31/713* (2013.01); *A61K 31/7105* (2013.01); *A61K 47/645* (2017.08); *A61K 47/65* (2017.08); *C12Q 1/6806* (2013.01)

(58) Field of Classification Search
None
See application file for complete search history.

(56) References Cited

U.S. PATENT DOCUMENTS

| | | | |
|---|---|---|---|
| 7,348,423 B2 | 3/2008 | Hoess et al. | |
| 2006/0137042 A1* | 6/2006 | Plesch | C12N 15/8242 800/288 |
| 2010/0022750 A1 | 1/2010 | Bishop et al. | |
| 2011/0201112 A1 | 8/2011 | Rome et al. | |

FOREIGN PATENT DOCUMENTS

| | | |
|---|---|---|
| FR | 2858772 | 2/2005 |
| WO | WO 99/16884 | 4/1999 |

OTHER PUBLICATIONS

Honkavuori et al., Dual role of the adenovirus pVl C terminus as a nuclear localization signal and activator of the viral protease, J. Gen. Virol. 85:3367-76 (2004).*
Wiethoff et al., Adenovirus Protein VI Mediates Membrane Disruption following Capsid Disassembly, J. Virol. 79:1992-2000 (2005).*
Raagel et al., "Peptide-mediated protein delivery—Which pathways are penetrable?," Biochim. Biophys. Acta Biomemb. 1798:2240-2248 (2010).*
Thurn et al., Rational therapeutic combinations with histone deacetylase inhibitors for the treatment of cancer, Fut. Oncol. 7:263-283 (2011).*
Singh et al., "Biotechnological applications of cyclodextrins," Biotech. Adv. 20:341-359 (2002).*

(Continued)

*Primary Examiner* — Julie Ha
*Assistant Examiner* — Kristina M Hellman
(74) *Attorney, Agent, or Firm* — Burns & Levinson, LLP; Richard B. Emmons

(57) ABSTRACT

The present invention relates to compositions which may comprise a molecular sled linked to cargo and uses thereof. In particular, the present invention relates to a non-naturally occurring or engineered composition which may comprise a molecular sled, linkers and a molecular cargo connected to the sled via the linkers. Methods involving the use of molecular sleds and their cargoes and pharmaceutical compositions, methods for treating cancer, a degenerative disease, a genetic disease or an infectious disease as well as diagnostic methods are also contemplated by the present invention.

14 Claims, 49 Drawing Sheets
(10 of 49 Drawing Sheet(s) Filed in Color)
Specification includes a Sequence Listing.

(56) References Cited

OTHER PUBLICATIONS

Zhou et al., "Generation of Induced Pluripotent Stem Cells Using Recombinant Proteins," Cell Press 4:381-384 (2009).*
Zhou et al. Supplemental Data, Cell Press, vol. 4, pp. 1-8 (2009).*
Dubikovskaya et al., "Overcoming multidrug resistance of small-molecule therapeutics through conjugation with releasable octaarginine transporters," PNAS 105:12128-12133 (2008).*
Hettiarachchi et al., "Toxicology and Drug Delivery by Cucurbit[n]uril Type Molecular Containers," PLOS one vol. 5, pp. 1-10 (2010).*
Futaki, "Membrane-permeable arginine-rich peptides and the translocation mechanisms," Adv. Drug Deliv. Rev. 57: 547-558 (2005).*
Wadia et al., "Transmembrane delivery of protein and peptide drugs by TAT-mediated transduction in the treatment of cancer," Adv. Drug. Deliv. Rev. 57:579-596 (2005).*
R. Abes, et al., Arginie-Rich Cell Penetrating Peptides: Design Structure-Activity, And Applications To Alter Pre-mRNA Splicing By Steric-Block Oligonucleotides, Journal of Peptide Science (2008) vol. 14, p. 455-460.
Mark T. Brown, et al., Interaction of Actin And Its 1 1-Amino Acid C-Terminal Peptide As Cofactors With The Adenovirus Proteinase; FEBS Letters (2004) vol. 563, p. 213-218.
Kariem Ezzat, et al., Peptide-Based Matrices As Drug Delivery Vehicles, Current Pharmaceutical Design (2010) vol. 16, p. 1167-1178.
Andrew W. Fraley, et al., Cationic Oligunucelotide-Peptide Conjugates With Aggregating Properties Enter Efficiently Into Cells While Maintaining Hybridization Properties And Enzymatic Recognition, J. Am. Chemical Society (2006) vol. 128, p. 10763-10771.
Stanislaw J. Kaczmarczyk, et al., Protein Delivery Using Engineered Virus-Like Particles, PNAS (2011) vol. 108, No. 41, p. 16998-17003.
Kersemans, et al, Cell Penetrating Peptides For In Vivo Molecular Imaging Applications, Current Pharmaceutical Design (2008) vol. 14, p. 2415-2427.
McGrath, et al., In The Virion, The 11-Amino-Acid Peptide Cofactor pVIc Is Covalently Linked To The Adenovirus Proteinase, Virology (2002) vol. 296, p. 234-240.
McGrath, et al. Human Adenovirus Proteinase: DNA Binding And Stimulation Of Proteinase Activity By DNA, Biochemistry (2001) vol. 40, p. 13237-13245.
Turkin, et al., Single-Molecule Studies Of Adenovirus Maturation, Biophysical Journal (Feb. 2-6, 2013) vol. 104, Nr. 2, Suppl. 1, p. 178A-179A, 57th Annual Meeting of the Biophysical Society, Philadelphia, PA, USA.

* cited by examiner

FIGS. 2A-B
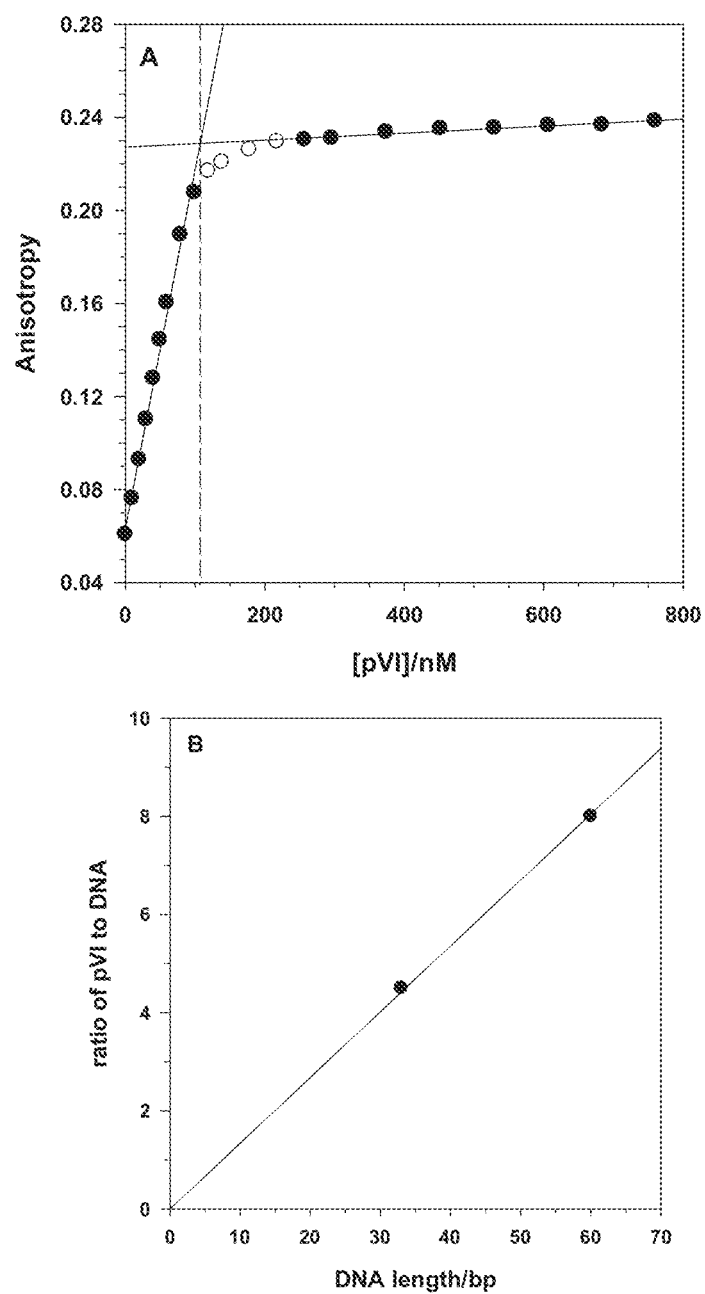

FIGS. 3A-B
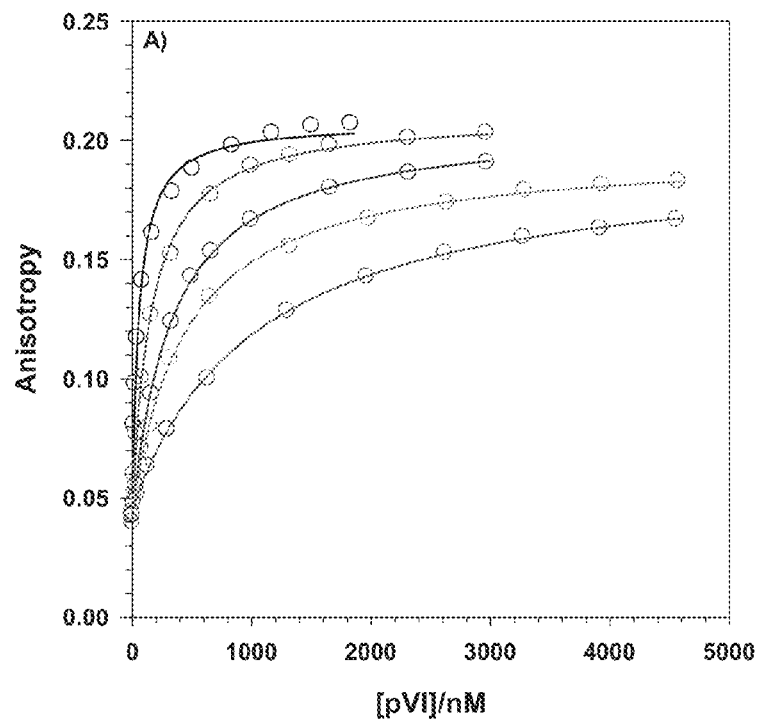
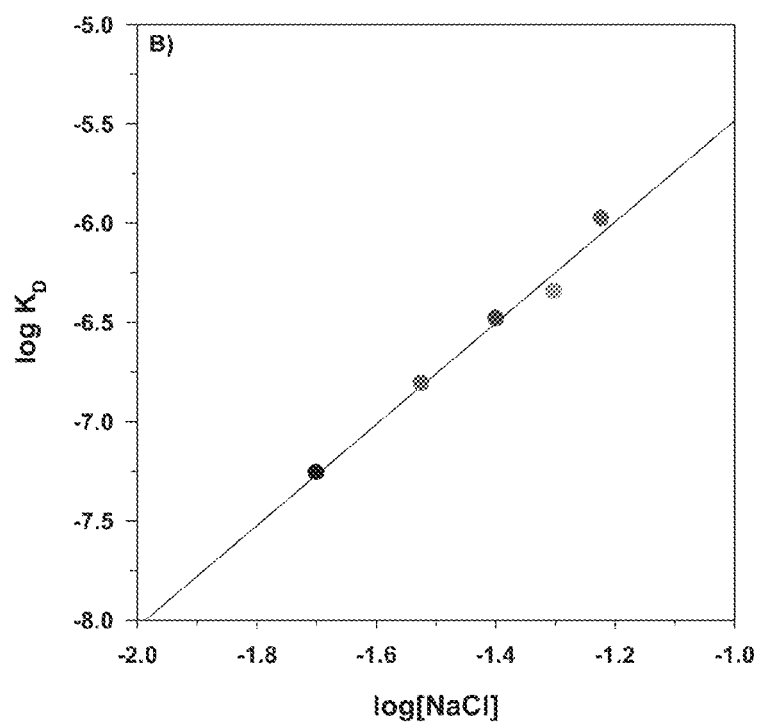

FIGS. 4A-B
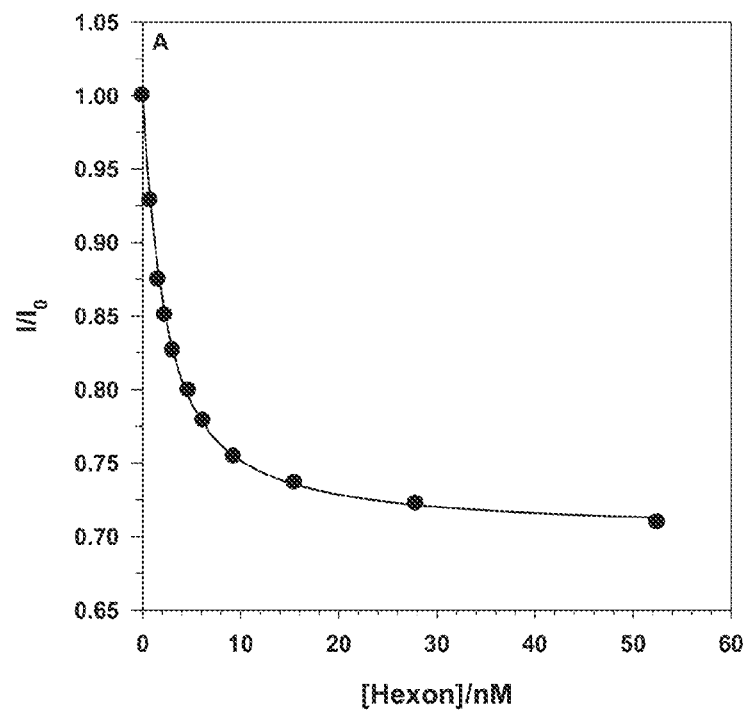
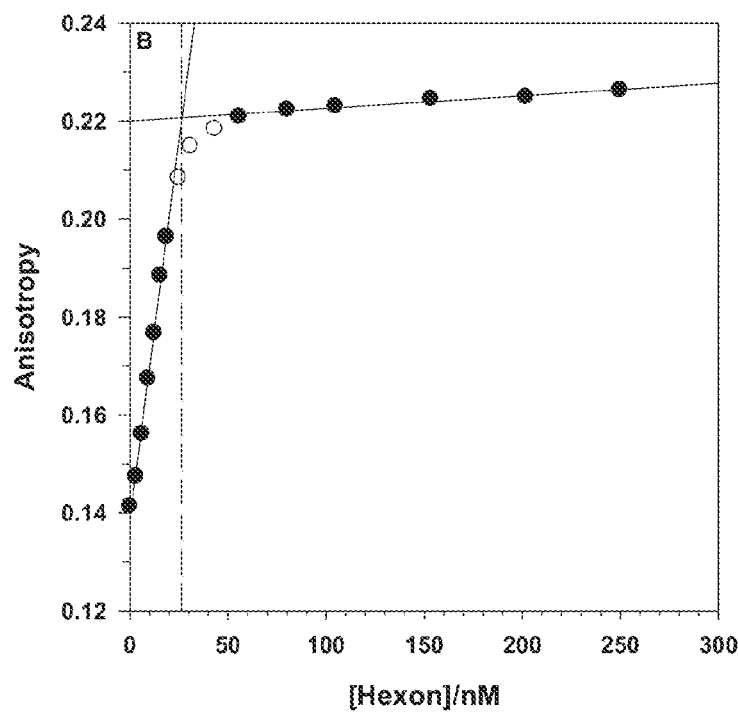

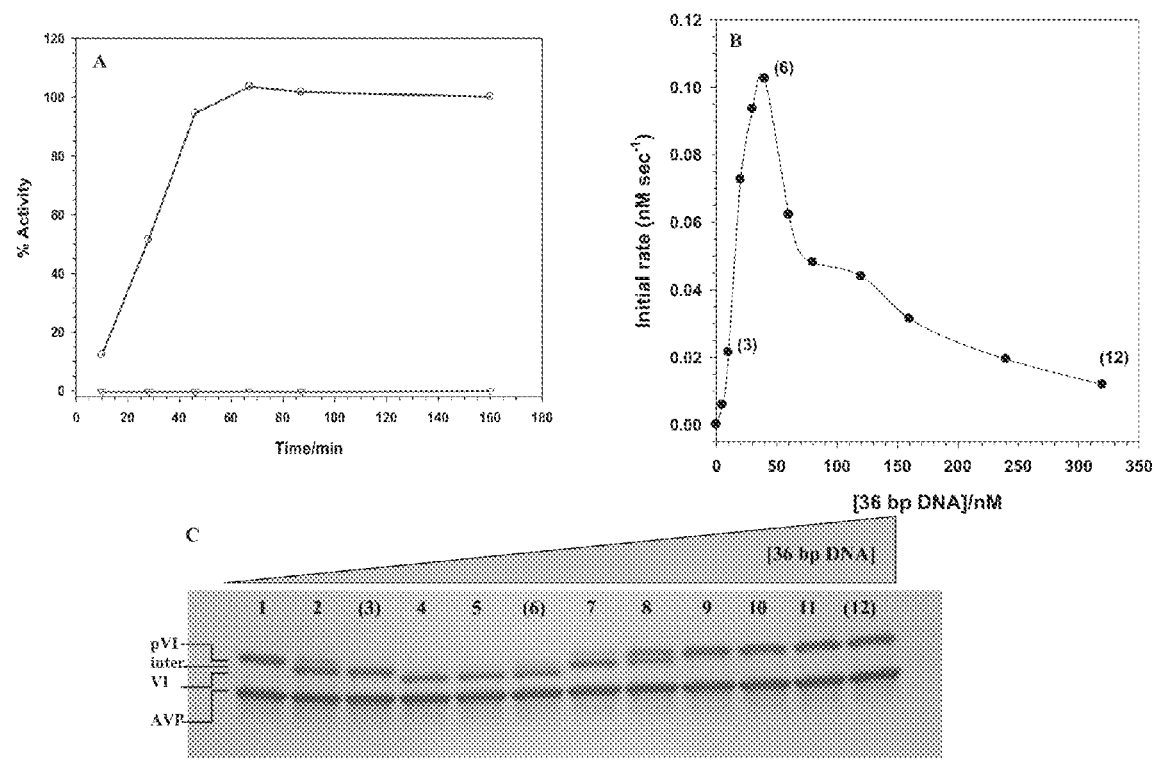
FIGS. 6A-C

FIGS. 7A-B
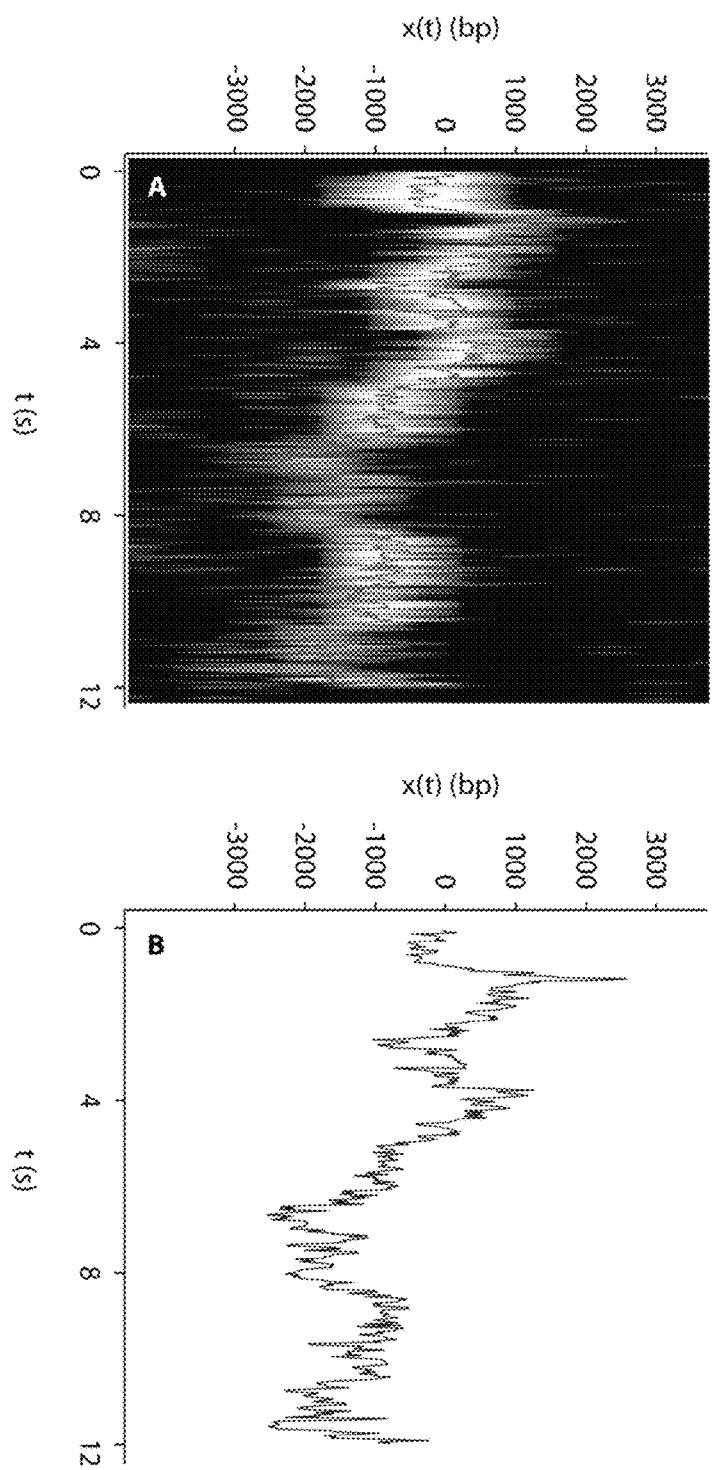

FIGS. 7C-D
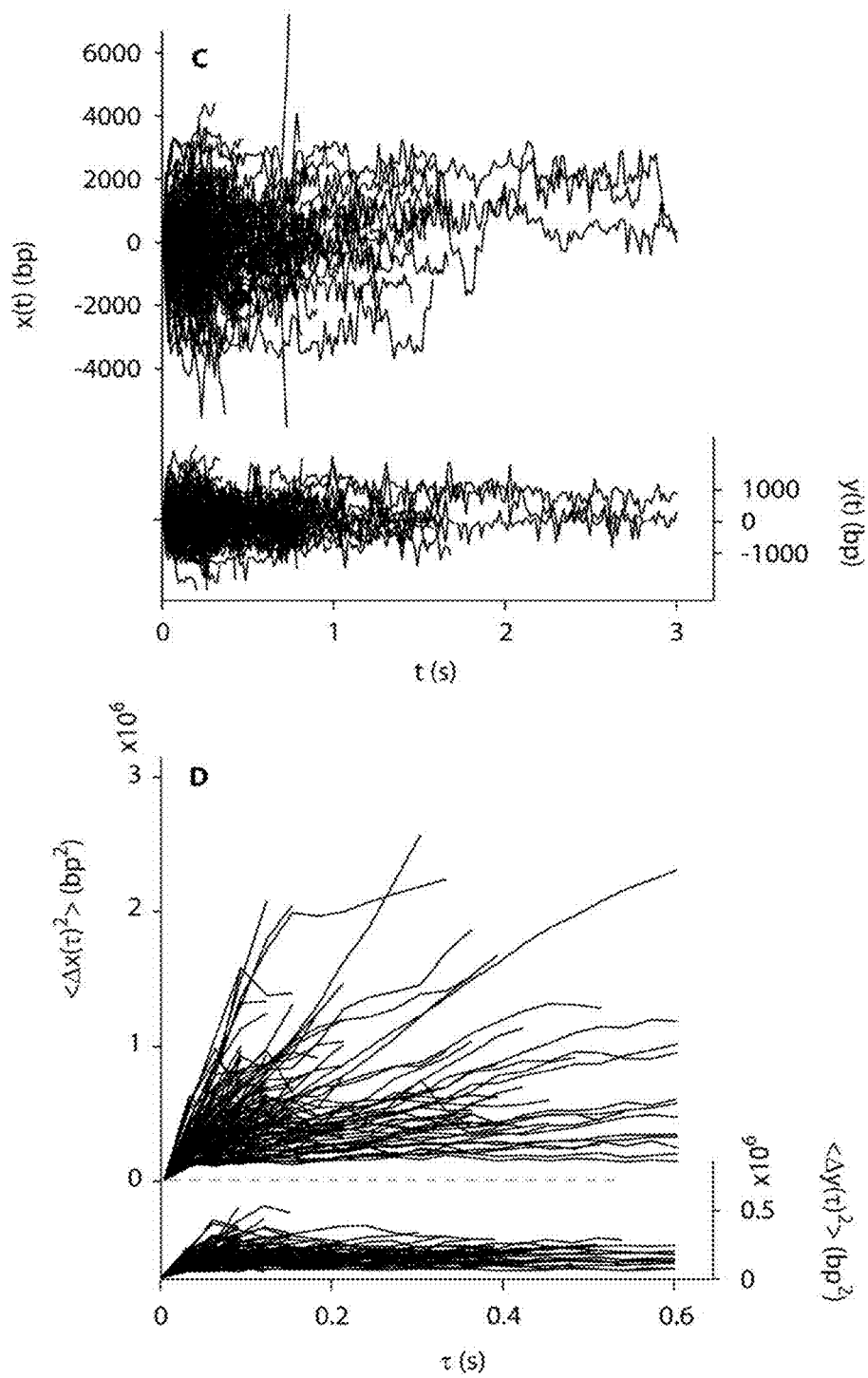

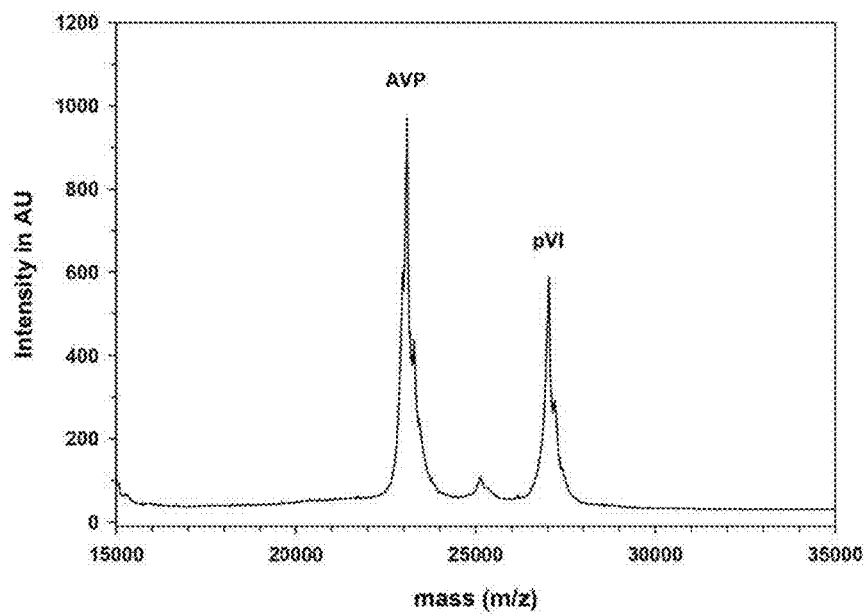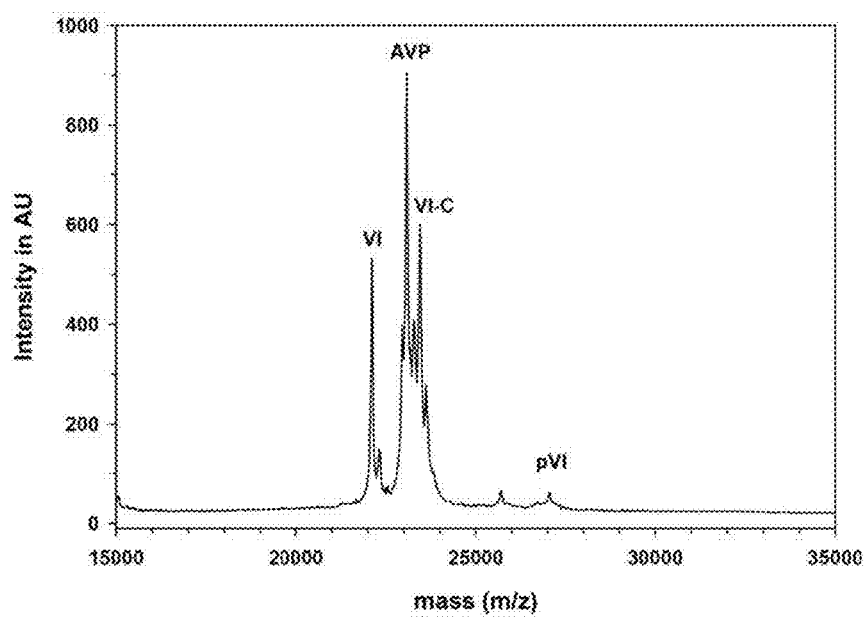
FIG. 8B-C

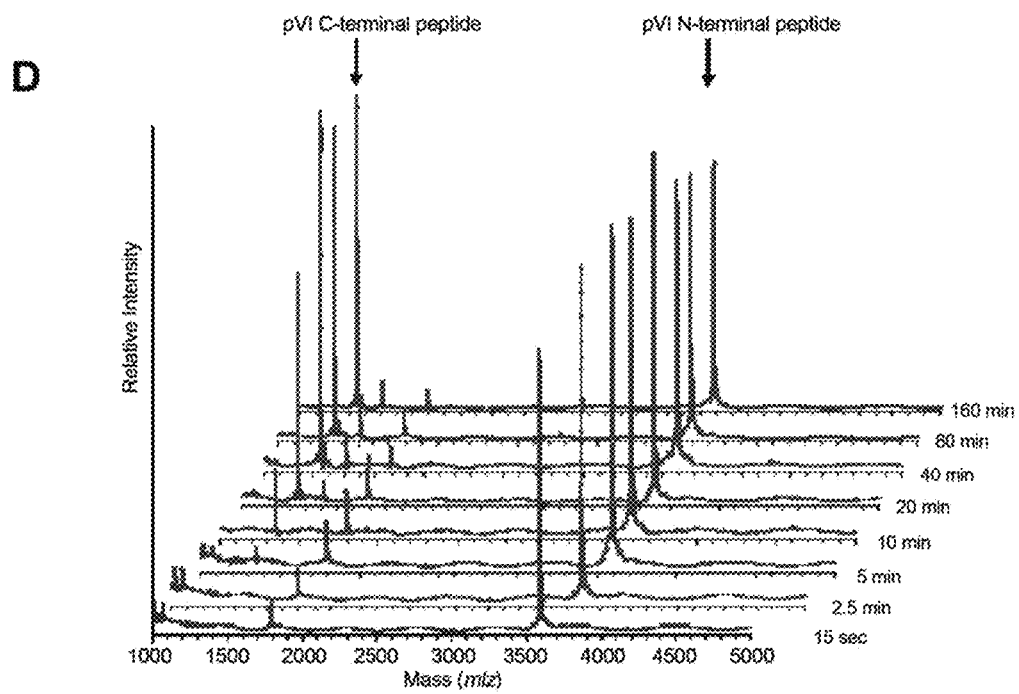
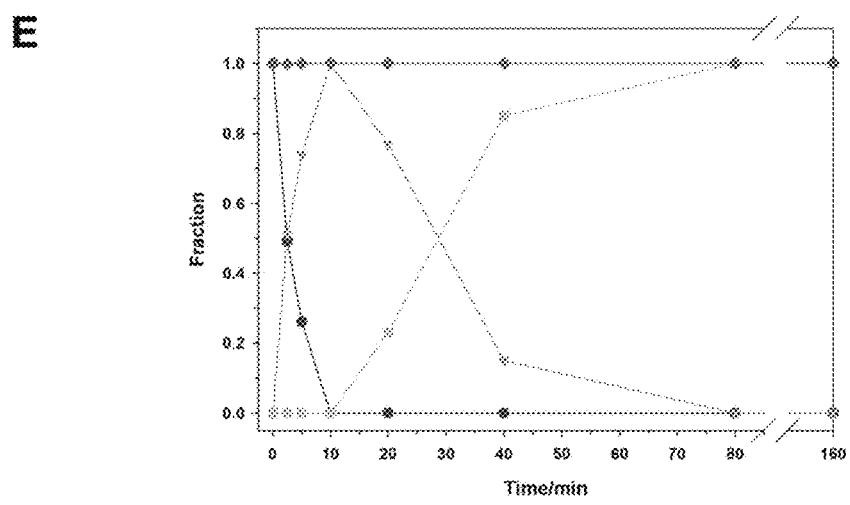
FIG. 8D-E

FIGS. 10A-B
A
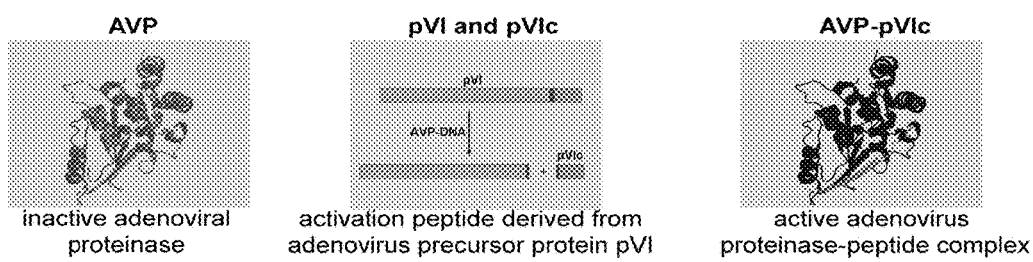
AVP — inactive adenoviral proteinase
pVI and pVIc — activation peptide derived from adenovirus precursor protein pVI
AVP-pVIc — active adenovirus proteinase-peptide complex
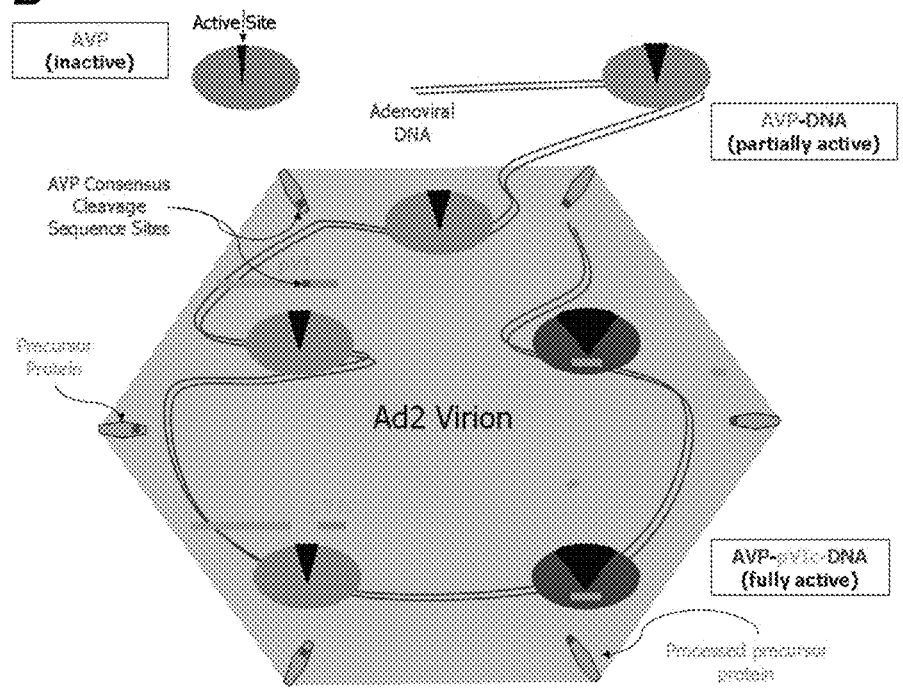

FIGS. 10C-E
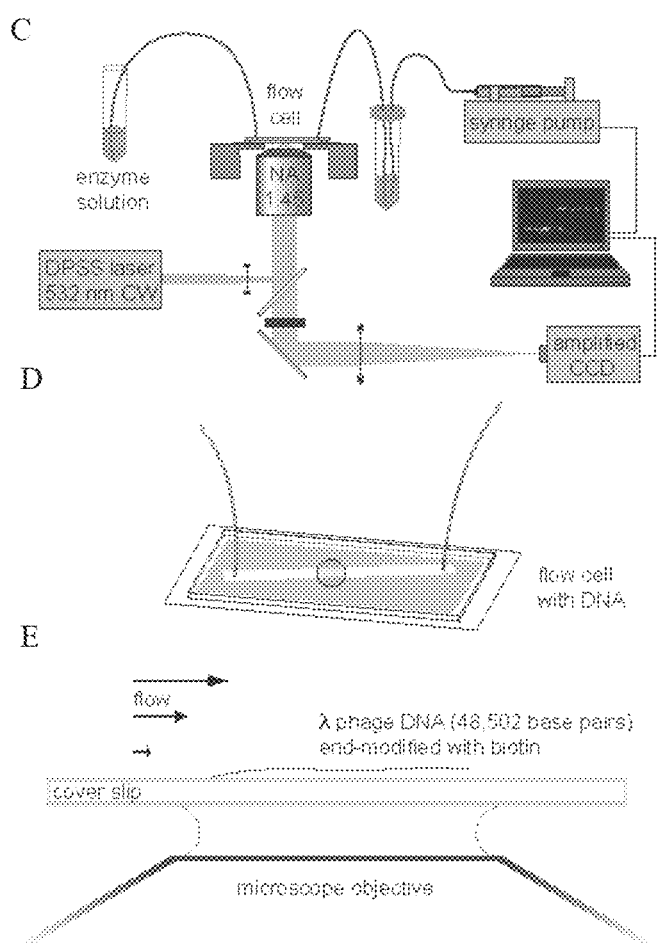

FIGS. 12A-B
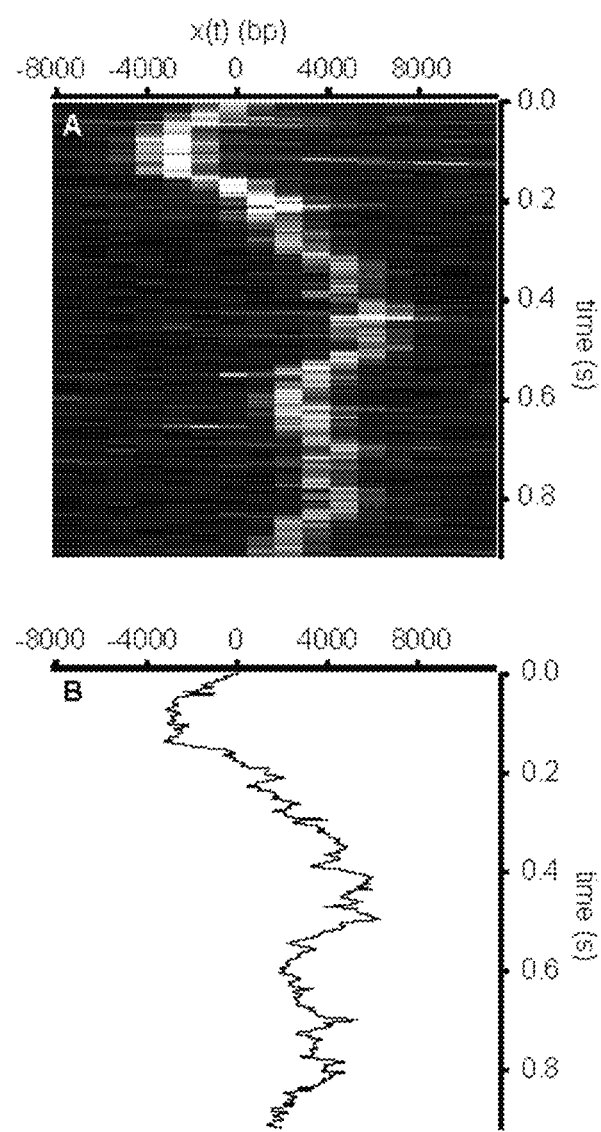

FIGS. 13A-B
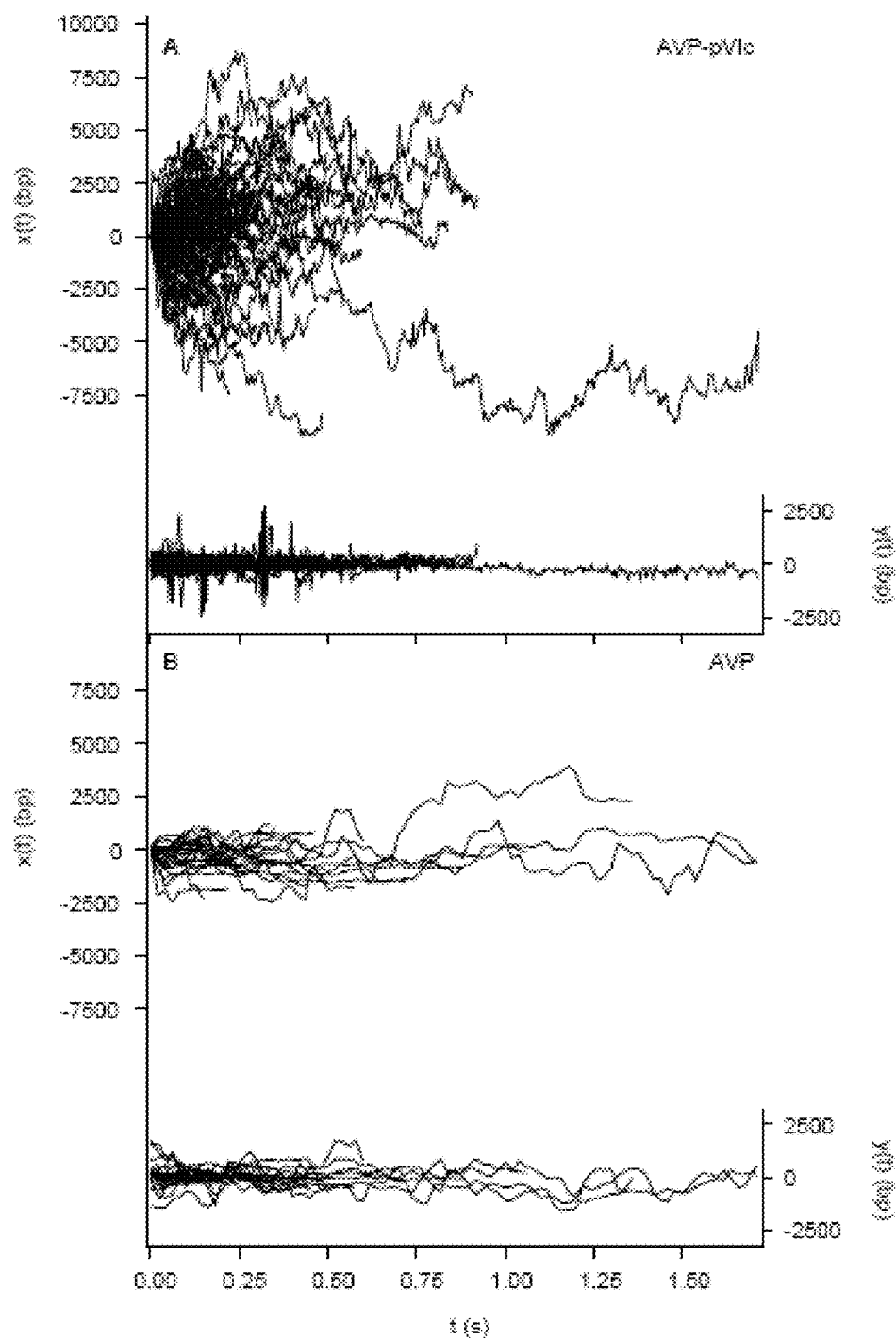

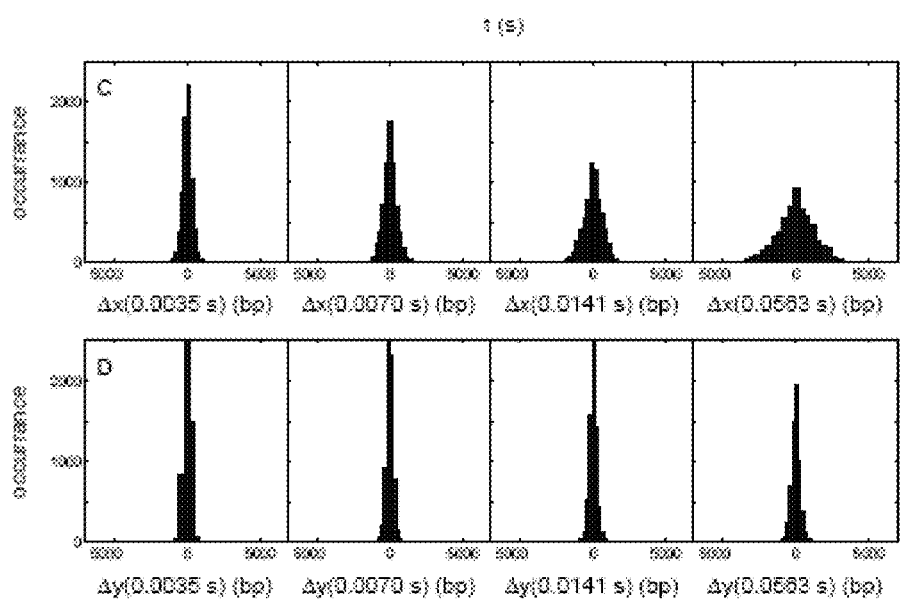
FIGS. 13C-D

FIGS. 14A-C
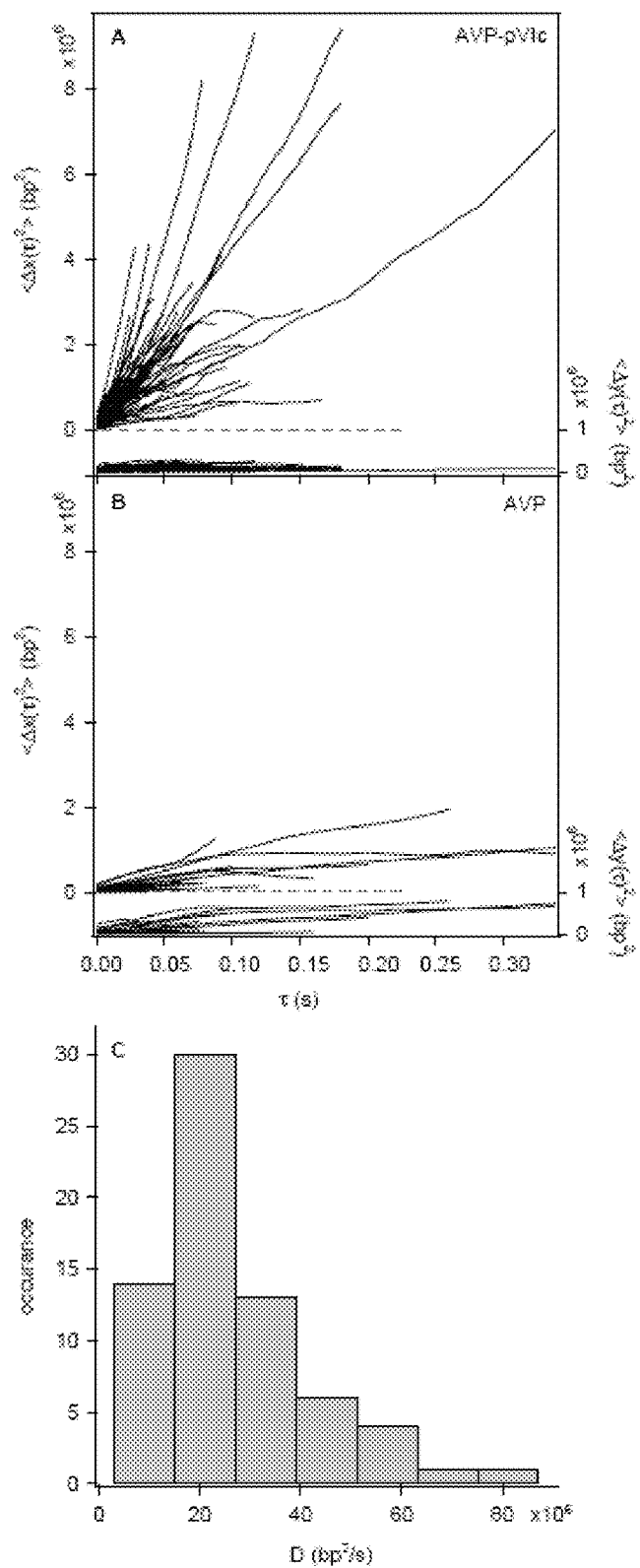

FIGS. 15A-B
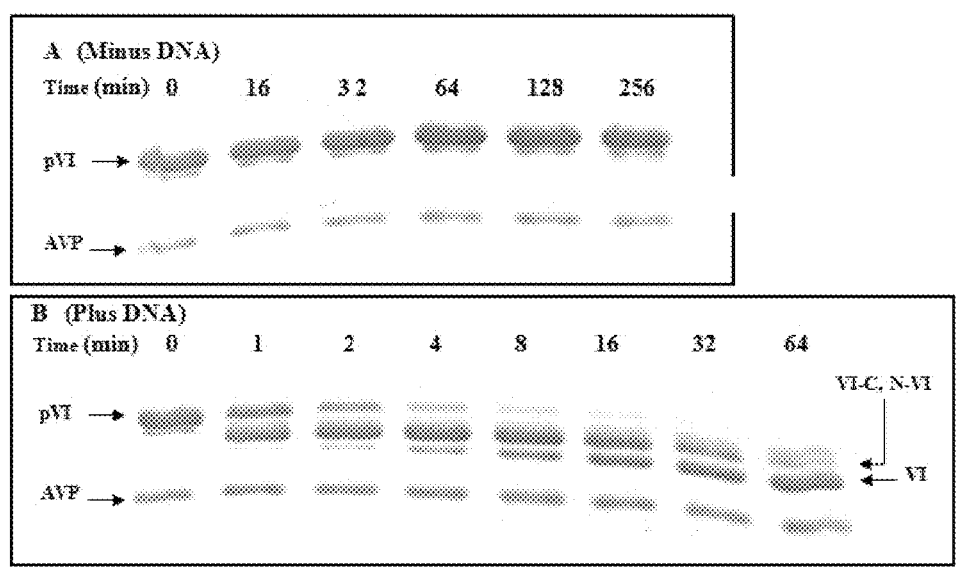

FIGS. 15C-E
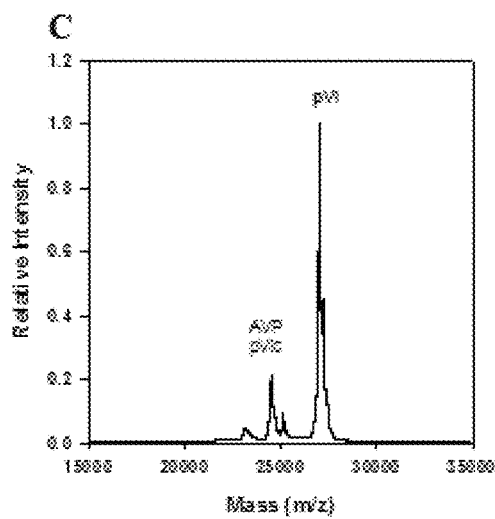
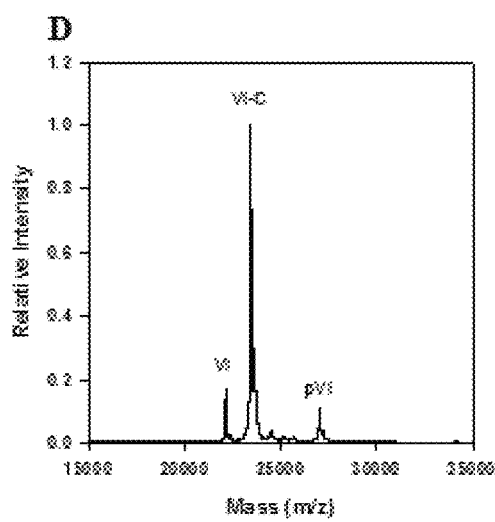
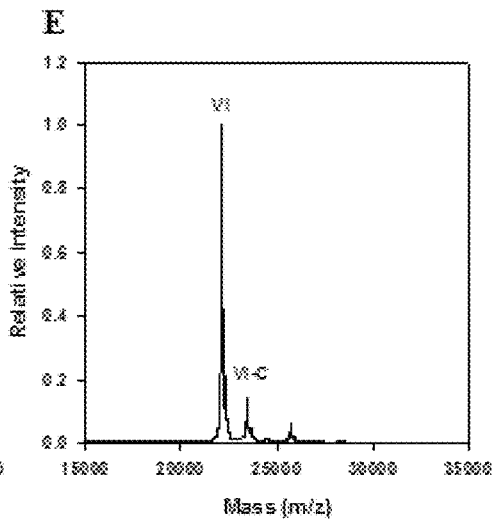

FIGS. 17A-B
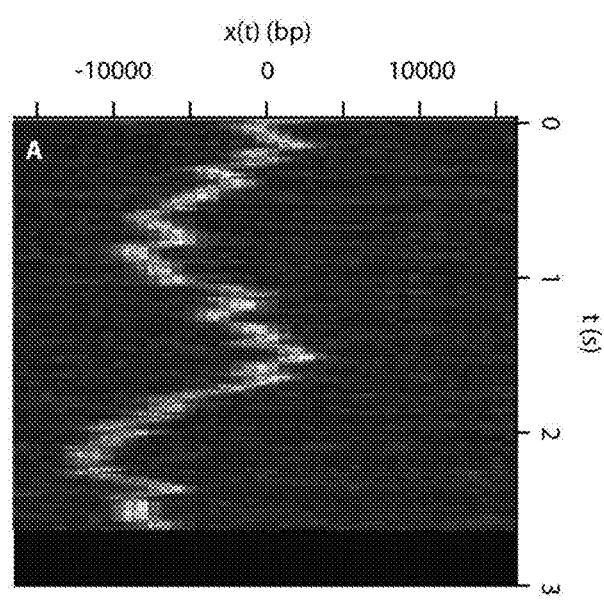
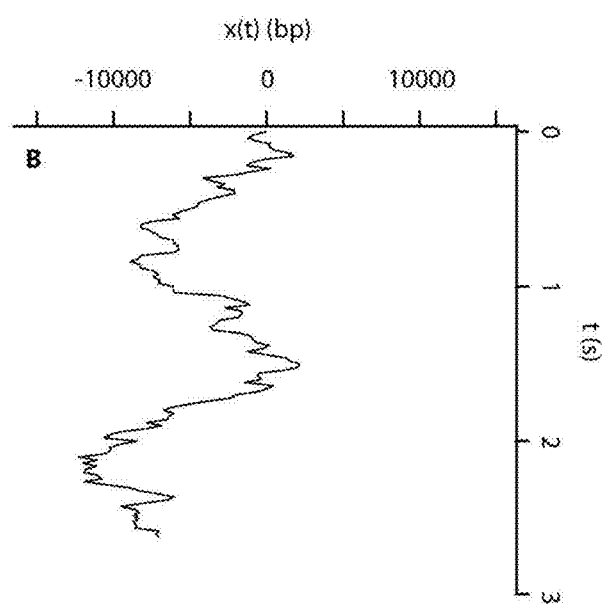

FIGS. 18A-C
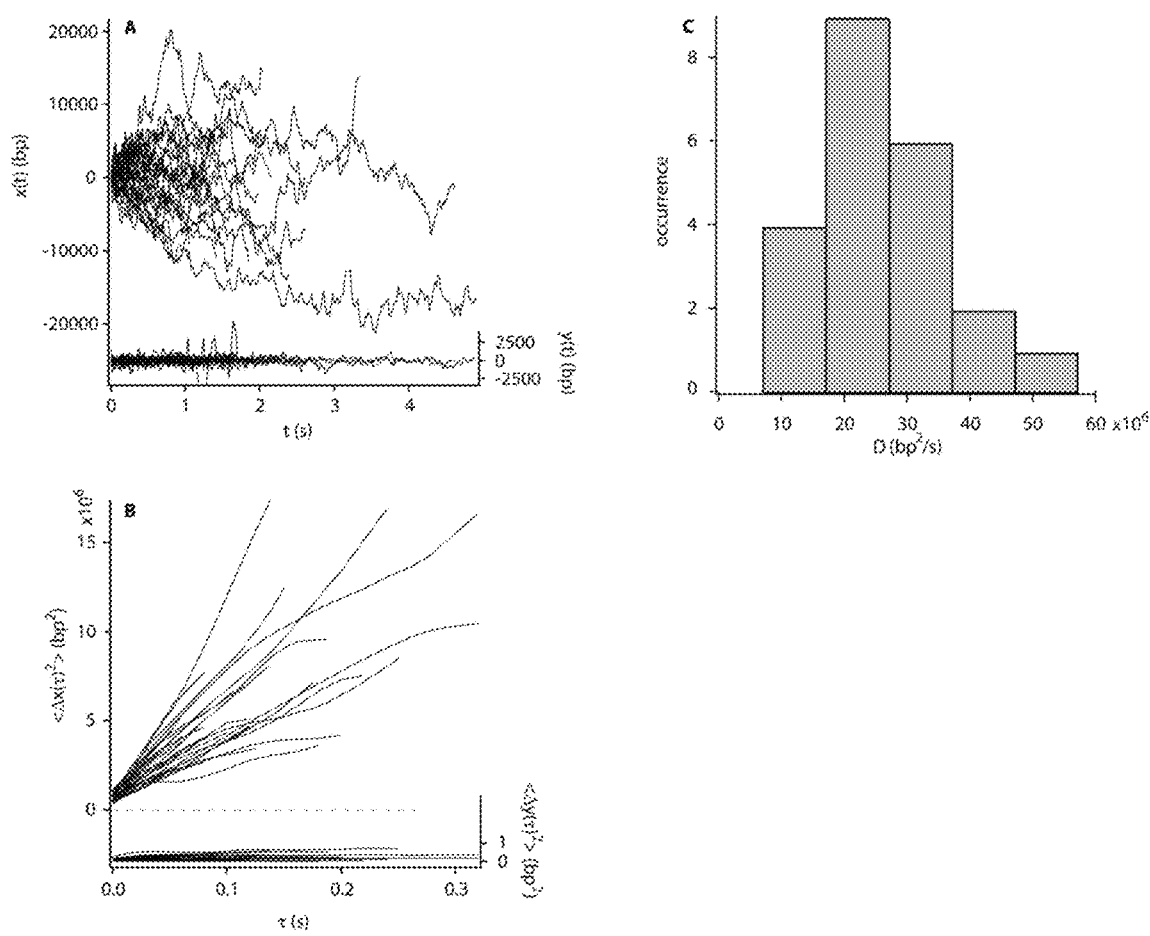

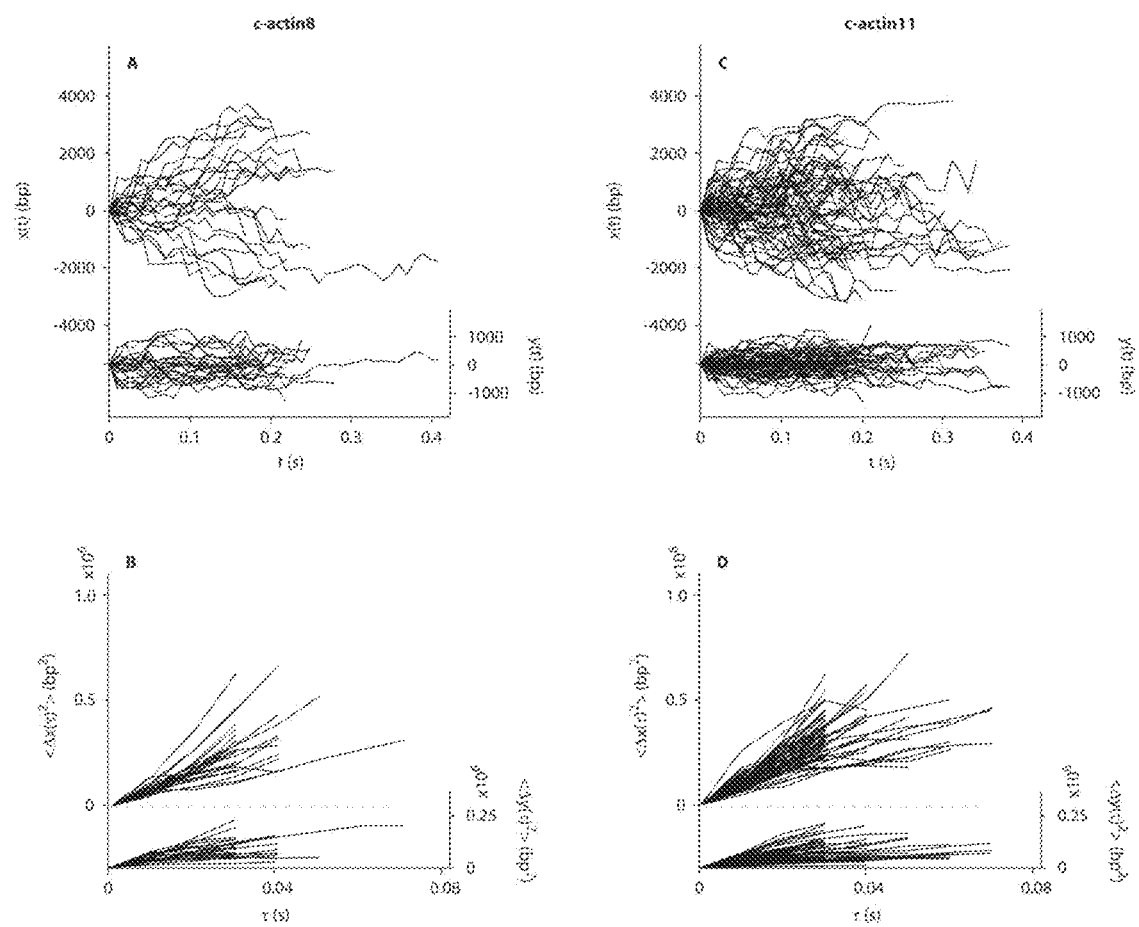
FIGS. 19A-D

FIGS. 20A-C
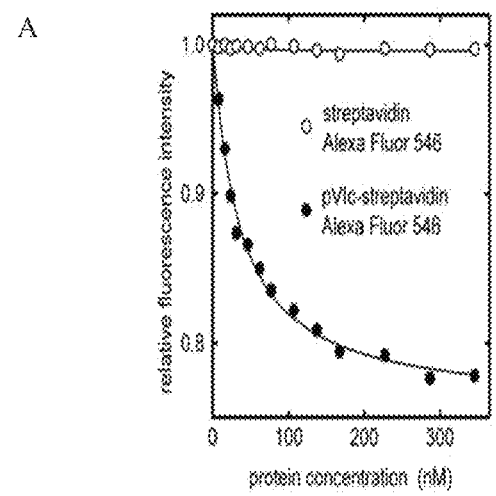
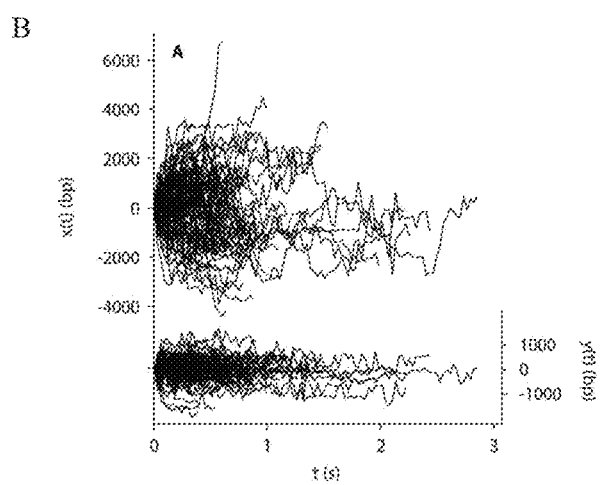
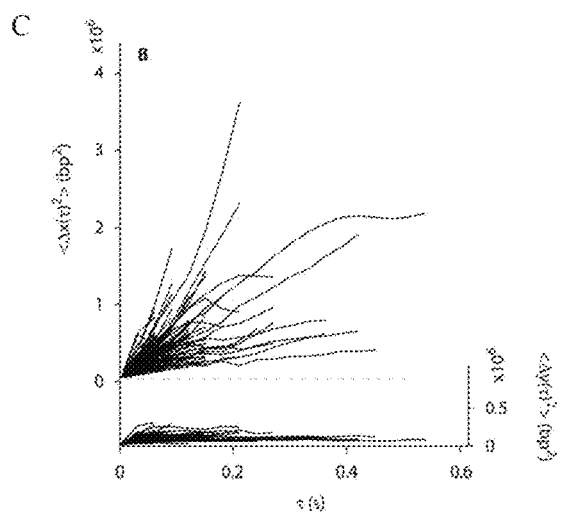

FIGS. 21A-B
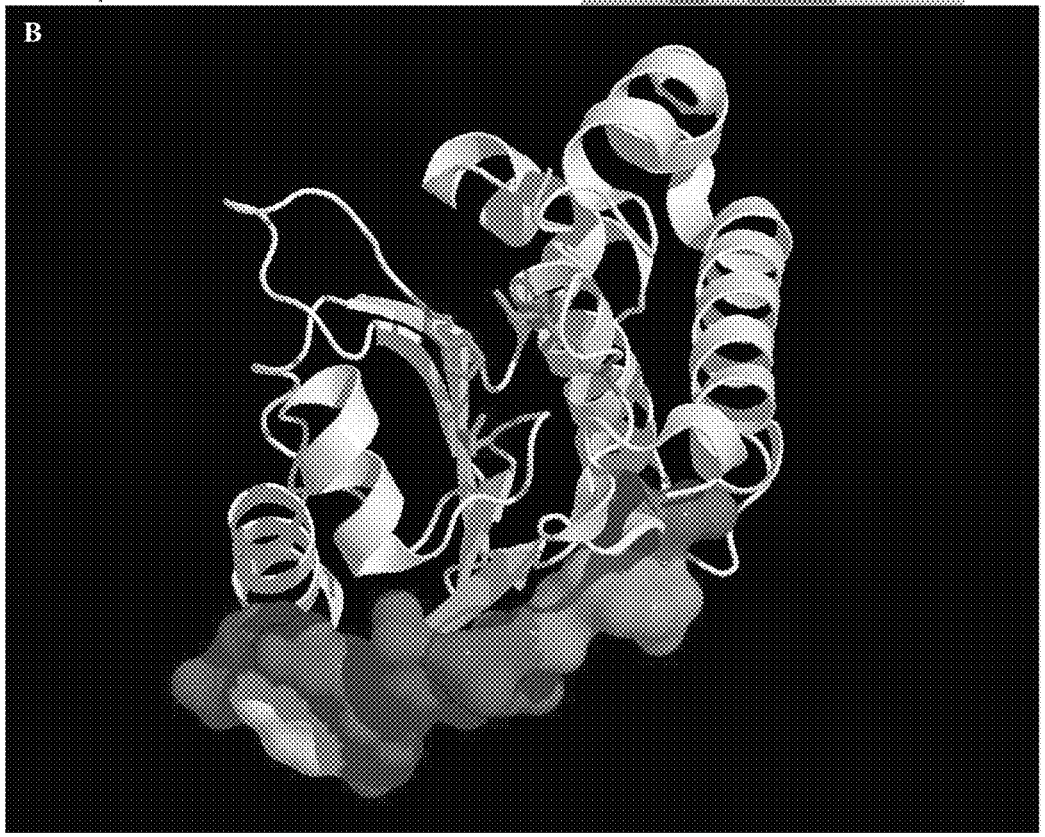

FIGS. 22A-D
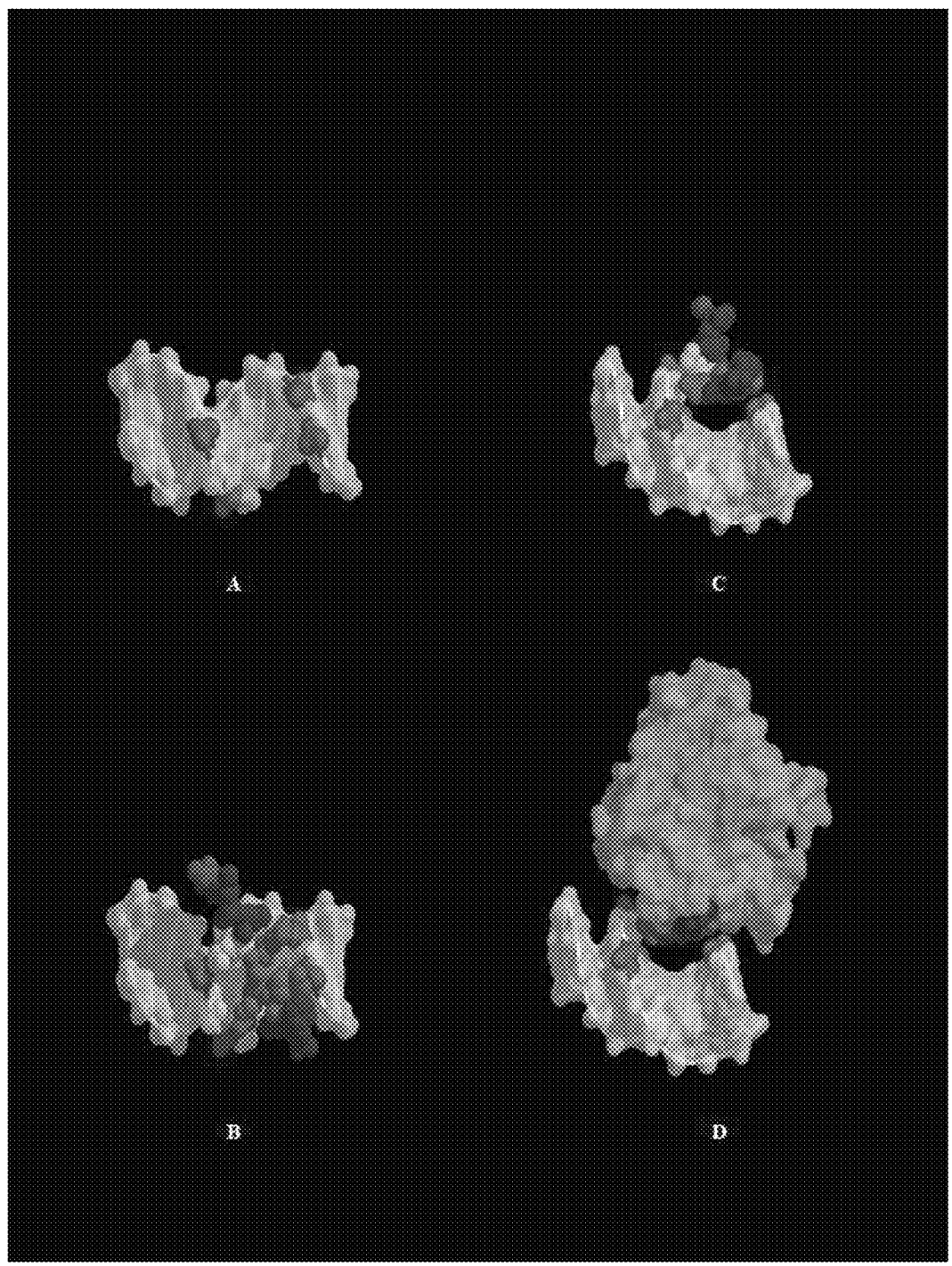

FIGS. 24A-D
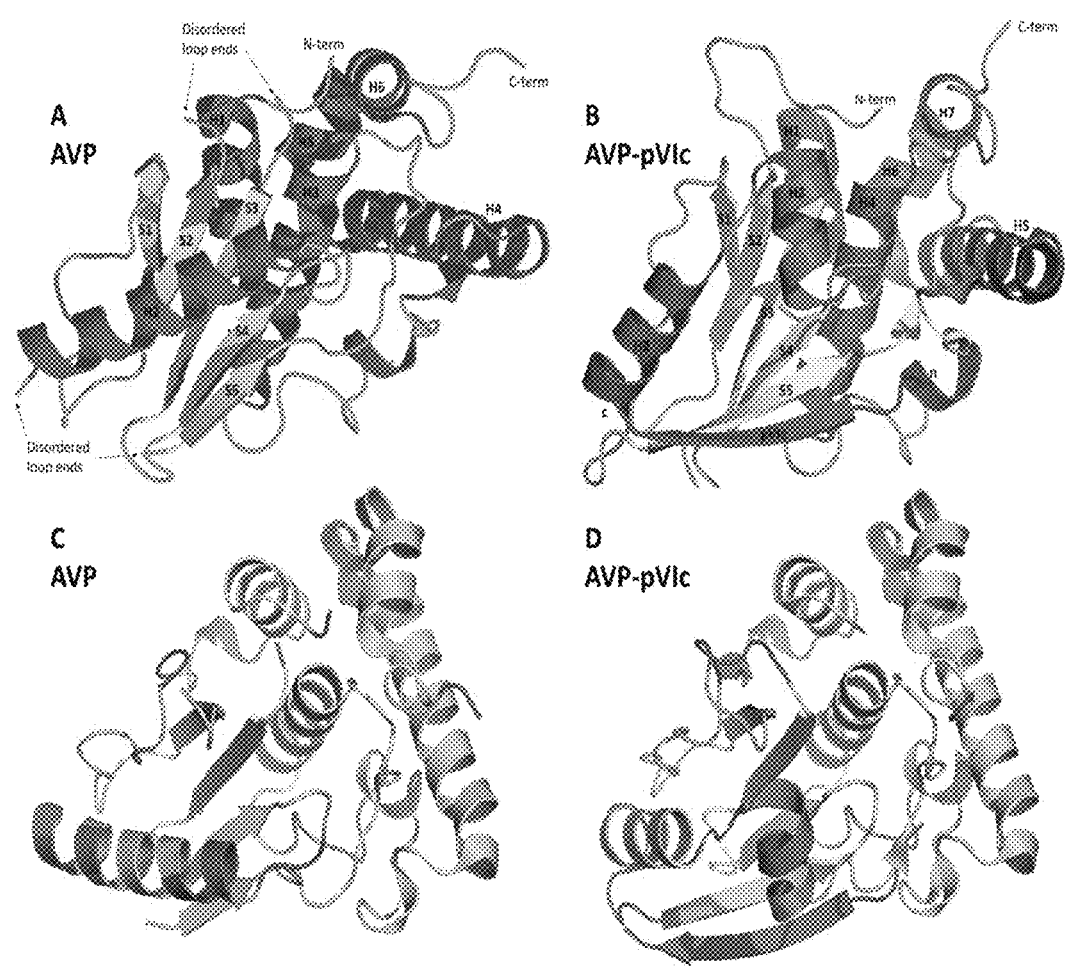

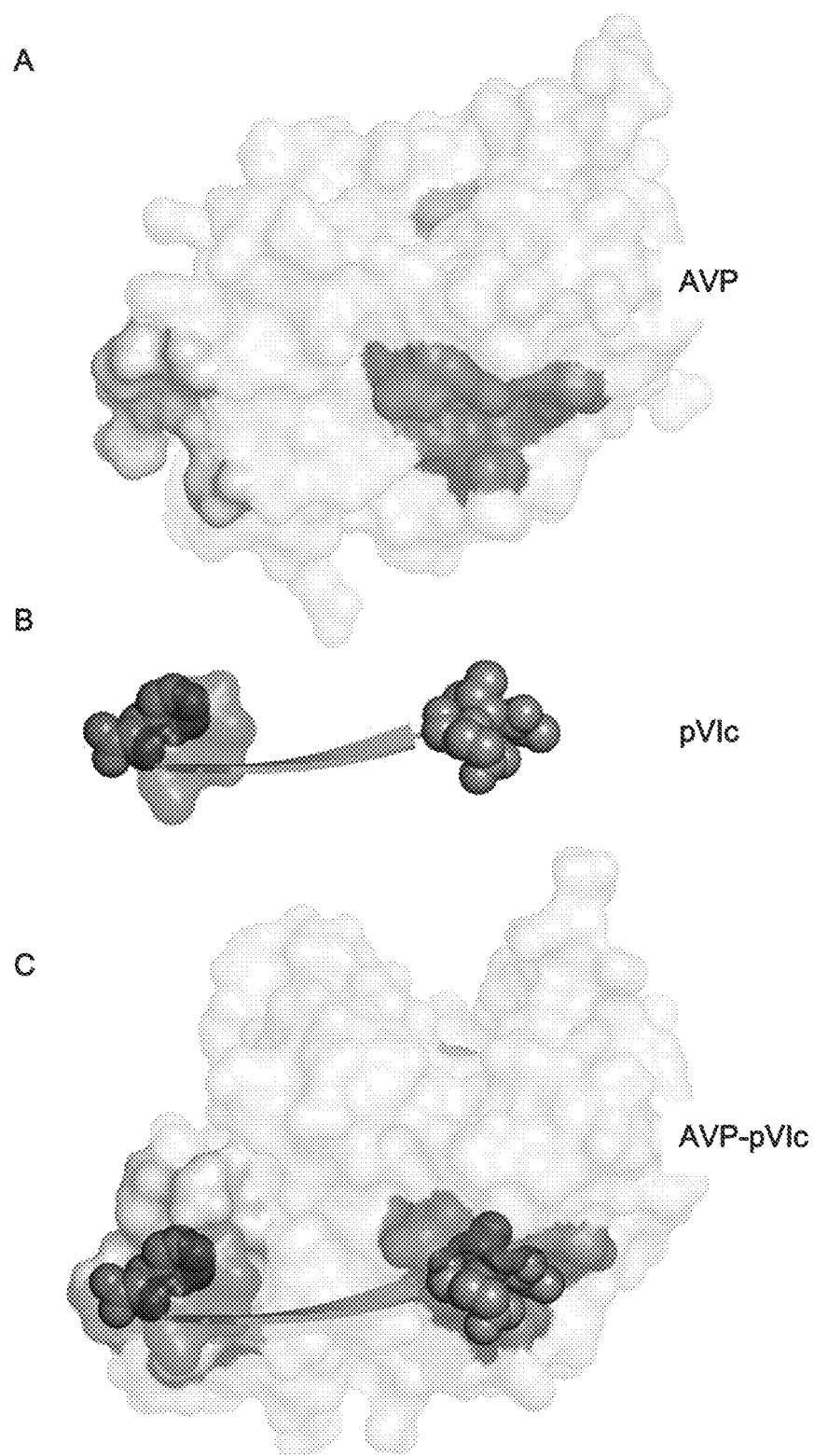
FIGS. 25A-C

FIGS. 26A-B
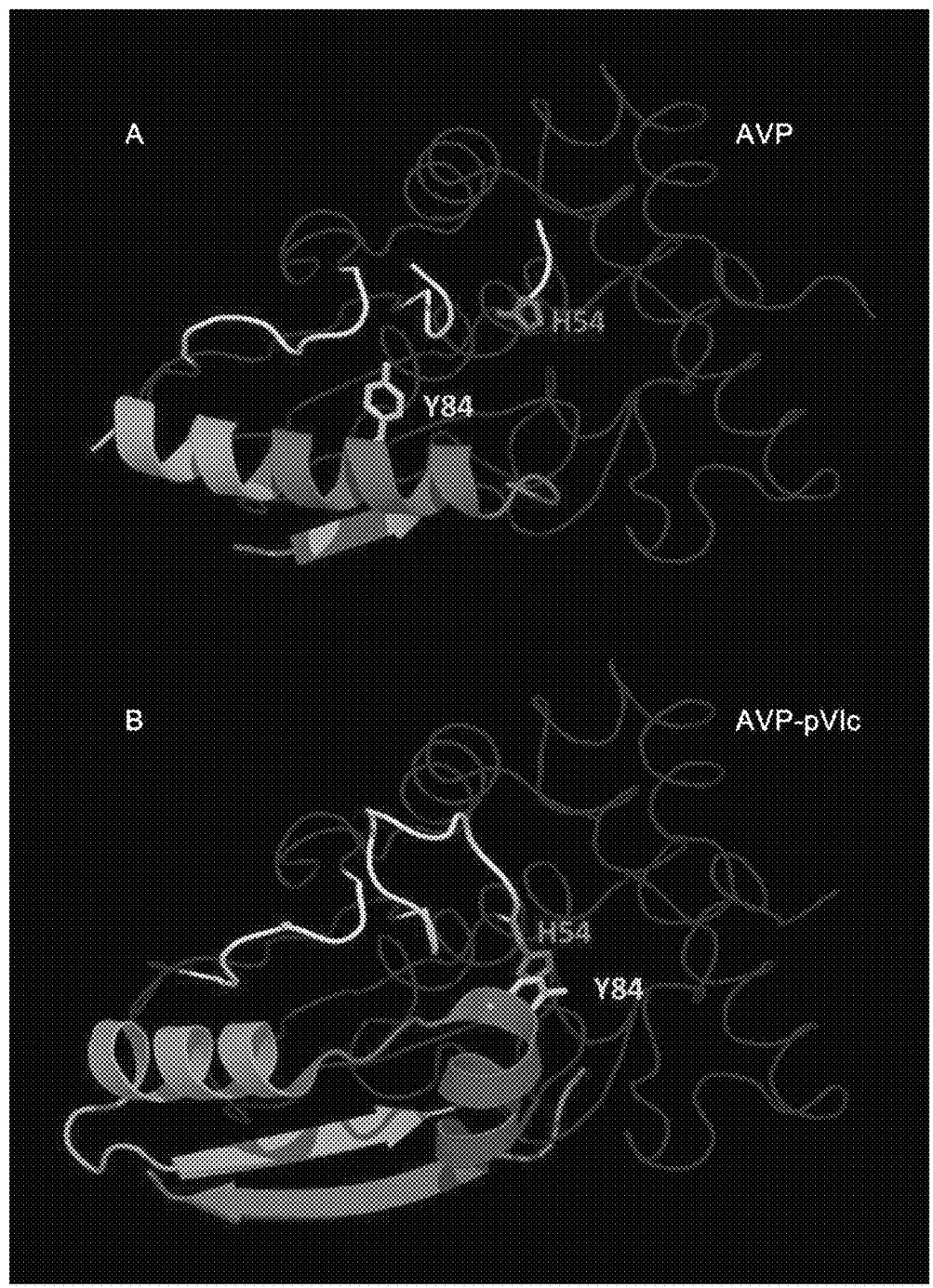

FIG. 28
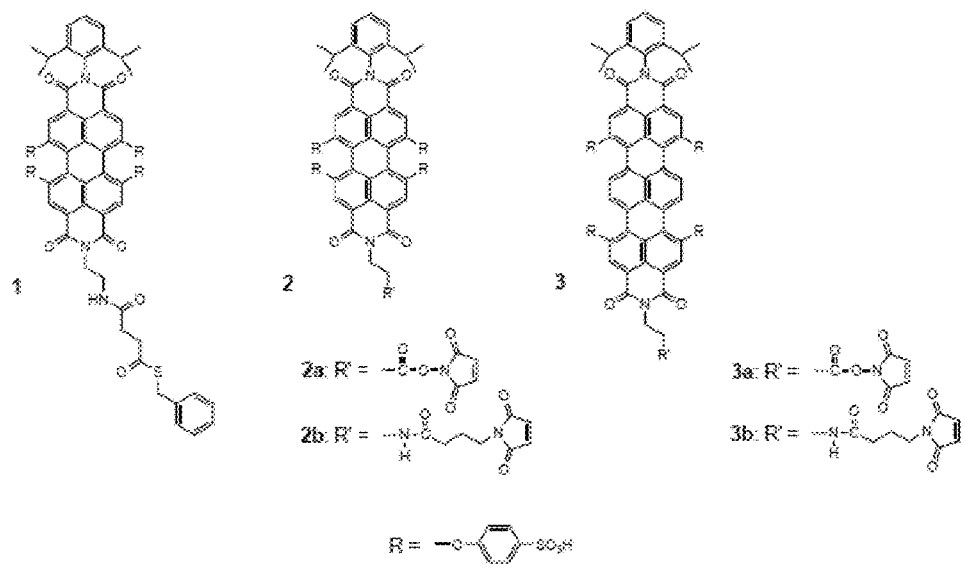
FIGS. 29A-C
A
B 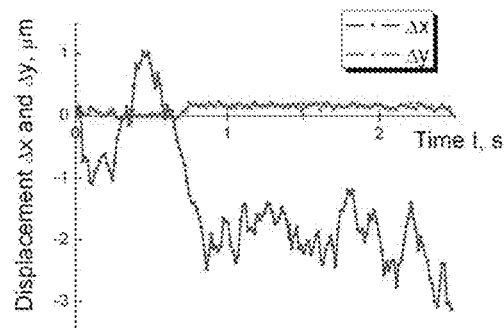
C 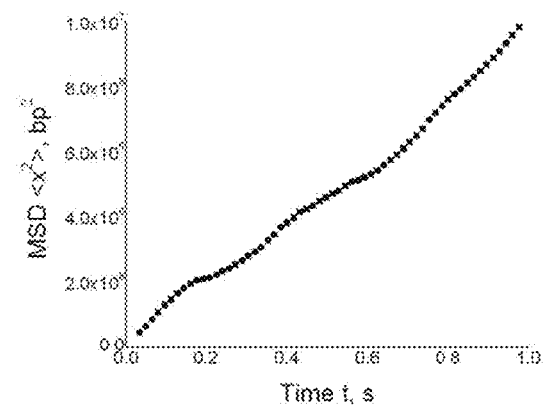

FIGS. 34A-B
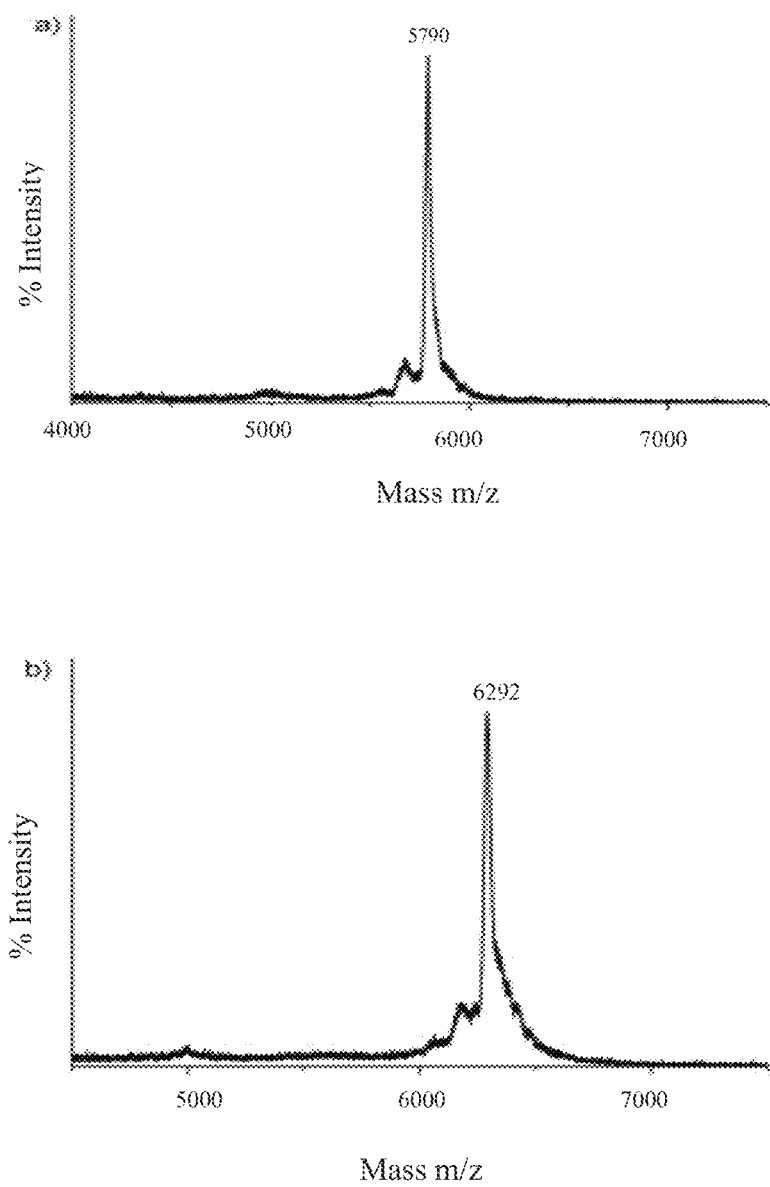

FIGS. 34C-D
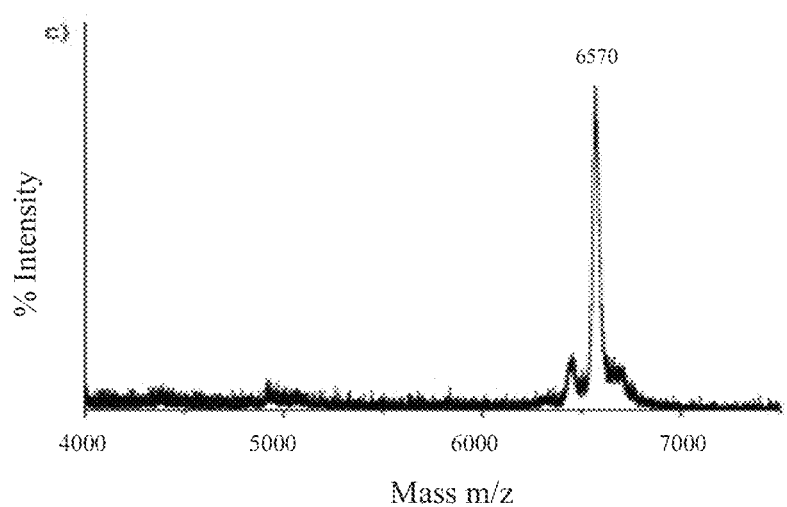
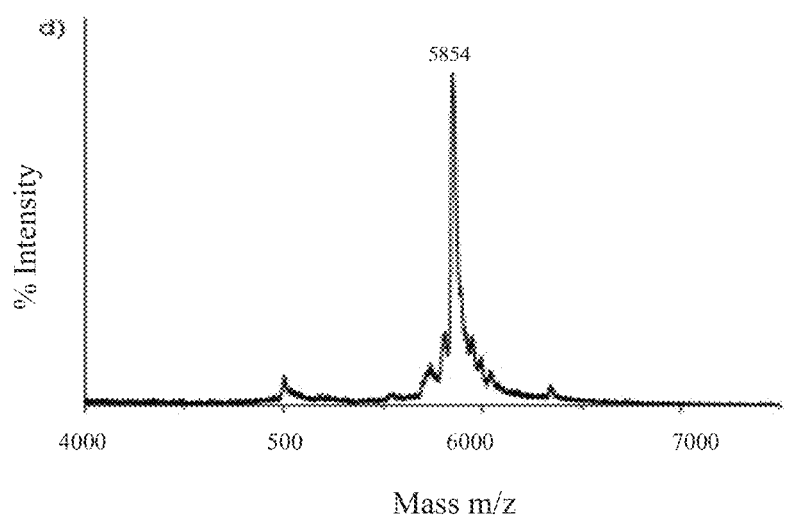

FIGS. 34E-F
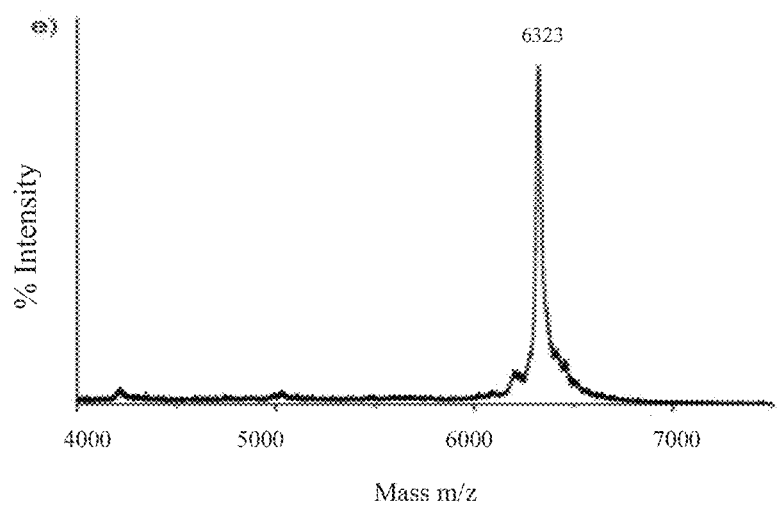
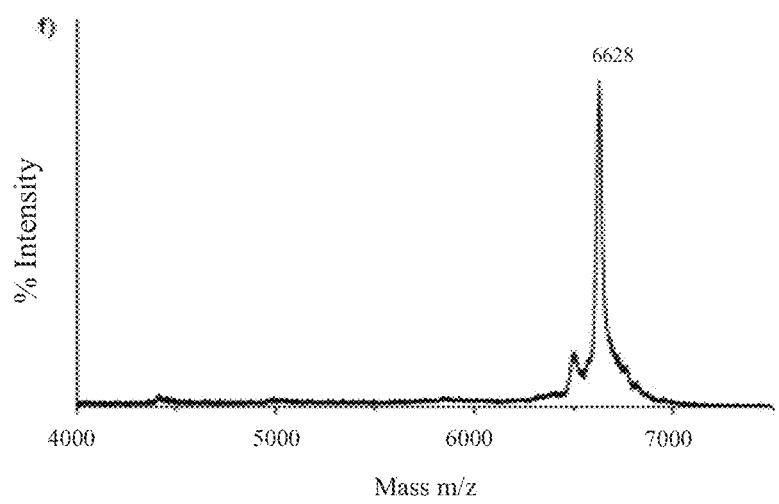

MOLECULAR SLEDS AND USES THEREOF

RELATED APPLICATIONS AND INCORPORATION BY REFERENCE

This application is a continuation-in-part application of international patent application Serial No. PCT/US2013/050451 filed Jul. 15, 2013, which published as PCT Publication No. WO 2014/012090 on Jan. 16, 2014, which claims benefit of and priority to U.S. provisional patent application Ser. No. 61/671,615 filed Jul. 13, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under 5DP1OD000277, awarded by the Department of Energy, 5R01AI041599 awarded by the National Institutes of Health, and 5P41RR012408 awarded by the National Institutes of Health. The government has certain rights in the invention.

FIELD OF THE INVENTION

The present invention relates to compositions which may comprise a non-naturally occurring or engineered molecular sled linked to cargo and uses thereof.

SEQUENCE LISTING

The instant application contains a Sequence Listing which has been submitted electronically in ASCII format and is hereby incorporated by reference in its entirety. Said ASCII copy, created on May 24, 2016, is named 46783.01.2001_SL.txt and is 7,663 bytes in size.

BACKGROUND OF THE INVENTION

Many viral proteins contain several, different domains that function at different steps during a virus infection. This is certainly true of the precursor to protein VI, pVI, and of its proteolytically processed product, protein VI, of adenovirus which are involved both early and late in infection. Early in infection, virus particles engage in a stepwise disassembly program coordinated in time and space during entry into cells leading to the delivery of the viral genome into the nucleus for replication. Protein VI is involved in endosome disruption. Late in infection, new virus particles are assembled and rendered infectious. pVI interacts with DNA to activate the adenovirus proteinase (AVP) and with hexon, the major structural proteins of adenovirus, to escort hexon into the nucleus.

Adenoviruses cause epidemic, endemic or sporadic disease and viremia, and are prevalent in the environment. They also cause fatal infections in immunosuppressed individuals. Adenovirus virions are assembled in part from precursor proteins. Of the 12 major virion proteins, 6 are precursor proteins in the young virion, an assembly intermediate.

Late in an adenovirus infection, the viral proteinase (AVP) becomes activated to process virion precursor proteins used in virus assembly. AVP is activated by pVIc, an 11-amino acid peptide from the C-terminus of the precursor protein pVI.

The high concentration of DNA inside the virion drives all the precursor proteins proteins and AVP onto the DNA by mass action. For AVP-pVIc complexes, the DNA-bound state predominates by at least one hundred thousand-fold over free AVP. This, in combination with the sieving action of the dense DNA, diminishes AVP's effective three-dimensional diffusion constant by at least one million-fold. Given these circumstances, a question is by what mechanism can vital bimolecular associations occur when both enzymes and substrates are essentially irreversibly bound to a fixed matrix, the viral DNA.

A model postulated that AVP-pVIc complexes slide along the viral DNA to locate and process the virion precursor proteins. In infectious wild-type virus, pVIc is covalently attached to AVP, indicating that the AVP-pVIc complex is the form of AVP that processes the virion precursor proteins.

Peptides with rapid sliding activity along DNA have the potential to considerably expand the biochemical repertoire of biological systems and offer the possibility of new regulatory mechanisms based on localization to and transport along regions of the genome. Such mechanisms have the potential to feed back on the cell state in many ways, including the variable quantity of DNA in the cell over the course of the cell cycle, its physical configuration within the cell, and its epigenetic state. The extent to which one-dimensional biochemistry extends beyond nucleic acid metabolism in nature is unknown beyond the initial example Applicants illustrate here in adenovirus. However, based on the discovery of human peptides with sliding activity, the possibility cannot be ignored.

Citation or identification of any document in this application is not an admission that such document is available as prior art to the present invention.

SUMMARY OF THE INVENTION

The invention is based, in part, in Applicants' observation that (a) AVP-pVIc complexes slide along DNA via one-dimensional diffusion and (b) AVP-pVIc complexes processed the virion precursor proteins in DNA-dependent reactions. There was no precedence for a proteinase to slide along DNA to locate and process its substrates.

The present invention relates to a non-naturally occurring or engineered composition which may comprise a molecular sled, linkers and a molecular cargo of the sled via the linkers.

The molecular sled may comprise a core sequence of amino acids XZ'ZZZX'X" wherein X, X' and X" is any amino acid, wherein X, X' or X" are optional Z' is any amino acid and is advantageously lysine (K), arginine (R) or histidine (H) and Z is lysine (K), arginine (R) or histidine (H)

Furthermore, the core sequence of amino acids XZ'ZZZX'X" may be capable of sliding on a negatively charged polymer track.

In an advantageous embodiment, the X of the core sequence may be lysine (K). In another advantageous embodiment, the X' of the core sequence may be cysteine (C). In another advantageous embodiment, the X" of the core sequence may be phenylalanine (F). In another advantageous embodiment, the core sequence may be XKRRRCX" (SEQ ID NO: 1). In another advantageous embodiment, the core sequence of the core sequence may be KKRRRCX" (SEQ ID NO: 2). In another advantageous embodiment, the core sequence of the core sequence may be XKRRRCF (SEQ ID NO: 3). In another advantageous embodiment, wherein the core sequence of the core sequence may be KKRRRCF (SEQ ID NO: 4). In yet another advantageous embodiment, core sequence may be KRRRCF (SEQ ID NO: 5).

The linkers of the present invention may be attached with a covalent bond, a non-covalent bond and/or a neutrally charged ionic bond. The linker may also include a disulfide bond. In another embodiment, the linkers may have at least 4, at least 5, at least 6, at least 10, at least 20, at least 30, at least 40, at least 50, at least 60, at least 70, at least 80, at least 90 up to about 100 linear or straight-chain or branched carbon, nitrogen, oxygen, phosphorous, and/or sulfur atoms.

In another embodiment, the linker may be an organic linker, such as, but not limited to, an amide, carbon-sulfide, ester or ether. In an advantageous embodiment, the linker may be part of the core sequence of the molecular sled. In another embodiment, the linker may be a small component, such as biotin or digoxigenin. In another embodiment, the linker may be a peptide, such as an epitope.

The cargo of the present invention may also encompass the linker. In an advantageous embodiment, the cargo is a therapeutic agent, such as a small molecule, a nucleic acid, a peptide, a protein or an analog or derivative thereof, or a particle, such as a nanoparticle, bed, organelle or large protein complex. Advantageously, the cargo is labeled.

The present invention also encompasses methods involving the use of molecular sleds and their cargoes. The present invention also involves pharmaceutical compositions, methods for treating cancer, a degenerative disease, a genetic disease or an infectious disease as well as diagnostic methods.

The present invention also encompasses methods for altering phenotype or genotype as well as genomic engineering.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent of application file contains at least one drawing executed in color. Copies of this patent or patent application publication with color drawings will be provided by the office upon request and payment of the necessary fees. The following detailed description, given by way of example, but not intended to limit the invention solely to the specific embodiments described, may best be understood in conjunction with the accompanying drawings.

FIG. 2A-B. Stoichiometry of binding of pVI to DNA. A. Stoichiometry of binding. Aliquots of pVI were added to solutions of buffer B containing 13.7 nM 60 bp DNA labeled at one 5' end with fluorescein. After each addition, the steady-state anisotropy was determined. The solid lines are linear fits to the data points represented by the filled circles. The point of intersection of the straight lines, the dashed vertical line, indicates that a minimum of 110 nM pVI was required to saturate 13.7 nM 60 bp dsDNA, a stoichiometry of binding of 8:1. The experiment was repeated but with 13.3 nM 33-mer dsDNA (data not shown); the stoichiometry of binding was 4:1. B. Number of base pairs occluded upon binding of pVI to DNA. The data from the experiments in A. were used to plot the ratio of pVI to DNA versus DNA length (bp). The average number of bp per pVI binding site was 8.

FIG. 3A-B. Thermodynamic parameters in the binding of pVI to DNA. A. Number of ion pairs involved in binding of pVI to DNA. Binding isotherms of pVI binding to 10 nM fluorescein-labeled 12 mer dsDNA in buffer B are shown as a function of the NaCl concentration: (black 0.02 M; red 0.03 M; blue 0.04 M; green 0.05 M, and pink 0.06 M). Binding was measured by changes in fluorescence anisotropy as the pVI concentration was increased. The solid curves are nonlinear least-squares fit of the data to a 1:1 binding model. B. Changes in nonelectrostatic free energy upon the binding of pVI to DNA. The log of the equilibrium dissociation constants calculated from the data in (A) are plotted versus −log [NaCl].

FIG. 4A-B. Binding of pVI to hexon. Equilibrium binding and tight binding of pVI to hexon. A. Change in Fluorescence intensity when 1 nM Cy3B-pVI is titrated with hexon in 20 mM Hepes, 150 mM NaCl, pH 7. Both pVI and hexon concentrations are reported as monomer concentrations. The dissociation constant ($K_d$) is determined by fitting the steady-state fluorescence intensity data to a single site receptor-ligand binding model. The $K_d$ is 1.8 nM. B. Binding data for pVI:hexon interaction under tight binding condition. Change in fluorescence anisotropy when 20 nM of Cy3B-pVI is titrated with increasing amounts of hexon (monomer concentration) in buffer containing 20 mM Hepes, 150 mM NaCl, pH 7. The stoichiometry of binding is determined by the intersection of the two linear regression lines from the first seven and last six data points.

FIG. 6A-C. Activation of AVP by pVI requires DNA and that both proteins be on the same DNA molecule. (A) DNA is required for the activation of AVP by pVI. Assays contained 3.38 µM pVI, 6.54 µM AVP and either 3.38 µM 36 bp dsDNA or no DNA. After the indicated time intervals, aliquots were removed and assayed for enzymatic activity. 100% activity is the enzyme activity of 3.38 µM AVP-pVIc complexes bound to DNA. (○) plus DNA, (▽) minus DNA. (B) For activation of AVP by pVI, both proteins must be on the same DNA molecule. Reactions contained 77 nM of pVI, 130 nM of AVP, and the indicated concentrations of 36-mer dsDNA. After 30 min. at 21° C., the amount of AVP-pVIc formed was assayed. (C) SDS-PAGE (15% polyacrylamide gel) analysis of the reactions in (B) except that the concentrations of pVI, AVP and DNA were 26-fold higher. The DNA concentration in the reactions fractionated on the gel increased from left to right. In B and C, parentheses including the same number indicates the ratio of protein to DNA in B and C is the same.

FIG. 7A-D. Sliding assays for pVI on flow-stretched DNA. (A) Rapid motion of a pVI molecule along flow-stretched dsDNA. Cinegraph generated from raw images showing motion along DNA (horizontal axis; each line is a strip of pixels from a movie frame) as function of time (vertical axis). (B) Trajectory of the molecule depicted in (A) produced by Gaussian centroid determination of the molecule's signal in each of 262 frames. (C) pVI molecules diffuse rapidly along DNA (x(t), left axis, 126 trajectories). (D) Mean-square displacement of the trajectories shown in (C) along the DNA ($<\Delta x(\tau)^2>$, left axis). In (C) and (D) motion transverse to the DNA (y(t) and $<\Delta y(\tau)^2>$, respectively, right axes) is represented on the same scale, as a control.

FIG. 8A-E. Sequence of events during the activation of AVP by pVI in the presence of DNA. During the activation of AVP by pVI in the presence of DNA depicted in (FIG. 5A), aliquots were removed after various time intervals and assayed: (A) SDS-PAGE (15% polyacrylamide gel) analysis. The first lane on the left contains the markers AVP, pVI, and VI. (B) MALDI-TOF analysis of the proteins in the reaction in (FIG. 1A) before the DNA was added; this represents the 0 min. time point. (C) The 20 minute time point is shown. (D) MALDI-TOF analysis of the peptides produced in the reaction mixture in (FIG. 5A) at each time point. The arrows point to the peaks representing the masses (m/z) of the C-terminal (MW 1,350, amino acids 240-250 from pVI) and N-terminal (MW 3583, amino acids 1-33 from pVI) peptides. (E) Summary of the sequence of events in the activation of AVP by pVI in the presence of DNA. The gel in (A) was scanned for protein density, and the data were plotted as the fraction of the initial amount of AVP or pVI versus time. AVP (♦), pVI (●), VI-C (▽), and VI (■).

FIG. 10A-E. Components of the adenovirus proteinase system. Model for the activation of AVP and cleavage of precursor proteins, and method to assay proteins sliding along DNA in vitro. (A) The adenovirus proteinase (AVP) is inactive. Partially activated by being bound to the viral DNA, AVP cleaves pVI to liberate the 11-amino acid peptide (pVIc), in green, which then binds to AVP forming an active AVP-pVIc complex. (B) AVP-pVIc complexes slide along the viral DNA processing virion precursor proteins also bound to the DNA[3]. Single molecule DNA sliding assay. (C) Inverted microscope fitted for total internal reflection fluorescence imaging with (D) mounted flow cell to which lambda DNA molecules (48,502 bp) had been attached at one end. (E) AVP-pVIc complexes, each labeled at Cys199 with one molecule of the fluorescent dye Cy3B, were continuously flowed over the surface of the cover slip. Single protein molecules bound to DNA or sliding along DNA were illuminated by evanescent laser excitation and tracked using a high speed CCD camera.

FIG. 12A-B. Rapid diffusion of AVP-pVIc complexes along flow-stretched dsDNA. (A) Rapid motion of an AVP-pVIc molecule sliding along flow-stretched dsDNA recorded at 284 Hz. Cinegraph generated from raw images showing motion along DNA (horizontal axis; each line is a strip of pixels from a movie frame) as a function of time (vertical axis). (B) Trajectory of the molecule depicted in (A) produced by Gaussian centroid determination of the molecule's signal in each of 262 frames.

FIG. 13A-D. Diffusion of the adenoviral proteinase along flow-stretched dsDNA. (A) AVP in complex with its cofactor pVIc diffuses rapidly along DNA (x(t), left axis, 72 trajectories). (B), AVP alone (without pVIc) binds to DNA but few of the molecules diffuse along DNA (x(t), left axis, 19 trajectories). In both parts (A) and (B), motion transverse to the DNA (y(t), right axis) is represented on the same scale as a control. (C) AVP-pVIc displacements along DNA grow as a function of time (Dx(t), top row of panels). (D) displacements of AVP-pVIc transverse to DNA (Dy(t), top row of panels) do not grow, as the protein is confined to the DNA.

FIG. 14A-C. Mean-square displacement of the adenoviral proteinase on dsDNA. (A) 72 AVP-pVIc complexes sliding along DNA ($<\Delta x(\tau)^2>$, left axis) and transverse to the DNA ($<\Delta y(\tau)^2>$, right axis). (B) 19 AVP complexes sliding along DNA ($<\Delta x(\tau)^2>$, left axis) and transverse to the DNA ($<\Delta y(i)^2>$, right axis). Mean-square displacements are plotted up to $\tau=20\%$ of the length of each trace. (C) Histogram of measured diffusion constants for AVP-pVIc diffusing along dsDNA. The mean diffusion constant is $21\times10^6$ bp$^2$/s.

FIG. 15A-E. DNA-dependent processing of pVI by AVP-pVIc complexes in vitro. DNA-dependent cleavage of pVI by AVP-pVIc complexes. (A, B) SDS-PAGE analysis of the cleavage of pVI by AVP-pVIc complexes in the absence (A) or presence (B) of DNA. A 100 μL reaction in Buffer A contained 6.7 μM pVI, 1.4 μM AVP-pVIc and either 3.4 μM 36 bp DNA or no DNA. After the indicated time intervals, aliquots were removed and the proteins fractionated on a 15% polyacrylamide gel by SDS-PAGE. The first lane on the left contains the markers pVI and AVP-pVIc complexes. MALDI-TOF analysis of the DNA-dependent processing of pVI by AVP-pVIc complexes. (C) The zero time point before DNA was added. (D) 2 minutes after DNA was added. (E) 4 minutes after DNA was added. The intermediate processing product VI-C (pVI fragment amino acids 34-250; 23450 m/z) is observed but the other intermediate product N-VI (pVI fragment amino acids 1-239; 25683 m/z) is not observed.

FIG. 17A-B. Tracking of pVIc sliding along dsDNA. (A) Rapid motion of a pVIc molecule along flow-stretched dsDNA recorded at 284 Hz. Cinegraph generated from raw images showing motion along DNA (horizontal axis; each line is a strip of pixels from a movie frame) as function of time (vertical axis). (B) Trajectory of the molecule depicted in (A) produced by Gaussian centroid determination of the molecule's signal in each of 262 frames.

FIG. 18A-C. Diffusion of pVIc along flow-stretched dsDNA in low salt (0.2-6 mM). (A) The 11-amino acid peptide pVIc diffuses rapidly along DNA (x(t), left axis, 35 trajectories). (B) Mean-square displacement of the trajectories shown in (A) along the DNA ($<\Delta x(\tau)^2>$, left axis). (C) Histogram of measured diffusion constants for pVIc diffusing along dsDNA in low salt with mean equal to $26.0\times10^6$ (bp)$^2$/s. In (A) and (B) motion transverse to the DNA (y(t) and $<\Delta y(\tau)^2>$, respectively, right axes) is represented on the same scale, as a control FIG. 19A-D. Diffusion of the C-terminus of actin along flow-stretched dsDNA. In (A) The 8-amino acid peptide from the C-terminus of β-actin, 8-Actin-C, diffuses-rapidly along DNA (x(t), left axis, 69 trajectories) and in (B) mean-square displacement of the trajectories shown in (A) along the DNA ($<\Delta x(\tau)^2>$, left axis). In (C) The 11-amino acid peptide from the C-terminus of β-actin, 11-Actin-C, diffuses rapidly along DNA (x(t), left axis, 102 trajectories) and in (D) mean-square displacement of the trajectories shown in (C) along the DNA ($<\Delta x(\tau)^2>$, left axis). In (A and C) motion transverse to the DNA (y(τ) and $<\Delta y(\tau)^2>$, respectively, right axes) is represented on the same scale, as a control.

FIG. 20A-C. Binding to DNA of (pVIc-biotin)-streptavidin complexes and diffusion of (pVIc-biotin)-streptavidin complexes along flow-stretched dsDNA. (A) The equilibrium dissociation constants for the binding of (pVIc-biotin)-strepavidin to 18-mer dsDNA were determined by fluorescence resonance energy transfer (FRET). The quenching of the fluorescence intensity of the donor molecule, fluorescein-labeled 18-dsDNA, as a function of the concentration of the acceptor molecule (pVIc-biotin)-strepavidin Alexa Fluor 546 is shown by the closed circles. The relative fluorescence intensity is the fluorescence intensity at a specific concentration of acceptor divided by $I_0$ which is the initial fluorescence intensity, i.e. the intensity of the donor in the absence of acceptor. The line through the closed circles represents the nonlinear regression fit of the experimental data to a 1:1 ligand-receptor model. When the experiment was repeated but with streptavidin-Alexa Fluor 546, the open circles represent the data from the titration of 10 nM fluorescein-labeled 18-mer dsDNA with strepavidin Alexa Fluor 546, the data indicate that strepavidin Alexa Fluor 546 did not bind to DNA. Both curves were corrected for inner filter effects, which were less than 10% at the highest concentration of acceptor. (B) (pVIc-biotin)-streptavidin complexes diffuse rapidly along DNA (x(t), left axis, 106 trajectories), 106 trajectories, DNA stretch factor 1.15. (C) Mean-square displacement of the trajectories shown in (A) along the DNA ($<\Delta x(z)^2>$, left axis). In (B and C) motion transverse to the DNA (y(t) and $<\Delta y(\tau)^2>$, respectively, right axes) is represented on the same scale, as a control.

FIG. 21A-B. Amino acid sequences of pVIcs and pVIc-like sequences and crystal structure of the AVP-pVIc complex. (A) Amino acid sequences of pVIcs from various adenoviruses and from the C-termini of actin and p53 (SEQ ID NOS 12, 12, 12, 27, 28, 28, 28, 28, 28, 28-33, 9 and 34, respectively, in order of appearance). Basic amino acids are colored in bright red, hydrophobic in light cyan, polar in light green, cysteine in light yellow, and glycine and proline in light gray. (B) Crystal structure of the AVP-pVIc complex. In the crystal structure of the AVP-pVIc complex the active site is in a groove; the four amino acids involved in catalysis are shown in purple. The van der Waals spheres of pVIc are colored using the same color scheme as in (A).

FIG. 22A-D. Models for the binding of pVIc and AVP-pVIc complexes to 12-mer dsDNA. (A) The structure of a DNA dodecamer (PDB id 1HQ7) is displayed with four, noncontiguous phosphate groups colored red. (B) The structure of pVIc obtained from the crystal structure of the AVP-pVIc complex (PDB id 1NLN) is shown docked to the DNA. The four basic residues of pVIc, the one lysine residue and the three arginine residues, are colored light blue and dark blue, respectively. (C) The DNA-pVIc complex was rotated approximately 90 degrees on its x-axis to show the contacts of the peptide with the major groove. (D) The AVP-pVIc structure (PDB id 1NLN) is displayed, showing that the DNA binding is dominated by the pVIc moiety. The active site of AVP is colored pink.

FIG. 24A-D. Structural comparisons between AVP and the AVP-pVIc complex. The two structures were superimposed by least-squares fitting. For A and B, helices are colored red, strands are colored yellow, and coils are colored green. In A, the secondary structure representation of AVP is shown. In B, the secondary structure representation of the AVP-pVIc complex is shown with the pVIc peptide depicted in magenta. In C & D, the aligned structures of A and B have been rotated approximately 60 degrees on the x-axis and 20 degrees on the y-axis to highlight the structural changes. In C, the aligned structural cartoon of AVP is shown with residues colored by rmsd using a spectrum from blue, similar in structure, through red, highly different in structure. Those amino acids residues that are essentially identical in structure are colored tan. In D, the alignment of AVP-pVIc with AVP is shown with residues colored as in C.

FIG. 25A-C. The NT- and CT-pockets on AVP and the AVP-pVIc complex into which the two termini of pVIc bind. In A, the accessible surface of AVP is shown with the active site cysteine colored orange, residues that form the NT pocket in the AVP-pVIc complex colored dark pink, and those residues whose positions could be determined in the structure that aid in forming the CT binding pocket are colored tan. In B, pVIc is shown in green with the residues which interact in the binding pockets shown as van der Waals spheres, the NT pocket residues in olive, the CT pocket residue in blue. Those residues of pVIc which aid in forming the CT pocket are shown as a light brown surface. In C, the AVP-pVIc complex with the NT and CT pockets colored as in A and the pVIc colored as in B. Three residues which aid in forming the CT pocket are undefined in the AVP structure.

FIG. 26A-B. Structural transition in the activation of AVP by pVIc—the activation pathways. A 'top' view of the aligned structures is shown in cartoon form. In A, AVP is shown with the residues involved in the common pathway colored green, the His54 pathway colored yellow and the Tyr84 pathway colored blue. His54 (pink) and Tyr84 (tan) are shown in stick form. In B, the orientation of those residues depicted in the AVP-pVIc structure. The cation-π interaction of His54 and Tyr84 is shown by the overlapping side chains and pVIc is colored red.

FIG. 28. Thioestermodified water soluble perylenediimide derivative 1, perylenes 2a and 2b and new analogous terrylen derivatives 3a and 3b functionalized with amine and thiol-reactive groups, respectively.

FIG. 29A-C. Data visualizing the rapid one-dimensional diffusive movement of individual, fluorescently labelled pVIc peptide molecules along DNA (panel A: fluorescence trace, B: high-precision tracked trace, C: mean-square displacement versus time).

FIG. 34A-G. MALDI-TOF mass spectra of primer-peptide conjugates. a) FP-K, b) FP-pVIc, c) FP-W, d) BP-K, e) BP-pVIc, f) BP-W, and g) FP-S.

DETAILED DESCRIPTION OF THE INVENTION

Figure 1:
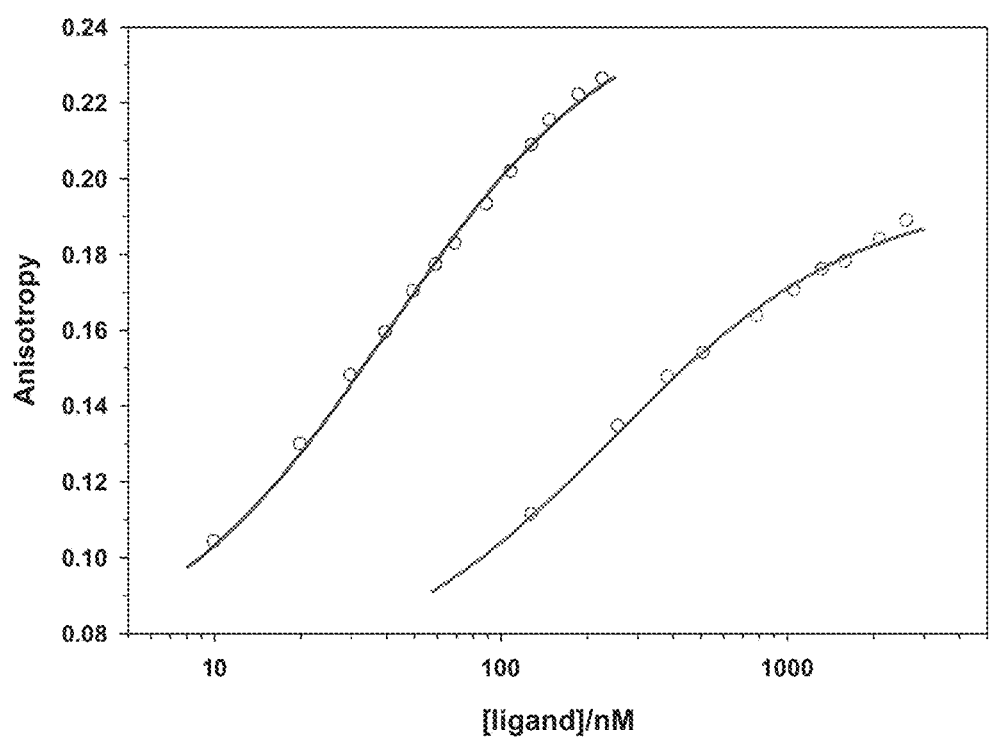
FIG. 1. Binding of pVI and VI to DNA. Equilibrium dissociation constants. Aliquots of pVI or VI were added to buffer B with 1 mM $MgCl_2$ containing 10 nM fluorescein labeled 33-mer dsDNA, and the steady-state anisotropy after each addition was measured at 21° C. The data are presented in the form of a Berjirim plot and yielded apparent equilibrium dissociation constants of 35±2 nM for pVI (blue open circles) and 241±14 nM for VI (red open circles).

The term "nucleic acid" or "nucleic acid sequence" refers to a deoxyribonucleic or ribonucleic oligonucleotide in either single- or double-stranded form. The term encompasses nucleic acids, i.e., oligonucleotides, containing known analogues of natural nucleotides. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" encompasses the ligation of nucleic acids having various coding regions or domains or promoter sequences from different sources into an expression cassette or vector for expression of, e.g., inducible or constitutive expression of polypeptide coding sequences in the vectors of invention.

The term "heterologous" when used with reference to a nucleic acid, indicates that the nucleic acid is in a cell or a virus where it is not normally found in nature; or, comprises two or more subsequences that are not found in the same relationship to each other as normally found in nature, or is recombinantly engineered so that its level of expression, or physical relationship to other nucleic acids or other molecules in a cell, or structure, is not normally found in nature. A similar term used in this context is "exogenous". For instance, a heterologous nucleic acid is typically recombinantly produced, having two or more sequences from unrelated genes arranged in a manner not found in nature; e.g., a human gene operably linked to a promoter sequence inserted into an adenovirus-based vector of the invention. As an example, a heterologous nucleic acid of interest can encode an immunogenic gene product, wherein the adenovirus is administered therapeutically or prophylactically as a carrier or drug-vaccine composition. Heterologous sequences can comprise various combinations of promoters and sequences, examples of which are described in detail herein.

A "therapeutic ligand" may be a substance which can bind to a receptor of a target cell with therapeutic effects.

A "therapeutic effect" may be a consequence of a medical treatment of any kind, the results of which are judged by one of skill in the field to be desirable and beneficial. The "therapeutic effect" may be a behavioral or physiologic change which occurs as a response to the medical treatment. The result may be expected, unexpected, or even an unintended consequence of the medical treatment. A "therapeutic effect" may include, for example, a reduction of symptoms in a subject suffering from infection by a pathogen.

A "target cell" may be a cell in which an alteration in its activity can induce a desired result or response.

An "antigen" may be a substance that is recognized by the immune system and induces an immune response.

An "immunogen" may be a substance that elicits an immune response from the immune system.

A "ligand" may be any substance that binds to and forms a complex with a biomolecule to serve a biological purpose. As used herein, "ligand" may also refer to an "antigen" or "immunogen". As used herein "antigen" and "immunogen" are used interchangeably.

As used herein, a "pathogen" may refer to a viral pathogen (e.g., virus) or a bacterial pathogen. "Pathogen" also encompasses "respiratory pathogens".

"Expression" of a gene or nucleic acid encompasses not only cellular gene expression, but also the transcription and translation of nucleic acid(s) in cloning systems and in any other context.

As used herein, a "vector" is a tool that allows or facilitates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. The present invention comprehends recombinant vectors that can include viral vectors, bacterial vectors, protozoan vectors, DNA vectors, or recombinants thereof.

With respect to exogenous DNA for expression in a vector (e.g., encoding an epitope of interest and/or an antigen and/or a therapeutic) and documents providing such exogenous DNA, as well as with respect to the expression of transcription and/or translation factors for enhancing expression of nucleic acid molecules, and as to terms such as "epitope of interest", "therapeutic", "immune response", "immunological response", "protective immune response", "immunological composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990, 091 and WO 98/00166 and WO 99/60164 and documents cited therein and documents of record in the prosecution of that patent and those PCT applications, and other documents cited herein or otherwise incorporated herein by reference, can be consulted in the practice of this invention; and, all exogenous nucleic acid molecules, promoters, and vectors cited therein can be used in the practice of this invention. In this regard, mention is also made of U.S. Pat. Nos. 6,706, 693; 6,716,823; 6,348,450; U.S. patent application Ser. Nos. 10/424,409; 10/052,323; 10/116,963; 10/346,021; and WO 99/08713, published Feb. 25, 1999, from PCT/US98/16739.

As used herein, the terms "drug composition" and "drug", "vaccinal composition", "vaccine", "vaccine composition", "therapeutic composition" and "therapeutic-immunologic composition" cover any composition that induces protection against an antigen or pathogen. In some embodiments, the protection may be due to an inhibition or prevention of infection by a pathogen. In other embodiments, the protection may be induced by an immune response against the antigen(s) of interest, or which efficaciously protects against the antigen; for instance, after administration or injection into the subject, elicits a protective immune response against the targeted antigen or immunogen or provides efficacious protection against the antigen or immunogen expressed from the inventive adenovirus vectors of the invention. The term "pharmaceutical composition" means any composition that is delivered to a subject. In some embodiments, the composition may be delivered to inhibit or prevent infection by a pathogen.

The terms "immunogenic composition" and "immunological composition" and "immunogenic or immunological composition" cover any composition that confers in a subject a therapeutic effect and/or elicits in a subject an immune response against the antigen, immunogen, or pathogen of interest; for instance, after administration into a subject, elicits an immune response against the targeted immunogen or antigen of interest.

An "immunological response" to a composition, vaccine, antigen, immunogen, pathogen or ligand is the development in the host of a cellular and/or antibody-mediated immune response to the composition, vaccine, antigen, immunogen, pathogen or ligand interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display both a rapid (e.g., within <24 hrs.) therapeutic effect and a long-term protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

A "therapeutically effective amount" or an "immunologically effective amount" is an amount or concentration of the recombinant vector encoding the gene of interest, that, when administered to a subject, produces a therapeutic response or an immune response to the gene product of interest.

A "circulating recombinant form" refers to recombinant viruses that have undergone genetic reassortment among two or more subtypes or strains. Other terms used in the context of the present invention is "hybrid form", "recombined form", and "reassortant form".

"Clinical isolates" refer to viruses or microbes isolated from infected subjects in a clinical setting.

"Field isolates" refer to viruses or microbes that are isolated from infected subjects or from the environment.

The term "viral vector" as used herein includes but is not limited to retroviruses, adenoviruses, adeno-associated viruses, alphaviruses, and herpes simplex virus.

The present invention encompasses a non-naturally occurring or engineered composition which may comprise a molecular sled, one or more linkers and a molecular cargo.

The molecular sled may comprise a core sequence of amino acids XZ'ZZZX'X" wherein X, X' and X" is any amino acid, wherein X, X' or X" are optional and/or may be part of a linker Z' is any amino acid and is advantageously lysine (K), arginine (R) or histidine (H) and Z is lysine (K), arginine (R) or histidine (H).

The core sequence of amino acids may be capable of sliding on a negatively charged polymer track.

In an advantageous embodiment, the X of the core sequence may be lysine (K). In another advantageous embodiment, the X' of the core sequence may be cysteine (C). In another advantageous embodiment, the X" of the core sequence may be phenylalanine (F). In another advantageous embodiment, the core sequence may be XKRRRCX" (SEQ ID NO: 1). In another advantageous embodiment, the core sequence of the core sequence may be KKRRRCX" (SEQ ID NO: 2). In another advantageous embodiment, the core sequence of the core sequence may be XKRRRCF (SEQ ID NO: 3). In another advantageous embodiment, wherein the core sequence of the core sequence may be KKRRRCF (SEQ ID NO: 4). In yet another advantageous embodiment, the core sequence may be KRRRCF (SEQ ID NO: 5).

In one embodiment, X, X' or X" may comprise one or more naturally-occurring or non-naturally occurring amino acids. The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The molecular sled and cargo of the present invention may be capable of penetrating a cell membrane. A classic example is the HIV TAT protein transduction domain, the peptide YGRKKRRQRRR (SEQ ID NO: 6). Such polycationic peptides are cell-penetrating. A subclass of cell penetrating peptides (CPP) with the K-K/R-X-K/R (classical monopartite) motif have additional signaling activity triggering nuclear import.

The molecular sled and cargo of the present invention may further comprise a nuclear localization signal (NLS). NLS is a sequence that has been identified in a variety of species of living organisms and viruses, and is generally a partial amino acid sequence rich in basic amino acids present in a variety of polypeptides that translocate into the nucleus within a cell. For instance, the literature of R. Truant and B. R. Cullen (MOLECULAR AND CELLULAR BIOLOGY, volume 19 (2), 1999, pp. 1210-1217) describes an NLS present in the human immunodeficiency virus (HIV). NLS sequences typically are small, mostly basic, amino acid sequences which can be classified into three general groups: (i) a monopartite NLS exemplified by the SV40 large T antigen NLS (PKKKRKV) (SEQ ID NO: 7); (ii) a bipartite motif consisting of two basic domains separated by a variable number of spacer amino acids and exemplified by the *Xenopus* nucleoplasmin NLS (KRXXXXXXXXXXK-KKL) (SEQ ID NO: 8); and (iii) noncanonical sequences such as M9 of the hnRNP A1 protein, the influenza virus nucleoprotein NLS, and the yeast Ga14 protein NLS (Dingwall and Laskey, Trends Biochem Sci 16:478-481, 1991).

The steps involved in the import mechanism of proteins into eukaryotic nuclei have been elucidated (Nigg, E. A., Nature, 386:779-87, 1997; Gorlich, D., EMBO J., 17:2721-7, 1998). To be transported, the NLS sequence is recognized by members of the importin family of proteins (also referred to as karyopherins), which then act as carriers to transport the substrate protein across the NPC. Inside the nucleus, the importin-substrate complex dissociates, liberating the substrate protein, and the importin carrier ultimately returns to the cytoplasm. The small GTPase Ran plays a pivotal role in this process by promoting, in its GTP-bound form, the dissociation of the import complex and the subsequent recycling of the importin carrier.

The invention contemplates any linker capable of connecting a molecular sled of the present invention with a molecular cargo.

The linkers of the present invention may be attached with a covalent bond, a non-covalent bond and/or a neutrally charged ionic bond. The linker may also include a disulfide bond. In another embodiment, the linkers may have at least 4, at least 5, at least 6, at least 10, at least 20, at least 30, at least 40, at least 50, at least 60, at least 70, at least 80, at least 90 up to about 100 linear or straight-chain or branched carbon, nitrogen, oxygen, phosphorous, and/or sulfur atoms.

In an advantageous embodiment, the linker may be poly (ethylene glycol).

In another advantageous embodiment, the linker may be

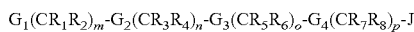

wherein $G_1$, $G_2$, $G_3$, and $G_4$ are each, independently, bifunctional groups selected from

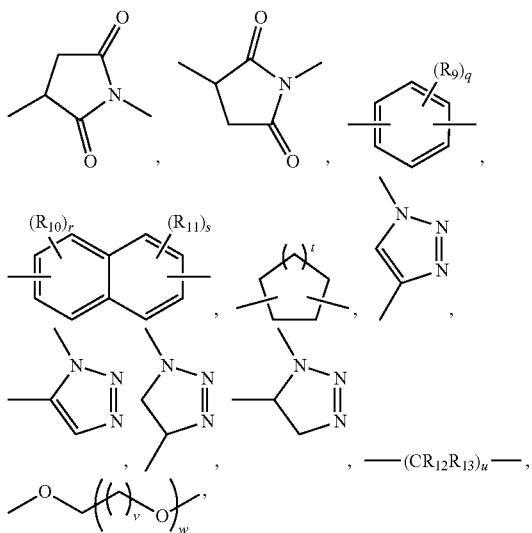

—(C=O)NR$_{14}$—, —NR$_{15}$(C=O), —O—, —O—O—, —O(C=O)—, —O(C=O)O—, —(C=O)O—, —(C=O)—, —P—, —O(PO$_2$)O—, —(PO)—, O(P—NR$_{16}$R$_{17}$)O—, —S—, —S—S—, —NR$_{18}$—NR$_{19}$—, —O(SO$_2$)—, —O(SO$_2$)O—, —(SO$_2$)O—, —(SO$_2$)—, —(SO)—, —(SO$_2$)NR$_{20}$—, —NR$_{21}$(SO$_2$)—, —NR$_{22}$—, a peptide, an oligonucleotide, and a combination thereof;

J is a capping group selected from —H, —OR$_{23}$, —NR$_{24}$R$_{25}$, —SR$_{26}$, —(C=O)NR$_{27}$R$_{28}$, (C=O)OR$_{29}$, a peptide, an oligonucleotide, biotin or a derivative thereof, and digoxigenin or a derivative thereof; or J is a bifunctional group selected from

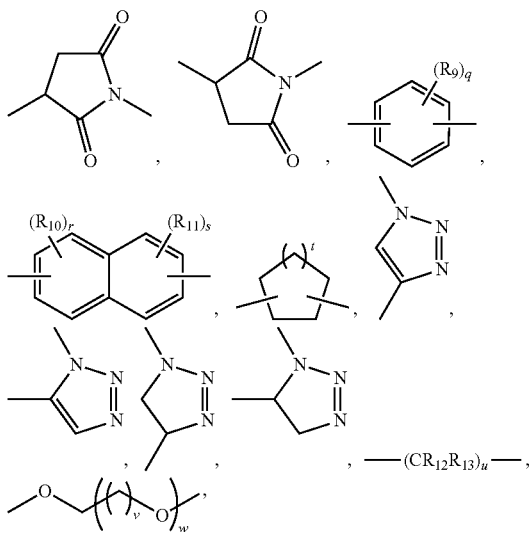

—(C=O)NR$_{14}$—, —NR$_{15}$(C=O), —O—, —O—O—, —O(C=O)—, —O(C=O)O-, —(C=O)O—, —(C=O)—, —P—, —O(PO$_2$)O—, —(PO)—, O(P—NR$_{16}$R$_{17}$)O—, —S—, —S—S—, —NR$_{18}$—NR$_{19}$—, —O(SO$_2$)—, —O(SO$_2$)O—, —(SO$_2$)O—, —(SO$_2$)—, —(SO)—, —(SO$_2$)NR$_{20}$—, —NR$_{21}$(SO$_2$)—, —NR$_{22}$—, a peptide, an oligonucleotide, and a combination thereof; m, n, o, p, u, v, and w are each, independently, an integer from 0 to 20;

q is an integer from 0 to 4;
r, s, and t are each, independently, an integer from 0 to 3;
R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, and R$_{22}$, are each, independently, hydrogen, halogen, cyano, nitro, C$_{1-10}$ alkyl, C$_{1-10}$ alkenyl, or C$_{1-10}$ alkynyl; wherein the C$_{1-10}$ alkyl, C$_{1-10}$ alkenyl, or C$_{1-10}$ alkynyl are each optionally substituted by one or more substituents selected from hydroxy, halogen, C$_{1-6}$ alkoxy, amino, and aryl and heteroaryl groups of 5 to 12 ring members.

Other linkers contemplated by the present invention include, but are not limited to, carbon with single and double bonds which encompass alkyl- and alkyne-containing linkers. Other chemical linkages may include aldehyde-amine, activated ester (eg NHS ester)—amine, Michael condensations (e.g., sulfahydryl with maleimide), and carboxylic acid-amine coupling (as in peptide synthesis, similar to addition to activated ester), "click" chemistry and coordination reactions (such as IDA with nickel or cobalt).

The linker of the present invention may be synthesized using chemical transformations and methods known to those of ordinary skill in the art. The chemical reactions described herein include using solvents, reagents, catalysts, protecting group and deprotecting group reagents, and certain reaction conditions. Synthetic chemistry transformations and protecting group methodologies (protection and deprotection) useful in synthesizing and/or attaching the linkers to the molecular sleds of the present invention are known in the art and include, for example, those disclosed in Advanced Organic Chemistry, second edition, Part B: Reactions and Synthesis, Carey and Sunberg, Plenum Press, N.Y. (1983); Advanced Organic Chemistry, Reactions, Mechanisms, and Structure, second edition, March, McGraw Hill, N.Y. (1977); and Comprehensive Organic Transformations, A Guide to Functional Group Preparations, second edition, Larock, N.Y. (1999); and reference cited therein. Suitable protection/deprotection methodologies and chemical reagents are further described, for example, in T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The linker according to the present invention may be synthesized using chemical transformations and methods known to those of ordinary skill in the art. The linker may comprise bifunctional groups and capping groups. Bifunctional groups are groups that have two valences available for bonding. Capping groups are groups that have one valence available for bonding. Examples of suitable functional groups appending such a bifunctional linker include, but are not limited to,

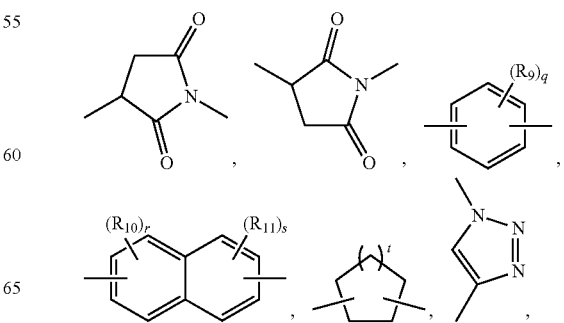

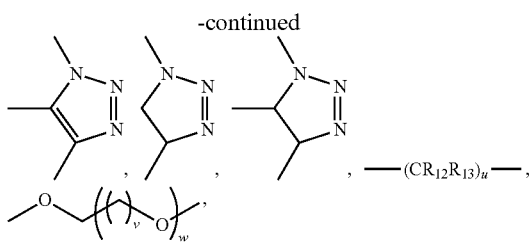

—(C=O)NR$_{14}$—, —NR$_{15}$(C=O)—, —O—, —O—O—, —O(C=O)—, —O(C=O)O—, —(C=O)O—, —(C=O)—, —P—, —O(PO$_2$)O—, —(PO)—, O(P—NR$_{16}$R$_{17}$)O—, —S—, —S—S—, —NR$_{18}$—NR$_{19}$—, —O(SO$_2$)—, —O(SO$_2$)O—, —(SO$_2$)O—, —(SO$_2$)—, —(SO)—, —(SO$_2$)NR$_{20}$—, —NR$_{21}$(SO$_2$)—, —NR$_{22}$—, a peptide, an oligonucleotide, and a combination thereof.

Examples of suitable capping groups include, but are not limited to, —H, —OR$_{23}$, —NR$_{24}$R$_{25}$, —SR$_{26}$, —(C=O)NR$_{27}$R$_{28}$, —(C=O)OR$_{29}$, a peptide, an oligonucleotide, biotin or a derivative thereof, and digoxigenin or a derivative thereof. R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, and R$_{22}$, are each defined herein.

The bifunctional and capping groups described herein may be assembled or synthesized using chemical transformations and methods known to those of ordinary skill in the art.

In another embodiment, the linker may be an organic linker, such as, but not limited to, an amide, carbon-sulfide, ester or ether. In an advantageous embodiment, the linker may be part of the core sequence of the molecular sled. In another embodiment, the linker may be a small component, such as biotin or digoxigenin. The linker may also be bioconjugated.

The present invention also contemplates peptides as linkers. For example, the core of the molecular sled may also be part of the linker.

In an advantageous embodiment, the peptide may be an epitope. Advantageously, the epitope may recognized by a FLAG or HIS5 antibody.

The molecular cargo may be covalently linked or hydrogen bonded to the one or more linkers. In another embodiment, capture of an endogenous protein/enzyme with an inhibitor, particularly a suicide inhibitor that covalently links with the enzyme, is also contemplated.

The cargo of the present invention may also encompass the linker. In an advantageous embodiment, the cargo is a therapeutic agent, such as a small molecule, a nucleic acid, a peptide, a protein or an analog or derivative thereof, or a particle, such as a nanoparticle, bed, organelle or large protein complex. Advantageously, the cargo is labeled.

The cargo may be naturally occurring. In an advantageous embodiment, the molecular cargo may be a therapeutic agent, such as a drug. The molecular cargo may be a small molecule, a nucleic acid, a peptide, a protein or an analog or derivative thereof.

If the cargo is a nucleic acid, the nucleic acid may be a double stranded DNA, single stranded DNA or RNA. Advantageously, the nucleic acid may contain a residue with a 2' O-Me, LNA, or a minor-grove-binding moiety modification.

In another advantageous embodiment, the cargo may be a protein, advantageously, an antibody. The antibody may target a nucleic acid binding protein. In another embodiment, the protein cargo may be a nucleic acid binding protein. Advantageously, the nucleic acid binding protein binds a specific sequence. In a particularly advantageous embodiment, the nucleic acid binding protein may be a DNA gyrase, a transcription activator-like effector (TALE) DNA binding protein, a transcription factor, chromatin remodeling factor, cell cycle promoting or inhibiting factor, epigenetic mark making or binding factor, DNA repair or other DNA metabolizing factor, or a zinc finger binding protein.

In another advantageous embodiment, the protein cargo may be an adenovirus proteinase (AVP), protein VI, pVi or streptavidin.

The cargo may also be modified with one or more gyrase inhibitors, such as but not limited to, Gemifloxacin or Norfloxacin.

The present invention also contemplates molecular capsules. In an advantageous embodiment, the molecular capsule may be a calixarene, cucurbituril, cyclodextrin or pillararene. The cucurbituril may comprise 5, 6, 7, 8 or 10 repeat units. George Church has an example of a capsule made of DNA (see, e.g., Douglas et al., Science 335, 831-834 (2012)).

The present invention also contemplates the cargo as a particle, such as, but not limited to, a nanoparticle, a bead, an organelle or a large protein complex.

In a particular advantageous embodiment, the molecular cargo may comprise a label. Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}$P, $^{14}$C, $^{125}$I $^{3}$H, and $^{131}$I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Labeling may be by fluorescent labeling selected from the group of, but not limited to, Cy3, Cy5, Bodipy Texas Red, Bodipy Far Red, *Lucifer* Yellow, Bodipy 630/650-X, Bodipy R6G-X and 5-CR 6G. The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen.

In an advantageous embodiment, the linkers and/or molecular cargo may be light sensitive, wherein the molecular cargo is light-activated and/or light cleaves the one or more linkers to release the molecular cargo. The light-activated molecular cargo may be a major light-harvesting complex (LHCII). In another embodiment, the fluorescent label may induce free radical formation.

The negatively charged polymer track along which the molecular sled is capable of sliding may be a double stranded DNA, single stranded DNA, engineered DNA nanostructures (ie "DNA origami"), a nucleosome, chromatin, or other natural or engineered DNA-protein complex, RNA, a ribosome or other natural or engineered ribonucleoprotein complex, a synthetic polymer (eg polyglutamic acid) or a natural polymer, organic nanowires or surfaces, inorganic nanowires, negatively charged nano tubes or surfaces, including two dimensional negatively charged surfaces such as glass. The natural polymer may be actin or tubulin. In an advantageous embodiment, the molecular sled may be linked to its cargo binds to the negatively charged polymer track by electrostatic binding. The molecular sleds of the present invention may encircle the DNA topologically by a combination of covalent and/or non-covalent bonds which may further increasing the processivity of the molecular sled.

In another embodiment, the molecular sled linked to its cargo is capable of sliding on actin. In this instance, the core amino acids X, Z', X' or X" may be S, I, V, H, R, K, C and/or F. Advantageously, X may be I, Z' may be V, ZZZ may be HRK, X' may be C and/or X" may be F. In a particularly advantageous embodiment, the core sequence may be SIVHRKCF (SEQ ID NO: 9). In another particularly advantageous embodiment, the core sequence may further comprise SGP.

The present invention also contemplates one or more additional sleds, linkers and/or cargos in addition to the molecular sled linked to its cargo. Advantageously, the molecular sled linked to its cargo may react with the one or more additional sleds, linkers and/or cargo. Such a reaction may occur on the polymer track, advantageously on a specific sequence of the polymer track. The polymer track may be DNA and the specific sequence may be a specific genomic locus. The reaction may be gene activation or epigenetic modification. For example, many transcription factors and histone deacetylase enzymes are known to bind to specific sequences. The DNA binding domains of transcription factors and histone deacetylase enzymes may be utilized as part of the molecular sled to bind a specific sequence.

The invention also contemplates the one or more additional sleds, linkers and/or cargo to comprise a PNA brake. The one or more additional sleds, linkers and/or cargo may contain a sled-PNA conjugate. For example, the sled-PNA conjugate may be a chromatin modifying factor.

The present invention also contemplates displaying the molecular sled on an exterior or inner membrane surface. A whole object (such as a vesicle, organelle, or entire cell) may constitute the cargo, or the surface may be used for the concentration of cargos or the recruitment of DNA/chromatin to the membrane surface.

The present invention also contemplates a nucleic acid encoding a molecular sled and a DNA, peptide or protein linker. In an advantageous embodiment, the expression of the sled may be inducible. In an advantageous embodiment, the nucleic acid may further encode the molecular cargo. Advantageously, the molecular cargo is a DNA, peptide or protein. The present invention also contemplates a virus particle which may comprise the above-disclosed nucleic acid. Advantageously, the virus particle is an adenovirus particle.

Also contemplated by the present invention are recombinant vectors and recombinant adenoviruses that can comprise subviral particles from more than one adenovirus serotype. For example, it is known that adenovirus vectors can display an altered tropism for specific tissues or cell types (Havenga, M. J. E. et al., 2002), and therefore, mixing and matching of different adenoviral capsids, i.e., fiber, or penton proteins from various adenoviral serotypes may be advantageous. Modification of the adenoviral capsids, including fiber and penton can result in an adenoviral vector with a tropism that is different from the unmodified adenovirus. Adenovirus vectors that are modified and optimized in their ability to infect target cells can allow for a significant reduction in the therapeutic or prophylactic dose, resulting in reduced local and disseminated toxicity.

Viral vector gene delivery systems are commonly used in gene transfer and gene therapy applications. Different viral vector systems have their own unique advantages and disadvantages. Viral vectors that may be used to express the pathogen-derived ligand of the present invention include but are not limited to adenoviral vectors, adeno-associated viral vectors, alphavirus vectors, herpes simplex viral vectors, and retroviral vectors, described in more detail below.

Additional general features of adenoviruses are such that the biology of the adenovirus is characterized in detail; the adenovirus is not associated with severe human pathology; the adenovirus is extremely efficient in introducing its DNA into the host cell; the adenovirus can infect a wide variety of cells and has a broad host range; the adenovirus can be produced in large quantities with relative ease; and the adenovirus can be rendered replication defective and/or non-replicating by deletions in the early region 1 ("E1") of the viral genome.

Adenovirus is a non-enveloped DNA virus. The genome of adenovirus is a linear double-stranded DNA molecule of approximately 36,000 base pairs ("bp") with a 55-kDa terminal protein covalently bound to the 5'-terminus of each strand. The adenovirus DNA contains identical inverted terminal repeats ("ITRs") of about 100 bp, with the exact length depending on the serotype. The viral origins of replication are located within the ITRs exactly at the genome ends. DNA synthesis occurs in two stages. First, replication proceeds by strand displacement, generating a daughter duplex molecule and a parental displaced strand. The displaced strand is single stranded and can form a "panhandle" intermediate, which allows replication initiation and generation of a daughter duplex molecule. Alternatively, replication may proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase, only the early gene products, encoded by regions E1, E2, E3 and E4, are expressed, which carry out a number of functions that prepare the cell for synthesis of viral structural proteins (Berk, A. J., 1986). During the late phase, the late viral gene products are expressed in addition to the early gene products and host cell DNA and protein synthesis are shut off. Consequently, the cell becomes dedicated to the production of viral DNA and of viral structural proteins (Tooze, J., 1981).

The E1 region of adenovirus is the first region of adenovirus expressed after infection of the target cell. This region consists of two transcriptional units, the E1A and E1B genes, both of which are required for oncogenic transformation of primary (embryonal) rodent cultures. The main functions of the E1A gene products are to induce quiescent cells to enter the cell cycle and resume cellular DNA synthesis, and to transcriptionally activate the E1B gene and the other early regions (E2, E3 and E4) of the viral genome. Transfection of primary cells with the E1A gene alone can induce unlimited proliferation (immortalization), but does not result in complete transformation. However, expression of E1A, in most cases, results in induction of programmed cell death (apoptosis), and only occasionally is immortalization obtained (Jochemsen et al., 1987). Co-expression of the E1B gene is required to prevent induction of apoptosis and for complete morphological transformation to occur. In established immortal cell lines, high-level expression of E1A can cause complete transformation in the absence of E1B (Roberts, B. E. et al., 1985).

The E1B encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene product exhibit a shortened infection cycle that is accompanied by excessive degradation of host cell chromosomal DNA (deg-phenotype) and in an enhanced cytopathic effect (cyt-phenotype; Telling et al., 1994). The deg and cyt phenotypes are suppressed when in addition the E1A gene is mutated, indicating that these phenotypes are a function of E1A (White, E. et al., 1988). Furthermore, the E1B 21 kDa protein slows down the rate by which E1A switches on the other viral genes. It is not yet known by which mechanisms EIB 21 kD quenches these E1A dependent functions.

In contrast to, for example, retroviruses, adenoviruses do not efficiently integrate into the host cell's genome, are able to infect non-dividing cells, and are able to efficiently transfer recombinant genes in vivo (Brody et al., 1994). These features make adenoviruses attractive candidates for in vivo gene transfer of, for example, an antigen or immunogen of interest into cells, tissues or subjects in need thereof.

Adenovirus vectors containing multiple deletions are preferred to both increase the carrying capacity of the vector and reduce the likelihood of recombination to generate replication competent adenovirus (RCA). Where the adenovirus contains multiple deletions, it is not necessary that each of the deletions, if present alone, would result in a replication defective and/or non-replicating adenovirus. As long as one of the deletions renders the adenovirus replication defective or non-replicating, the additional deletions may be included for other purposes, e.g., to increase the carrying capacity of the adenovirus genome for heterologous nucleotide sequences. Preferably, more than one of the deletions prevents the expression of a functional protein and renders the adenovirus replication defective and/or non-replicating and/or attenuated. More preferably, all of the deletions are deletions that would render the adenovirus replication-defective and/or non-replicating and/or attenuated. However, the invention also encompasses adenovirus and adenovirus vectors that are replication competent and/or wild-type, i.e. comprises all of the adenoviral genes necessary for infection and replication in a subject.

Embodiments of the invention employing adenovirus recombinants may include E1-defective or deleted, or E3-defective or deleted, or E4-defective or deleted or adenovirus vectors comprising deletions of E1 and E3, or E1 and E4, or E3 and E4, or E1, E3, and E4 deleted, or the "gutless" adenovirus vector in which all viral genes are deleted. The adenovirus vectors can comprise mutations in E1, E3, or E4 genes, or deletions in these or all adenoviral genes. The E1 mutation raises the safety margin of the vector because E1-defective adenovirus mutants are said to be replication-defective and/or non-replicating in non-permissive cells, and are, at the very least, highly attenuated. The E3 mutation enhances the immunogenicity of the antigen by disrupting the mechanism whereby adenovirus down-regulates MHC class I molecules. The E4 mutation reduces the immunogenicity of the adenovirus vector by suppressing the late gene expression, thus may allow repeated re-vaccination utilizing the same vector. The present invention comprehends adenovirus vectors of any serotype or serogroup that are deleted or mutated in E1, or E3, or E4, or E1 and E3, or E1 and E4. Deletion or mutation of these adenoviral genes result in impaired or substantially complete loss of activity of these proteins.

The "gutless" adenovirus vector is another type of vector in the adenovirus vector family. Its replication requires a helper virus and a special human 293 cell line expressing both E1a and Cre, a condition that does not exist in a natural environment; the vector is deprived of all viral genes, thus the vector as a vaccine carrier is non-immunogenic and may be inoculated multiple times for re-vaccination. The "gutless" adenovirus vector also contains 36 kb space for accommodating antigen or immunogen(s) of interest, thus allowing co-delivery of a large number of antigen or immunogens into cells.

Adeno-associated virus (AAV) is a single-stranded DNA parvovirus which is endogenous to the human population. Although capable of productive infection in cells from a variety of species, AAV is a dependovirus, requiring helper functions from either adenovirus or herpes virus for its own replication. In the absence of helper functions from either of these helper viruses, AAV will infect cells, uncoat in the nucleus, and integrate its genome into the host chromosome, but will not replicate or produce new viral particles.

The genome of AAV has been cloned into bacterial plasmids and is well characterized. The viral genome consists of 4682 bases which include two terminal repeats of 145 bases each. These terminal repeats serve as origins of DNA replication for the virus. Some investigators have also proposed that they have enhancer functions. The rest of the genome is divided into two functional domains. The left portion of the genome codes for the rep functions which regulate viral DNA replication and vital gene expression. The right side of the vital genome contains the cap genes that encode the structural capsid proteins VP1, VP2 and VP3. The proteins encoded by both the rep and cap genes function in trans during productive AAV replication.

AAV is considered an ideal candidate for use as a transducing vector, and it has been used in this manner. Such AAV transducing vectors comprise sufficient cis-acting functions to replicate in the presence of adenovirus or herpes virus helper functions provided in trans. Recombinant AAV (rAAV) have been constructed in a number of laboratories and have been used to carry exogenous genes into cells of a variety of lineages. In these vectors, the AAV cap and/or rep genes are deleted from the viral genome and replaced with a DNA segment of choice. Current vectors can accommodate up to 4300 bases of inserted DNA.

To produce rAAV, plasmids containing the desired vital construct are transfected into adenovirus-infected cells. In addition, a second helper plasmid is cotransfected into these cells to provide the AAV rep and cap genes which are obligatory for replication and packaging of the recombinant viral construct. Under these conditions, the rep and cap proteins of AAV act in trans to stimulate replication and packaging of the rAAV construct. Three days after transfection, rAAV is harvested from the cells along with adenovirus. The contaminating adenovirus is then inactivated by heat treatment.

Herpes Simplex Virus 1 (HSV-1) is an enveloped, double-stranded DNA virus with a genome of 153 kb encoding more than 80 genes. Its wide host range is due to the binding of viral envelope glycoproteins to the extracellular heparin sulphate molecules found in cell membranes (WuDunn & Spear, 1989). Internalization of the virus then requires envelope glycoprotein gD and fibroblast growth factor receptor (Kaner, 1990). HSV is able to infect cells lytically or can establish latency. HSV vectors have been used to infect a wide variety of cell types (Lowenstein, 1994; Huard, 1995; Miyanohara, 1992; Liu, 1996; Goya, 1998).

There are two types of HSV vectors, called the recombinant HSV vectors and the amplicon vectors. Recombinant HSV vectors are generated by the insertion of transcription units directly into the HSV genome, through homologous recombination events. The amplicon vectors are based on plasmids bearing the transcription unit of choice, an origin of replication, and a packaging signal.

HSV vectors have the obvious advantages of a large capacity for insertion of foreign genes, the capacity to establish latency in neurons, a wide host range, and the ability to confer transgene expression to the CNS for up to 18 months (Carpenter & Stevens, 1996).

Retroviruses are enveloped single-stranded RNA viruses, which have been widely used in gene transfer protocols. Retroviruses have a diploid genome of about 7-10 kb, composed of four gene regions termed gag, pro, pol and env. These gene regions encode for structural capsid proteins, viral protease, integrase and viral reverse transcriptase, and envelope glycoproteins, respectively. The genome also has a packaging signal and cis-acting sequences, termed long-terminal repeats (LTRs), at each end, which have a role in transcriptional control and integration.

The most commonly used retroviral vectors are based on the Moloney murine leukaemia virus (Mo-MLV) and have varying cellular tropisms, depending on the receptor binding surface domain of the envelope glycoprotein.

Recombinant retroviral vectors are deleted from all retroviral genes, which are replaced with marker or therapeutic genes, or both. To propagate recombinant retroviruses, it is necessary to provide the viral genes, gag, pol and env in trans.

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Alphaviruses, including the prototype Sindbis virus (SIN), Semliki Forest virus (SFV), and Venezuelan equine encephalitis virus (VEE), constitute a group of enveloped viruses containing plus-stranded RNA genomes within icosahedral capsids.

The viral vectors of the present invention are useful for the delivery of nucleic acids expressing antigens or immunogens to cells both in vitro and in vivo. In particular, the inventive vectors can be advantageously employed to deliver or transfer nucleic acids to animal cells, more preferably avian and mammalian cells. Nucleic acids of interest include nucleic acids encoding peptides and proteins, preferably therapeutic (e.g., for medical or veterinary uses) or immunogenic (e.g., for vaccines) peptides or proteins.

Preferably, the codons encoding the antigen or immunogen of interest are "optimized" codons, i.e., the codons are those that appear frequently in, e.g., highly expressed genes in the subject's species, instead of those codons that are frequently used by, for example, an influenza virus. Such codon usage provides for efficient expression of the antigen or immunogen in animal cells. In other embodiments, for example, when the antigen or immunogen of interest is expressed in bacteria, yeast or another expression system, the codon usage pattern is altered to represent the codon bias for highly expressed genes in the organism in which the antigen or immunogen is being expressed. Codon usage patterns are known in the literature for highly expressed genes of many species (e.g., Nakamura et al., 1996; Wang et al., 1998; McEwan et al. 1998).

As a further alternative, the viral vectors can be used to infect a cell in culture to express a desired gene product, e.g., to produce a protein or peptide of interest. Preferably, the protein or peptide is secreted into the medium and can be purified therefrom using routine techniques known in the art. Signal peptide sequences that direct extracellular secretion of proteins are known in the art and nucleotide sequences encoding the same can be operably linked to the nucleotide sequence encoding the peptide or protein of interest by routine techniques known in the art. Alternatively, the cells can be lysed and the expressed recombinant protein can be purified from the cell lysate. Preferably, the cell is an animal cell, more preferably a mammalian cell. Also preferred are cells that are competent for transduction by particular viral vectors of interest. Such cells include PER.C6 cells, 911 cells, and HEK293 cells.

A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types can be found at the American Type Culture Collection (ATCC) or the European Collection of Cell Cultures (ECACC). Culture media can be supplemented with amino acids such as L-glutamine, salts, anti-fungal or anti-bacterial agents such as Fungizone®, penicillin-streptomycin, animal serum, and the like. The cell culture medium can optionally be serum-free.

The present invention also contemplates diagnostic methods for detecting cancer, a degenerative disease, a genetic disease or an infectious disease which may comprise any of the compositions disclosed herein to a suspected cancer cell, genetically diseased cell or infected cell and detecting the molecular sled in the suspected cancer cell or infected cell, thereby detecting cancer, a genetic disease or an infectious disease. The targeting may be to a marker specific to a cancer cell, genetically diseased cell or infected cell, wherein the targeting is by attachment to cargo of a particular size, by attachment via a pH-sensitive cleavable linker, or by a cargo with molecular recognition capability to target a cancer biomarker or a singular cargo or a second, additional cargo.

In particular, the present invention contemplates conjugating the molecular sled of the present invention on an oligomer. Therefore, any polymerase-chain reaction (PCR) diagnostic method may be modified by adding the molecular sled of the present invention to oligomeric primers. Allowing the DNA primers to move along DNA rapidly allow them to arrive at hybridization sites much more rapidly than conventional three-dimensional diffusion allow them to. In this way, the overall reaction time for PCR to be significantly reduced. Moreover, the reversibility of the ternary complex allows improved protocols for purification and immobilization of amplicons. Applicants believe that the PCR process, especially the annealing step, can be speeded up significantly by preparing single stranded (ss) DNA-pVIc conjugates that act as primers in PCR. These conjugates are able to reach their position for DNA strand invasion much faster than the unfunctionalized primers. The performance of oligonucleotide (ODN)-pVIc hybrids is assessed in real-time PCR experiments with a standard molecular beacon that efficiently reports amplicon formation. Special attention is paid to how much the annealing time of primers and primer concentration is reduced. Applicants are well aware of the fact that during the denaturation step the template gets fully or partially separated depending on the sequence composition. The presence of ssDNA should not impair the action of the molecular sled since binding of the oligopeptide was recently also suggested to take place on ss substrates. Assuming duration of 30 seconds for annealing during a standard PCR protocol (30 cycles), Applicants estimate a decrease in the whole PCR procedure by 7 to 10 minutes by employing molecular sled modified primers, which has tremendous economic potential taking into account the widespread use of this technique.

In clinical diagnostic embodiments, the molecular sleds of the present invention may be used in combination with an appropriate means, such as a label, to detect cancer, a degenerative disease, a genetic disease or an infectious disease. Typical methods of detection might utilise, for example, radioactive species, enzyme-active or other marker ligands such as avidin/biotin, which are detectable directly or indirectly. In preferred diagnostic embodiments, one will likely desire to employ an enzyme tag such as alkaline phosphatase or peroxidase rather than radioactive or other reagents that may have undesirable environmental effects. Enzyme tags, for example, often utilise calorimetric indicator substrates that are readily detectable spectrophotometrically, many in the visible wavelength range. Luminescent substrates could also be used for increased sensitivity. However, fluorescent tags may be preferred. The present invention further encompasses a diagnostic composition comprised of the methods of the present invention in the form of a kit. The diagnostic composition may comprise the components as defined hereinabove. The diagnostic composition of the present invention may be used as a kit, inter alia, for carrying out the methods of the present invention, for example diagnostic kits or research tools. Additionally, the kit of the invention may contain suitable means for any other scientific, medical and/or diagnostic purposes. Diagnostic compositions and kits of the present invention may be manufactured by standard procedures that are well known to one of skill in the art. Kits may advantageously include instructions for use and/or admixture of ingredients.

Finally, Applicants contemplate the use of the molecular sled in a number of in vivo applications. First, Applicants display the sled on the bacterial surface to speed up transformation. By allowing plasmid DNA to transiently bind to the outer membrane of E. coli, Applicants increase the uptake of plasmids upon electroporation or salt treatment. Secondly, the molecular sled is presented on the inner cell surface in order to accelerate the production of membrane proteins. By positioning the plasmid at the periphery of the membrane the initial step of membrane protein biogenesis is located at the final destination of the mature protein. In this way, Applicants significantly reduce or even avoid the diffusion of the ribosome nascent chain complex. Thirdly, Applicants couple the sled to antibiotics. By using antibiotics that target DNA-bound proteins (such as gyrase inhibitors), Applicants drastically decrease the time required to find gyrase proteins inside the crowded environment of the cell. An improvement in these kinetics may lead to higher efficacies of this class of antibiotics and to potentially much lower dosages needed for treatment.

Bacterial transformation is a technique widely applied in molecular biology to introduce foreign plasmid DNA into bacteria. In molecular cloning, the ligation of inserts into vectors is an extremely low yielding process and therefore requires high transformation efficiencies for successful gene incorporation. Moreover, in protein evolution a low transfection efficiency is a major bottleneck hampering sampling of large sequence space. The successful uptake of plasmids by transformation of competent cells is in essence determined by a kinetic barrier. Currently, standard protocols rely on having a high concentration of plasmid in the bacterial cultures while electroporation or exposure to calcium chloride transiently permeates the bacterial membrane. One improvement is to locally increase the plasmid concentration by allowing the DNA to bind non-specifically to DNA-binding moieties expressed on the bacterial surface.

Here, Applicants display the molecular sled on the surface of Gram negative bacteria by fusion to outer membrane proteins. Well suited targets include, but are not limited to, Int550 (C-terminal fusion), FhuA (N- and C-terminal fusion) and the AIDA-I autotransporter. Especially the latter has been shown to be suited for surface exposure of passenger peptides and even a stable presentation of functional lactamase on the E. coli outer membrane was achieved. With such a presenting system the DNA is stably localized and kept in a mobile state at the cell surface. These combined features result in enhanced DNA uptake through transiently induced pores in the cell wall compared to wild type cells.

The corresponding transformation efficiency is determined by adding equal amounts of plasmid DNA containing an antibiotic resistance gene to the same number of cells. Subsequent spreading of dilution series on plates supplemented with and without the corresponding antibiotic allow calculating the transformation efficiency.

Instead of presenting the molecular sled to the outside of the cell, displaying the sliding peptide on the inner surface of the cytoplasmic membrane offers exciting opportunities as well. Fusion of the molecular sled to cytoplasmic termini of inner membrane proteins such as, but not limited to, YidC (N- or C terminus), the N-terminus of FtsQ or YddG (N- and C-terminus) results in localization of plasmid or genomic DNA close to the inner cell surface. This situation enables bringing the first step of membrane protein biogenesis, the transcription, closer to the mature protein's final destination. Usually, the translation of mRNA into the membrane protein is stalled as soon as the first hydrophobic transmembrane segment emerges from the ribosome. Subsequently, this complex is transported to the membrane and transferred to the insertion pore (SecYEG). Upon this binding event translation is restarted and the protein is cotranslationally inserted into the membrane. By bringing the first step of membrane protein biogenesis close to the membrane a significant acceleration of protein production is anticipated. The overexpression of membrane proteins in contrast to soluble proteins is still a major obstacle in current biotechnological research and industry.

Another in vivo application is increasing the efficiency of antibiotics with the molecular sled. For that purpose known antimicrobial agents are selected that interfere with the bacterial DNA machinery. The conjugation of the molecular sled with DNA gyrase inhibitors lead to improved drug efficiency. DNA gyrase is an important protein involved in bacterial DNA replication, because it helps to release the strain that arises from unwinding of the ds DNA by helicase. The mode of action of bacterial topoisomerase II inhibitors is the stabilization of the cleavage complexes in an open form with the generation of chromosome breaks. The bacterial DNA gyrases convert into potent cellular toxins leading to cell death. The molecular sled is attached to the amino group of gemifloxacin, a gyrase inhibitor of the 4th generation. The attachment point of the molecular sled is chosen in such a way that it is well separated from the pharmacophore scaffold and therefore should not interfere with drug action. Alternatively, the molecular sled may be coupled to Norfloxacin (2nd generation inhibitor). In both conjugates, the antibiotic activity is strongly increased due to the fact that the 3D diffusion of the drugs is reduced to a one dimensional search process. After the synthesis of the novel conjugate its antimicrobial activity may be tested against $E.\ coli$ ATCC 25922, which is a standard strain to evaluate the efficiency of antibiotics. Two methods, the Kirby-Bauer Disk Test and the determination of the Minimal Inhibitory Concentration (MIC) are employed for that purpose.

Another example of the application of the molecular sled is potency enhancement of the antibiotics from gyrase and topoisomerase inhibitor classes. Antibiotics from this group form stable complexes with the aforementioned proteins once they cleave bacterial DNA, preventing them from reconnecting DNA strands. Left with chromosomal breaks, bacteria are unable to survive.

However, this class of antibiotics is notorious for its side-effects: phototoxicity, QTc interval prolongation, tendon tear etc. Here Applicants reduce the required dosage of the drug by increasing its potency by chemically attaching a molecular sled to gyrase and topoisomerase inhibitors. Molecules of antibiotic need to find and inactivate their targets that are situated on DNA. Instead of relying only on three dimensional (3D) diffusion, antibiotic with pVIc attached to it slide along bacterial DNA in one dimension (1D). Thus, the search process is much more effective.

One of the antibiotics from gyrase and topoisomerase inhibitor class is gemifloxacin.

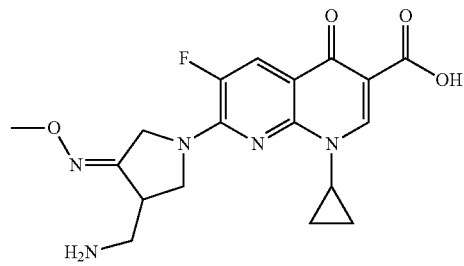 [SMILES: CO/N=C1\CN(c2nc3c(cc2F)c(=O)c(C(=O)O)cn3C2CC2)CC1CN]

Applicants attach pVIc to the primary amine of gemifloxacin because this position is situated far from the pharmacophore of the drug and therefore does not interfere with its action.

The modification is conducted in two steps, the first one being an attachment of a PEG linker

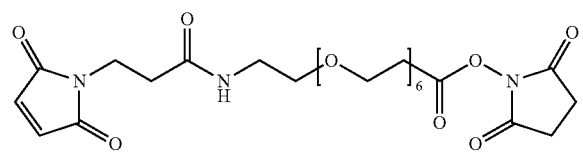

to the primary amine of gemifloxacin by performing a conventional click chemistry of NHS ester to primary amine coupling. The resulting compound GFX-PEG is purified by HPLC.

The second step is a direct coupling of the maleimide group of GFX-PEG to the Cys10' of the pVIc. The final product (gemifloxacin-pVIc) is purified by cation exchange chromatography.

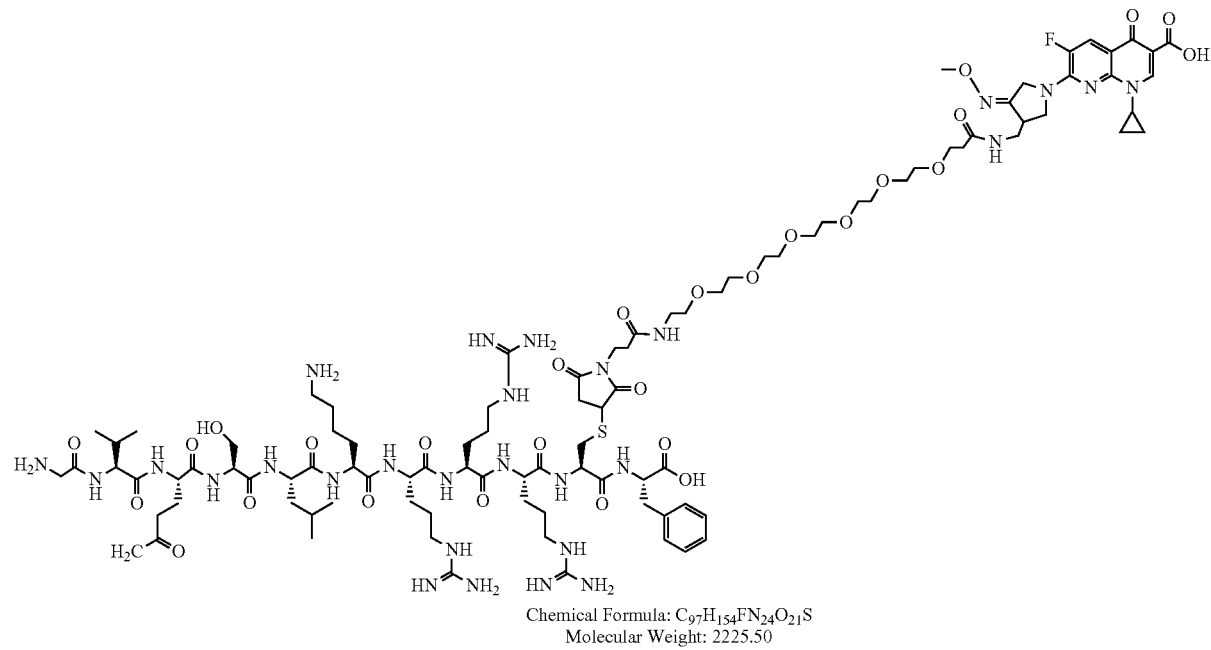 [SMILES: CO/N=C1\CN(c2nc3c(cc2F)c(=O)c(C(=O)O)cn3C2CC2)CC1CNC(=O)CCOCCOCCOCCOCCOCCOCCNC(=O)CCN1C(=O)CC(SC[C@H](NC(=O)[C@H](CCCNC(=N)N)NC(=O)[C@H](CCCNC(=N)N)NC(=O)[C@H](CCCNC(=N)N)NC(=O)[C@H](CCCCN)NC(=O)[C@H](CC(C)C)NC(=O)[C@H](CO)NC(=O)[C@H](CCC(C)=O)NC(=O)[C@@H](NC(=O)CN)C(C)C)C(=O)N[C@@H](Cc2ccccc2)C(=O)O)C1=O]

Chemical Formula: $C_{97}H_{154}FN_{24}O_{21}S$
Molecular Weight: 2225.50

The pVIc peptide influences bacterial uptake of the antibiotic. To have a valid comparison the same modification of gemifloxacin is carried out with a scrambled pVIc peptide with a sequence SFRRCGLRQVK (SEQ ID NO: 10), or other highly basic peptide sequences such as longer, fusions of natural cell penetrating peptides with NLS sequences (for example PKKRKRRLYGRKKRRQRRR (SEQ ID NO: 11) from Johnson et al. 2010, Journal of Investigative Dermatology (2011) 131, 753-761 which do not slide or slide rapidly along DNA. Other basic peptides may not necessarily slide or slide rapidly along DNA (see, e.g., Robillard et al., J. Comb. Chem. 2003, 5, 821-825; Robillard et al., Journal of Inorganic Biochemistry 96 (2003) 331-338 and Wang et al., J. Med. Chem. 2001, 44, 3682-3691) and some other basic peptides do not make it into the nucleus or help with isoform specificity (see, e.g., Canzoneri et al., Bioorganic & Medicinal Chemistry Letters 19 (2009) 6588-6590).

The antimicrobial activity of the three compounds, gemifloxacin-pVIc, gemifloxacin-random pVIc and gemifloxacin is tested against *E. coli* ATCC 25922, which is a standard strain to evaluate the efficiency of antibiotics. Two methods, the Kirby-Bauer Disk Test and the determination of the Minimal Inhibitory Concentration (MIC), is employed for that purpose.

The advantages of this system to speed up antibiotic recognition is to avoid liver delivery passage, avoid gastrointestinal degradation, reduce the IC50 and required concentration to be delivered (such as, but not limited to, about 25%, about 30%, about 35%, about 40%, about 45%, about 50%, about 55%, about 60%, about 65%, about 70% or about 75% reduction of the antibiotic delivered when compared to a conventional antibiotic administration system). Methods of antibiotic administration are known in the art and when coupled with the methods of the present invention, one of skill in the art can adjust the dosage of the antibiotic delivered by the molecular sled of the present invention.

In another embodiment of the present invention, DNA amplification may be accelerated with primers modified with the molecular sleds of the present invention. When PCR primers are modified with the molecular sleds of the invention, the PCR primers find their complementary position on the template more quickly than unmodified primers. Applicants found that primers modified with the molecular sleds of the present invention speed up DNA amplification as compared to DNA primers without a molecular sled. Therefore, the present invention also encompasses methods of accelerating PCR amplification comprising attaching a molecular sled to a PCR primer. A primer-molecular sled may be synthesized by methods known in the art (see, e.g., Ching-Hsuan Tung; M. Jonathan Rudolph; Stanley Stein. Bloconjugate Chem. 1991, 2, 464-465 and Andrew W. Fraley; Benedicte Pons; Deniz Dalkara; Gerard Nullans; Jean-Paul Behr; Guy Zuber. J. Am. Chem. Soc. 2006, 128, 10763-10771).

The present invention will be further illustrated in the following Examples which are given for illustration purposes only and are not intended to limit the invention in any way.

EXAMPLES

Example 1: Binding to DNA and to Hexon of the Precursor to Protein VI, pVI, of Human Adenovirus Adenovirus protein pVI escorts hexon into the nucleus and activates the adenovirus proteinase by sliding along the DNA via one-dimensional diffusion. pVI had not been purified before. Applicants quantitatively characterized the interaction of purified pVI with hexon and with DNA. pVI binds tightly to hexon, $K_d$ 1.9 nM, with a 1:1 stoichiometry. pVI binds as a monomer tightly to DNA, $K_d$ 35 nM, releasing 3 sodium ions and occluding 8 base pairs. Characterizing these binding interactions is crucial towards understanding how this protein escorts hexon into the nucleus and how it activates the adenovirus proteinase.

The precursor to adenovirus protein VI, pVI, is a multifunctional protein with different roles early and late in virus infection. Here Applicants focus on two roles late in infection, binding of pVI to DNA and to the major capsid protein hexon. pVI bound to DNA as a monomer independent of DNA sequence with an apparent equilibrium dissociation constant, $K_{d(app.)}$, of 35 nM. Bound to double-stranded DNA, one molecule of pVI occluded 8 base pairs. Upon the binding of pVI to DNA, 3 sodium ions were displaced from the DNA. A $\Delta G_0^0$ of −4.54 kcal for the nonelectrostatic free energy of binding indicated that a substantial component of the binding free energy resulted from nonspecific interactions between pVI and DNA. The proteolytically processed, mature form of pVI, protein VI, also bound to DNA; its $K_{d(app.)}$ was much higher, 241 nM. The binding assays were performed in 1 mM $MgCl_2$, because in the absence of magnesium, the binding to pVI or protein VI to DNA was too tight to determine a $K_{d(app.)}$. Three molecules of pVI bound to one molecule of the hexon trimer with an equilibrium dissociation constant $K_{d(app.)}$ of 1.85 nM.

Many viral proteins contain several, different domains that function at different steps during a virus infection. This is certainly true of the precursor to protein VI, pVI, and of its proteolytically processed product, protein VI, of adenovirus which are involved in both early and late in infection. Early in infection, virus particles engage in a stepwise disassembly program coordinated in time and space during entry into cells leading to the delivery of the viral genome into the nucleus for replication (Greber, U. F., Wiletts, M., Webster, P., and Helenius, A. (1993) Cell 75, 477-486; Strunze, S., Engelke, M. F., Wang, I. H., Puntener, D., Boucke, K., Schleich, S., Way, M., Schoenenberger, P., Burckhardt, C. J., and Greber, U. F. (2011) Cell Host Microbe 10(3), 210-223; Burckhardt, C. J., Suomalainen, M., Schoenenberger, P., Boucke, K., Hemmi, S., and Greber, U. F. (2011) Cell Host Microbe 10(2), 105-117 and Puntener, D., Engelke, M. F., Ruzsics, Z., Strunze, S., Wilhelm, C., and Greber, U. F. (2011) J. Virol. 85(1), 481-496). Protein VI is involved in endosome disruption (Wiethoff, C. M., Wodrich, H., Gerace, L., and Nemerow, G. R. (2005) J. Virol. 79(4), 1992-2000 and Moyer, C. L., Wiethoff, C. M., Maier, O., Smith, J. G., and Nemerow, G. R. (2011) J Virol 85(6), 2631-2641). Late in infection, new virus particles are assembled and rendered infectious. pVI interacts with DNA to activate the adenovirus proteinase (AVP) (Graziano, V., Luo, G., Blainey, P. C., Pérez-Berná, A. J., McGrath, W. J., Flint, S. J., San Martin, C., Xie, X. S., and Mangel, W. F. (2012)) and with hexon, the major structural proteins of adenovirus, to escort hexon into the nucleus (Wodrich, H., Guan, T., Cingolani, G., Seggern, D. V., Nemerow, G., and Gerace, L. (2003) EMBO J. 22, 6245-66255 and Honkavuori, K. S., Pollard, B. D., Rodriguez, M. S., Hay, R. T., and Kemp, G. D. (2004) J Gen Virol 85 (Pt 11), 3367-3376).

Adenoviruses (Russell, W. C. (2009) J. Gen. Virol. 90, 1-20) are non-enveloped, icosahedral eukaryotic viruses that infect a wide range of species, from hamsters to human, and of tissues, from the kidney to the eye.

They cause epidemic, endemic or sporadic disease and viremia, and are prevalent in the environment (Schmitz, H., Wigand, R., and Heinrich, W. (1983) Am J Epidemiol 117(4), 455-466; Munoz, F. M., Piedra, P. A., and Demmler, G. J. (1998) Clin Infect Dis 27(5), 1194-1200 and Pina, S., Puig, M., Lucena, F., Jofre, J., and Girones, R. (1998) Appl Environ Microbiol 64(9), 3376-3382). They also cause fatal infections in immunosuppressed individuals (Krilov, L. (2005) Pediatr Infect Dis J. 24, 555-556). The species C human adenoviruses (HAdV) Ad2 or Ad5 are the best characterized adenoviruses. They have an ~36 kb double-stranded DNA genome (Philipson, L. (1995) Curr Top Microbiol Immunol 199 (Pt 1), 1-24). The Ad2/Ad5 particle is about 90 nm in diameter and consists of an outer capsid surrounding an inner nucleoprotein core. Hexon, penton base, and fiber are the major structural proteins in the outer capsid. Hexon is the major protein of the facets of the icosahedral virus. Penton base and fiber are the major constituents of the vertices. Several minor proteins play roles in cementing the capsid. Adenovirus protein IX resides on the outer surface of the capsid between hexons, while proteins IIIa, VIII and VI sit on the inner surface of the capsid (Liu, H., Jin, L., Koh, S. B., Atanasov, I., Schein, S., Wu, L., and Zhou, Z. H. (2010) Science 329(5995), 1038-1043). The size of the hexon molecule can vary with the serotype—the largest, from Ad2, has 967 amino acids (Russell, W. C. (2009) J. Gen. Virol. 90, 1-20). There are 720 copies of hexon present as 240 homotrimers per virion. One face of the hexon trimers in the capsid is exposed to the core of the virus and hence the viral DNA. Protein VI is thought to lie within the internal cavity of each hexon trimer (Liu, H., Jin, L., Koh, S. B., Atanasov, I., Schein, S., Wu, L., and Zhou, Z. H. (2010) Science 329(5995), 1038-1043; Saban, S. D., Silvestry, M., Nemerow, G. R., and Stewart, P. L. (2006) J Virol 80(24), 12049-12059; Silvestry, M., Lindert, S., Smith, J. G., Maier, O., Wiethoff, C. M., Nemerow, G. R., and Stewart, P. L. (2009) J. Virol. 83(15), 7375-7383; Stewart, P. L., Fuller, S. D., and Burnett, R. M. (1993) EMBO J. 12, 2589-2599; van Oostrum, J. V., and Burnett, R. M. (1985) J. Virol. 56, 439-448 and San Martin, C., Glasgow, J. N., Borovjagin, A., Beatty, M. S., Kashentseva, E. A., Curiel, D. T., Marabini, R., and Dmitriev, I. P. (2008) J Mol Biol 383(4), 923-934). There are 360 copies of protein VI which contains 206 amino acids. Protein VI has been shown to bind to DNA independent of nucleotide sequence (Russell, W. C., and Precious, B. (1982) J Gen. Virol. 63, 69-79).

Initiation of an Ad2/Ad5/infection occurs when the capsid binds to high affinity receptors on the cell surface (Burckhardt, C. J., Suomalainen, M., Schoenenberger, P., Boucke, K., Hemmi, S., and Greber, U. F. (2011) Cell Host Microbe 10(2), 105-117; Bergelson, J. M., Cunningham, J. A., Droguett, G., Kurt-Jones, E. A., Krithivas, A., Hong, J. S., Horwitz, M. S., Crowell, R. L., and Finberg, R. W. (1997) Science 275(5304), 1320-1323; Tomko, R. P., Xu, R., and Philipson, L. (1997) Proc Natl Acad Sci USA 94(7), 3352-3356 and Freimuth, P., Philipson, L., and Carson, S. D. (2008) Curr Top Microbiol Immunol 323, 67-87), and the virus particle is internalized via clathrin-mediated endocytosis (Meier, O., Boucke, K., Hammer, S. V., Keller, S., Stidwill, R. P., Hemmi, S., and Greber, U. F. (2002) J Cell Biol 158(6), 1119-1131; Gastaldelli, M., Imelli, N., Boucke, K., Amstutz, B., Meier, O., and Greber, U. F. (2008) Traffic 9(12), 2265-2278 and Wang, K., Huang, S., Kapoor-Munshi, A., and Nemerow, G. (1998) J Virol 72(4), 3455-3458). After internalization, protein VI, the proteolytically processed from of pVI, is rapidly exposed (Burckhardt, C. J., Suomalainen, M., Schoenenberger, P., Boucke, K., Hemmi, S., and Greber, U. F. (2011) Cell Host Microbe 10(2), 105-117 and Wodrich, H., Henaff, D., Jammart, B., Segura-Morales, C., Seelmeir, S., Coux, O., Ruzsics, Z., Wiethoff, C. M., and Kremer, E. J. (2010) PLoS Pathog 6(3), e1000808). Protein VI mediates endosome disruption, so the partially uncoated capsid can enter the cytoplasm (Wiethoff, C. M., Wodrich, H., Gerace, L., and Nemerow, G. R. (2005) J. Virol. 79(4), 1992-2000 and Moyer, C. L., Wiethoff, C. M., Maier, O., Smith, J. G., and Nemerow, G. R. (2011) J Virol 85(6), 2631-2641).

Late in adenovirus infection, the genes for pVI, AVP (adenovirus proteinase) and hexon are transcribed from the L3 transcription region on the viral DNA (Akusjarvi, G., Alestrom, P., Pettersson, M., Lager, M., Jornvall, H., and Pettersson, U. (1984) J Biol Chem 259(22), 13976-13979). AVP is synthesized as an inactive enzyme (Mangel, W. F., McGrath, W. J., Toledo, D. L., and Anderson, C. W. (1993) Nature 361, 274-275 and Webster, A., Hay, R. T., and Kemp, G. (1993) Cell 72, 97-104). The nuclear transport of hexon is mediated by pVI as hexon does not have a nuclear localization signal (NLS). pVI contains two nuclear export signals (NESs) and two NLSs (Wodrich, H., Guan, T., Cingolani, G., Seggern, D. V., Nemerow, G., and Gerace, L. (2003) EMBO J. 22, 6245-66255; Mathews, D. A., and Russell, W. C. (1994) J. Gen. Virol. 75, 3365-3374 and Mathews, D. A., and Russell, W. C. (1995) J. Gen. Virol. 76, 1959-1969). pVIc, the last 11-amino acids of pVI, contains an NLS. It has been shown that the nuclear import of hexon in cultured cells occurs via pVI, which shuttles between the nucleus and the cytoplasm and appears to provide an adaptor for hexon import (Wodrich, H., Guan, T., Cingolani, G., Seggern, D. V., Nemerow, G., and Gerace, L. (2003) EMBO J. 22, 6245-66255).

Adenovirus virions are assembled in part from precursor proteins. Of the 12 major virion proteins, 6 are precursor proteins in the young virion, an assembly intermediate. The penultimate step before the appearance of infectious virus is the activation of the adenovirus proteinase (AVP), a 23 kDa cysteine proteinase (Ding, J., McGrath, W. J., Sweet, R. M., and Mangel, W. F. (1996) EMBO J. 15, 1778-1783 and McGrath, W. J., Ding, J., Sweet, R. M., and Mangel, W. F. (2003) Biochem. Biophys. Acta 1648, 1-11), followed by the processing of the virion precursor proteins. AVP is activated by two cofactors, pVIc (GVQSLKRRRCF (SEQ ID NO: 12)) (Webster, A., Hay, R. T., and Kemp, G. (1993) Cell 72, 97-104 and Mathews, D. A., and Russell, W. C. (1994) J. Gen. Virol. 75, 3365-3374), the 11-amino acid peptide from the C-terminus of pVI, and the viral DNA genome (Mangel, W. F., McGrath, W. J., Toledo, D. L., and Anderson, C. W. (1993) Nature 361, 274-275). In pVI, an AVP consensus cleavage site, IVGL-G (SEQ ID NO: 35), immediately precedes pVIc and is cleaved by AVP between L and G to release pVIc (Graziano, V., Luo, G., Blainey, P. C., Pérez-Berná, A. J., McGrath, W. J., Flint, S. J., San Martin, C., Xie, X. S., and Mangel, W. F. (2012)). The other cofactor, the viral DNA genome (Mangel, W. F., McGrath, W. J., Toledo, D. L., and Anderson, C. W. (1993) Nature 361, 274-275; 37,38), consists of 35,937 bp of linear DNA in the case of Ad2. The viral cofactors dramatically stimulate the macroscopic kinetic constants for substrate hydrolysis (McGrath, W. J., Baniecki, M. L., Li, C., McWhirter, S. M., Brown, M. T., Toledo, D. L., and Mangel, W. F. (2001) Biochemistry 40, 13237-13245; Mangel, W. F., Toledo, D. L., Brown, M. T., Martin, J. H., and McGrath, W. J. (1996) J. Biol. Chem. 271, 536-543 and Baniecki, M. L., McGrath, W. J., McWhirter, S. M., Li, C., Toledo, D. L., Pellicena, P., Barnard, D. L., Thorn, K. S., and Mangel, W. F. (2001) Biochemistry 40, 12349-12356). The relative $k_{cat}/K_m$ of AVP is enhanced 110-fold in the presence of DNA and 1130-fold in the presence of pVIc. When both cofactors are bound to AVP, the $k_{cat}/K_m$ increases synergistically, by 16,000-fold. AVP, pVI, pVIc, and AVP-pVIc complexes bind tightly to DNA with nanomolar equilibrium dissociation constants; binding is independent of nucleic acid sequence (Table 1) (Graziano, V., Luo, G., Blainey, P. C., Pérez-Berná, A. J., McGrath, W. J., Flint, S. J., San Martin, C., Xie, X. S., and Mangel, W. F. (2012); Mangel, W. F., McGrath, W. J., Toledo, D. L., and Anderson, C. W. (1993) Nature 361, 274-275; McGrath, W. J., Baniecki, M. L., Li, C., McWhirter, S. M., Brown, M. T., Toledo, D. L., and Mangel, W. F. (2001) Biochemistry 40, 13237-13245; Bajpayee, N. S., McGrath, W. J., and Mangel, W. F. (2005) Biochemistry 44(24), 8721-8729 and Gupta, S., Mangel, W. F., McGrath, W. J., Perek, J. L., Lee, D. W., Takamoto, K., and Chance, M. R. (2004) Mol. Cell. Proteomics 3.10, 950-959).

A question is how does pVI activate AVP, and how does an activated AVP-pVIc complex process virion precursor proteins. In the newly assembled virion, AVP is bound to the viral DNA (Graziano, V., Luo, G., Blainey, P. C., Pérez-Berná, A. J., McGrath, W. J., Flint, S. J., San Martin, C., Xie, X. S., and Mangel, W. F. (2012); Mangel, W. F., McGrath, W. J., Toledo, D. L., and Anderson, C. W. (1993) Nature 361, 274-275 and McGrath, W. J., Baniecki, M. L., Li, C., McWhirter, S. M., Brown, M. T., Toledo, D. L., and Mangel, W. F. (2001) Biochemistry 40, 13237-13245). pVI, also bound to the viral DNA, slides via one-dimensional diffusion into AVP. Its one-dimensional diffusion constant is $1.45 \pm 0.13 \times 10^6$ $(bp)^2/s$. AVP, partially activated by being bound to DNA, cleaves pVI first at its N-terminus, to release amino acids 1-33, and then at its C-terminus, to release amino acids 239-250, i.e. pVIc. The pVIc then binds and forms a disulfide bond with the AVP that excised it. pVIc is a "molecular sled" that slides along DNA via one-dimensional diffusion by itself or with cargos attached to it such as protein VI or AVP (Blainey, P. C., Graziano, V., McGrath, W. J., Luo, G., Xie, X. S., and Mangel, W. F. (2012)). Thus, although AVP does not slide, the AVP-pVIc complex does slide. It slides along the viral DNA cleaving the precursor proteins more than 1900 times to render the virus particle infectious (Blainey, P. C., Graziano, V., Pérez-Berná, A. J., McGrath, W. J., Flint, S. J., San Martin, C., Xie, X. S., and Mangel, W. F. (2012)).

Here, Applicants clone and express the gene for pVI and a gene for its proteolytically processed, mature product, protein VI, and purify the proteins from E. coli. Because the interaction of pVI with DNA leads to the activation of AVP (Graziano, V., Luo, G., Blainey, P. C., Pérez-Berná, A. J., McGrath, W. J., Flint, S. J., San Martin, C., Xie, X. S., and Mangel, W. F. (2012)), Applicants quantitatively characterize the binding of pVI to DNA, including determining the equilibrium dissociation constant. And, since pVI has been shown to be required for the shuttling of hexon into the nucleus (Wodrich, H., Guan, T., Cingolani, G., Seggern, D. V., Nemerow, G., and Gerace, L. (2003) EMBO J. 22, 6245-66255), Applicants quantitatively characterize the interaction of pVI and hexon.

Materials—

The 11-amino acid peptide pVIc (GVQSLKRRRCF (SEQ ID NO: 12)) was purchased from New England Peptide Inc. (Gardner, Mass.). The 5'-fluorescein-labeled 33 mer DNA, 36-mer DNA, 60 mer DNA, and the strands complementary to these DNAs were purchased from Invitrogen (Carlsbad, Calif.) as was streptavidin Alexa Fluor 546. Annealing of complementary DNAs was done as described previously (Baniecki, M. L., McGrath, W. J., McWhirter, S. M., Li, C., Toledo, D. L., Pellicena, P., Barnard, D. L., Thorn, K. S., and Mangel, W. F. (2001) Biochemistry 40, 12349-12356). The 1500 mer dsDNA was obtained by sonicating Cupriavidus metallidurans $CH_{34}$ genomic DNA. n-Dodecyl-β-D-Maltopyranoside (DDM) was purchased from Anatrace (Maumee, Ohio). Cy3B mono maleimide was purchased from GE Healthcare (Piscataway, N.J.). 5-Iodoacetamidofluorescein was purchased from Pierce (Rockford, Ill.). The complex (pVIc-biotin):streptavidin was synthesized as described (Blainey, P. C., Graziano, V., McGrath, W. J., Luo, G., Xie, X. S., and Mangel, W. F. (2012)). The fluorogenic substrates (Leu-Arg-Gly-Gly-NH)$_2$—Rhodamine (SEQ ID NO: 13) and (Cbz-Leu-Arg-Gly-Gly-NH)$_2$—Rhodamine (SEQ ID NO: 13) were synthesized and purified as described previously (Mangel, W. F., McGrath, W. J., Toledo, D. L., and Anderson, C. W. (1993) Nature 361, 274-275 and 44). AVP and the AVP mutant Cys122Ala (McGrath and Mangel, unpublished) were purified using published procedures (Mangel, W. F., McGrath, W. J., Toledo, D. L., and Anderson, C. W. (1993) Nature 361, 274-275 and Mangel, W. F., Toledo, D. L., Brown, M. T., Martin, J. H., and McGrath, W. J. (1996) J. Biol. Chem. 271, 536-543). Coomassie-blue stained or silver stained protein gels were scanned on a flatbed scanner and the bands quantitated with the Molecular Dynamics ImageQuant software. Buffer A was 20 mM Hepes (pH 7.0), 0.025% (w/v) DDM, and 0.1 mM DTT. Buffer B was 20 mM Tris-HCl (pH 8.0), 0.025% DDM, and 0.1 mM DTT. pVIc was labeled with Cy3B as described previously (Blainey, P. C., Graziano, V., McGrath, W. J., Luo, G., Xie, X. S., and Mangel, W. F. (2012)).

Cloning of pVI and VI—

Expression plasmids containing the pVI or VI open reading frames were acquired in two steps. First, pcr products were synthesized using Ad2 genomic DNA (Sigma) as template: The pVI ORF pcr product was inserted between a Bsa I site and a blunt end. The VI ORF pcr product was inserted between NdeI and Bam HI sites. Primers were purchased from Invitrogen (Carlsbad, Calif.). Sequences of the primers were as follows: for pVI, the forward primer, pVIf, was 5'-AAG GGT CTC ACA TGG AAG ACA TCA ACT TTG CGT CTC TG-3' (SEQ ID NO: 14) and incorporated a Bsa I site (underlined). The reverse primer, pVIr, was 5'-GAA GCA TCG TCG GCG CTT CAG GGA TTG-3' (SEQ ID NO: 15) with a blunt end. For VI, the forward primer, VIf, was 5'-ATT CCA TAT GGC CTT CAG CTG GGG CTC GCT G-3' (SEQ ID NO: 16) and incorporated a Nde I site (underlined), and the reverse primer, VIr, 5'-GGT TGG ATC CTT ACA GAC CCA CGA TGC TGT TCA G-3' (SEQ ID NO: 17) incorporated a Bam HI site (underlined). For efficient VI expression, VIf contained an initiator Met codon just prior to the Ala codon at the site of the N-terminal consensus cleavage site of the adenovirus proteinase, and VIr contained a stop codon after the Leu codon at the consensus cleavage site of the adenovirus proteinase near the C-terminus of pVI. After restriction. protein VI was ligated into a pET13a vector while pVI was ligated into a pREX-S31 vector. The resultant plasmids were subcloned into Top10 cells. Sequence verification was performed to insure the presence of the correct reading frame and absence of mutations. pVI and VI expressing bacteria were obtained by transformation of Escherichia coli BL21 (DE3) RIL Codon Plus cells for both constructs.

Expression of pVI and VI—

The genes for pVI and VI were expressed overnight at 37° C. by autoinduction in ZYM-5052 medium (Studier, F. W. (2005) Protein Expr. Purif. 41, 207-234). The bacterial cells were collected by centrifugation at 20,000×g for 20 min and stored at −20° C. Protein expression was confirmed by SDS-PAGE on bacterial lysates.

Purification of pVI and VI—

Frozen E. coli cell paste (~5 g) was suspended in 50 mL of lysis buffer containing 50 mM Tris-HCl (pH 7.5), 100 mM NaCl, 5 mM EDTA, 1% DDM, 1 mM DTT, 1 mM PMSF, 1 mM benzamidine-HCl and 1 tablet of Complete, EDTA-free protease inhibitor cocktail (Roche). Lysozyme to 0.01 mg/mL was added, and the cell suspension mixed by end-over-end rotation at room temperature for 60 min. The cell lysate was then sonicated intermittently for 5 min. on ice. Nucleic acids were further digested by the addition of 2.5 units of benzonase. The suspension was clarified by centrifugation at 10° C. in an SS-34 rotor for 30 min. at 30,000×g. The supernatant was diluted two-fold to lower the salt concentration and with a peristaltic pump loaded onto a low-pressure 40 mL Macro-Prep high S cation exchange cartridge. The cartridge had previously been equilibrated in 25 mM MES (pH 6.5), 0.1 mM EDTA, 1 mM DTT and 0.05% DDM. The flow rate was 3 mL/min. Proteins were eluted using 15 column volumes of a linear salt gradient between 0 and 1 M NaCl. Protein elution was monitored at 280 nm, and 1 min fractions were collected. Fractions containing pVI were identified by SDS-PAGE on a 15% polyacrylamide gel and pooled; protein in the pool was concentrated in an Amicon Ultra 10K MWCO membrane. The pVI was then diluted 3-fold with 25 mM MES (pH 6.5), 0.1 mM EDTA, 1 mM DTT and 0.05% DDM and loaded onto a 15 mL POROS 20 HS cation-exchange column at a flow rate of 2 mL/min. Proteins were eluted in a 20 column volume linear gradient from 0 to 500 mM NaCl. Fractions containing pVI were identified by SDS-PAGE and pooled; the pVI was concentrated to about 1 mL. pVI was further purified by size exclusion chromatography on a HiLoad 16/60 Superdex 200 prep grade column (Amersham Biosciences). The column was equilibrated with 25 mM Tris-HCl (pH 7.5), 150 mM NaCl, 0.1 mM EDTA, 1 mM DTT, and 0.05% DDM. The flow rate was 0.75 mL/min; 1 mL of sample was injected; the protein elution profile was obtained from the O.D. at 280 nm; 2 min fractions were collected. Fractions with pVI greater than 98% pure were identified by SDS-PAGE and pooled. The pooled fractions were diluted five-fold with 25 mM MES (pH 6.5), 0.025% DDM, 0.1 mM EDTA, and 1 mM DTT and then loaded onto a small cation-exchange column. The column was washed extensively and the pVI eluted with 0.8 M NaCl, 25 mM MES (pH 6.5), 0.1 mM EDTA, and 1 mM DTT. This step not only led to pVI being more concentrated but also insured that the concentration of DDM in the buffer was 0.025%. Fractions with pure pVI were then dialyzed against storage buffer which contained 12.5 mM MES (pH 6.5), 0.025% DDM, 25 mM NaCl, 0.1 mM EDTA, and 1 mM DTT. The concentration of pVI was determined using a calculated molar extinction coefficient of 30480 $M^{-1}$ $cm^{-1}$. Aliquots of pVI were frozen in liquid nitrogen and stored at −80° C. Protein VI was purified by the same procedure.

Equilibrium Dissociation Constants—

Equilibrium dissociation constants from anisotropy experiments and enzymatic activity assays were calculated as described previously (McGrath, W. J., Baniecki, M. L., Li, C., McWhirter, S. M., Brown, M. T., Toledo, D. L., and Mangel, W. F. (2001) Biochemistry 40, 13237-13245)

Purification of Hexon—

Hexon was purified by modifications of the procedures of Burnett (Rux, J., and Burnett, R. M. (2007) Large-scale purification and crystallization of adenovirus hexon. In: Tollefson, W. W. S. W. a. A. E. (ed). Methods in Molecular Medicine, Adenovirus Methods and Protocols, 2nd Ed., Humana Press Inc., Totowa, N.Y.). CsCl top fractions from a crude extract of Ad2 infected HelaS3 cells were thawed and dialyzed overnight against 1 liter of 10 mM Tris-HCl, pH 8 at 4° C. After dialysis, the solution was centrifuged for 30 min. at 4° C. at 6700×g to remove any insoluble material. All further chromatography steps were carried out at 21° C. The clarified solution was loaded onto a 15 mL Fractogel EMD TMAE Hicap (M) strong anion-exchange column at a flow rate of 2 mL/min. The column was washed extensively with 10 mM Bis-Tris-Propane, pH 7, and bound proteins were eluted with a linear salt gradient from 0 mM to 500 mM NaCl. Hexon enriched fractions were identified by SDS-PAGE and eluted from the column around 0.4 M NaCl. The fractions were pooled (~20 mL), diluted 1:2 with 10 mM Bis-Tris-Propane, pH 7 and loaded onto a 15 mL POROS 20 HQ strong anion-exchange column, previously equilibrated in the same buffer. Hexon was eluted from the column with a linear salt gradient as described above except that it eluted at 0.65 M NaCl. Pure hexon fractions were identified by SDS-PAGE, pooled, and dialyzed against 1 liter of storage buffer consisting of 10 mM sodium phosphate, pH 7, 0.02% sodium azide. Hexon was quantitated spectrophotometrically using a calculated extinction coefficient of 156430 $M^{-1}$ $cm^{-1}$ and stored on ice.

Steady-State Fluorescence Intensity and Anisotropy Measurements—

Steady-state fluorescence intensity and anisotropy measurements were performed on an ISS PC-1 spectrofluorometer with 19 A lamp current, 564 nm excitation wavelength, and 580 nm emission filter. The G factor for anisotropy experiments was measured before the beginning of each experiment. 1 mL of Cy3B labeled pVI was placed inside a quartz cuvette in buffer containing 20 mM Hepes, pH 7, 150 mM NaCl. After each addition of hexon, the liquid was mixed by pipetting the solution up and down four times and allowed to reach equilibrium for two minutes before opening the shutters to acquire data. Steady-state fluorescence intensity data were acquired in the absence of polarizers in order to increase the fluorescence signal Photobleaching Data Analysis—

Fluorescence images of an isolated and immobilized single-molecule of (pVIc-biotin):streptavidin-Alexa Fluor 546 complex or Cy3B-pVI were processed as follows: For each image frame, the average fluorescence peak intensity was calculated by summing all neighboring pixels with intensity values above a certain threshold and then dividing by the number of neighbors. All remaining pixels in that frame were considered background noise and were processed in a similar manner. The net peak intensity was obtained by subtracting the average background noise from the average peak intensity.

Cloning, Expression and Purification of pVI and VI—

The T7-based system (Studier, F. W. (2005) Protein Expr. Purif. 41, 207-234) was employed for the cloning and expression of the adenovirus precursor protein pVI and its proteolytically processed, mature form, protein VI as described in Materials and Methods. Briefly, the gene for pVI and an expressible gene of VI were synthesized by PCR and inserted into expression vectors. The vectors for pVI and VI were used to transform Escherichia coli BL21 (DE3) Codon Plus cells. Recombinant proteins were expressed in autoinduction media (Studier, F. W. (2005) Protein Expr. Purif. 41, 207-234). Purification of pVI and VI was accomplished by cation-exchange and size exclusion chromatography. The proteins were about 99% pure. pVI and VI required a detergent to keep them in solution. Below a concentration of DDM of 0.0125%, the proteins were insoluble, as determined by dynamic light scattering.

Binding of pVI and Protein VI to DNA—

The interactions of pVI and VI with DNA have not been previously characterized. Applicants used fluorescence anisotropy to measure the $K_{d(app.)}$, for the binding of pVI to dsDNA. Aliquots of pVI were added to a solution of 33-mer dsDNA in which one of the strands was labeled at its 5'-end with Fluorescein, and the fluorescence anisotropy was determined as described in Materials and Methods. The data are presented in FIG. 1 in the form of a Bejirim plot. The $K_{d(app.)}$ was 35±2 nM, Table 1. A similar experiment was performed with protein VI, FIG. 1. The $K_{d(app.)}$ was much higher, 241±14 nM, Table 1. These binding assays were done in 1 mM MgCl$_2$, because in the absence of magnesium, the binding to DNA was too tight to determine a $K_{d(app.)}$.

Stoichiometry of Binding of pVI to DNA—

A question is how many molecules of pVI bind to one molecule of 60-mer dsDNA. The stoichiometry of binding of pVI to DNA was ascertained using fluorescence anisotropy under "tight" binding conditions, conditions in which the concentration of one of the ligands was at least 10-fold greater than its $K_{d(app.)}$. Increasing amounts of pVI were added to a constant amount of 5' fluorescein-labeled 60-mer dsDNA, and the change in anisotropy upon each addition was measured. The concentration of fluorescein-labeled dsDNA was much higher than the $K_{d(app.)}$. Under these "tight" binding conditions, at pVI concentrations below saturation of DNA, all pVI present will be bound to DNA; above saturation, no added pVI will be able to bind to DNA. As shown in FIG. 2A, as the concentration of pVI was increased, the anisotropy increased linearly. Once saturation was reached, there was no further increase in anisotropy as additional pVI was added. The data points could be characterized by two straight lines using a linear fitting routine. The intersection point of the two lines is the minimal concentration of pVI required to saturate the DNA. Since this occurred at a concentration of pVI of 110 nM and the concentration of 60 mer dsDNA was 13.7 nM, the stoichiometry of binding of pVI to 60-mer dsDNA was 8:1, eight molecules of pVI per molecule of 60-mer dsDNA. A similar experiment with pVI and 33-mer dsDNA indicated a 4:1 stoichiometry (data not shown). When the maximal number of molecules of pVI bound to one DNA molecule is plotted versus the DNA length in base pairs, a straight line through the origin was observed, FIG. 2B. This implied that one molecule of pVI occluded eight base pairs of DNA. Most important, these data also indicated that pVI bound to DNA independent of the sequence of the DNA.

Number of Ion Pairs in the Binding of pVI to DNA—

To further characterize the DNA binding interface, Applicants determined the number of ion pairs involved in the binding of pVI to DNA. At different ionic strengths, 12-mer dsDNA labeled at one of its 5' ends with fluorescein was incubated with increasing concentrations of pVI. The equilibrium dissociation constants ($K_d$) were determined by fluorescence anisotropy, FIG. 3A. The log ($K_d$) was plotted versus log [NaCl], FIG. 3B. The following equation describes the resultant straight line:

$$-\frac{\partial \log K_d}{\partial \log (M^+)} = m'\psi$$

where M+ is the monovalent counterion concentration, m' is the number of ion pairs formed, and $\psi$ is the fraction of a counterion associated, in the thermodynamic sense, with each phosphate of DNA in solution. For dsDNA, $\psi$ is 0.88 (Record, M. T., Jr., Lohman, T. M., and De Haseth, P. (1976) J. Mol. Biol. 107, 145-158). The number of ion pairs formed upon binding of a pVI to 12-mer dsDNA was 2.9.

Nonelectrostatic Free Energy of Binding of pVI to dsDNA—

The nonelectrostatic change in free energy, $\Delta G_0^0$, upon binding of pVI to DNA was also calculated. The line in FIG. 3B was extrapolated to a Na+ concentration of 1 M. Then, the following equation was used:

$$\Delta G_0^0 = -RT \ln K_o$$

where $K_o$ is $K_A$ in 1 M Na$^+$. The $\Delta G_0^0$ (1 M Na$^+$) was −4.0 kcal. By correction for three lysine-like ion pairs, which have a $\Delta G_0^0$ (1 M Na$^+$) of 3×0.18 kcal, the nonelectrostatic free energy of binding was calculated to be −4.54 kcal. The $K_D$ values from FIG. 3A were 55, 155, 328, 449, and 1044 nM in 0.02, 0.03, 0.04, 0.05 and 0.06 M NaCl, respectively. By extrapolation of the line in FIG. 3B, the $K_d$ in 1 M NaCl was 1154 M.

pVI Slides Along DNA as a Monomer—

The oligomeric state of pVI was difficult to determine, because pVI requires detergent to be soluble. For this reason, Applicants resorted to an indirect assay, a single-molecule photobleaching assay, to see whether pVI is a monomer or an oligomer.

In the movies of pVI sliding along DNA, occasionally a labeled molecule of pVI would be seen to stick irreversibly to the glass surface of the coverslip (Graziano, V., Luo, G., Blainey, P. C., Pérez-Berná, A. J., McGrath, W. J., Flint, S. J., San Martin, C., Xie, X. S., and Mangel, W. F. (2012)). If the exciting light remained on, eventually the fluorophore would bleach. Before the Cy3B-labeled molecule of pVI stuck to a spot on the glass, the fluorescence intensity at that spot was zero. Upon pVI sticking to the glass, the fluorescence intensity abruptly increased. The fluorescence intensity remained constant for about 0.5 seconds and then abruptly decreased to zero. Abrupt, one-step photo bleaching of a molecule irreversibly bound to the glass slide is characteristic of the visualization of a protein molecule labeled with a single dye molecule. Were the fluorescence from more than one dye molecule on a protein or from more than one labeled protein, upon bleaching, the fluorescence would have diminished in multiple steps as several colocalized dye molecules would not likely bleach simultaneously. One-step photo bleaching was observed in 30 out of 30 bleaching events. Since in the same microscope field the fluorescence intensities of the molecules that were sliding on DNA were the same as those that stuck to the glass whose bleaching was observed, Applicants conclude that under these conditions, pVI was sliding along DNA as a monomer.

pVI Binding to Hexon—

The interactions of purified pVI to the hexon trimer have not been quantitatively characterized. Applicants used fluorescence quenching to measure the $K_{d(app.)}$, for the binding of pVI to hexon. Aliquots of hexon were added to a solution of pVI labeled with Cy3B and the intensity of fluorescence was determined as described in Materials and Methods. The data are presented in FIG. 4A. The $K_{d(app.)}$ Was 1.8±0.08 nM, Table 1.

TABLE 1

Adenovirus proteins: Binding to DNA and sliding along DNAs via one-dimensional diffusion

| Species MW | Ligand For $K_{D(app.)}$ Analysis | $K_{D(app.)}$ [nM] | DNA Binding Site Length [bp] | One-Dimensional Diffusion Constant[‡] [(bp)$^2$/s × 10$^{-6}$] |
|---|---|---|---|---|
| pVI 27014 | 33-mer ds DNA | 35 ± 2 | 8 | 1.45 ± 0.13[†] |
| pVI 27014 | hexon | 1.8 ± 0.08 | | |
| Protein VI 22118 | 33-mer ds DNA | 241 ± 14 | | |
| pVIc* 1350 | 12-mer ds DNA | 264 ± 25 | | 26.0 ± 1.8 |
| AVP[#] 23087 | 12-mer ds DNA | 63.08 ± 5.79 | | |
| AVP-pVIc 24437 | 36-mer ds DNA | 4.65 ± 2.16[#] | 6[#] | 21.0 ± 1.9[¶] |

[†](Graziano, V., Luo, G., Blainey, P. C., Pérez-Berná, A. J., McGrath, W. J., Flint, S. J., San Martin, C., Xie, X. S., and Mangel, W. F. (2012))
*(Blainey, P. C., Graziano, V., McGrath, W. J., Luo, G., Xie, X. S., and Mangel, W. F. (2012))
[#](McGrath, W. J., Baniecki, M. L., Li, C., McWhirter, S, M., Brown, M. T., Toledo, D. L., and Mangel, W. F. (2001) Biochemistry 40, 13237-13245)
[¶]( Blainey, P. C., Graziano, V., Pérez-Berná, A. J., McGrath, W. J., Flint, S. J., San Martin, C., Xie, X. S., and Mangel, W. F. (2012))
[‡]To convert from bp to nm: 10$^6$ (bp)$^2$/s = 102,400 (nm)$^2$/s Stoichiometry of Binding of pVI to Hexon—

A question is how many molecules of pVI bind to one molecule of hexon. The stoichiometry of binding of pVI to hexon was ascertained using fluorescence anisotropy under "tight" binding conditions. In this case, the concentration of Cy3B-labeled pVI, 20 nM, was more than 10-fold greater than its $K_{d(app.)}$ for binding to hexon. Experimentally, increasing amounts of hexon were added to a constant amount of Cy3b-labeled pVI, and the change in anisotropy upon each addition was measured. As shown in FIG. 4B, as the concentration of hexon was increased, the anisotropy increased linearly. Once saturation was reached, there was no further increase in anisotropy as additional hexon was added. The data points could be characterized by two straight lines using a linear fitting routine. The intersection point of the two lines is the minimal concentration of hexon required to saturate pVI. Since this occurred at a concentration of hexon of 25 nM, and the concentration of pVI was 20 nM, the stoichiometry of binding of pVI to hexon monomer was 1:1.

The Form of Hexon to which pVI Binds—

Figure 5:
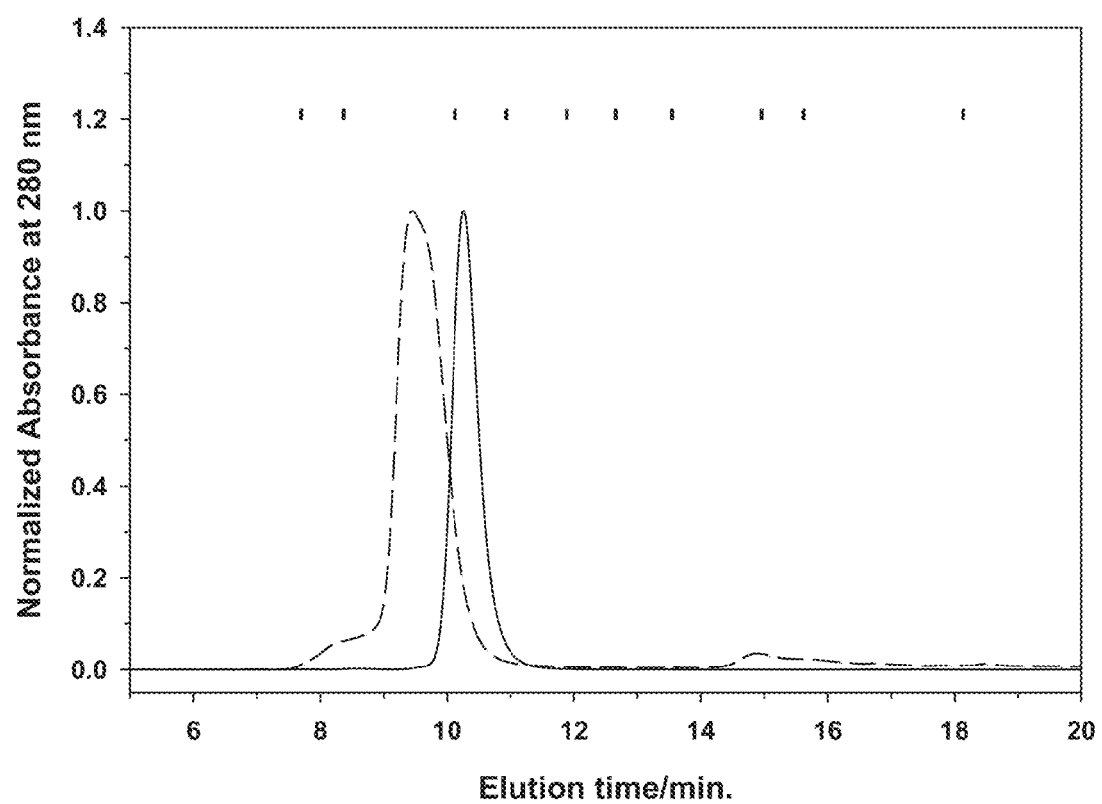
FIG. 5. Size exclusion chromatography of pVI-hexon complexes. Gel filtration of hexon and pVI-hexon complexes. The samples were injected onto a 7.8 mm×30 cm TSK-GEL G3000SWXL analytical size-exclusion column and eluted with 25 mM MES, pH 6.5 containing 250 mM NaCl. The vertical marks on top correspond to elution times of known molecular weight standards (from left to right: void volume, thyroglobulin (669000), apoferritin (443000), B-amylase (200000), alcohol dehydrogenase (150000), BSA (66000), ovalbumin (45000), carbonic anhydrase (29000), myoglobin (17000) and vitamin B-12 (1200). The apparent molecular weights of Ad2 hexon and Ad2 hexon:pVI were determined by interpolation from the standard curve. Ad2 hexon (solid line) and Ad2 hexon:pVI complex (dash line).

In solution and in the crystal structure, hexon is a trimer. Applicants' data showed one molecule of pVI binds to one molecule of hexon. A question is if it means that 3 molecules of pVI bind to one molecule of hexon trimer. It is possible the binding of pVI to the hexon trimer could cause the trimer to dissociate into monomers. To determine the molecular mass of the pVI-hexon complex, Applicants fractionated hexon and pVI-hexon complexes via gel filtration, FIG. 5. Based upon molecular weight standards, the molecular weight of hexon was 331,000, consistent with it being a homotrimer (3×109,000). The molecular weight of the pVI-hexon complex was 602,065. This is considerably higher than that predicted from 3 molecules of pVI binding to 1 molecule of the hexon trimer which would be 408,000 (327,000+3×27,000). Perhaps the binding of 3 molecules of pVI to the hexon trimer induces a rather large conformational change (Mangel, W. F., Lin, B., and Ramakrishnan, V. (1990) Science 248, 69-73).

The gene for pVI was cloned and expressed in E. coli and the resultant protein purified and characterized. pVI was purified to homogeneity. pVI had not been purified before, and some of the previous experiments with pVI and protein VI were done with proteins that had at one time been denatured (Russell, W. C., and Precious, B. (1982) J. Gen. Virol. 63, 69-79). The binding of pVI to DNA was independent of DNA sequence and was very tight. The $K_{d(app.)}$ for the binding of pVI to DNA was 35 nM. However, the binding assays had to be done in 1 mM MgCl$_2$, because in the absence of magnesium, the binding to DNA was too tight to determine a $K_{d(app.)}$. A similar problem arose in characterizing the binding of pVI to hexon. At 10 nM, Applicants observed tight binding; this implied that the $K_{d(app.)}$ was probably much lower. The binding of pVI to DNA was mediated by ionic contacts as the binding was sensitive to ionic strength. On the other hand, the binding of pVI to hexon can occur even in the presence of 1 M NaCl. However, that binding appeared to be due to hydrophobic interactions as that interaction was sensitive to detergents (data not shown).

pVI is a monomer at nM concentrations. Previously, Applicants had shown that pVI slides along DNA via one-dimensional diffusion (Graziano, V., Luo, G., Blainey, P. C., Pérez-Berná, A. J., McGrath, W. J., Flint, S. J., San Martin, C., Xie, X. S., and Mangel, W. F. (2012)); its one-dimensional diffusion constant is 1.45×10$^6$ (bp)/s. In the sliding assays, Applicants observed photo bleaching of pVI. Since the drop in fluorescence due to bleaching occurred in a single step, Applicants concluded that pVI was siding as a monomer. Both pVI and VI required a detergent to be soluble. As judged by dynamic light scattering, the minimum amount of DDM required for pVI to remain in solution was 0.0125%.

pVI may bind to DNA mostly through its pVIc moiety. The $K_{d(app.)}$ for the binding of pVI to DNA was 35 nM. AVP-pVIc complexes also bind tightly to DNA. The $K_{d(app.)}$ is 4.65 nM. Both protein VI and AVP bind less tightly to DNA. Their $K_{d(app.)}$ values are almost 10-fold higher, 241 and 63 nM respectively. Secondly, the number of base pairs covered while bound to DNA is similar; pVI covers 8 bp and AVP-pVIc complexes cover 6 bp (McGrath, W. J., Baniecki, M. L., Li, C., McWhirter, S. M., Brown, M. T., Toledo, D. L., and Mangel, W. F. (2001) Biochemistry 40, 13237-13245). In contrast, the virion precursor protein pIIIa covers 33 bp (Graziano & Mangel, data not shown). Third, some thermodynamics parameters of pVI binding to DNA are similar to those of AVP-pVIc complexes binding to DNA (McGrath, W. J., Baniecki, M. L., Li, C., McWhirter, S. M., Brown, M. T., Toledo, D. L., and Mangel, W. F. (2001) Biochemistry 40, 13237-13245), namely the number of ion pairs formed and the nonelectrostatic free energy of binding.

The non-sequence specific interaction between pVI and DNA exhibited a substantial dependence on monovalent sodium ion concentration. This dependence reflects the electrostatic component of the binding reaction (Record, M. T., Jr., Lohman, T. M., and De Haseth, P. (1976) J. Mol. Biol. 107, 145-158). The electrostatic component originates from the formation of ion pairs between positively charged groups on pVI and negatively charged phosphate groups on DNA. After binding occurs, there is a concomitant release of counterions from the DNA and, possibly, from pVI. From an analysis of the equilibrium association constants for the binding of pVI to 12-mer dsDNA as a function of the Na$^+$ concentration, an accurate estimate of the number of ion pairs involved in the interaction was obtained. Three ion pairs were involved in binding to 12-mer dsDNA. For comparison, two ions pairs of AVP-pVIc complexes are involved in its interaction with DNA (McGrath, W. J., Baniecki, M. L., Li, C., McWhirter, S. M., Brown, M. T., Toledo, D. L., and Mangel, W. F. (2001) Biochemistry 40, 13237-13245).

There also seems to be a substantial, favorable nonelectrostatic component of the binding interaction. Upon extrapolation to 1 M Na$^+$ of the line in FIG. 3B, the $\Delta G_0^0$ was −4.0 kcal for pVI. The $\Delta G_0^0$ is −4.2 kcal for AVP-pVIc complexes (McGrath, W. J., Baniecki, M. L., Li, C., McWhirter, S. M., Brown, M. T., Toledo, D. L., and Mangel, W. F. (2001) Biochemistry 40, 13237-13245). Correction for three lysine-like ion pairs makes the nonelectrostatic free energy of binding −4.5 for pVI. This indicates that a substantial component of the binding free energy under physiological conditions results from nonspecific interactions between pVI and base or sugar residues on the DNA and that the dominant factor driving the nonspecific interaction between pVI and DNA is the entropic contribution from the release of counterions.

Although it had been known that pVI binds to hexon (Russell, W. C., and Precious, B. (1982) J. Gen. Virol. 63, 69-79), pVI had not, heretofore, been purified so that its interaction with hexon could be quantitatively characterized. In the virion, hexon appears as a homotrimer and is the major component of the capsid, forming the faces of the icosahedral surface. The arrangement of the hexon trimers alters at the vertices of the capsid, where the peri-pentoneal hexons interact with the penton base. Applicants' data on the binding of pVI to hexon showed that one molecule of pVI binds to one hexon molecule. A gel filtration experiment indicated three molecules of pVI per hexon trimer. Perhaps after pVI escorts hexon into the nucleus, pVI dissociates from hexon and binds to the viral DNA, because the local viral DNA concentration is so high. pVI then activates AVP on the DNA and the resultant protein VI, given its 10-fold higher $K_{d(ass.)}$ dissociates from the DNA and binds to its final position in infectious virus.

There are multiple functions at the two ends of pVI. pVI is processed by AVP first at its N-terminus and then at its C-terminus (Graziano, V., Luo, G., Blainey, P. C., Pérez-Berná, A. J., McGrath, W. J., Flint, S. J., San Martin, C., Xie, X. S., and Mangel, W. F. (2012)). Upon processing by AVP, some of these functions may be terminated and others de-repressed. The N-terminus of pVI has membrane lytic activity (Wiethoff, C. M., Wodrich, H., Gerace, L., and Nemerow, G. R. (2005) J. Virol. 79(4), 1992-2000). Initially, AVP cleaves off a peptide from pVI that contains amino acids 1-33. This may expose a predicted amphipathic alpha-helix (residues 36-53) that has been shown to be essential for membrane lytic activity in protein VI. Alternatively, the membrane lytic activity at the N-terminus of pVI may be buried within hexon and exposed only after pVI dissociates from hexon. The last 11 amino acids of pVI, amino acids 239-250, facilitate binding to DNA. Their removal is reflected in the almost 10-fold higher $K_{d(app.)}$ for protein VI relative to that of pVI. Also, the removed C-terminal peptide, pVIc, activates AVP (Mangel, W. F., McGrath, W. J., Toledo, D. L., and Anderson, C. W. (1993) Nature 361, 274-275 and Webster, A., Hay, R. T., and Kemp, G. (1993) Cell 72, 97-104) and enables it to slide along DNA via one-dimensional diffusion to process the virion precursor proteins (Blainey, P. C., Graziano, V., Pérez-Berná, A. J., McGrath, W. J., Flint, S. J., San Martin, C., Xie, X. S., and Mangel, W. F. (2012)). Premature exposure of the membrane lytic activity before virion assembly or premature activation of AVP may be harmful to the infected cell and possibly abort the infection. For example, if pVIc is added to cells along with adenovirus, the yield of infectious virus is down by more than 99% (Baniecki, M. L., McGrath, W. J., McWhirter, S. M., Li, C., Toledo, D. L., Pellicena, P., Barnard, D. L., Thorn, K. S., and Mangel, W. F. (2001) Biochemistry 40, 12349-12356).

pVI and its processed form protein VI are remarkable proteins, because they exhibit many, quite different functions at various stages of an adenovirus infection. Two of those functions, binding to DNA and sliding along DNA require nonspecific binding to DNA, which Applicants have characterized here. And pVI binds tightly to hexon so that they can enter the nucleus together. It will be interesting to see how during virion assembly pVI dissociates from being tightly bound to hexon and binds tightly to the viral DNA to activate AVP.

Example 2. Adenovirus Proteinase is Activated in an Unusual One-Dimensional Biochemical Reaction Late in an adenovirus infection, the viral proteinase (AVP) becomes activated to process virion precursor proteins used in virus assembly. AVP is activated by pVIc, an 11-amino acid peptide from the C-terminus of the precursor protein pVI. Here Applicants show how AVP is activated by pVI in the virion where both AVP and pVI are essentially irreversibly bound to the viral DNA genome. pVI, a substrate, slides on DNA via one-dimensional diffusion, $D_1=1.45\times10^6$ (bp)$^2$/s, until it comes into contact with AVP. This encounter enables AVP to excise and bind the released cofactor pVIc. AVP was also activated by pVI in DNA-dependent reactions in heat-disrupted immature virus. These activities illustrate new paradigms for virion maturation and for the formation of bimolecular complexes by proteins that do not participate in nucleic acid metabolism.

Human adenovirus, a eukaryotic virus with an ~36,000 bp, linear DNA genome, encodes the adenovirus proteinase (AVP), a 204 amino acid cysteine proteinase (J. Ding, W. J. McGrath, R. M. Sweet, W. F. Mangel, EMBO J. 15, 1778 (1996)) whose activity is essential for the synthesis of infectious virus particles (J. Weber, J. Virol. 17, 462 (1976)). One of the functions of the proteinase, after virion assembly, is to cleave six virion precursor proteins to the mature counterparts found in wild-type virions (J. Weber, J. Virol. 17, 462 (1976)). Recombinant AVP exhibited little or no enzymatic activity (W. F. Mangel, W. J. McGrath, D. L. Toledo, C. W. Anderson, Nature 361, 274 (1993) and A. Webster, R. T. Hay, G. Kemp, Cell 72, 97 (1993)), prompting a search for cofactors. One cofactor is pVIc, the 11-amino acid residue peptide (GVQSLKRRRCF (SEQ ID NO: 12)) originating from the C-terminus of the 250 amino acid adenovirus precursor protein pVI. A second cofactor is the viral DNA (W. F. Mangel, W. J. McGrath, D. L. Toledo, C. W. Anderson, Nature 361, 274 (1993); W. J. McGrath et al., Biochemistry 40, 13237 (2001); N. S. Bajpayee, W. J. McGrath, W. F. Mangel, Biochemistry 44, 8721 (2005) and S. Gupta et al., Mol. Cell. Proteomics 3.10, 950 (2004)). The cofactors stimulate the macroscopic kinetic constants for substrate hydrolysis (W. J. McGrath et al., Biochemistry 40, 13237 (2001); W. F. Mangel, D. L. Toledo, M. T. Brown, J. H. Martin, W. J. McGrath, J. Biol. Chem. 271, 536 (1996); M. L. Baniecki et al., Biochemistry 40, 12349 (2001) and M. L. Baniecki et al., Biochemistry 41, 430 (2001)).

pVIc is cleaved from pVI inside immature particles to activate AVP, i.e. to form AVP-pVIc complexes. Restricting any model for the activation of AVP by pVI in such particles is the prediction that AVP and pVI can no longer undergo bimolecular interactions by diffusion in three-dimensional space. Both AVP and pVI are sequence-independent DNA binding proteins (W. F. Mangel, W. J. McGrath, D. L. Toledo, C. W. Anderson, Nature 361, 274 (1993); W. J. McGrath et al., Biochemistry 40, 13237 (2001); M. L. Baniecki et al., Biochemistry 40, 12349 (2001) and W. C. Russell, B. Precious, J. Gen. Virol. 63, 69 (1982)). The high concentration of DNA inside the virion (>500 g/L)) (S. Casjens, in Structural biology of viruses W. Chiu, R. M. Burnett, R. L. Garcea, Eds. (Oxford University Press, Oxford, 1997) pp. 3-37) drives both AVP and pVI onto the DNA by mass action. For AVP, the DNA-bound state predominates by at least one hundred thousand-fold over free AVP (W. J. McGrath et al., Biochemistry 40, 13237 (2001)); this in combination with the sieving action in the dense DNA environment (S. Mangenot, S. Keller, J. Radler, Biophys J 85, 1817 (2003), diminishes AVP's effective three-dimensional diffusion constant by at least one million-fold. The DNA genome cannot move either. The pressure exerted by the tightly packed genome on the shell of the virion creates considerable friction, leading to freezing the DNA in place and rendering DNA-bound proteins likewise immobile. Given this situation inside the virion, it is not clear how a bimolecular interaction between AVP and pVI can occur leading to the cleavage of pVI and the activation of the enzyme by released pVIc.

Here Applicants solve this conundrum by presenting evidence that these two proteins can form a bimolecular interaction in the one-dimensional compartment present along the viral DNA by sliding via one-dimensional diffusion; they do not diffuse in three-dimensional space to meet. The activation reaction takes place by a novel biochemistry, one-dimensional biochemistry (P. C. Blainey et al. (2012)). This mechanism for promoting bimolecular interactions is a new paradigm for how substrates interact with 'non nucleic acid' enzymes and a new paradigm for virion maturation.

A question is which components are required for the activation of AVP by pVI leading to the formation of the enzymatically active AVP-pVIc complex. If only a simple bimolecular interaction between AVP and pVI were needed, then mixing purified AVP (W. F. Mangel, D. L. Toledo, M. T. Brown, J. H. Martin, W. J. McGrath, J. Biol. Chem. 271, 536 (1996)) with purified pVI (V. Graziano et al. (2012)) should result in the cleavage of pVI to yield pVIc followed by the formation of active AVP-pVIc complexes. However, when this was done, no enzymatic activity was detected (FIG. 6A). Both AVP and pVI bind to DNA with apparent equilibrium dissociation constants of 63 nM (W. J. McGrath et al., Biochemistry 40, 13237 (2001)) and 35 nM (V. Graziano et al. (2012)), respectively. Another question is if DNA is required for the activation of AVP by pVI. Applicants repeated the experiment but in the presence of dsDNA. By one hour, 100% of the pVI was cleaved and used to form active AVP-pVIc complexes. Thus, activation of AVP to AVP-pVIc complexes by pVI required the presence of DNA.

To see if both enzyme (AVP) and substrate (pVI) must be on the same molecule of DNA for activation to occur or whether they can interact when bound to different DNA molecules, Applicants incubated increasing concentrations of DNA with a mixture of AVP and pVI, each at a concentration such that both should bind to DNA at any DNA concentration. And then Applicants assayed for enzyme activation (FIG. 6B). At low DNA concentrations, the DNA was saturated with AVP and pVI; the rate of AVP activation was proportional to the DNA concentration. The rate of activation of AVP reached a peak at the concentration of DNA at which all the AVP and pVI were bound to all the DNA molecules. Beyond the peak, the rate of AVP activation progressively decreased. For example, at a DNA concentration of 320 nM, the rate of AVP activation was 12% of the rate exhibited at the DNA concentration at the peak, 50 nM. This is the type of curve expected if AVP and pVI must be on the same DNA molecule for activation to occur. Beyond the peak, as the concentration of DNA was progressively increased, the probability that both an AVP and a pVI molecule would be bound to the same DNA molecule would progressively decrease. If an AVP on one DNA molecule can be activated by a pVI on another DNA molecule, one would predict an initial curve similar to that in (FIG. 6B), but, beyond the peak, the rate of activation would have remained constant. This is because all the AVP and pVI would have been bound to DNA and, therefore, the bound protein concentration would not have changed as the DNA concentration was increased. These conclusions were corroborated by the SDS-PAGE analysis of the proteins present at the various DNA concentrations in (FIG. 6C); pVI was not processed at the higher DNA concentrations. Thus for AVP to be activated by pVI, both AVP and pVI must be on the same molecule of DNA.

In a single molecule total internal reflection fluorescence microscopy DNA sliding assay, Applicants found that AVP does not slide effectively along DNA (see SOM). This implied that for a bimolecular interaction to occur between AVP and pVI, pVI must slide. Applicants labeled pVI molecules with the fluorophore Cy3B and observed the molecules binding to DNA as monomers (V. Graziano et al. (2012)) at random locations. Most important, the molecules slid rapidly over tens of thousands of base pairs before dissociating from the DNA. For example, the molecule whose motion is shown in the raw image data in (FIG. 7A), upon centroid analysis (FIG. 7B), had traveled more than 10,000 base pairs during a 12 sec binding event. The trajectories of 126 pVI molecules sliding on DNA are plotted in (FIG. 7C); the mean square displacement (MSD) of each trajectory shown versus diffusion time is shown in (FIG. 7D). The MSD for each molecule is approximately linear with diffusion time, indicating transport dominated by Brownian motion. From the MSD slopes, the mean diffusion constant was calculated to be $1.45 \pm 0.13 \times 10^6$ (bp)$^2$/s (Table 2).

TABLE 2

Adenovirus proteins: Binding to DNA, $K_d$, and sliding along DNA via one-dimensional diffusion, $D_1$

| Species MW [aa] | Ligand For $K_{D(app.)}$ Analysis | $K_{D(app.)}$ [nM] | DNA Binding Site Length [bp] | One-Dimensional Diffusion Constant[‡] [(bp)$^2$/s × 10$^{-6}$] |
|---|---|---|---|---|
| pVI 27014 [1-250] | 33-mer ds DNA | $(35 \pm 2)^a$ | 8 | 1.45 ± .13 |
| Protein VI 22118 [34-239] | 33-mer ds DNA | $(241 \pm 14)^a$ | | |
| pVIc[b] 1350 [240-250] | 12-mer ds DNA | 264 ± 25 | 7 | 26.0 ± 1.8 |
| AVP 23087 [1-204] | 12-mer ds DNA | $(63.08 \pm 5.79)^c$ | | $(0.02 \pm 0.07)^d$ |
| AVP-pVIc 24435 [215] | 36-mer ds DNA | $(4.65 \pm 2.16)^c$ | 6 | 21.0 ± 1.9$^e$ |

TABLE 2-continued

Adenovirus proteins: Binding to DNA, $K_d$, and sliding along DNA via one-dimensional diffusion, $D_1$

| Species MW [aa] | Ligand For $K_{D(app.)}$ Analysis | $K_{D(app.)}$ [nM] | DNA Binding Site Length [bp] | One-Dimensional Diffusion Constant[‡] [(bp)$^2$/s × $10^{-6}$] |
|---|---|---|---|---|
| pVIc-biotin: streptavidin~57000 | 18-mer ds DNA | 35 ± 5.0[b] | | 2.21 ± 0.21[b] |

[‡]To convert from bp to nm: $10^6$ (bp)$^2$/s = 102,400 (nm)$^2$/s
[a](V. Graziano et al. (2012))
[b](P. C. Blainey et al. (2012))
[c](W. J. McGrath et al., Biochemistry 40, 13237 (2001))
[d]Whole population-mean $D_1$ calculated from one population (99-96% of the molecules bound to DNA) have a $D_1$ of zero and another population (1-4% of the molecules bound to DNA) having a $D_1$ of $1.7 \times 10^6$ (bp)$^2$/s, with SD of $1.9 \times 10^6$ (bp)$^2$/s. See SOM.
[e](P. C. Blainey et al. (2012))

Figure 8A:
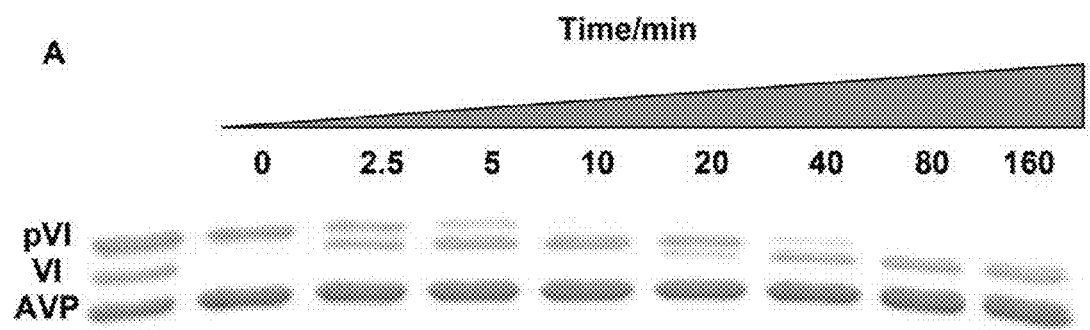

To determine the sequence of events in the activation of AVP by pVI in the presence of DNA, Applicants assayed aliquots of the reaction in (FIG. 6A) for processing intermediates. SDS-polyacrylamide gel electrophoresis (FIG. 8A) showed that by 2.5 minutes, an intermediate in the processing of pVI to protein VI appeared. By 10 minutes, all the pVI had disappeared. At 20 minutes protein VI began to appear and by 40 minutes almost all the intermediate had been converted to protein VI. A similar analysis of the reaction in the absence of DNA showed that pVI is not cleaved by AVP (data not shown). MALDI-TOF mass spectroscopic analysis of the reactions in (FIG. 6A) showed that before the addition of DNA, two masses were present, AVP and pVI, (FIG. 8B). At the 20 minute time point, the pVI mass had disappeared, (FIG. 8C). Masses corresponding to VI-C (pVI from which the N-terminal peptide, amino acids 1-33, was cleaved) and VI had appeared. A MALDI-TOF mass spectroscopic analysis of the peptides generated at each time point is shown in (FIG. 8D). By 15 sec., the peptide from the N-terminus of pVI, amino acids 1-33, began to appear. At 5 min., the peptide from the C-terminus of pVI, amino acids 239-250, began to appear. Thus, the processing of pVI by AVP occurred in two steps, first cleavage at the N-terminus of pVI and then at its C-terminus. The sequence of events is summarized in (FIG. 8E).

Figure 9A:
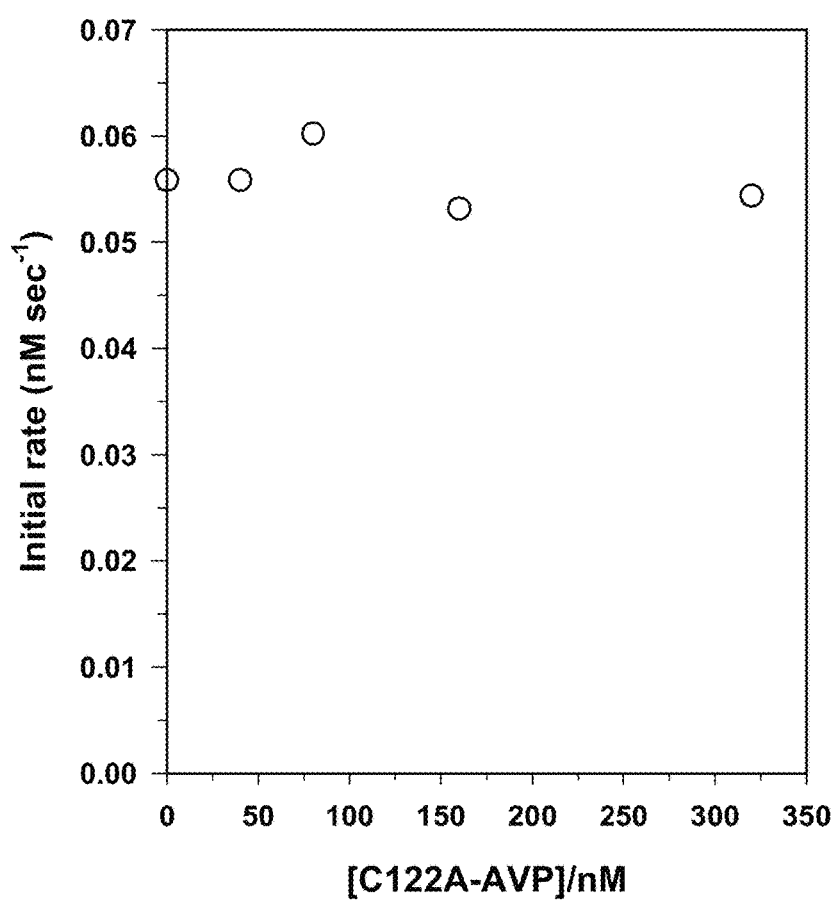
FIG. 9A-D. pVIc binds to the AVP that cut it out, in heat-disrupted ts-1 virus particles activation of AVP requires DNA, and a model on the activation of AVP. (A) pVI binds to the AVP that cut it out. Increasing amounts of the AVP mutant Cys122Ala were added to reaction mixtures in buffer A containing 130 nM pVI, 130 nM AVP, and 2.8 nM 1500-mer ds DNA. After a 5 min incubation at 21° C., the formation of active AVP-pVIc complexes was assayed. (B) The precursor proteins, their cleavage sites, (▼), and the processed precursor proteins are labeled and color coded. (C) In heat-disrupted ts-1 virus particles, activation of AVP requires DNA. Proteins were fractionated on PhastGel 8-25% gradient gels. pVI is cleaved to protein VI via an intermediate iVI. pVIII, the precursor to protein VIII, migrates like protein VI. Lane 1 contained heat-disrupted ts-1 virus incubated for 24 hours. Lanes 2 and 3 contained heat-disrupted ts-1 virus incubated with AVP for 2 h or 24 h, respectively. Lanes 4 and 5 contained heat-disrupted ts-1 virus treated with DNase and then incubated with AVP for 2 h or 24 h, respectively. Lanes 6 and 7 contained heat-disrupted ts-1 virus treated with DNase, the DNase inactivated, the DNA returned, and then the reactions incubated with AVP for 2 h or 24 h, respectively. Lane 8 contained wild-type virus (Ad5GL). Ovals next to bands refer to the specific precursor proteins and their products that are color-coded as in (B). (D) A model, based upon the data in this Example, on the activation of AVP by pVI on DNA.

During the activation reaction on DNA, it is a question if the pVIc generated bind to any AVP bound to DNA or just to the AVP molecule that cut it out. Applicants incubated AVP, pVI and DNA with increasing concentrations of the Cys122Ala mutant of AVP and then assayed for AVP-pVIc complex activity, (FIG. 9A). This mutant of AVP lacks enzymatic activity as the nucleophilic cysteine has been substituted; however, it binds pVIc and binds to DNA like wild-type AVP (data not shown). No decrease in AVP-pVIc complex activity was observed regardless of the mutant AVP concentration. That no decrease in enzyme activity was observed indicated that the released pVIc did not bind to any AVP molecule bound to DNA but only to the active AVP molecule that cut it out. If it could bind to any AVP molecule, as the concentration of Cys122Ala was increased, the pVIc would have a greater probability to bind to the inactive mutant and the amount of enzyme activity observed would decrease. Thus, pVIc binds to the AVP molecule that cut it out from pVI.

Figure 9B:
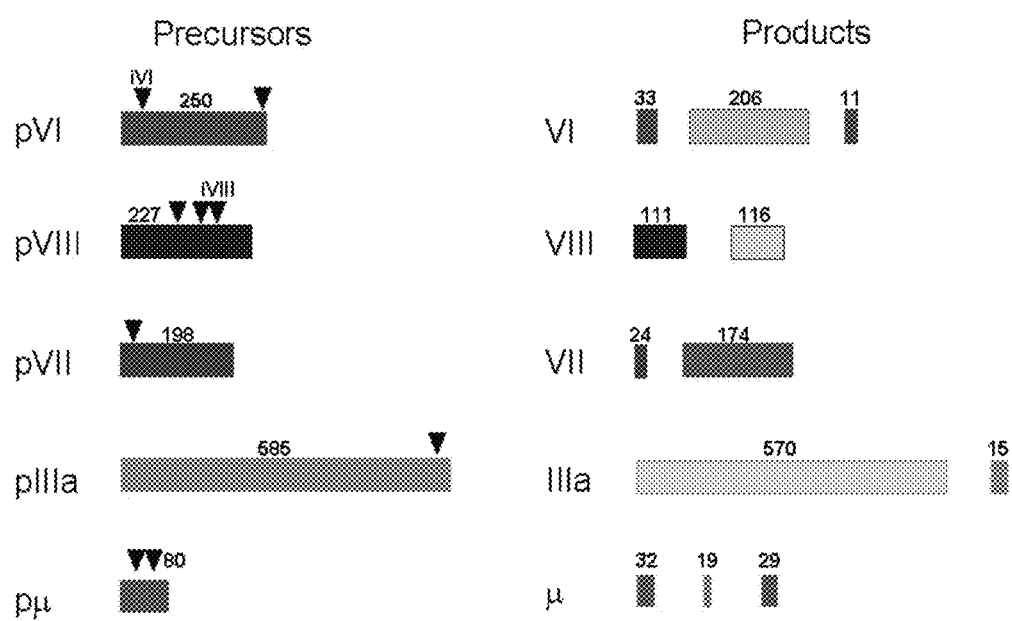
Figure 9C:
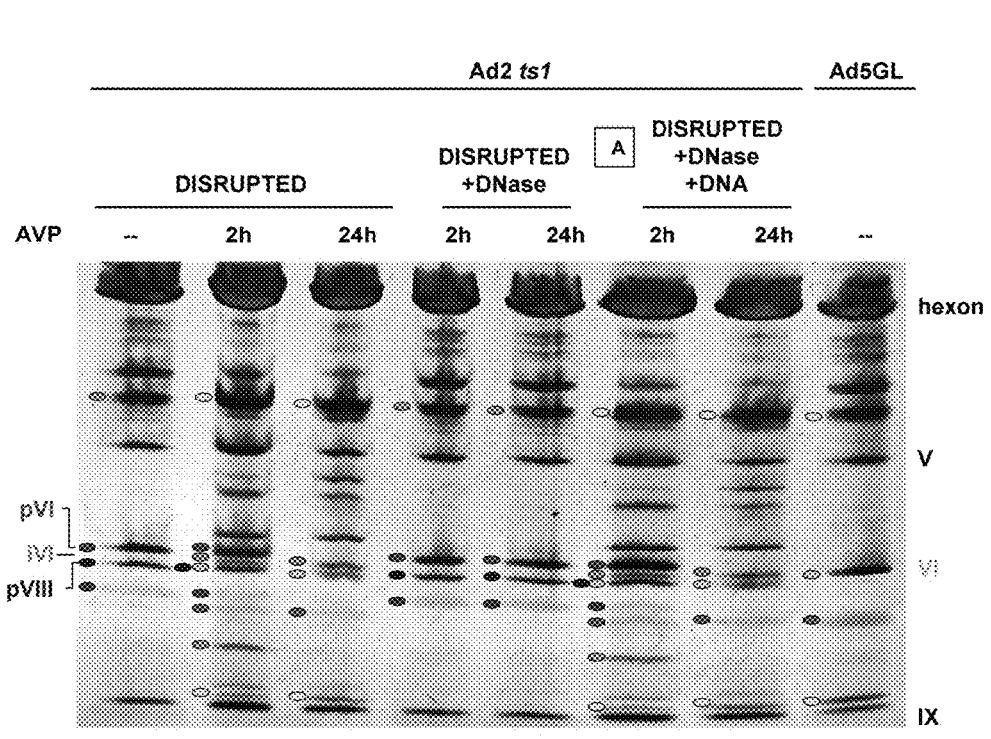

A question is whether DNA required for the activation of AVP in vivo, inside immature particles where the viral DNA is decorated with tightly bound proteins such as pVII and protein V (S. J. Flint, L. W. Enquist, V. R. Racaniello, principles of virology (ASM Press, ed. third, 2009), pp. 1028). Sliding does occur in vivo at a DNA concentration not unlike that inside the adenovirus virion by the lac repressor inside E. coli (J. Elf, G.-W. Li, X. S. Xie, Science 316, 1191 (2007)). Applicants do see DNA-dependent activation of AVP in a quasi in vivo situation, using heat-disrupted ts-1 virus particles (A. J. Pérez-Berná et al., J. Mol. Biol. 392, 547 (2009)). Ts-1 virus is a temperature-sensitive mutant of adenovirus that when grown at the nonpermissive temperature produces virions devoid of AVP; as such, all the virion precursor proteins are intact (J. Weber, J. Virol. 17, 462 (1976)). The cartoon in (FIG. 9B) depicts the precursor proteins, the processing sites, and the mature proteins. In one experiment, AVP was incubated with heat disrupted ts-1 virus for 2 and 24 hours before fractionating the proteins on an SDS-polyacrylamide gel. The results, (FIG. 9C), indicated that some pVI was processed within 2 hours and all of it processed within 24 hours as indicated by the disappearance of the pVI band. During the processing of pVI, AVP-pVIc complexes were formed, because other precursor proteins (pIIIa, pVII, and pVIII) were observed to be processed. If, before adding AVP, heat disrupted ts-1 virus was incubated with DNase, no processing of pVI or the other precursor proteins was observed, 2 or 24 hours after adding AVP. Most convincing was the experiment in which heat disrupted ts-1 virus was incubated with DNase, the DNase inactivated, and ts-1 viral DNA added back. Here, upon adding AVP and incubating for 2 or 24 hours, the processing pattern of pVI and the other precursor proteins was identical to that observed with heat disrupted ts-1 virus particles just incubated with AVP. Thus, in heat disrupted virus, DNA is required for the activation of AVP.

Figure 9D:
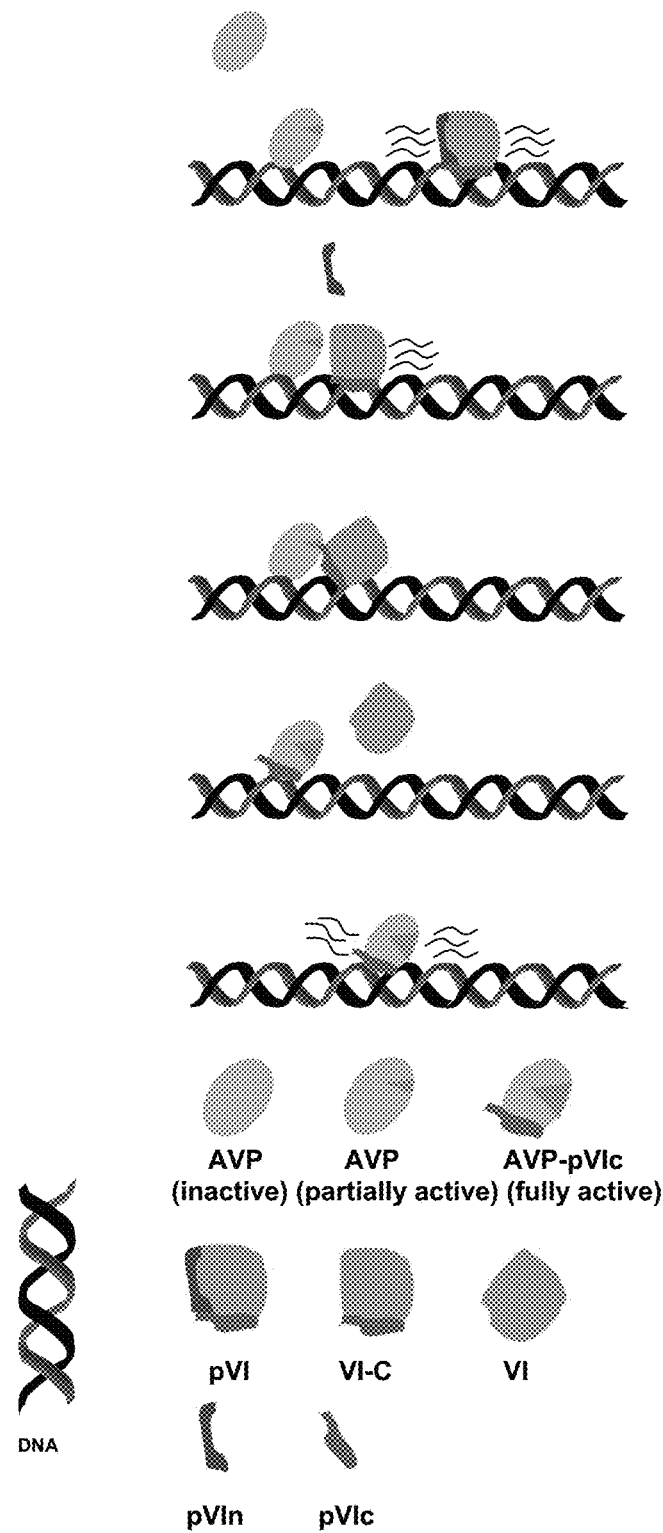

Applicants have shown how AVP can be activated by pVI, i.e. how an AVP-pVIc complex can form in the DNA dense environment of the core of the immature virion, (FIG. 9D). AVP, synthesized as an inactive proteinase, binds to the viral DNA and does not slide. pVI binds to the viral DNA and slides via one-dimensional diffusion into AVP. AVP, partially activated by being bound to its cofactor DNA (W. F. Mangel, W. J. McGrath, D. L. Toledo, C. W. Anderson, Nature 361, 274 (1993); W. J. McGrath et al., Biochemistry 40, 13237 (2001); N. S. Bajpayee, W. J. McGrath, W. F. Mangel, Biochemistry 44, 8721 (2005) and S. Gupta et al., Mol. Cell. Proteomics 3.10, 950 (2004)), cleaves DNA-bound pVI twice, first near its N-terminus to generate the processing intermediate VI-C and liberate a 33 amino acid peptide. Since pVI probably binds to DNA via its pVIc moiety (P. C. Blainey et al. (2012) and V. Graziano et al. (2012)) to stay on the DNA, pVI must first be cleaved at its N-terminus; presumably a rate limiting, conformational change then occurs to make the C-terminal cleavage site accessible. Next, AVP cleaves VI-C near its C-terminus generating protein VI and liberating pVIc, an 11-amino acid peptide. pVIc then preferentially binds to the AVP that cut it out (see SOM). Next, pVIc forms a disulfide bond with AVP keeping the now fully activated enzyme, the AVP-pVIc complex bound to DNA, permanently activated (M. L. Baniecki et al., Biochemistry 40, 12349 (2001); W. J. McGrath, M. L. Baniecki, E. Peters, D. T. Green, W. F. Mangel, Biochemistry 40, 14468 (2001) and W. J. McGrath, K. S. Aherne, W. F. Mangel, Virology 296, 234 (2002)). Consistent with the conclusion that activation of AVP by pVI with purified components requires DNA in vitro is the conclusion that DNA is required for activation of AVP in heat disrupted virus.

Binding to and sliding along DNA are required for the activation of AVP by pVI. Binding of AVP to DNA partially activates the enzyme allowing it to cleave pVI also bound to DNA. And binding of AVP and pVI to DNA must orient them such that a productive collision occurs when the substrate binding site at the N-terminus of pVI slides into the active site of AVP. This is a novel type of biochemistry, one-dimensional biochemistry (P. C. Blainey et al. (2012)). Sliding on DNA is required for the activation of AVP by pVI. In the absence of DNA, AVP will not even bind to pVI (Graziano and Mangel, unpublished). That both AVP and pVI must be on the same DNA molecule for formation of AVP-pVIc complexes is consistent with a requirement for sliding. Since AVP binds to DNA and does not slide, the only way AVP could become activated via pVI is for pVI to slide on DNA into AVP. Applicants had recently shown that molecules sliding along DNA, including AVP-pVIc complexes, diffuse along a helical path defined by the double helix and rotate in order to keep the DNA-binding face of the protein in contact with DNA (B. Bagchi, P. C. Blainey, X. S. Xie, J Phys Chem B 112, 6282 (2008) and P. C. Blainey et al., Nat Struct Mol Biol 16, 1224 (2009)).

A conundrum about the assembly of adenovirus virions arises when it is realized that AVP and the six virion precursor proteins are essentially, irreversibly bound to the viral DNA inside the immature virion. Yet, under these conditions, somehow AVP becomes activated by pVIc and the virion precursor proteins become processed by AVP-pVIc complexes. Here Applicants addressed the part of the conundrum as to how AVP becomes activated by pVI under these conditions. The solution is an unprecedented series of reactions between a proteinase and its substrate. In a different communication, Applicants address the remaining enigma of how fully activated AVP-pVIc complexes process the virion precursor proteins (P. C. Blainey et al. (2012)). AVP-pVIc complexes slide along the DNA via one-dimensional diffusion processing the virion precursor proteins also bound to the DNA. And finally, Applicants address the issue of how pVI and AVP-pVIc complexes slide along the DNA. The element they both have in common is pVIc, and Applicants show that pVIc is a "molecular sled" (P. C. Blainey et al. (2012)) that slides by itself or with different cargos attached to it such as protein VI or AVP.

While proteins, including viral proteins (S. J. Flint, L. W. Enquist, R. M. Krug, V. R. Racaniello, A. M. Skalka, Principles of Virology: Molecular Biology, Pathogenesis, and Control (ASM Press, Washington, D C, 2000), pp. 804), have been shown to slide on DNA, all the examples to date have been of 'nucleic acid' proteins and enzymes with functions relevant to specific loci or features in the genome. pVI, by contrast, is an adenovirus structural protein tasked with no known functions at particular genomic loci. Not only is there no precedence for a 'non-nucleic acid' protein sliding on DNA, there is no precedence for a substrate sliding along DNA into an enzyme that will cleave it. Given this novel exploitation by pVIc of the ability of DNA to present a sliding surface, it is not difficult to imagine that other substrates and enzymes will be found that make non-canonical use of facilitated diffusion along DNA.

Example 3: Viral Proteinase Slides Along DNA to Locate and Process its Substrates Many different viruses, including human adenovirus, utilize precursor proteins during virion assembly. These must later be processed by virus-coded proteinases to render the virus particles infectious (Weber, J. Genetic analysis of adenovirus type 2, III. Temperature-sensitivity of processing of viral proteins. J. Virol. 17, 462-471 (1976)). How this occurs inside a nascent virion has been an enigma: The adenovirus proteinase (AVP) and its precursor protein substrates are tightly bound to the highly concentrated and immobilized viral DNA such that bimolecular interactions cannot occur by three-dimensional diffusion. Applicants uncovered a solution when Applicants observed complexes of AVP covalently attached to its 11-amino acid cofactor pVIc (GVQSLKRRRCF (SEQ ID NO: 12)) exhibiting directionless sliding on viral DNA lasting more than one second and covering more than 20,000 base pairs. The one-dimensional diffusion constant, $21.0 \pm 1.9 \times 10^6$ (bp)$^2$/s, was the fastest yet observed for a protein sliding along DNA. In principle, one-dimensional diffusion can provide a means for DNA-bound proteinases to locate and process DNA-bound substrates. And here Applicants show this is correct: in vitro, AVP-pVIc complexes processed a purified virion precursor protein in a DNA-dependent reaction; in a quasi in vivo environment, heat-disrupted ts-1 virions, AVP-pVIc complexes processed five different precursor proteins in DNA-dependent reactions. The sliding of AVP-pVIc complexes along DNA illustrates a new biochemical mechanism by which a proteinase can locate its substrates, represents a new paradigm for virion maturation, and reveals a new way of exploiting the ability of DNA to present a sliding surface.

Late in adenovirus infection immature particles are assembled with multiple copies of six, different precursor proteins (Weber, J. Genetic analysis of adenovirus type 2, III. Temperature-sensitivity of processing of viral proteins. J. Virol. 17, 462-471 (1976)); then, the adenovirus proteinase (Ding, J., McGrath, W. J., Sweet, R. M. & Mangel, W. F. Crystal structure of the human adenovirus proteinase with its 11 amino acid cofactor. EMBO J. 15, 1778-1783 (1996)) (AVP), a 23 kDa cysteine proteinase (FIG. 10A), is activated and cleaves the virion precursor proteins to produce the mature forms found in wild-type, infectious virions. Maximal activation of AVP in vitro requires two cofactors (Mangel, W. F., McGrath, W. J., Toledo, D. L. & Anderson, C. W. Viral DNA and a viral peptide can act as cofactors of adenovirus virion proteinase activity. Nature 361, 274-275 (1993) and Webster, A., Hay, R. T. & Kemp, G. The adenovirus protease is activated by a virus-coded disulphide-linked peptide. Cell 72, 97-104 (1993)). One cofactor is pVIc, the 11-amino acid peptide (GVQSLKRRRCF (SEQ ID NO: 12)) from the C-terminus of virion precursor protein pVI, FIG. 10A. The other cofactor is the entire viral DNA genome of 36,000 bp of linear DNA (Mangel, W. F., McGrath, W. J., Toledo, D. L. & Anderson, C. W. Viral DNA and a viral peptide can act as cofactors of adenovirus virion proteinase activity. Nature 361, 274-275 (1993); McGrath, W. J. et al. Human adenovirus proteinase: DNA binding and stimulation of proteinase activity by DNA. Biochemistry 40, 13237-13245 (2001) and Bajpayee, N. S., McGrath, W. J. & Mangel, W. F. Interaction of the adenovirus proteinase with protein cofactors with high negative charge densities. Biochemistry 44, 8721-8729 (2005)). Together, the viral cofactors dramatically increase the relative $k_{cat}/K_m$ for substrate hydrolysis by AVP more than 15,000-fold (McGrath, W. J. et al. Human adenovirus proteinase: DNA binding and stimulation of proteinase activity by DNA. Biochemistry 40, 13237-13245 (2001); Mangel, W. F., Toledo, D. L., Brown, M. T., Martin, J. H. & McGrath, W. J. Characterization of three components of human adenovirus proteinase activity in vitro. J. Biol. Chem. 271, 536-543 (1996) and Baniecki, M. L. et al. Interaction of the human adenovirus proteinase with its 11-amino-acid cofactor pVIc. Biochemistry 40, 12349-12356 (2001)).

A conundrum in the processing of the virion precursor proteins by an AVP-pVIc complex, FIG. 10A, bound to DNA is how can about 50 molecules (Brown, M. T., McGrath, W. J., Toledo, D. L. & Mangel, W. F. Different modes of inhibition of human adenovirus proteinase, probably a cysteine proteinase, by bovine pancreatic trypsin inhibitor. FEBS Lett. 388, 233-237 (1996)) of the fully active proteinase (both cofactors bound) cleave multiple copies (about 1440) of six different virion precursor proteins at about 1900 processing sites (van Oostrum, J. V. & Burnett, R. M. Molecular composition of the adenovirus type 2 virion J. Virol. 56, 439-448 (1985); Lehmberg, E. et al. Reversed-phase high-performance liquid chromatographic assay for the adenovirus type 5 proteome. J Chromatogr B Biomed Sci Appl 732, 411-23 (1999) and Pérez-Berná, A. J. et al. Structure and uncoating of immature adenovirus. J. Mol. Biol. 392, 547-557 (2009)) within the tightly packed interior of a nascent particle under conditions in which no three-dimensional diffusion can occur. Like AVP-pVIc complexes (Mangel, W. F., McGrath, W. J., Toledo, D. L. & Anderson, C. W. Viral DNA and a viral peptide can act as cofactors of adenovirus virion proteinase activity. Nature 361, 274-275 (1993); McGrath, W. J. et al. Human adenovirus proteinase: DNA binding and stimulation of proteinase activity by DNA. Biochemistry 40, 13237-13245 (2001) and Baniecki, M. L. et al. Interaction of the human adenovirus proteinase with its 11-amino-acid cofactor pVIc. Biochemistry 40, 12349-12356 (2001)), the adenoviral precursor proteins pVI, pTP, pVII, pIIIa and pi are sequence-independent DNA-binding proteins (Russell, W. C. & Precious, B. Nucleic acid-binding properties of adenovirus structural polypeptides. J. Gen. Virol. 63, 69-79 (1982); Chatterjee, P. K., Vayda, M. E. & Flint, S. J. Identification of proteins and protein domains that contact DNA within adenovirus nucleoprotein cores by ultraviolet light crosslinking of oligonucleotides $^{32}$P-labeled in vivo. J. Mol. Biol. 188, 23-37 (1986); Webster, A., Leith, I. R. & Hay, R. T. Activation of adenovirus-coded protease and processing of preterminal protein. J. Virol. 68, 7292-7300 (1994) and Greber, U. F. Virus assembly and disassembly: the adenovirus cysteine protease as a trigger factor. Rev. Med. Virol. 8, 213-222 (1998)). The high concentration of DNA inside the virion (>500 g/L) (Casjens, S. in Structural biology of viruses (eds. Chiu, W., Burnett, R. M. & Garcea, R. L.) 3-37 (Oxford University Press, Oxford, 1997)) drives all these proteins onto the DNA by mass action. For AVP-pVIc complexes, the DNA-bound state predominates by at least one hundred thousand-fold over free AVP (McGrath, W. J. et al. Human adenovirus proteinase: DNA binding and stimulation of proteinase activity by DNA. Biochemistry 40, 13237-13245 (2001)). This, in combination with the sieving action of the dense DNA (Mangenot, S., Keller, S. & Radler, J. Transport of nucleosome core particles in semidilute DNA solutions. Biophys J 85, 1817-25 (2003)), diminishes AVP's effective three-dimensional diffusion constant by at least one million-fold. Given these circumstances, a question is by what mechanism can vital bimolecular associations occur when both enzymes and substrates are essentially irreversibly bound to a fixed matrix, the viral DNA.

A model proposing a solution to the conundrum was published in 1993 (Mangel, W. F., McGrath, W. J., Toledo, D. L. & Anderson, C. W. Viral DNA and a viral peptide can act as cofactors of adenovirus virion proteinase activity. Nature 361, 274-275 (1993)). That model, FIG. 10B, postulated that AVP-pVIc complexes slide along the viral DNA to locate and process the virion precursor proteins. Applicants know that in infectious wild-type virus, pVIc is covalently attached to AVP (McGrath, W. J., Aherne, K. S. & Mangel, W. F. In the virion, the 11-amino acid peptide cofactor pVIc is covalently linked to the adenovirus proteinase. Virology 296, 234-240 (2002)), indicating that the AVP-pVIc complex is the form of AVP that processes the virion precursor proteins. There are two key predictions from the model: 1) AVP-pVIc complexes slide along the viral DNA via one-dimensional diffusion and 2) AVP-pVIc complexes bound to DNA cleave virion precursor proteins also bound to DNA. Here Applicants test these predictions directly. Not only did Applicants observe AVP-pVIc complexes sliding along DNA via one-dimensional diffusion, but, Applicants also saw that AVP-pVIc complexes processed the virion precursor proteins in DNA-dependent reactions. There is no precedence for a proteinase sliding along DNA to locate and process its substrates.

Figure 16A:
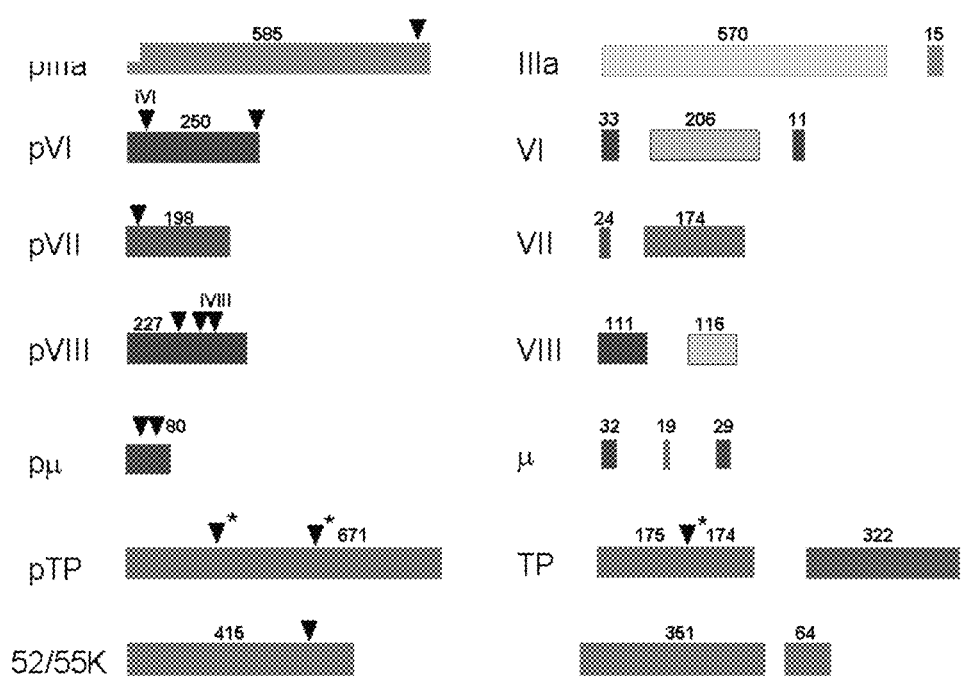
FIG. 16A-C. DNA-dependent processing of the precursor proteins by AVP-pVIc complexes in heat-disrupted ts1 virus particles. (A) Virion precursor proteins and their processed forms in wild-type virus. The precursor proteins, their cleavage sites (▼), and the processed precursor proteins are color coded. (▼*) indicates AVP consensus cleavage sites where processing has not been confirmed experimentally, because there are only two copies of pTP per virion. (B) DNA-dependent cleavage of the precursor proteins by AVP-pVIc complexes in heat-disrupted ts1 virus. Reaction conditions are in SI. Proteins were fractionated on PhastGel 8-25% gradient gels. Lane 1 contained heat-disrupted ts-1 virus incubated for 24 hours. Lanes 2 and 3 contained heat-disrupted ts-1 virus incubated with AVP-pVIc complexes for 2 h or 24 h, respectively. Lanes 4 and 5 contained heat-disrupted ts-1 virus treated with DNase and then incubated with AVP-pVIc complexes for 2 h or 24 h, respectively. Lanes 6 and 7 contained heat-disrupted ts-1 virus treated with DNase, the DNase inactivated, the DNA returned, and then the reactions incubated with AVP-pVIc complexes for 2 h or 24 h, respectively. Lane 8 contained mature Ad5 virus. (C) The proteins in the reactions in (B) were fractionated on a 24% polyacrylamide gel to be able to visualize the processing of pX (p) which consists of 80 amino acids and is cleaved twice. The positions of MW standards are indicated with arrowheads in the left.
Figure 16B:
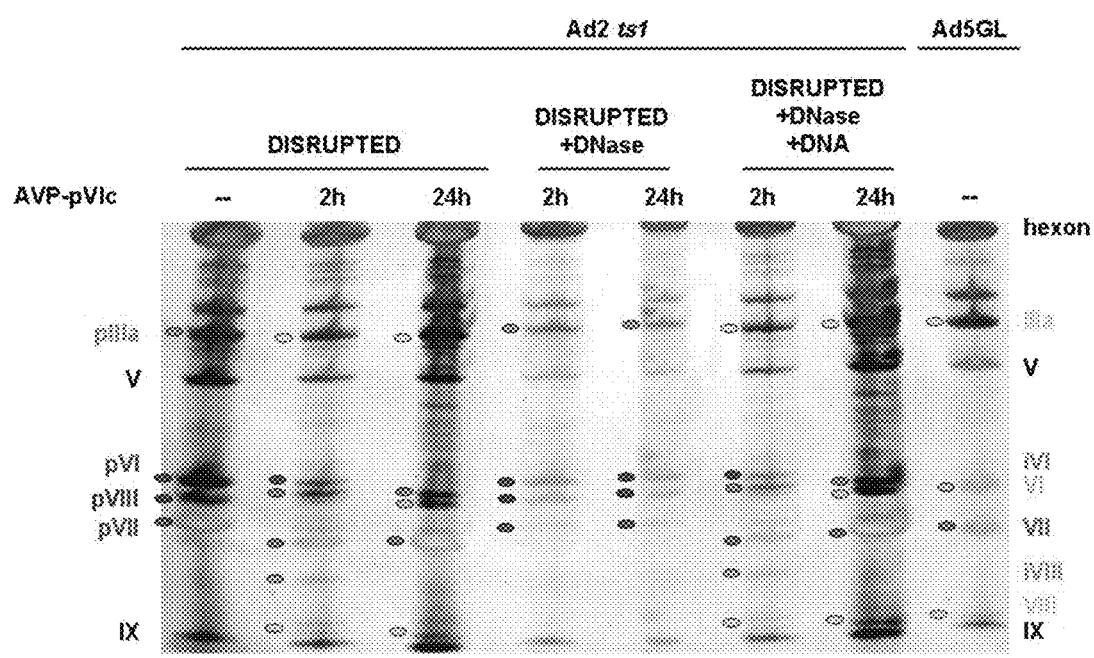
Figure 16C:
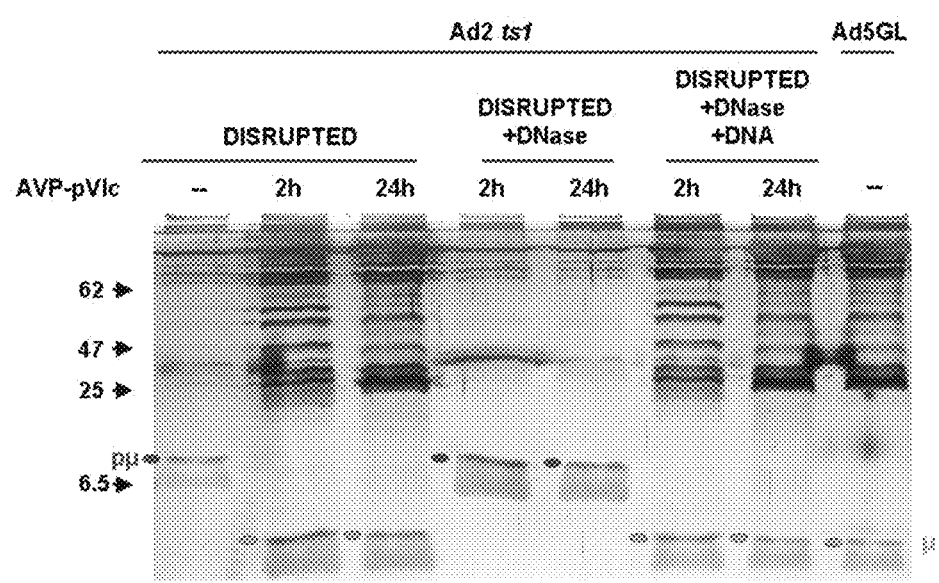

To determine whether AVP-pVIc complexes slide on DNA, Applicants used single-molecule fluorescence microscopy (FIG. 10C) with flow-stretched DNA, (FIG. 10D,E) (Kabata, H. et al. Visualization of single molecules of RNA polymerase sliding along DNA. Science 262, 1561-3 (1993); Harada, Y. et al. Single-molecule imaging of RNA polymerase-DNA interactions in real time. Biophys. J. 76, 709-715 (1999) and Blainey, P. C., van Oijen, A. M., Banerjee, A., Verdine, G. L. & Xie, X. S. A base-excision DNA-repair protein finds intrahelical lesion bases by fast sliding in contact with DNA. Proc Natl Acad Sci USA 103, 5752-7 (2006)). In the DNA sliding assay (Blainey, P. C., van Oijen, A. M., Banerjee, A., Verdine, G. L. & Xie, X. S. A base-excision DNA-repair protein finds intrahelical lesion bases by fast sliding in contact with DNA. Proc Natl Acad Sci USA 103, 5752-7 (2006)), AVP-pVIc molecules labeled with one molecule of Cy3B at Cys199 were observed to bind DNA at random locations, as predicted (Mangel, W. F., McGrath, W. J., Toledo, D. L. & Anderson, C. W. Viral DNA and a viral peptide can act as cofactors of adenovirus virion proteinase activity. Nature 361, 274-275 (1993) and McGrath, W. J. et al. Human adenovirus proteinase: DNA binding and stimulation of proteinase activity by DNA. Biochemistry 40, 13237-13245 (2001)), and furthermore to diffuse rapidly over tens of thousands of base pairs before dissociating from the DNA. For example, the molecule whose motion is shown in the raw image data in FIG. 12A traveled more than 20,000 base pairs during a 0.9 sec binding event. Despite the optical resolution limit imposed by diffraction, the centroid position of each signal in each frame was determined with 11 nm spatial precision at 3.5 ms time resolution (Gelles, J., Schnapp, B. J. & Sheetz, M. P. Tracking kinesin-driven movements with nanometer-scale precision. Nature 331, 450-3 (1988) and Thompson, R. E., Larson, D. R. & Webb, W. W. Precise nanometer localization analysis for individual fluorescent probes. Biophys J 82, 2775-83 (2002)), FIG. 12B. Control experiments showed that the images were due to a single fluorophore (FIG. 15), and that sliding occurred in persistent contact with DNA (FIG. 16).

The quality of the data was sufficient to be able to obtain one-dimensional diffusion constants. The trajectories of 72 AVP-pVIc complexes sliding on DNA are plotted in FIG. 13A. The mean square displacement (MSD) of each molecular trajectory in FIG. 13A is plotted versus diffusion time in FIG. 14A. The MSD for each molecule was approximately linear with diffusion time, indicating transport dominated by Brownian motion. From the MSD slopes, one-dimensional diffusion constants ($D_1$) were calculated according to $D_1 = <\Delta x^2>/2\Delta\tau$ and are displayed in the histogram in FIG. 14C. Another indication the one-dimensional diffusion was due to Brownian motion was that the AVP-pVIc complex displacements along DNA increased as a function of time, FIG. 13C, whereas the displacements transverse to the DNA did not, FIG. 13D as expected for particles confined to diffuse in one dimension only, i.e. along the DNA. AVP-pVIc diffusion did not seem to be biased by the direction of flow; at long times, the mean displacements along DNA were indistinguishable from zero. The mean diffusion constant was $21.0 \pm 1.9 \times 10^6$ (bp)$^2$/s with the variation among $D_1$ measured for individual AVP-pVIc complexes yielding a standard deviation (SD) of $15.6 \times 10^6$ (bp)$^2$/s (Table 3). This one-dimensional diffusion constant is the fastest yet reported.

TABLE 3

One-dimensional diffusion constants on lambda DNA, equilibrium dissociation constants, $K_d$, on DNA, and size of DNA binding site

| Protein*[†] [MM in kDa] | mean $D_1$[‡] ± SEM (bp)$^2$/s × 10$^{-6}$ | SD $D_1$ (bp)$^2$/s × 10$^{-6}$ | $K_{d(app.)}$ nM | size of DNA binding site (bp) |
|---|---|---|---|---|
| AVP [23.1] | (0.02–0.97)[a] | | (63.1 ± 5.8)[b] | |
| pVIc[c] [1.35] | 26.1 ± 1.8 | 11 | (264 ± 25)[‡] | 7 |
| AVP-pVIc [24.4] | 21.0 ± 1.9 | 15.6 | (4.65 ± 2.16)[b] | 6 |
| (High salt) | (17.1 ± 3.5) | (16.2) | | |
| pIIIa[d] [64.3] | | | (19.4 ± 3.9)[¶] | 33 |
| pVI [27.0] | (1.45 ± 0.13)[a] | 1.61 | (35 ± 2.0)[•,e] | 8 |

*AVP and AVP-pVIc complexes were labeled with Cy3B at Cys199; pVIc was labeled at Cys10' with Cy3B. pVI was labeled at Cys249 with Cy3B.
[‡]To convert from bp to nm: $10^6$ (bp)$^2$/s = 102,400 (nm)$^2$/s
[†]The NaCl concentration in assay buffer (see Materials and Methods in SI) was 2-6 mM NaCl; in high salt assay buffer, 20-25 mM NaCl was added to assay buffer.
[¶]Determined in 50 mM NaCl.
[•]Determine in 1 mM MgCl$_2$
[a](Graziano, V. et al. Binding to DNA and to hexon of the precursor to protein VI, pVI, of human adenovirus. (2012))
[b](McGrath, W. J. et al. Human adenovirus proteinase: DNA binding and stimulation of proteinase activity by DNA. Biochemistry 40, 13237-13245 (2001))
[c](Blainey, P. C. et al. "Molecular sled"-11-amino acid peptide mediates one-dimensional biochemistry by sliding enzymes and substrates on DNA. (2012))
[d](Graziano and Mangel, unpublished)
[e](Graziano, V. et al. Binding to DNA and to hexon of the precursor to protein VI, pVI, of human adenovirus. (2012))

If sliding by AVP-pVIc complexes on DNA is required for the processing of the virion precursor proteins, then, one would predict that processing of virion precursor proteins would occur only in the presence of DNA. Previously, Applicants had cloned, expressed and purified the precursor to protein VI, pVI (Graziano, V. et al. Binding to DNA and to hexon of the precursor to protein VI, pVI, of human adenovirus. (2012)). Applicants showed that pVI binds tightly to DNA independent of DNA sequence, $K_{d(app.)}=35$ nM, (Table 1). pVI contains 250 amino acids and must be cleaved twice, liberating amino acids 1-33 from the N-terminus and amino acids 239-250 from the C-terminus, to become protein VI (van Oostrum, J. V. & Burnett, R. M. Molecular composition of the adenovirus type 2 virion J. Virol. 56, 439-448 (1985) and Lehmberg, E. et al. Reversed-phase high-performance liquid chromatographic assay for the adenovirus type 5 proteome. J Chromatogr B Biomed Sci Appl 732, 411-23 (1999)). To see if the processing of pVI to protein VI by AVP-pVIc complexes requires DNA, Applicants incubated AVP-pVIc complexes with pVI in the presence of DNA. At various time intervals, Applicants withdrew aliquots of the reactions and assayed them for the presence of protein VI using SDS-polyacrylamide gel electrophoresis and MALDI-TOF mass spectrometry. In the presence of 36-mer dsDNA, after 1 minute, an intermediate in the processing of pVI to VI appeared, FIG. 15B. By 4 minutes, most of the pVI had disappeared. At 2 minutes protein VI began to appear and by 64 minutes there was more protein VI than intermediate. In the absence of DNA, no conversion of pVI to VI was observed, even after 256 minutes, FIG. 15A. Thus, for processing of pVI to protein VI to occur via AVP-pVIc complexes in vitro, DNA is required.

To identify the specific intermediates during the processing reaction depicted in the gel in FIG. 15B, Applicants performed MALDI-TOF mass spectroscopic analysis. Before the addition of DNA, two masses were present, AVP-pVIc complexes and pVI, FIG. 15C. At the 2 minute time point, FIG. 15D, much of the pVI mass had disappeared. Masses corresponding to VI-C (pVI from which the N-terminal peptide, amino acids 1-33, was cleaved) and VI had appeared. At 4 minutes, FIG. 15E, no pVI was observed and there was more protein VI than VI-C. Thus, the processing of pVI by AVP-pVIc complexes occurred sequentially, in two steps, first cleavage at the N-terminus of pVI and then at its C-terminus.

A question is if DNA is required for the processing of virion precursor proteins by AVP-pVIc complexes in vivo, inside immature virions where the viral DNA compacted and decorated with tightly bound proteins such as pVII and protein V (Flint, S. J., Enquist, L. W. & Racaniello, V. R. Principles of Virology (ASM Press, 2009)). Previously, Applicants had obtained heat disrupted ts-1 virus, added AVP, and observed the time-dependent processing of the virion precursor proteins (Mangel, W. F., Toledo, D. L., Brown, M. T., Martin, J. H. & McGrath, W. J. Characterization of three components of human adenovirus proteinase activity in vitro. J. Biol. Chem. 271, 536-543 (1996) and Blainey, P. C. et al. "Molecular sled"—11-amino acid peptide mediates one-dimensional biochemistry by sliding enzymes and substrates on DNA. (2012)). Ts-1 virus is a temperature-sensitive mutant of adenovirus that when grown at the nonpermissive temperature produces virions devoid of AVP; as such, all the virion precursor proteins are intact (Weber, J. Genetic analysis of adenovirus type 2, III. Temperature-sensitivity of processing of viral proteins. J. Virol. 17, 462-471 (1976)). Heat disruption of purified adenovirus virions renders the viral DNA accessible to the action of DNase and other proteins (Russell, W. C., Valentine, R. C. & Pereira, H. G. The effect of heat on the anatomy of the adenovirus. J. Gen. Virol. 1, 509-522 (1967)). The precursor proteins and their mature forms in wild-type virus are shown in the cartoon in FIG. 16A. In one experiment, AVP-pVIc complexes were incubated with heat disrupted ts-1 virus particles for 2 and 24 hours before fractionating the proteins on an SDS-polyacrylamide gel, FIG. 16B. Some pVI was processed within 2 hours and all of it was processed within 24 hours. On the other hand, most of pVII was processed by 2 hours, all of it by 24 hours. Processing of pIIIa is difficult to resolve due to the small relative change in mass on processing. As for pVIII, at two hours, a band consistent with a ~17 kDa processing intermediate is visible; the band disappears at 24 h, leaving only one band corresponding to the large (12 kDa) fragment of mature VIII (Liu, H. et al. Atomic structure of human adenovirus by cryo-EM reveals interactions among protein networks. Science 329, 1038-43 (2010)). The processing of pµ was observed with a 24% polyacrylamide gel, FIG. 16C. p was processed by AVP-pVIc complexes within two hours.

But, a question is if processing of the precursor proteins in heat-disrupted ts1 virus is DNA dependent. If, before adding AVP-pVIc complexes, the heat disrupted ts-1 virus particles were incubated with DNase, no processing of pVI or the other precursor proteins was observed 2 or 24 hours after adding AVP-pVIc complexes. Most convincing was the experiment in which heat disrupted ts-1 virus particles were incubated with DNase, the DNase inactivated, and ts-1 viral DNA added back. Here, upon adding AVP-pVIc complexes and incubating for 24 hours, the processing of pVI and the other precursor proteins was identical to that observed with heat disrupted ts-1 virus particles incubated with AVP-pVIc complexes for 24 hours. The remaining precursor protein, pre-terminal protein (pTP), was not detectable in these experiments, because of its low abundance, only two copies per virion.

Applicants' results present a solution to the enigma of how bimolecular associations can occur between enzymes and substrates inside an immature virus particle. The solution, sliding of an enzyme along DNA to locate and process its substrates, is sufficient to enable all the precursor proteins to be processed. The adenovirus genome contains 36,000 base pairs. Each of the 50 molecules of AVP present in the virion (Brown, M. T., McGrath, W. J., Toledo, D. L. & Mangel, W. F. Different modes of inhibition of human adenovirus proteinase, probably a cysteine proteinase, by bovine pancreatic trypsin inhibitor. FEBS Lett. 388, 233-237 (1996)) need interrogate only about 700 base pair segments of viral DNA for the entire genome to be scanned for bound precursor protein molecules. Many of the AVP-pVIc slides Applicants observed covered tens of thousands of base pairs, a distance much longer than the interrogation distance.

A question is if sliding along DNA occurs in the core of the immature adenovirus virion. The highly compacted and protein-decorated DNA in the core of the adenovirus virion is not unlike that of the DNA inside a bacterium (Thanbichler, M. & Shapiro, L. Chromosome organization and segregation in bacteria. J. Struc. Biol. 156, 292-303 (2006)) or in the nucleus of a eukaryotic cell (Lieberman-Aiden, E. et al. Comprehensive mapping of long-range interactions reveals folding principles of the human genome. Science 326, 289-93 (2009)). Applicants calculate the double-stranded DNA concentration inside adenovirus virions to be 178-500 g/L, which is similar to the concentration of DNA in double-stranded DNA bacteriophages (Earnshaw, W. C. & Casjens, S. R. DNA packaging by the double-stranded DNA bateriophages. Cell 21, 319-331 (1980)). The concentration of double-stranded DNA in the nucleoidal regions of *E. coli* is estimated at 50-100 g/L (Zimmerman, S. B. Shape and compaction of *Escherichia coli* nucleoids. J. Struc. Biol. 156, 255-261 (2006) and Murphy, L. D. & Zimmerman, S. B. Condensation and cohesion of lambda DNA in cell extracts and other media: Implications for the structure and function of DNA in prokaryotes. Biophys. Chem. 57, 71-92 (1995)). In a living *E. coli* cell, labeled lac repressor molecules have been observed binding to chromosomal lac operator sites (Elf, J., Li, G.-W. & Xie, X. S. Probing transcription factor dynamics at the single-molecule level in a living cell. Science 316, 1191-1194 (2007)). In searching for operator sequences, the lac repressor spends ~90% of its time nonspecifically bound to and diffusing along DNA. Given the high density of DNA inside the *E. coli* nucleoid (Thanbichler, M. & Shapiro, L. Chromosome organization and segregation in bacteria. J. Struc. Biol. 156, 292-303 (2006)), significant coverage by DNA-binding proteins, and in vivo observations of the lac repressor consistent with sliding and facilitated diffusion (Elf, J., Li, G.-W. & Xie, X. S. Probing transcription factor dynamics at the single-molecule level in a living cell. Science 316, 1191-1194 (2007)); the feasibility of small proteins sliding along DNA in the core of an immature adenovirus virion can be recognized.

A model on the role of AVP in maturation of the virus particle, based upon recent and extensive evidence, including data presented here, proposes: (1) AVP is synthesized in a catalytically inactive form (Mangel, W. F., McGrath, W. J., Toledo, D. L. & Anderson, C. W. Viral DNA and a viral peptide can act as cofactors of adenovirus virion proteinase activity. Nature 361, 274-275 (1993) and Webster, A., Hay, R. T. & Kemp, G. The adenovirus protease is activated by a virus-coded disulphide-linked peptide. Cell 72, 97-104 (1993)). If AVP were synthesized as an active enzyme, it could cleave virion precursor protein before virion assembly, and this would abort the infection (Baniecki, M. L. et al. Interaction of the human adenovirus proteinase with its 11-amino-acid cofactor pVIc. Biochemistry 40, 12349-12356 (2001)). (2) Binding of AVP to DNA inside immature virions partially activates the enzyme (Mangel, W. F., McGrath, W. J., Toledo, D. L. & Anderson, C. W. Viral DNA and a viral peptide can act as cofactors of adenovirus virion proteinase activity. Nature 361, 274-275 (1993) and McGrath, W. J. et al. Human adenovirus proteinase: DNA binding and stimulation of proteinase activity by DNA. Biochemistry 40, 13237-13245 (2001)). (3) pVI slides via one-dimensional diffusion on DNA into AVP, and (4) the partially activated AVP cuts out pVIc from pVI (Graziano, V. et al. Adenovirus proteinase is activated in an unusual one-dimensional biochemical reaction. (2012)). (5) The released pVIc binds to and (6) forms a disulfide bond with the AVP that cut it out forming the covalent AVP-pVIc complex. (7) AVP-pVIc complexes bind tightly to DNA (McGrath, W. J. et al. Human adenovirus proteinase: DNA binding and stimulation of proteinase activity by DNA. Biochemistry 40, 13237-13245 (2001)), and the resultant ternary complex is the most active form of the enzyme (McGrath, W. J. et al. Human adenovirus proteinase: DNA binding and stimulation of proteinase activity by DNA. Biochemistry 40, 13237-13245 (2001); Mangel, W. F., Toledo, D. L., Brown, M. T., Martin, J. H. & McGrath, W. J. Characterization of three components of human adenovirus proteinase activity in vitro. J. Biol. Chem. 271, 536-543 (1996) and Baniecki, M. L. et al. Interaction of the human adenovirus proteinase with its 11-amino-acid cofactor pVIc. Biochemistry 40, 12349-12356 (2001)). (8) Although AVP binds to but does not slide on DNA (Graziano, V. et al. Binding to DNA and to hexon of the precursor to protein VI, pVI, of human adenovirus. (2012)), the fully active proteinase, the AVP-pVIc complex bound to DNA, does slide along the DNA via one-dimensional diffusion as it searches for, (9) binds to, and (10) processes its substrates, the DNA-bound precursor proteins. In a different communication, Applicants address the mechanism of sliding by pVI and AVP-pVIc complexes showing that pVIc is a "molecular sled," capable of sliding by itself or carrying heterologous cargos such as protein VI and AVP (Blainey, P. C. et al. "Molecular sled"—11-amino acid peptide mediates one-dimensional biochemistry by sliding enzymes and substrates on DNA. (2012)).

This solution to the conundrum establishes a new paradigm for virion maturation. The surprising discovery of the robust sliding activity of AVP-pVIc complexes illustrates how sliding, a conspicuous feature of cellular proteins with functions related to nucleic acid metabolism, can operate in a completely different context: to facilitate bimolecular interactions between enzymes and substrates that are forced by thermodynamic imperatives to bind tightly to a fixed matrix, in this case a viral DNA genome. Given this novel exploitation of the "sliding properties" on the DNA contour by AVP described here, it is not difficult to imagine that other proteins and peptides will be found that make non-canonical use of facilitated diffusion along DNA.

DNA Sliding Assay Conditions.

Flow cells containing bacteriophage lambda DNA immobilized at one end were constructed as described previously (Blainey, P. C., van Oijen, A. M., Banerjee, A., Verdine, G. L. & Xie, X. S. A base-excision DNA-repair protein finds intrahelical lesion bases by fast sliding in contact with DNA. Proc Natl Acad Sci USA 103, 5752-7 (2006)). Labeled samples of AVP-pVIc complexes were infused at concentrations of 1-2 nM at rates of 20-50 mL/hour. Flow rates were chosen to drive the longitudinal DNA fluctuation faster than the imaging frame rate (Blainey, P. C., van Oijen, A. M., Banerjee, A., Verdine, G. L. & Xie, X. S. A base-excision DNA-repair protein finds intrahelical lesion bases by fast sliding in contact with DNA. Proc Natl Acad Sci USA 103, 5752-7 (2006)). The assay buffers consisted of 10 mM MES (pH 6.5), 2-25 mM NaCl, 50 µM EDTA, 20 mM ethanol, 5 percent glycerol, and, where indicated in the text, reducing agent (DTT and mercaptoethanol gave equivalent results). "Low salt" measurements were conducted with 2-6 mM NaCl; "high salt" measurements were conducted with 20-25 mM NaCl.

Processing of Virion Precursor Proteins by AVP-pVIc Complexes in Heat Disrupted Ad2 ts-1 Virions.

All reactions were carried out in 10 mM Tris-HCl (pH 8.2), 5 mM $MgCl_2$ buffer. Ad2 ts-1 virions at a concentration of $1.6 \times 10^{12}$ particles/ml were disrupted by heating at 60° C. for 10 minutes. When present, reactions contained 0.25 µM AVP-pVIc complexes. To remove DNA, heat disrupted virus was incubated with 50 µg/ml DNase I (SIGMA D5025) at 37° C. for 24 hours. DNase was inactivated by adding 10 mM EDTA. After 30 min, 0.25 µM AVP-pVIc-complexes was added, and the samples were incubated at 37° C. for either 2 or 24 hours. In the indicated cases, purified Ad2 ts-1 DNA was added after DNase inactivation at a final concentration of 50 ng/ml. For DNA isolation, $25 \times 10^{10}$ Ad2 ts-1 viral particles were treated with proteinase K at a final concentration of 400 µg/ml, and the DNA was extracted by phenol/chloroform precipitation. Proteins were fractionated by SDS-PAGE on an 8-25% gradient PhastGel and visualized by silver staining. For pX (pµ), a 24% polyacrylamide gel was used.

The gene for AVP was expressed in *Escherichia coli* and the resultant protein purified as described previously (Mangel, W. F., McGrath, W. J., Toledo, D. L. & Anderson, C. W. Viral DNA and a viral peptide can act as cofactors of adenovirus virion proteinase activity. Nature 361, 274-275 (1993) and Mangel, W. F., Toledo, D. L., Brown, M. T., Martin, J. H. & McGrath, W. J. Characterization of three components of human adenovirus proteinase activity in vitro. J. Biol. Chem. 271, 536-543 (1996)). pVI was purified as described (Graziano, V. et al. Adenovirus proteinase is activated in an unusual one-dimensional biochemical reaction. (2012).). AVP concentrations were determined using a calculated (Gill, S. G. & von Hippel, P. H. Calculation of protein extinction coefficients from amino acid sequence data. Anal. Biochem. 182, 319-326 (1989)) extinction coefficient of 26,510 $M^{-1}$ $cm^{-1}$ at 280 nm. pVIc (GVQS-LKRRRCF (SEQ ID NO: 12)), the 5'-fluorescein-labeled 12-mer DNA (Fl-GACGACTAGGAT (SEQ ID NO: 18)), and 5'-Fluorescein-labeled 18-mer DNA (Fl-CAG-GAAACAGCTATGACC (SEQ ID NO: 19)) were purchased from Invitrogen (Carlsbad, Calif.). Fluorescent DNAs were annealed to their complimentary strands according to standard protocols. Cy3B-maleimide was purchased from GE HealthCare (Piscataway, N.J.). pVIc concentrations were determined by titration of the cysteine residue with Ellman's reagent (Riddles, P. W., Blakeley, R. L. & Zerner, B. Reassessment of Ellman's reagent. Methods Enzymol. 91, 49-60 (1983)) using an extinction coefficient of 14,150 $M^{-1}cm^{-1}$ at 412 nm for released thionitrobenzoate. Octylglucoside (Fisher Scientific; Faden, N.J.) and endoproteinase Glu-C(Sigma; St. Louis, Mo.) were both obtained from commercial sources. Where indicated, buffer A was 20 mM Hepes (pH 7.0), 10 mM NaCl, 0.025% DDM, and 0.1 mM DTT and buffer B was 20 mM Tris-HCl (pH 8.0), 0.025% DDM, 10 mM NaCl, and 0.1 mM DTT. pVIc was labeled with Cy3B as described previously (Blainey, P. C. et al. "Molecular sled"—11-amino acid peptide mediates one-dimensional biochemistry by sliding enzymes and substrates on DNA. (2012)).

AVP-pVIc Complex Formation.

Disulfide-linked AVP-pVIc complexes were prepared by overnight incubation at 4° C. of 75 µM AVP and 75 µM pVIc in 20 mM Tris-HCl (pH 8.0), 250 mM NaCl, 0.1 mM EDTA and 20 mM β-mercaptoethanol. Under these conditions, Cys104 of AVP and Cys10' of pVIc undergo oxidative condensation (McGrath, W. J., Aherne, K. S. & Mangel, W. F. In the virion, the 11-amino acid peptide cofactor pVIc is covalently linked to the adenovirus proteinase. Virology 296, 234-240 (2002) and McGrath, W. J., Baniecki, M. L., Peters, E., Green, D. T. & Mangel, W. F. Roles of two conserved cysteine residues in the activation of human adenovirus proteinase. Biochemistry 40, 14468-14474 (2001)).

Fluorescent Labeling.

Disulfide-linked AVP-pVIc complexes, 75 M, were labeled in 25 mM HEPES (pH 7.0), 50 mM NaCl, and 20 mM ethanol by the addition of Cy3B maleimide to 225 µM. Labeling reactions were incubated at room temperature in the dark for 2.5 hours. Excess reagents were removed from the labeled sample by passage through Bio-Spin 6 Chromatography columns (Bio-Rad; Hercules, Calif.) equilibrated in the labeling buffer. The degree of labeling was determined using $\varepsilon_{280nm}^{AVP}=26,510$ $M^{-1}cm^{-1}$, $\varepsilon_{558nm}^{Cy3B}=130,000$ $M^{-1}$ $cm^{-1}$, and $\varepsilon_{280nm}^{Cy3B}=10,400$ $M^{-1}cm^{-1}$. The ratio of labeled AVP-pVIc to total AVP-pVIc was determined to be 0.84. The labeled materials were characterized by matrix-assisted laser desorption ionization time of flight mass spectrometry (MALDI-TOF) mass spectrometry.

Location of Cy3B Label.

Specific enzymatic digestions followed by MALDI-TOF mass spectrometry were used to locate cysteinyl-Cy3B conjugates in AVP-pVIc complexes. 1.2 µg labeled AVP-pVIc complexes was digested by incubation with 0.01 µg each endoproteinase Glu-C or trypsin at 21° C. in 25 mM Tris-HCl (pH 7.5). At 1, 2, 4, and 22 hours, 0.5 µL of each reaction were removed and added to 4.5 µL of a saturated matrix solution (a-cyano-4-hydroxycinnamic acid) in 50% acetonitrile and 0.1% TFA. The matrix-analyte solution was then immediately spotted onto a 100-well stainless-steel sample plate. The sample plate was calibrated using Applied Biosystems peptide calibration mixtures 1 and 2. Mass spectrometric characterization was carried out on a Voyager-DE Biospectrometry Workstation (Applied Biosystems; Foster City, Calif.). The m/z peak list generated for each chromatogram was analyzed by the FindPept Tool (Gasteiger, E. et al. ExPASy: the proteomics server for in-depth protein knowledge and analysis Nucleic Acids Res 31, 3784-3788 (2003)). The Cy3B modification was entered as a post-translational modification with an atomic composition of $C_{37}H_{38}N_4O_7S$ (MM 682.785). AVP-pVIc complexes were found to be labeled at Cys199 (data not shown).

Centroid Determination and Analysis of Molecular Trajectories.

Due to the speed and duration of sliding by AVP-pVIc complexes, these events were readily identifiable manually. All AVP-pVIc complex DNA-binding events noted were included in the analyses. Once events had been identified, signals were tracked using Gaussian centroid determination in the Matlab environment. Molecular trajectories were analyzed in Matlab by methods similar to those previously published (Blainey, P. C., van Oijen, A. M., Banerjee, A., Verdine, G. L. & Xie, X. S. A base-excision DNA-repair protein finds intrahelical lesion bases by fast sliding in contact with DNA. Proc Natl Acad Sci USA 103, 5752-7 (2006)).

Example 4: "Molecular Sled"—11-Amino Acid Peptide that Mediates One-Dimensional Biochemistry by Sliding Enzymes and their Substrates Along DNA During an adenovirus infection, inside a young virion, a substrate (pVI) slides along the DNA via one-dimensional diffusion to activate the adenovirus proteinase (AVP) (Graziano et al., 2012, Adenovirus proteinase is activated in an unusual one-dimensional biochemical reaction); once activated, the proteinase (the AVP-pVIc complex) then slides along the viral DNA cleaving multiple copies of virion precursor proteins to render the virus particle infectious (Blainey et al., activated Adenovirus Proteinase Slides Along Viral DNA Via One-Dimensional Diffusion to Locate and Process its Substrates). Here Applicants address the mechanism by which both substrate and enzyme slide along DNA. In doing so, the concept of a "molecular sled" emerges as well as a new type of biochemistry, one-dimensional biochemistry. The "molecular sled" is pVIc, an 11-amino acid peptide activator of AVP that originates from the C-terminus of the precursor to protein VI, pVI. Applicants show here that pVIc is capable of sliding along DNA by itself or with different cargos attached to it. The one-dimensional diffusion constants of individual pVIc molecules were the highest yet reported for any object sliding along DNA; the mean was $26 \times 10^6$ (bp)$^2$/s. When pVIc was attached to an heterologous cargo, Streptavidin tetramers, it slid them as well. One-dimensional diffusion of enzyme and their substrates along DNA, including those that have nothing to do with DNA metabolism, enables a different kind of chemistry, one that might not be characterized by simple Michaelis-Menten kinetics. One-dimensional biochemistry, in a milieu where the DNA defines reaction space and constrains the orientations of the reactants, may be the only way bimolecular reactions between proteins can efficiently occur in the presence of extremely high concentrations of DNA such as in a virus particle or the nucleus of a cell.

Peptides with rapid sliding activity along DNA have the potential to considerably expand the biochemical repertoire of biological systems and offer the possibility of new regulatory mechanisms based on localization to and transport along regions of the genome. Such mechanisms have the potential to feed back on the cell state in many ways, including the variable quantity of DNA in the cell over the course of the cell cycle, its physical configuration within the cell, and its epigenetic state. The extent to which one-dimensional biochemistry extends beyond nucleic acid metabolism in nature is unknown beyond the initial example Applicants illustrate here in adenovirus. However, based on the discovery of human peptides with sliding activity, the possibility cannot be ignored.

Late in adenovirus infection, young virions are assembled in part from precursor proteins. Of the 12 major virion proteins, 6 are precursor proteins. The penultimate step before the appearance of infectious virus is the activation of the adenovirus proteinase (AVP), a 23 kD cysteine proteinase (Ding et al., 1996, Crystal structure of the human adenovirus proteinase with its 11 amino acid cofactor. EMBO J 15, 1778-1783 and McGrath et al., 2003, Crystallographic structure at 1.6-Å resolution of the human adenovirus proteinase in a covalent complex with its 11-amino-acid peptide cofactor: insights on a new fold. Biochem Biophys Acta 1648, 1-11), followed by the processing of the virion precursor proteins. AVP is activated by two cofactors, pVIc (GVQSLKRRRCF (SEQ ID NO: 12)) (Mangel et al., 1993, Viral DNA and a viral peptide can act as cofactors of adenovirus virion proteinase activity. Nature 361, 274-275 and Webster et al., 1993, The adenovirus protease is activated by a virus-coded disulphide-linked peptide. Cell 72, 97-104), the 11-amino acid peptide from the C-terminus of the precursor to protein VI, pVI, and the viral DNA genome (Mangel et al., 1993, Viral DNA and a viral peptide can act as cofactors of adenovirus virion proteinase activity. Nature 361, 274-275). In pVI, an AVP consensus cleavage site, IVGL-G (SEQ ID NO: 35), immediately precedes pVIc and is cleaved by AVP between L and G to release pVIc (Graziano et al., 2012, Adenovirus proteinase is activated in an unusual one-dimensional biochemical reaction). The other cofactor, the viral DNA genome (Bajpayee et al., 2005, Interaction of the adenovirus proteinase with protein cofactors with high negative charge densities. Biochemistry 44, 8721-8729; Mangel et al., 1993, Viral DNA and a viral peptide can act as cofactors of adenovirus virion proteinase activity. Nature 361, 274-275; McGrath et al., 2001, Human adenovirus proteinase: DNA binding and stimulation of proteinase activity by DNA. Biochemistry 40, 13237-13245), consists of 36,000 bp of double-stranded, linear DNA. The viral cofactors dramatically stimulate the macroscopic kinetic constants for substrate hydrolysis (Baniecki et al., 2001, Interaction of the human adenovirus proteinase with its 11-amino-acid cofactor pVIc. Biochemistry 40, 12349-12356; Mangel et al., 1996, Characterization of three components of human adenovirus proteinase activity in vitro. J Biol Chem 271, 536-543 and McGrath et al., 2001, Human adenovirus proteinase: DNA binding and stimulation of proteinase activity by DNA. Biochemistry 40, 13237-13245). The relative $k_{cat}/K_m$ of AVP is stimulated 110-fold in the presence of DNA and 1130-fold in the presence of pVIc. When both cofactors are bound to AVP, the $k_{cat}/K_m$ increases synergistically, by 16,000-fold. AVP, pVI, pVIc, and AVP-pVIc complexes bind tightly to DNA with nanomolar equilibrium dissociation constants; binding is independent of nucleic acid sequence (Table 4) (Bajpayee et al., 2005, Interaction of the adenovirus proteinase with protein cofactors with high negative charge densities. Biochemistry 44, 8721-8729; Graziano et al., 2012, Adenovirus proteinase is activated in an unusual one-dimensional biochemical reaction; Gupta et al., 2004, DNA binding provides a molecular strap activating the adenovirus proteinase. Mol Cell Proteomics 3.10, 950-959; Mangel et al., 1993, Viral DNA and a viral peptide can act as cofactors of adenovirus virion proteinase activity. Nature 361, 274-275 and McGrath et al., 2001, Human adenovirus proteinase: DNA binding and stimulation of proteinase activity by DNA. Biochemistry 40, 13237-13245).

TABLE 4

One-dimensional diffusion constants, $D_1$, on lambda DNA, equilibrium dissociation constants, $K_d$, on dsDNA, and size of binding site on DNA.

| Protein (bp DNA) MW [aa] | Mean $D_1 \pm$ SEM $(bp)^2/s \times 10^{-6}$ | SD $D_1$ $(bp)^2 \times 10^{-6}$ | $K_{d(app.)}$ nM | Binding Site Size (bp) | pH for $K_d$s | Additional information/ References |
|---|---|---|---|---|---|---|
| pVIc (12) 1350 [11] | ND | ND | 693 ± 84 | 7 | pH 8 | 1, 2, 3 |
| pVIc | 26.0 ± 1.8 | 11 | 264 ± 25 | 7 | pH 7 | 1, 4 |
| pVIc (High salt) | 17.9 ± 3.5 | 10.7 | ND | ND | pH 7 | 1, 4 |
| AVP | (0.02 ± 0.07) | | 63.1 ± 5.8 | ND | pH 7 | 1, 3, 5, 6 |
| AVP-pVIc (36) 24435 [215] | 21.0 ± 1.9 | 15.6 | 4.65 ± 2.16 | 6 | pH 7.5 | 1, 3, 7, 8 |
| AVP-pVIc (High salt) | 17.1 ± 3.5 | 16.2 | ND | ND | pH 7 | 1, 4, 7 |
| pVIc-biotin: streptavidin (18) ~57000 | 2.21 ± 0.21 | 1.99 | 35 ± 5.0 | ND | pH 7.5 | 1, 8 |
| pVI (33) 27014 [250] | 1.45 ± 0.13 | 1.61 | 35 ± 2.0 | 8 | pH 8 | 1, 2, 6, 9 |
| Protein VI (33) 22249 [207] | ND | ND | 241 ± 14 | ND | pH 8 | 1, 2, 9 |
| 8-Actin-C (12) 988 [8] | 5.45 | 3.63 | 5.0 ± 0.78 | ND | pH 7 | 1 |
| 11-Actin-C (12) 1230 [11] | 6.40 | 3.29 | ND | ND | pH 7 | 1 |
| Random peptide (12) 1350 [11] | No Diffusion | — | 646 ± 75 | ND | pH 8 | 1 |

1 To convert from bp to nm: $10^6$ $(bp)^2/s = 102,400$ $(nm)^2/s$. ND—not determined. For $K_{d(app.)}$ determinations, at pH 7.5 or 8, the dye was Fluorescein, and the label was on the DNA; at pH 7 the dye was Cy3B and the label was on the protein. For pVIc-biotin: streptavidin experiments at pH 7.5, the dye used was Alexa Fluor 546, and there were two dye molecules per streptavidin. pVIc was labeled with Cy3B at Cys10'. AVP and AVP-pVIc were labeled with Cy3B at Cys199. The actin C-terminal peptides were labeled on their cysteine residue with Cy3B. The random peptide was labeled at Cys5' with Cy3B. pVI was labeled at Cys249 with Cy3B.
2 Assay buffer was 20 mM Tris-HCl, pH 8, 0.025% DDM, 0.1 mM DTT
3 (McGrath et al., 2001, Human adenovirus proteinase: DNA binding and stimulation of proteinase activity by DNA. Biochemistry 40, 13237-13245)
4 Assay buffer was 20 mM Hepes, pH 7, 0.025% DDM, 10 mM NaCl, 0.1 mM DTT, The NaCl concentration in the assay buffer (see Materials and Methods in SOM) was 2-6 mM NaCl; in the high salt assay buffer, 20-25 mM NaCl was present.
5 Whole population-mean $D_1$ calculated from one population (99-96% of the molecules bound to DNA) having a $D_1$ of zero and another population (1-4% of the molecules bound to DNA) having a $D_1$ of 1.7 × $10^6$ $(bp)^2/s$, with SD of 1.9 × $10^6$ $(bp)^2/s$.
6 (Graziano et al., 2012, Adenovirus proteinase is activated in an unusual one-dimensional biochemical reaction)
7 (Blainey et al., 2012, Activated Adenovirus Proteinase Slides Along Viral DNA Via One-Dimensional Diffusion to Locate and Process its Substrates)
8 Assay buffer was 20 mM Na Phosphate, pH 7.5, 0.05% DDM
9 (Graziano et al., 2012, Binding to DNA and to hexon of the precursor to protein VI, pVI, of human adenovirus)

How AVP becomes activated by cleavage of pVIc from pVI and how the active AVP-pVIc complexes process the virion precursor proteins has been a conundrum: In the tightly packed interior of the virion, there are about 50 molecules (Brown et al., 1996, Different modes of inhibition of human adenovirus proteinase, probably a cysteine proteinase, by bovine pancreatic trypsin inhibitor. FEBS Lett 388, 233-237) of the fully active proteinase (both cofactors bound) and multiple copies (about 1440 molecules) of six different virion precursor proteins that must be cleaved at about 1900 processing sites (Pérez-Berná et al., 2009, Structure and uncoating of immature adenovirus. J Mol Biol 392, 547-557) Since there is about 40-fold more substrate than enzyme, for all the precursor proteins to be processed, either enzymes or substrates must move for processing to go to completion. However, this must take place in the tightly packed interior of the virus particle where three-dimensional diffusion is extremely limited, almost nil. The effective diffusion constants are extremely small because, like AVP (Baniecki et al., 2001, Interaction of the human adenovirus proteinase with its 11-amino-acid cofactor pVIc. Biochemistry 40, 12349-12356; Mangel et al., 1993, Viral DNA and a viral peptide can act as cofactors of adenovirus virion proteinase activity. Nature 361, 274-275 and McGrath et al., 2001, Human adenovirus proteinase: DNA binding and stimulation of proteinase activity by DNA. Biochemistry 40, 13237-13245), the adenovirus precursor proteins pIIIa, pVI, pTP, pVII, and p (pX) are sequence-independent DNA-binding proteins (Chatterjee et al., 1986, Identification of proteins and protein domains that contact DNA within adenovirus nucleoprotein cores by ultraviolet light cross-linking of oligonucleotides $^{32}$P-labeled in vivo. J Mol Biol 188, 23-37; Graziano et al., 2012, Adenovirus proteinase is activated in an unusual one-dimensional biochemical reaction; Greber, 1998, Virus assembly and disassembly: the adenovirus cysteine protease as a trigger factor. Rev Med Virol 8, 213-222; Russell and Precious, 1982, Nucleic acid-binding properties of adenovirus structural polypeptides. J Gen Virol 63, 69-79 and Webster et al., 1994, Activation of adenovirus-coded protease and processing of preterminal protein. J Virol 68, 7292-7300). The high concentration of DNA inside the virion (>500 g/L) (Casjens, 1997, Principles of virion structure, function and assemble, In Structural biology of viruses, W. Chiu, R. M. Burnett, and R. L. Garcea, eds. (Oxford: Oxford University Press), pp. 3-37) drives all these proteins onto the DNA by mass action. For AVP, the DNA-bound state predominates by at least one hundred thousand-fold over free AVP; that plus the sieving effect of DNA (Mangenot et al., 2003, Transport of nucleosome core particles in semidilute DNA solutions. Biophys J 85, 1817-1825) diminishes AVP's effective three-dimensional diffusion constant by more than one million-fold. The DNA genome cannot move as it is jammed inside the virion due to being packaged under pressure, a pressure possibly in excess of 100 atm (Purohit et al., 2003, Mechanics of DNA packaging in viruses. Proc Natl Acad Sci USA 100, 3173-3178). The pressure exerted by the DNA on the virion walls results in a large friction between the DNA and the inner surface of the virion, freezing the DNA in place and rendering DNA-bound proteins likewise immobile. Given these circumstances, a question is by what mechanism can vital bimolecular associations occur when both enzymes and substrates are essentially irreversibly bound to a fixed matrix, the viral DNA.

Recently, Applicants solved this conundrum after having observed pVI (Graziano et al., 2012, Adenovirus proteinase is activated in an unusual one-dimensional biochemical reaction) and AVP-pVIc complexes (Blainey et al., 2012, Activated Adenovirus Proteinase Slides Along Viral DNA Via One-Dimensional Diffusion to Locate and Process its Substrates) slide along DNA over tens of thousands of base pairs via one-dimensional diffusion. Applicants went on to show that AVP is activated by pVI by the following mechanism: AVP binds randomly to DNA and does not slide (Graziano et al., 2012, Adenovirus proteinase is activated in an unusual one-dimensional biochemical reaction). pVI also binds randomly to DNA, but it slides along DNA with a one-dimensional diffusion constant of $1.45 \times 10^6$ (bp)$^2$/s. pVI slides into AVP. AVP, partially activated by being bound to the viral DNA, cleaves pVI first at its N-terminus and then at its C-terminus. pVIc, released by cleavage of pVI at its C-terminus, binds to the AVP that cut it out, and then a disulfide bond is formed between pVIc's Cys10' and Cys104 of AVP thereby keeping AVP permanently activated. The processing of the virion proteins by AVP-pVIc complexes occurs by the following mechanism: Covalent, active AVP-pVIc complexes slide along the viral DNA with a one-dimensional diffusion constant of $21.0 \times 10^6$ (bp)$^2$/s (Blainey et al., 2012, Activated Adenovirus Proteinase Slides Along Viral DNA Via One-Dimensional Diffusion to Locate and Process its Substrates) and process the precursor proteins which are also nonspecifically bound to the viral DNA (Blainey et al., 2012, Activated Adenovirus Proteinase Slides Along Viral DNA Via One-Dimensional Diffusion to Locate and Process its Substrates).

A question is by what mechanism do pVI and AVP-pVIc complexes slide along DNA to render virus particles infectious. Both have in common the 11-amino acid peptide pVIc. This raised the possibility that pVIc is a modular component that confers sliding ability. Here, Applicants showed that pVIc alone can slide along DNA via one-dimensional diffusion and further discovered that pVIc is a "molecular sled" that can slide heterologous cargoes along DNA. This ability to slide enzyme and substrates along DNA to promote bimolecular interactions empowers a different kind of chemistry that has some advantageous characteristics.

pVIc, by Itself, Slides Robustly

A question is does pVIc by itself slide on DNA. To address this possibility, Applicants performed a sliding assay (Blainey et al., 2012, Activated Adenovirus Proteinase Slides Along Viral DNA Via One-Dimensional Diffusion to Locate and Process its Substrate and Blainey et al., 2009, Nonspecifically bound proteins spin while diffusing along DNA. Nat Struct Mol Biol 16, 1224-1229 and Blainey et al., 2006, A base-excision DNA-repair protein finds intrahelical lesion bases by fast sliding in contact with DNA. Proc Natl Acad Sci USA 103, 5752-5757) using pVIc labeled with Cy3B at Cys10'. In the SOM, showed that pVIc labeled Cys10' with Cy3B had an apparent equilibrium dissociation constant for dsDNA of 264±25 nM and that one molecule of pVIc covered 7 base pairs of DNA, Table 4. The sliding assay, based upon total internal reflection fluorescence microscopy, used phage λ DNA molecules (48,502 base pairs) attached at one end to a glass cover slip surface by a biotin-streptavidin linkage. The area of the cover slip with DNA was placed within a flow cell. Laminar flow (~10 mL/hr) stretches the DNA in the direction of flow and positions the DNA parallel to the surface of the glass cover slip. Evanescent waves from a LASER are used to illuminate a very small volume (1 pL) within 100 nm of the glass surface. The interaction of a single, fluorescently-labeled protein with DNA can then be visualized with a low background by wide field imaging. Individual pVIc molecules were observed not only binding to DNA as predicted (McGrath et al., 2001, Human adenovirus proteinase: DNA binding and stimulation of proteinase activity by DNA. Biochemistry 40, 13237-13245), but, surprisingly, they were observed diffusing along the DNA as well. Indeed, pVIc exhibited robust sliding activity, with many molecules remaining bound to the DNA for much longer than a second, some up to 6 s, while sliding over tens of thousands of base pairs. For example, the molecule whose motion is shown in the raw image data in FIG. 17A traveled over more than 30,000 base pairs during a 3 sec binding event. Despite the optical resolution limit imposed by diffraction, the centroid position (see Experimental Procedures) of each signal in each frame was determined with sub-diffraction-limited resolution, FIG. 17B.

One-Dimensional Diffusion Constant.

The trajectories of 35 pVIc molecules sliding on DNA are plotted in FIG. 18A. The mean square displacement (MSD) of each molecular trajectory shown in FIG. 18A is plotted in FIG. 18B versus diffusion time. The MSD for each molecule was approximately linear with diffusion time, indicating transport dominated by Brownian motion. From the MSD slopes, one-dimensional diffusion constants ($D_1$) were calculated according to $D_1 = <\Delta x^2>/2\Delta\tau$ and are displayed in the histogram in FIG. 18C. The one-dimensional diffusion constants of individual pVIc molecules were the highest yet reported for any object sliding along DNA; the mean was $26 \pm 1.8 \times 10^6$ (bp)$^2$/s with SD of $11 \times 10^6$ (bp)$^2$/s (Table 4). In a control experiment, in the SOM, Applicants showed that sliding was occurring here, i.e. one-dimensional translocation along the DNA with the protein in continuous contact with the DNA rather than hopping. The $D_1$ did not increase at higher ionic strengths.

C-Terminal Peptides of β-Actin Slide on DNA.

A peptide similar in sequence to pVIc is present at the C-terminus of a major cellular protein, actin. And actin can act as a cofactor for AVP (Brown and Mangel, 2004, Interaction of actin and its 11-amino acid C-terminal peptide as cofactors with the adenovirus proteinase. FEBS Lett 563, 213-218 and Brown et al., 2002, Actin can act as a cofactor for a viral proteinase, in the cleavage of the cytoskeleton. J Biol Chem 277, 46298-46303). The sequence of the actin peptide is SIVHRKCF (SEQ ID NO: 9). Of the last 8 amino acids of β-actin, 4 are identical and 3 are homologous to the last 8 amino acids of pVIc. Applicants labeled this peptide, 8-Actin-C, at Cys7' with Cy3B. 8-Actin-C bound to dsDNA with a $K_{d(app.)}$ of 5.0±0.78 nM, Table 4 (data not shown). In a sliding assay, 8-Actin-C was observed to slide along the DNA via one-dimensional diffusion. The trajectories of 69 8-Actin-C molecules sliding on DNA are plotted in FIG. 19A. The mean square displacement (MSD) of each molecular trajectory shown in FIG. 19A is plotted versus diffusion time in FIG. 19B. The MSD for each molecule was approximately linear with diffusion time, indicating transport dominated by Brownian motion. From the MSD slopes, one-dimensional diffusion constants ($D_1$) were calculated according to $D_1=<\Delta x^2>/2\Delta\tau_1$. The mean one-dimensional diffusion constant was 5.45×. ×10$^6$ (bp)$^2$/s with SD of 3.63×10$^6$ (bp)$^2$/s (Table 4). Applicants also looked into the sliding properties of a peptide containing the last 11-amino acids of β-actin, 11-Actin-C, SGPSIVHRKCF (SEQ ID NO: 20). The trajectories of 102 11-actin-C molecules sliding on DNA are plotted in FIG. 19C. The MSDs are plotted versus diffusion time in FIG. 19D. The mean one-dimensional diffusion constant was 6.40×. ×10$^6$ (bp)$^2$/s with SD of 3.29×10$^6$ (bp)$^2$/s (Table 4).

A Question is if the Amino Acid Sequences of pVIc and the Actin-C Peptides are Important for Sliding Ability.

A question is does pVIc slide just because it is a basic peptide or is the amino acid sequence important. Applicants synthesized a peptide with the same amino acids in pVIc but in a randomly defined sequence, SFRRCGLRQVK (SEQ ID NO: 10). This peptide, up to a concentration of 60 M, did not act like a cofactor in stimulating AVP (Brown and Mangel, 2004, Interaction of actin and its 11-amino acid C-terminal peptide as cofactors with the adenovirus proteinase. FEBS Lett 563, 213-218). A question is does this peptide bind to DNA. Applicants labeled the peptide with Cy3B at Cys5' using Cy3B maleimide. In a DNA binding assay, the peptide exhibited a $K_{d(app.)}$ of 646±75 nM, Table 4, (data not shown). A question is does this peptide slide along DNA. No one-dimensional diffusion of the peptide was observed under conditions in which extensive binding and sliding of pVIc was observed. Thus, Applicants conclude that the primary sequence of pVIc is tuned for sliding activity and that basic peptides with random sequences show little or no sliding activity. A corollary to this statement is that the conserved C-terminus of actin probably did not acquire sliding activity by chance, although Applicants have not identified a biological function dependent upon this activity.

pVIc is a "Molecular Sled" that can Transport a Heterologous Cargo Along DNA.

Since AVP-pVIc complexes (Blainey et al., 2012, Activated Adenovirus Proteinase Slides Along Viral DNA Via One-Dimensional Diffusion to Locate and Process its Substrates), pVI (Graziano et al., 2012, Adenovirus proteinase is activated in an unusual one-dimensional biochemical reaction) and pVIc slide on DNA, and since AVP does not slide (Blainey et al., 2012, Activated Adenovirus Proteinase Slides Along Viral DNA Via One-Dimensional Diffusion to Locate and Process its Substrates) a question is if this implies that pVIc might be an 11-amino acid "molecular sled" carrying as cargos AVP and protein VI along DNA. And, if so, will pVIc carry an heterologous cargo. To answer this question, Applicants attached streptavidin (MM 52.8 kDa) to pVIc (MM 1.35 kDa) and assayed the complex for DNA binding and sliding activity. The attachment was done by derivatizing Cys10' of pVIc with PEG-biotin and then incubating that with Alexa Fluor 546-labeled streptavidin to form the fluorescently-labeled (pVIc-biotin)-streptavidin complex. Labeled streptavidin alone did not bind to DNA, FIG. 20A. However, (pVIc-biotin)-streptavidin complexes (MM ~57 kDa) did bind to DNA; the equilibrium dissociation constant was 35±5 nM (FIG. 20A and Table 4). In sliding assays, Applicants observed (pVIc-biotin)-streptavidin sliding along DNA FIG. 20B; the mean square displacements are shown in FIG. 20C. From the MSD slopes, one-dimensional diffusion constants (D1) were calculated according to $D_1=<\Delta x^2>/2\Delta\tau$. The average one-dimensional diffusion constant was 2.21±0.21×10$^6$ (bp)$^2$/s with a SD of 1.99×10$^6$ (bp)$^2$/s with a DNA stretch factor of 1.15 (Table 4). Applicants expected the (pVIc-biotin)-streptavidin complex to have a lower one-dimensional diffusion constant than that of pVIc, in part because its frictional coefficient is surely much larger due to the 42-fold gain in molecular weight. Thus, pVIc indeed appears to be a "molecular sled" that can slide along DNA by itself or slide with different cargos attached to it, e.g. AVP, protein VI or streptavidin.

pVIc is a "Molecular Sled".

Ic is an 11-amino acid "molecular sled," a short peptide that binds to DNA independent of sequence and slides via one-dimensional diffusion on DNA either by itself or with different cargos attached to it: pVIc had been shown to bind to DNA independent of the DNA sequence, e.g. the number of pVIc molecules binding to DNA was proportional to the length of the DNA (Graziano et al., 2012, Binding to DNA and to hexon of the precursor to protein VI, pVI, of human adenovirus). Because AVP-pVIc complexes (Blainey et al., 2012, Activated Adenovirus Proteinase Slides Along Viral DNA Via One-Dimensional Diffusion to Locate and Process its Substrates) as well as pVI slide (Graziano et al., 2012, Adenovirus proteinase is activated in an unusual one-dimensional biochemical reaction) on DNA and AVP does not (Blainey et al., 2012, Activated Adenovirus Proteinase Slides Along Viral DNA Via One-Dimensional Diffusion to Locate and Process its Substrates), this implied that the pVIc moiety may be solely responsible for the sliding activity of both AVP-pVIc complexes and pVI and raised the possibility that pVIc alone may slide on DNA. That seemed unlikely, because the 11-amino acid peptide lacks the large, structured DNA-binding interface present in proteins shown to slide on DNA (Blainey et al., 2006, A base-excision DNA-repair protein finds intrahelical lesion bases by fast sliding in contact with DNA. Proc Natl Acad Sci USA 103, 5752-5757; Elf et al., 2007, Probing transcription factor dynamics at the single-molecule level in a living cell. Science 316, 1191-1194; Harada et al., 1999, Single-molecule imaging of RNA polymerase-DNA interactions in real time. Biophys J 76, 709-715 and Kabata et al., 1993, Visualization of single molecules of RNA polymerase sliding along DNA. Science 262, 1561-1563). However, Applicants observed both robust and persistent sliding activity by pVIc on DNA. The mean one-dimensional diffusion constant was the highest yet reported for any object sliding along DNA, 26±1.8×10$^6$ (bp)$^2$/s (Table 4). If pVIc can slide by itself or slide carrying cargos such as AVP or protein VI, then it may be an 11-amino acid "molecular sled" able to carry non-viral, heterologous cargos as well. When streptavidin, which does not bind to DNA, was attached to biotinylated pVIc, the (pVIc-biotin)-streptavidin complex bound to and slid robustly along DNA. Thus, pVIc is a "molecular sled."

Conservation of Amino Acids in pVIc and their Presence in Other Proteins.

e amino acid sequence of pVIc is highly conserved among adenoviruses and homologous sequences are even present at the C-terminus of other proteins. Across human adenovirus serotypes, as well as among simian, porcine, and murine adenoviruses, there is strict conservation of the KRRR motif (SEQ ID NO: 21), FIG. 21A. Furthermore, these four contiguous amino acids serve as a functional nuclear localization signal (NLS) (Wodrich et al., 2003, Switch from capsid protein import to adenovirus assembly by cleavage of nuclear transport signals. EMBO J 22, 6245-66255). pVIc constitutes the C-terminal 11 amino acids of pVI, and Applicants have shown that the adenovirus precursor protein pVI slides on DNA (Graziano et al., 2012, Adenovirus proteinase is activated in an unusual one-dimensional biochemical reaction). The C-terminal region of the human tumor suppressor p53, whose structure has not yet been solved, contains the sequence (TSRHKKLMF (SEQ ID NO: 22)) which has an NLS. p53 has been shown to slide on DNA (Tafvizi et al., 2011, A single-molecule characterization of p53 search on DNA. Proc Natl Acad Sci USA 108, 563-568 and Tafvizi et al., 2008, Tumor suppressor p53 slides on DNA with low friction and high stability. Biophys J 95, L01-03), in particular, a region at the C-terminus has been shown to confer sliding activity on the protein (McKinney et al., 2004, p53 linear diffusion along DNA requires its C terminus. Cell 16, 413-424 and Tafvizi et al., 2011, A single-molecule characterization of p53 search on DNA. Proc Natl Acad Sci USA 108, 563-568). It is not obvious why a sliding module appears to be at the C-terminus of a protein.

The C-terminus of actin is similar in sequence to pVIc, and that sequence is conserved among the various forms of actin. Of the last eleven amino acids at the C-terminus of actin (SGPSIVHRKCF) (SEQ ID NO: 20), four are identical and four homologous to the amino acid sequence in pVIc (GVQSLKRRRCF) (SEQ ID NO: 12) (FIG. 21A). Like pVIc, actin and its C-terminal peptide are cofactors for AVP; they stimulate the enzymatic activity of AVP (Brown and Mangel, 2004, Interaction of actin and its 11-amino acid C-terminal peptide as cofactors with the adenovirus proteinase. FEBS Lett 563, 213-218 and Brown et al., 2002, Actin can act as a cofactor for a viral proteinase, in the cleavage of the cytoskeleton. J Biol Chem 277, 46298-46303). Applicants have shown here that peptides with the last 11 and 8 amino acids of β-actin slide on DNA with rather large one-dimensional diffusion constants, Table 4. If actin itself slides on DNA, the function of this is not clear. Actin has been found in the nucleus (Visa and Percipalle, 2010, Nuclear functions of actin. Cold Spring Harb Perspect Biol 2, 1-13) and in virus particles (Wong and Chen, 1998, Evidence for the internal location of actin in the pseudorabies virion. Virus Res 56, 191-197).

pVIc Probably Mediates the Sliding Contacts Between DNA and pVI, AVP-pVIc Complexes, and Streptavidin-pVIc Chimeras.

pVIc probably contributes the majority or the entirety of the sliding contacts between DNA and pVI, AVP-pVIc complexes, and (pVIc-biotin)-streptavidin complexes. All bind to DNA with low nM $K_{d(app.)}$ values and all exhibit a similar binding footprint of about 6 base pairs, Table 4. Without pVIc, the $K_{d(app.)}$ for DNA for protein VI is 7-fold higher and for AVP it is 13-fold higher. The pVIc moiety in the AVP-pVIc-DNA complex has been shown to interact with the DNA, by protection against oxidation of pVIc residues by DNA in synchrotron protein footprinting experiments (Gupta et al., 2004, DNA binding provides a molecular strap activating the adenovirus proteinase. Mol Cell Proteomics 3.10, 950-959). Most convincingly, pVIc in a complex with the heterologous protein streptavidin slid robustly on DNA, Table 4. In control experiments, streptavidin alone did not even bind to DNA, FIG. 20A. The $K_d$ of the (pVIc-biotin)-streptavidin complex binding to DNA is almost identical to the $K_d$ for pVI, 35 nM, Table 4.

Electrostatic Forces Mediate Binding of pVIc to DNA.

Experiments on the ionic strength dependence for the sliding of AVP-pVIc complexes and of pVI on DNA are consistent with the pVIc moiety mediating the binding to DNA. The major factor driving the nonspecific interaction between AVP-pVIc complexes (McGrath et al., 2001, Human adenovirus proteinase: DNA binding and stimulation of proteinase activity by DNA. Biochemistry 40, 13237-13245) or pVI (Graziano et al., 2012, Adenovirus proteinase is activated in an unusual one-dimensional biochemical reaction) and DNA comes from the entropic contribution upon the release of counterions. The non-sequence specific interactions between AVP-pVIc complexes or pVI and DNA exhibit a substantial dependence on the monovalent sodium ion concentration. This dependence reflects the electrostatic component of the binding reaction (Record et al., 1976, Ion Effects on ligand-nucleic acid interactions. J Mol Biol 107, 145-158). The electrostatic component originates from the formation of ion pairs between positively charged groups on the AVP-pVIc complex or on pVI and negatively charged phosphate groups on DNA. After binding occurs, there is a concomitant release of counterions from the DNA and, possibly, from AVP-pVIc complexes or pVI. From an analysis of the equilibrium association constants for the binding of AVP-pVIc complexes or pVI to 12-mer dsDNA as a function of the $Na^+$ concentration, an accurate estimate of the number of ion pairs involved in the interaction was obtained. For AVP-pVIc complexes and for pVI, 2.2 (McGrath et al., 2001, Human adenovirus proteinase: DNA binding and stimulation of proteinase activity by DNA. Biochemistry 40, 13237-13245) and 2.9 (Graziano et al., 2012, Adenovirus proteinase is activated in an unusual one-dimensional biochemical reaction) ion pairs respectively were involved in complex formation with 12-mer dsDNA. There is also a favorable nonelectrostatic component of the binding interaction between these two proteins and DNA; the nonelectrostatic change in free energy, $\Delta G^o_o$, upon binding to DNA was −4.4 kcal for AVP-pVIc complexes (McGrath et al., 2001, Human adenovirus proteinase: DNA binding and stimulation of proteinase activity by DNA. Biochemistry 40, 13237-13245) and −4.5 kcal for pVI (Graziano et al., 2012, Adenovirus proteinase is activated in an unusual one-dimensional biochemical reaction). That both the number of ion pairs released upon binding to DNA and the nonelectrostatic change in free energy upon binding to DNA are the same for AVP-pVIc complexes and for pVI is consistent with binding being mediated by the pVIc moiety in both proteins. That an 11-amino acid peptide, presumably lacking a well-defined secondary structure, can slide on DNA suggests that established concepts of the structural requirements for sliding activity (Breyer and Matthews, 2001, A structural basis for processivity. Protein Sci 10, 1699-1711) need to be extended.

Interaction Between pVIc and AVP, the Sliding Interface.

Proteins capable of carrying out facilitated diffusion are thought to be highly tuned machines. Very low free energy barriers to sliding (comparable to $k_BT$) are needed for effective searching along DNA (Slutsky et al., 2004, Diffusion in correlated random potentials, with applications to DNA. Phys Rev E Stat Nonlin Soft Matter Phys 69, 061903 and Slutsky and Mirny, 2004, Kinetics of protein-DNA interaction: facilitated target location in sequence-dependent potential. Biophys J 87, 4021-4035). Sliding rates are highly sensitive to modification of the DNA-binding interfaces by mutation and changing solution conditions (Blainey et al., 2006, A base-excision DNA-repair protein finds intrahelical lesion bases by fast sliding in contact with DNA. Proc Natl Acad Sci USA 103, 5752-5757 and Blainey et al., 2009, Nonspecifically bound proteins spin while diffusing along DNA. Nat Struct Mol Biol 16, 1224-1229). Features such as interfacial water, interactions between helix dipoles and the DNA, bridged or out-of-register positively charged side chains can be understood to 'buffer' the protein-DNA contacts support rapid sliding. Such observations naturally lead one to expect that such precision-tuned three-dimensional structures evolved in part to support the high-speed sliding necessary for efficacious search of the genome under the constraint to maintain a protein's other functional activities Recently, Applicants showed that molecules sliding along DNA, including AVP-pVIc complexes, diffuse along a helical path defined by DNA; they rotate in order to keep the DNA-binding face of the protein in contact with DNA (Bagchi et al., 2008, Diffusion constant of a nonspecifically bound protein undergoing curvilinear motion along DNA. J Phys Chem B 112, 6282-6284; Blainey et al., 2009, Nonspecifically bound proteins spin while diffusing along DNA. Nat Struct Mol Biol 16, 1224-1229 and Schurr, 1979, The one-dimensional diffusion coefficient of proteins absorbed on DNA. Hydrodynamic considerations. Biophys Chem 9, 413-414). The one-dimensional diffusion constants scale as the reciprocal of the cube of the radius of the protein. However, AVP-pVIc complexes slide nearly as fast as pVIc alone despite the additional hydrodynamic friction imposed by the presence of the 17-fold larger protein. This suggests that the peptide's configuration in the AVP-pVIc complex is further optimized by AVP to minimize free energy barriers to diffusion along DNA.

Model of the Sliding Interface Between pVIc and DNA if pVIc is a Molecular Sled.

A possible mechanism for sliding of pVIc, AVP-pVIc complexes, and pVI along DNA invokes the interaction of the basic residues of pVIc and the phosphate groups in the backbones in the major groove of the DNA. The model is based upon the assumption that the majority of the binding enthalpy between pVIc and DNA is likely to originate as a consequence of electrostatic interactions involving 2 or 3 ion pairs and that sliding occurs along a helical path defined by the DNA (Blainey et al., 2009, Nonspecifically bound proteins spin while diffusing along DNA. Nat Struct Mol Biol 16, 1224-1229). The crystal structure of the covalent complex of AVP with pVIc (Ding et al., 1996, Crystal structure of the human adenovirus proteinase with its 11 amino acid cofactor. EMBO J 15, 1778-1783 and McGrath et al., 2003, Crystallographic structure at 1.6-Å resolution of the human adenovirus proteinase in a covalent complex with its 11-amino-acid peptide cofactor: insights on a new fold. Biochem Biophys Acta 1648, 1-11) reveals extensive interactions between the peptide cofactor and the protein, one covalent bond (Cys10' to Cys104), six main chain hydrogen bonds and 24 side-chain hydrogen bonds, FIG. 21B. As part of the AVP-pVIc complex, the 8 amino acids at the C-terminus of pVIc are part of a β-sheet. The crystal structure of a 12-mer dsDNA (1HQ7) is shown in FIG. 22A. Applicants assume that the binding of AVP-pVIc complexes to DNA occurs via the pVIc moiety; therefore, the pVIc moiety in the AVP-pVIc complex is in its sliding conformation. The structure of pVIc, taken from the atomic coordinates of the AVP-pVIc complex (Ding et al., 1996, Crystal structure of the human adenovirus proteinase with its 11 amino acid cofactor. EMBO J 15, 1778-1783 and McGrath et al., 2003, Crystallographic structure at 1.6-Å resolution of the human adenovirus proteinase in a covalent complex with its 11-amino-acid peptide cofactor: insights on a new fold. Biochem Biophys Acta 1648, 1-11), is depicted in FIG. 22B with its van der Waals spheres; the structure was manually moved to the DNA. Since the basic amino acid residues of pVIc are part of an extended beta-strand, alternate side chains extend to opposite sides of the peptide backbone. The distance between the positive charge at the end of the side chain of Lys6' and the positive charge at the end of the side chain of Arg7 is 14 Å. This is approximately the same distance as that between the two phosphate backbones across the major groove of the B-form of double-stranded DNA. With no modification of either structure, each basic residue of pVIc could be positioned next to one of the four phosphates in the DNA major groove, giving rise to 4 ion pairs. A rotation of the DNA, giving a view down the major groove of the helix, shows that the contacts between pVIc and the DNA are solely between the basic residues on pVIc and the phosphate groups on the DNA, FIG. 22C. This model implies the sequence of amino acids in pVIc is important for sliding and that not just any peptide with basic amino acids will slide. Consistent with this conclusion is the observation that an 11-amino acid peptide with the same amino acid composition as in pVIc but in a randomly chosen sequence, (SFRRCGLRQVK (SEQ ID NO: 10)), binds to DNA with a $K_d$ of 646±75 nM (unpublished observations), Table 4. However, that peptide does not slide along the DNA. The randomly chosen sequence contained only 2 contiguous basic amino acids.

Model of the Binding of AVP-pVIc Complexes to DNA.

If instead of placing the structure of pVIc taken from the atomic coordinates of the AVP-pVIc complex on to DNA, FIG. 22B, the structure of the entire AVP-pVIc complex is manually moved to the DNA, FIG. 22C, no additional contacts between the protein and DNA were made beyond those between pVIc and DNA, i.e. it appears that AVP-pVIc complexes can bind to DNA solely via the pVIc moiety. This may be why the sizes of the footprints from the binding of pVIc, AVP-pVIc complexes, or pVI to DNA are similar. The size of the binding site between pVIc and DNA is 7 bp; between AVP-pVIc complexes and DNA, 6 bp (McGrath et al., 2001, DNA binding and stimulation of proteinase activity by DNA. Biochemistry 40, 13237-13245); and between pVI and DNA, 8 bp (Graziano et al., 2012, Adenovirus proteinase is activated in an unusual one-dimensional biochemical reaction), Table 4. During movement of the sled along DNA, one or more of the four ion pairs could break and reform elsewhere; concomitantly, the other ion pairs could remain intact, keeping the moving peptide bound to at least one part of the DNA at all times. From a study on the electrostatic components of binding, Applicants showed that 2.2 ion pairs for AVP-pVIc complexes (McGrath et al., 2001, DNA binding and stimulation of proteinase activity by DNA. Biochemistry 40, 13237-13245) and 2.9 ion pairs for pVI (Graziano et al., 2012, Adenovirus proteinase is activated in an unusual one-dimensional biochemical reaction) are involved in complex formation with 12-mer dsDNA. Multiple binding sites used simultaneously could explain the high processivity observed in these single molecule translocation experiments. In Applicants' model, sliding is dependent not only upon the flexibility of the peptide but also on the flexibility of the DNA. The model implies that a stiff tertiary structure is not a basic engineering requirement of DNA-binding interfaces that support rapid sliding, because preventing the movement of basic side chains to form very low-energy contacts with DNA would give rise to enormous barriers to translocation.

Relationship Between the Active Site of AVP and the pVIc Sliding Interface.

Heretofore, the AVP-pVIc structure was thought to be unusual in that pVIc, which exerts powerful control on the rate of catalysis, binds quite far away from the active-site residues involved in catalysis, FIG. 21B. The disulfide bond between Cys104 of AVP and Cys10' of pVIc is 32 Å from Cys122, the active site nucleophile. Because pVIc both activates the enzyme and serves as a "molecular sled," there must be constraints as to where the active site is located relative to the sliding interface. Sliding along DNA must not physically interfere with the ability of the active site to recognize and cleave a precursor protein aligned along the DNA. Perhaps this is why the position of "molecular sled," pVIc, in the AVP-pVIc complex is quite far away from the active-site residues involved in catalysis. Most proteins that slide along DNA are looking for specific sequences, and hence they need to recognize the DNA sequences they are sliding over. AVP does not have to look for a specific DNA sequence and thus does not have to continually interrogate the DNA; this may relieve functional constraints and allow its sliding surface to be different than that in sequence specific DNA binding proteins.

A Question is What does Diffusion Limited Mean Inside the Virus Particle.

It has been persuasively argued that at physiological ionic strength (Kao-Huang et al., 1977, Nonspecific DNA binding of genome-regulating proteins as a biological control mechanism: measurement of DNA-bound *Escherichia coli* lac repressor in vivo. Proc Natl Acad Sci USA 74, 4228-4232 and Richey et al., 1987, Variability of the intracellular ionic environment of *Escherichia coli*. Differences between in vitro and in vivo effects of ion concentrations on protein-DNA interactions and gene expression. J Biol Chem 262, 7157-7164), association rate constants mediated by facilitated diffusion are unlikely to exceed $10^8$ $M^{-1}$ $s^{-1}$, the three-dimensional diffusion limited rate constant (Halford, 2009, An end to 40 years of mistakes in DNA-protein association kinetics. Biochem Soc Trans 37, 343-348) and that therefore one-dimensional diffusion is not a faster alternative to promote bimolecular interactions. But, a question is what does three-dimensional diffusion limited mean inside an adenovirus virion. Within the capsid of the virion, there are 50 AVP molecules at a concentration of about 750 µM, 150,000-fold higher than the $K_d$ for AVP-pVIc complexes binding to DNA. Table 4. The concentration of viral DNA is 500 g/L (Casjens, 1997, Principles of virion structure, function and assemble, In Structural biology of viruses, W. Chiu, R. M. Burnett, and R. L. Garcea, eds. (Oxford: Oxford University Press), pp. 3-37). Thus, both the concentration of DNA and AVP-pVIc complexes drive this sequence independent DNA-binding protein onto the DNA. For AVP-pVIc complexes, based upon their $K_d$ for DNA, the DNA-bound state predominates by at least one hundred thousand-fold over the DNA-unbound state, and this would diminish the three-dimensional diffusion constant by a similar factor. Furthermore, Applicants calculate the mesh size or dynamic porosity of the DNA inside the virion to be less than 1 nm (Mangenot et al., 2003, Transport of nucleosome core particles in semidilute DNA solutions. Biophys J 85, 1817-1825). Three-dimensional diffusion has been shown to be reduced by as much as an order of magnitude when the mesh size of a dynamic polymer network equals the size of the diffusing object. The AVP-pVIc complex is ovoid with dimensions of 41×44×55 Å (McGrath et al., 2003, Crystallographic structure at 1.6-Å resolution of the human adenovirus proteinase in a covalent complex with its 11-amino-acid peptide cofactor: insights on a new fold. Biochem Biophys Acta 1648, 1-11). Since the diameter of the AVP-pVIc complex is much larger than the mesh size, another factor of 10 in the reduction of the diffusion constant is a conservative estimate as to the effect of the DNA concentration on the three-dimensional diffusion of AVP-pVIc complexes. From these points of view, inside the virion, the three-dimensional diffusion limited rate constant for AVP-pVIc complexes is reduced by at least one-million fold over that outside the virion. And this argues that sliding on DNA inside the virion via one-dimensional diffusion is a faster alternative to promote bimolecular interactions than three-dimensional diffusion.

One-Dimensional Diffusion Occurs In Vivo.

Sliding along DNA has been shown to occur in vivo, inside *E. coli* (Elf et al., 2007, Probing transcription factor dynamics at the single-molecule level in a living cell. Science 316, 1191-1194). In searching for the operator, a lac repressor spends about 90% of time nonspecifically bound to and diffusing along DNA with a residence time of <5 milliseconds. The search time of the lac repressor for its operator is less than 270 seconds. Up until now, diffusion, mediated by hopping, jumping and sliding, has been used to explain how DNA-grooming proteins can quickly search for target sites in DNA. Most protein-DNA interactions in the cell involve a protein e.g. a repressor, transcription factor, DNA repair enzyme, initially binding to randomly encountered sites on DNA, and then subsequently hopping or jumping on and off the DNA and/or sliding via one-dimensional diffusion along the DNA, in search of a specific locus, e.g. an operator, promoter, or DNA lesion (Berg et al., 1981, Diffusion-driven mechanisms of protein translocation on nucleic acids. 1. Models and theory. Biochemistry 20, 6929-6948; Elf et al., 2007, Probing transcription factor dynamics at the single-molecule level in a living cell. Science 316, 1191-1194 and Riggs et al., 1970, The lac repressor-operator interaction. III. Kinetic studies. J Mol Biol 53, 401-417). Now, however, if the structural basis for sliding of pVIc on DNA is solely the four contiguous basic amino acids, all proteins with an NLS, not just DNA-grooming proteins, would be predicted not only to bind to DNA but to slide on it as well.

New Paradigm for Virion Maturation.

Adenovirus exploits the sliding behavior of pVIc by incorporating it into a substrate (pVI) and attaching it to an enzyme (AVP-pVIc complexes) thereby promoting their interaction and activation of the enzyme. This illustrates how sliding, a behavior crucial to the biology of cellular proteins with functions related to nucleic acid metabolism, can operate in a completely different context. In this case, the context is to facilitate bimolecular interactions between enzymes and substrates in the crowded, highly charged, environment of a virion where the enzymes and substrates are forced by thermodynamic imperatives to bind tightly to a fixed matrix, the viral DNA genome. How these bimolecular interactions can occur is defined by the biological constraints of infection, by the physical constraints of the adenovirus virion, and by the biochemical constraints imposed by the maturation process. The solution to the problem was to have both enzymes and substrates bind tightly to a fixed matrix, the immobilized viral DNA genome, and the evolution of an elegant mechanism whereby catalysis and motility are regulated by the cleavage product of AVP's own reaction with pVI. That reaction gives rise to pVIc, both an activator of AVP's catalytic activity and a molecular sled to carry the activated AVP along the DNA to search for its substrates. The solution required a "molecular sled" on both enzyme and substrate and a new mechanism as to how a proteinase locates its substrates and how substrates locate a proteinase—a new paradigm for virion maturation.

Biochemistry in One-Dimensional Space.

Heretofore, the one-dimensional compartment defined by the DNA contour provided a region in which transactions upon the DNA could occur. This work extends the use of that compartment to provide transactions among DNA-bound proteins and further provides a vehicle for that purpose, a molecular sled. Reduced dimensionality and compartmentalization in regions of the genome defined by different and varying physical, chemical, and biological factors are expected to have strong effects on specificities and on chemical kinetics of protein-protein bimolecular interactions, hence on biological outcomes. And that enables a different kind of chemistry. For example, pVI is not cleaved by highly active AVP-pVIc complexes in solution; both components must be bound to the same DNA molecule for bimolecular processing reactions to occur via sliding (Graziano et al., 2012, Adenovirus proteinase is activated in an unusual one-dimensional biochemical reaction). Michaelis-Menten kinetic analysis may not be applicable to interactions between enzymes and substrates in the one-dimensional compartment defined by the DNA contour. Equilibrium dissociation constants that characterize bimolecular interactions in three dimensional space are less predictive of productive collisions than the individual equilibrium dissociation constants for the binding of the two components to DNA and the one-dimensional diffusion constants. AVP-pVIc complexes and their substrates bound to DNA are highly constrained, both in space and in orientation. That plus the constraint that within the virus particle AVP-pVIc complexes move only in the one-dimensional space of the viral DNA greatly reduces the number of possible orientations of AVP and its precursor protein substrates relative to each other, compared to both being free in solution. It is possible that the orientation of AVP-pVIc complexes sliding on DNA and the orientation of their substrates also bound to DNA are such that almost every collision between enzyme and substrate will be productive, i.e. lead to catalysis. In three-dimensional space, productive bimolecular collisions require correct orientations and velocities and are thus tens of orders of magnitude less probable. This one-dimensional biochemistry, in a milieu where DNA defines space, may be the only way bimolecular reactions between proteins can efficiently occur inside a virus particle or in the nucleus of a cell.

Experimental Procedures.

pVIc (GVQSLKRRRCF (SEQ ID NO: 12)), streptavidin Alexa Fluor 546 conjugate, 5'-fluorescein-labeled 12-mer ssDNA (GACGACTAGGAT (SEQ ID NO: 18)), 5'-fluorescein-labeled 18-mer ssDNA (CAGGAAACAGCTATGACC (SEQ ID NO: 19)), and 5'-fluorescein-labeled-36-mer ssDNA (GATTGCATGATTAGAGTGTGCTGGATGTGATAGTGA (SEQ ID NO: 23)) were purchased from Invitrogen (Carlsbad, Calif.). Labeled ss-DNAs were annealed to their complimentary strands according to standard protocols. 8-Actin-C(SIVHRKCF (SEQ ID NO: 9)), 11-Actin-C(SGP-SIVHRKCF (SEQ ID NO: 20)), and the random-sequence-peptide (SFRRCGLRQVK (SEQ ID NO: 10)) were purchased from Research Genetics (Huntsville, Ala., USA). Cy3B-maleimide was purchased from GE Healthcare (Piscataway, N.J.). Octylglucoside was purchased from Fisher Scientific (Faden, N.J.). n-dodecyl-β-D-maltopyranoside (DDM) was purchased from Anatrace (Maumee, Ohio).

Concentration of Unlabeled Peptides.

The concentrations of pVIc, 8-Actin-C, 11-Actin-C, and random peptide were determined by titration of the cysteine residue with Ellman's reagent (Riddles et al., 1979, Ellman's reagent: 5,5'-dithiobis(2-nitrobenzoic acid)-a reexamination. Anal Biochem 94, 75-81 and Riddles et al., 1983, Reassessment of Ellman's reagent. Methods Enzymol 91, 49-60) using an extinction coefficient of 14,150/M/cm at 412 nm for released thionitrobenzoate.

Fluorescent Labeling of Peptides.

pVIc, and random peptide were labeled at a concentration of 200 μM in 25 mM HEPES (pH 7.0), 25 mM NaCl, and 20 mM ethanol by the addition of Cy3B maleimide to 600 M. Labeling reactions were incubated at 21° C. in the dark for 2.5 hours. Dye-conjugated peptides were purified from unreacted dye and peptide on a 15 cm×4.6 mm Discovery C18, 5 m column. Peptides were eluted via a linear acetonitrile-gradient from 0 to 40% in 0.1% TFA. The conjugated peptide peak was identified by MALDI-TOF analysis. The fractions were evaporated to dryness on a LABCONCO Centrivap Console and resuspended in water. The concentration of the dye-conjugated peptide was determined by measuring the dye concentration spectrophotometrically using $\varepsilon_{558nm}^{Cy3B}=130,000$ M$^{-1}$ cm$^{-1}$. The conjugated peptide was aliquoted, dried and stored at $-20°$ C.

Synthesis of Alexa Fluor 546-Streptavidin-Biotinylated pVIc Conjugates.

Alexa Fluor 546-streptavidin-biotinylated pVIc conjugates were formed as follows: pVIc was biotinylated by incubating 3.4 mM pVIc in 100 mM sodium phosphate (pH 7.0) and 20 mM ethanol with 7.8 mM biotin-PEG-maleimide in the dark for 16 h at room temperature. The reaction was quenched by the addition of DTT to 10 mM. The biotinylated pVIc was purified on a Discovery C18 column equilibrated in 0.1% (v/v) TFA using a linear gradient of acetonitrile. Fractions off the column that stimulated AVP activity and were unreactive to Ellman's reagent were pooled. Next, approximately 850 pmol of the biotin-PEG-pVIc were serially diluted 1:2 with acetonitrile and each dilution lyophilized to dryness using a Labconco Centrivap. Then, a constant volume of 16.7 μM Streptavidin-Alexa Fluor 546 was added resulting in molar ratios of (pVIc-biotin)-Streptavidin-Alexa Fluor 546 of 1:1, 2:1, 4:1, 8:1, and 16:1. After incubation for 1 hr, the conjugates were stored at 4 C.

Fluorescence Anisotropy.

Steady-state fluorescence anisotropy measurements were performed using an ISS model PC-1 photon counting spectrofluorometer (ISS, Champaign, Ill.) equipped with polarization accessories. Measurements were made in L-format using a 300-W xenon arc lamp with 10 mm and 14 mm Glan-Thompson polarizers in the excitation and emission channels, respectively. For Cy3B dye, the excitation wavelength was 564 nm, with 8 nm slits placed before and after a monochromator. The parallel and vertical emission components were measured through a 580 nm bandpass filter with a FWHM of 10 nm. For fluorescein dye, the excitation wavelength was 495 nm, with 8 nm slits placed before and after a monochromator. The parallel and vertical emission components were measured through a 530 nm longpass filter.

Calculation of $K_d$ Values.

The $K_d$ was calculated by fitting the fluorescence anisotropy data to a one-to-one stoichiometry binding model according to the equation:

$$r_{obs} = r_f + (r_b - r_f) \frac{([P]_T + [D]_T + K_D) - \sqrt{(([P]_T + [D]_T + K_D)^2 - 4[P]_T[D]_T}}{2[D]_T}$$

where $r_{obs}$ is the observed anisotropy; $r_f$ the anisotropy of free 12-mer ssDNA; $r_b$ the anisotropy of protein bound DNA; $[P]_T$ the total protein concentration; $[D]_T$ the total DNA concentration (10 nM); and $K_d$ is the equilibrium dissociation constant. The parameters in the nonlinear regression analysis were $r_f$, $r_b$, and $K_d$.

Fluorescence Resonance Energy Transfer (FRET).

Steady state fluorescence measurements were measured with an ISS PC1 spectrofluorometer (ISS, Champaign, Ill.) with a 300-W xenon arc lamp and 19 amp lamp current. The excitation and emission wavelengths were 490 and 520 nm, respectively, using 8 nm excitation and emission slits. A 1 mL solution of 10 nM fluorescein-labeled 18-mer dsDNA in 20 mM sodium phosphate, pH 7.5, 0.05% DDM was placed inside a 1 cm standard quartz cuvette and was titrated with increasing amounts of streptavidin Alexa Fluor 546 or the complex (pVIc-biotin)-streptavidin Alexa Fluor 546. The solution was mixed and allowed to equilibrate for 2 minutes before measuring the fluorescence intensity for a maximum of 10 seconds (corresponds to an average of eleven measurements). To correct for the decrease in fluorescence intensity due to inner filter effects, a 10 nM solution of fluorescein was titrated with streptavidin Alexa Fluor 546.

Sliding Assay Conditions

Flow cells containing lambda DNA immobilized at one end were constructed as described previously (Blainey et al., 2006, A base-excision DNA-repair protein finds intrahelical lesion bases by fast sliding in contact with DNA. Proc Natl Acad Sci USA 103, 5752-5757). Labeled peptides or proteins were infused at concentrations of 1-2 nM at rates of 20-50 mL/hour. High flow rates were chosen to drive the longitudinal DNA fluctuation faster than the imaging frame rate (Blainey et al., 2006, A base-excision DNA-repair protein finds intrahelical lesion bases by fast sliding in contact with DNA. Proc Natl Acad Sci USA 103, 5752-5757). The assay buffer consisted of 10 mM MES (pH 6.5), 2-25 mM NaCl, 50 M EDTA, 20 mM ethanol, 5 percent glycerol, and, where indicated in the text, reducing agent (DTT and mercaptoethanol gave equivalent results). "Low salt" measurements were conducted with 2-6 mM NaCl; "high salt" measurements were conducted with 20-25 mM NaCl.

Fluorescence Imaging.

pVIc was labeled with Cy3B at Cys10'. Individual, fluorescently labeled molecules were imaged by total internal reflection fluorescence microscopy as previously described (Blainey et al., 2006, A base-excision DNA-repair protein finds intrahelical lesion bases by fast sliding in contact with DNA. Proc Natl Acad Sci USA 103, 5752-5757), with the exception that a faster EMCCD camera (Photometrics Cascade: 128+) was used for the highest time-resolution measurements. Lambda DNA was tethered to a glass surface at one end and stretched by a laminar flow of buffer. Single molecules that bound to and diffused along the DNA were illuminated by an evanescent wave via laser beam (532 nm) and imaged with a fluorescence microscope.

Centroid Determination and Analysis of Molecular Trajectories.

Due to the speed and duration of sliding, all such events were readily identifiable manually. All pVIc DNA-binding events noted were included in the analyses. Once events had been identified, signals were tracked using Gaussian centroid determination in the Matlab environment. Molecular trajectories were analyzed in Matlab by methods similar to those previously published (Blainey et al., 2006, A base-excision DNA-repair protein finds intrahelical lesion bases by fast sliding in contact with DNA. Proc Natl Acad Sci USA 103, 5752-5757).

Example 5: Structure of the Adenovirus Proteinase at Atomic Resolution (0.98 Å)

The adenovirus proteinase (AVP) is essential for the production of infectious virus particles. AVP, an inactive enzyme, requires two cofactors for maximal activity-pVIc, an 11 amino acid peptide and the viral DNA. Here Applicants present the crystal structure of AVP at 0.98 Å-resolution. Comparison of the structure of AVP with that of an active form of the enzyme, the AVP-pVIc complex, reveals why AVP is inactive. In AVP, the general base, His54, is no longer close enough to the active site nucleophile to render it nucleophilic and its cation-π interaction with Tyr84 has been disrupted. Applicants present a model postulating that activation of AVP by pVIc occurs via a 62-amino acid long activation pathway in which the binding of pVIc initiates contiguous conformational changes, like falling dominos: There is a common pathway that branches into a pathway leads to the repositioning of His54 and another pathway that leads to the repositioning of Tyr84. This high resolution structure of AVP should facilitate identification of inhibitors of AVP that will act as antiviral agents.

The adenovirus proteinase (AVP) is essential for the production of infectious virus (Weber, 1976, Genetic analysis of adenovirus type 2, III. Temperature-sensitivity of processing of viral proteins. J. Virol., 17, 462-471). AVP, whose structure Applicants describe here, is synthesized as a relatively inactive enzyme (Mangel et al., 1993, Viral DNA and a viral peptide can act as cofactors of adenovirus virion proteinase activity. Nature, 361, 274-275 and Webster et al., 1993, The adenovirus protease is activated by a virus-coded disulphide-linked peptide. Cell, 72, 97-104). Late in adenovirus infection, AVP becomes activated inside young virions and cleaves multiple copies of six, different virion precursor proteins (Weber, 1976, Genetic analysis of adenovirus type 2, III. Temperature-sensitivity of processing of viral proteins. J. Virol., 17, 462-471). AVP is synthesized in an inactive form, because if it were not, it would cleave virion precursor proteins before virion assembly thereby aborting an infection (Baniecki et al., 2001, Interaction of the human adenovirus proteinase with its 11-amino-acid cofactor pVIc. Biochemistry, 40, 12349-12356). Two viral cofactors have been discovered that stimulate proteinase activity. One cofactor is pVIc, the 11-amino acid peptide from the C-terminus of adenovirus precursor protein pVI (Baniecki et al., 2001, Interaction of the human adenovirus proteinase with its 11-amino acid cofactor pVIc. Biochemistry, 41, 430; Mangel et al., 1993, Viral DNA and a viral peptide can act as cofactors of adenovirus virion proteinase activity. Nature, 361, 274-275 and Webster and Kemp, 1993, The active adenovirus protease is the intact L3 23K protein. J. Gen. Virol., 74, 1415-1420). Its primary sequence is GVQSLKRRRCF (SEQ ID NO: 12). Cys104 of AVP can form a disulfide bond with Cys10' of pVIc in vitro (Ding et al., 1996, Crystal structure of the human adenovirus proteinase with its 11 amino acid cofactor. EMBO J., 15, 1778-1783 and McGrath et al., 2003, Crystallographic structure at 1.6-Å resolution of the human adenovirus proteinase in a covalent complex with its 11-amino-acid peptide cofactor: insights on a new fold. Biochem. Biophys. Acta, 1648, 1-11) and does so in vivo in the virus particle (McGrath et al., 2002, In the virion, the 11-amino acid peptide cofactor pVIc is covalently linked to the adenovirus proteinase. Virology, 296, 234-240). A second cofactor is the viral DNA (Mangel et al., 1993, Viral DNA and a viral peptide can act as cofactors of adenovirus virion proteinase activity. Nature, 361, 274-275 and McGrath et al., 2001, Human adenovirus proteinase: DNA binding and stimulation of proteinase activity by DNA. Biochemistry, 40, 13237-13245). The two viral cofactors increase the specificity constant ($k_{cat}/K_m$) for substrate hydrolysis (Mangel et al., 1993, Viral DNA and a viral peptide can act as cofactors of adenovirus virion proteinase activity. Nature, 361, 274-275 and McGrath et al., 2001, DNA binding and stimulation of proteinase activity by DNA. Biochemistry, 40, 13237-13245; Baniecki et al., 2001, Interaction of the human adenovirus proteinase with its 11-amino-acid cofactor pVIc. Biochemistry, 40, 12349-12356 and Mangel et al., 1996, Characterization of three components of human adenovirus proteinase activity in vitro. J. Biol. Chem., 271, 536-543). In the presence of Ad2 DNA, the $k_{cat}/K_m$ for AVP increases 110-fold (Baniecki et al., 2001, Interaction of the human adenovirus proteinase with its 11-amino-acid cofactor pVIc. Biochemistry, 40, 12349-12356; Mangel et al., 1996, Characterization of three components of human adenovirus proteinase activity in vitro. J. Biol. Chem., 271, 536-543 and McGrath et al., 2001, Human adenovirus proteinase: DNA binding and stimulation of proteinase activity by DNA. Biochemistry, 40, 13237-13245); in the presence of pVIc, 1130-fold. With all three components together, AVP, pVIc and Ad2 DNA, the $k_{cat}/K_m$ increases 15,800.

How AVP becomes activated by cleavage of pVIc from pVI and how the active AVP-pVIc complexes process the virion precursor proteins has been a conundrum: AVP and pVI are sequence-independent DNA-binding proteins (Graziano et al., 2012, Binding to DNA and to hexon of the precursor to protein VI, pVI, of human adenovirus; Mangel et al., 1993, Viral DNA and a viral peptide can act as cofactors of adenovirus virion proteinase activity. Nature, 361, 274-275 and McGrath et al., 2001, Human adenovirus proteinase: DNA binding and stimulation of proteinase activity by DNA. Biochemistry, 40, 13237-13245). In the tightly-packed interior of a young virion, the concentration of viral DNA is 500 g/L (Casjens, 1997, Principles of virion structure, function and assemble. In Chiu, W., Burnett, R. M. and Garcea, R. L. (eds.), Structural biology of viruses. Oxford University Press, Oxford, pp. 3-37); that plus the sieving effect of DNA (Mangenot et al., 2003, Transport of nucleosome core particles in semidilute DNA solutions. Biophys J, 85, 1817-1825) diminishes the effective three-dimensional diffusion constants of AVP and pVI by more than one million-fold (Blainey et al., 2012, "Molecular sled"—11-amino acid peptide mediates one-dimensional biochemistry by sliding enzymes and substrates on DNA). A model solving the conundrum as to how AVP is activated and how AVP-pVIc complexes cleave the virion precursor proteins has been presented (Blainey et al., 2012, "Molecular sled"—11-amino acid peptide mediates one-dimensional biochemistry by sliding enzymes and substrates on DNA; Blainey et al., 2012, Interaction of the human adenovirus proteinase with its 11-amino acid cofactor pVIc. Biochemistry, 41, 430 and Graziano et al., 2012, Adenovirus proteinase is activated in an unusual one-dimensional biochemical reaction). AVP binds randomly to DNA and does not slide along the DNA via one-dimensional diffusion (Graziano et al., 2012, Adenovirus proteinase is activated in an unusual one-dimensional biochemical reaction). pVI also binds randomly to DNA, but it slides along DNA with a one-dimensional diffusion constant of $1.45 \times 10^6$ $(bp)^2$/s. pVI slides into AVP. AVP, partially activated by being bound to the viral DNA, cleaves pVI first at its N-terminus and then at its C-terminus. pVIc, released by cleavage of pVI at its C-terminus, binds to the AVP that cut it out, and then a disulfide bond is formed between pVIc's Cys10' and Cys104 of AVP thereby keeping AVP permanently activated. The processing of the virion proteins by AVP-pVIc complexes occurs by the following mechanism: Covalent, active AVP-pVIc complexes slide along the viral DNA with a one-dimensional diffusion constant of $21.0 \times 10^6$ $(bp)^2$/s (Blainey et al., 2012, Viral proteinase slides along DNA to locate and process its substrates) and process the precursor proteins which are also nonspecifically bound to the viral DNA (Blainey et al., 2012, Viral proteinase slides along DNA to locate and process its substrates). Both pVI and AVP-pVIc complexes slide along DNA via one-dimensional diffusion, because pVIc is a "molecular sled."

The AVP-pVIc complex has been crystallized (Keefe et al., 1995, Crystallization and preliminary X-ray diffraction studies of human adenovirus serotype 2 proteinase with peptide cofactor. Protein Sci., 4, 1658-1660 and McGrath et al., 1996, Preparation and crystallization of a complex between human adenovirus serotype 2 proteinase and its 11-amino-acid cofactor pVIc. J. Struct. Biol., 117, 77-79) and its structure determined at 2.6 Å resolution [Ding, 1996 #241] and at 1.6 Å resolution (McGrath et al., 2003, Crystallographic structure at 1.6-Å resolution of the human adenovirus proteinase in a covalent complex with its 11-amino-acid peptide cofactor: insights on a new fold. Biochem. Biophys. Acta, 1648, 1-11). The AVP-pVIc complex is a cysteine proteinase. Comparison of the amino acid residues involved in catalysis by the canonical cysteine proteinase papain with those amino acids in similar positions in the AVP-pVIc complex revealed they can be superimposed. However, even with these juxtapositions, because the order along the polypeptide chain of these amino acids in AVP and papain is different, AVP is the first member of a new class of cysteine proteinases. The remarkable juxtaposition of catalytic elements strongly suggests that AVP employs the same catalytic mechanism as papain (Polgar, 1974, Mercaptide-imidazolium ion-pair: The reactive nucleophile in papain catalysis. FEBS Lett., 47, 15-18). And because the fold of AVP is different from the fold of papain, yet the positions of the residues involved in catalysis are the same, AVP is an example of convergent evolution. Recently, other proteinases have been added to the AVP family. Among viruses, this includes vaccinia virus (Ansarah-Sobrinho and Moss, 2004, Role of the 17 protein in proteolytic processing of vaccinia virus membrane and core components. J. Virol., 78, 6335-6343) and African Swine Fever virus (Andres et al., 2001, African swine fever virus protease, a new viral member of the SUMO-1-specific protease family. J. Biol. Chem., 276, 780-787). *Chlamydia trachomatis* has a gene similar to that of AVP (Stephens et al., 1998, Genome sequence of an obligate intracellular pathogen of humans: *Chlamydia trachomatis*. Science, 282, 754-759) as does Ulp1, a proteinase involved in de-sumoylation (Li and Hochstrasser, 1999, A new protease required for cell-cycle progression in yeast. Nature, 398, 246-251). YopJ from *Yersinia pestis* is an acetyltransferase involved in the inhibition of mitogen-activated protein kinase and nuclear factor κB signaling in animal cells and in the induction of localized cell death in plants (Mukherjee et al., 2006, *Yersinia* YopJ acetylates and inhibits kinase activation by blocking phosphorylation. Science, 312, 1211-1214).

Applicants crystallized AVP (Baniecki et al., 2002, Adenovirus proteinase-crystallization and preliminary x-ray diffraction studies to atomic resolution. Acta Crystallogr., D58, 1462-1464) and here present its structure at a resolution of 0.98 Å as determined by X-ray diffraction. With the structure of the inactive form of the enzyme, comparison of it with the structure of the active form of the enzyme, the AVP-pVIc complex, should reveal at the structural level why AVP is inactive and how AVP is activated upon the binding of pVIc. Furthermore, this high resolution structure should reveal novel targets for AVP inhibitors that will act as antiviral agents (McGrath et al., 2012, Highly specific and selective inhibitors of the adenovirus proteinase).

X-Ray Diffraction Data.

The unit cell dimensions and mass of the molecular species in the crystal were consistent with there being one 23,087 Da monomer of AVP per asymmetric unit, which gives a Matthew's coefficient of 1.75 Å$^3$/Da. This corresponds to a solvent content of 29.2%, which may be why this crystal diffracted to such high resolution. The data collection statistics are listed in Table 5.

TABLE 5

AVP crystal data collection and processing statistics.
Summary of data collection and processing statistics

| | |
|---|---|
| Space Group | P2$_1$ |
| Unit Cell (Å) | a = 36.270, b = 54.54, c = 42.41, β = 100.1 |
| Wavelength (Å) | 0.90 |
| Resolution (Å) | 20-0.98 (1.0-0.98) |
| Total reflections | 611496 |
| Unique reflections | 92247 |
| Overall (Highest Shell): | |
| Completeness (%) | 99.1 (97.1) |
| $^a$ R(I) merge (%) | 5.7 (59.4) |
| I/σ(I) | 25.4 (1.6) |

$^a$ The merging R(I) factor is defined as Σ |I-<I>|/ΣI.

Quality of the Model.

Figure 23:
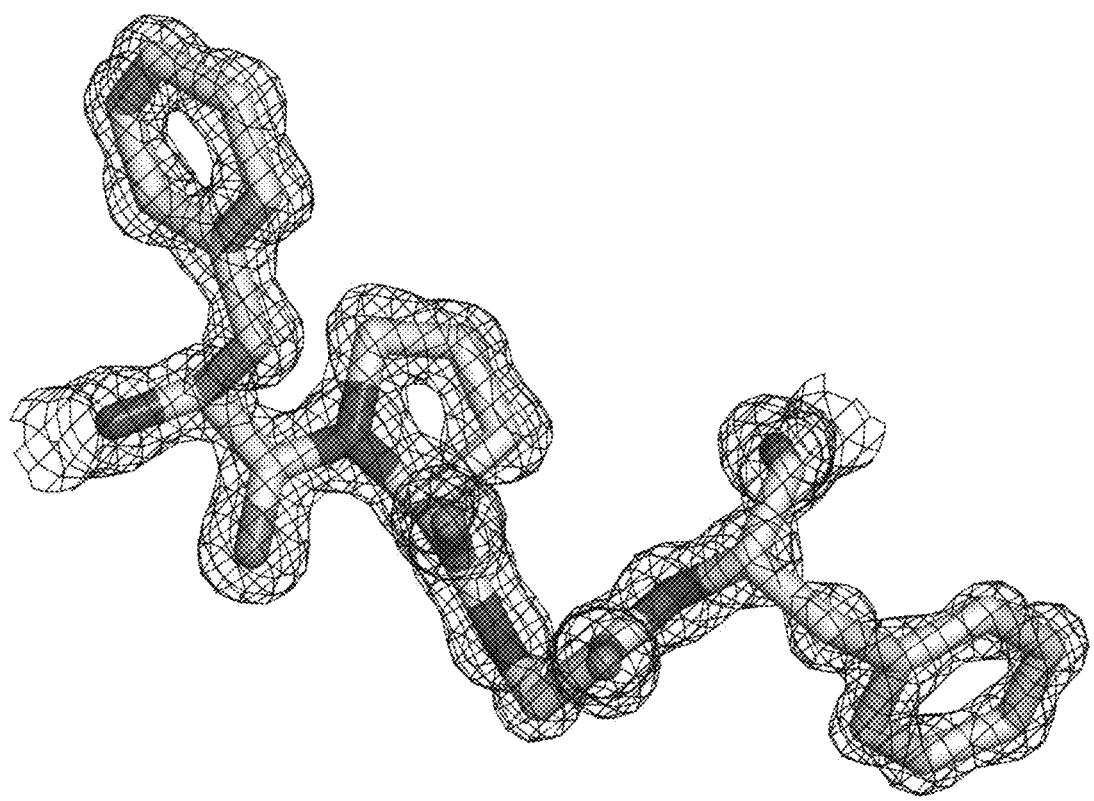
FIG. 23. Example of high resolution (0.98 Å) data. A region of the AVP structure is depicted with the 2 $F_o$-$F_F$ map contoured at 1.5 sigma. The amino acid residues, F29, P30, G31 and F32, are conserved among AVP genes and lie in the His activation pathway.
Figure 27A:
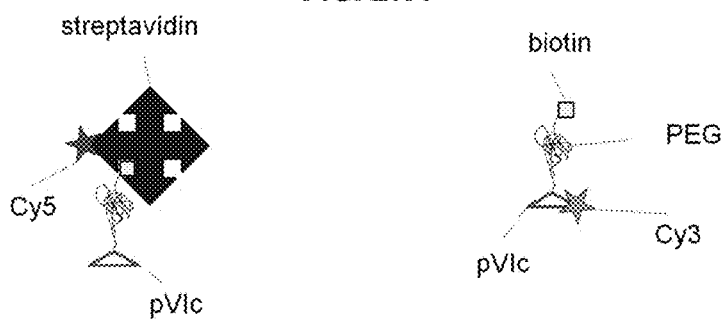
FIG. 27A. Schematic design of the two components. Left: fluorescently (Cy5) labeled streptavidin with a pVIc sled (coupled to the streptavidin through a biotin-poly(ethylene glycol) linker. Right: fluorescently (Cy3) labeled pVIc sled coupled to a biotin through a poly(ethylene glycol) linker.
Figure 27B:
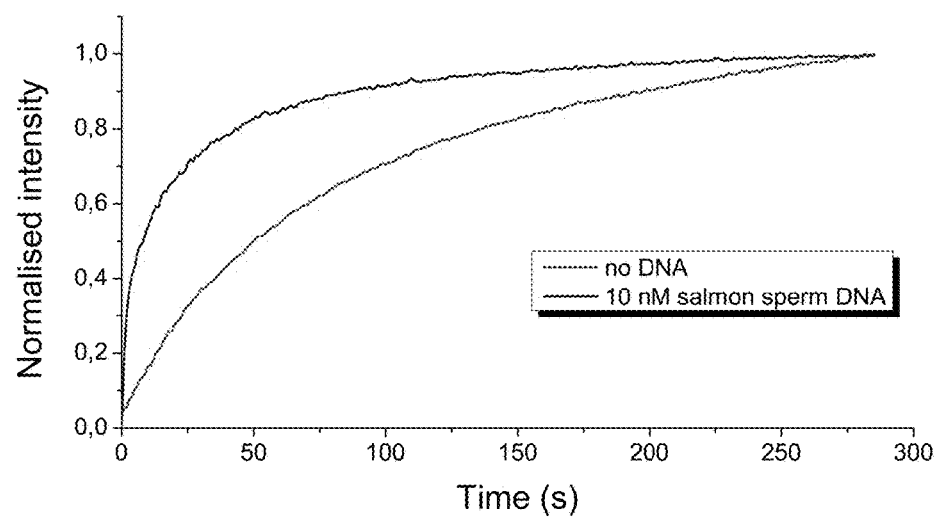
FIG. 27B. Equimolar amounts of the Cy5-labeled streptavidin-pVIc and Cy3-labeled biotin-pVIc are combined while the Cy3 label is excited and Cy5 emission is monitored as a function of the time. The increase in signal represents fluorescence resonance energy transfer (FRET) between the two fluorophores and indicates biomolecular association. In the presence of DNA (blue), this association process is significantly faster than in the absence of DNA (red). All experiments were done in an aqueous solution with high viscosity to gain better access to the dynamics of the process.
Figure 27C:
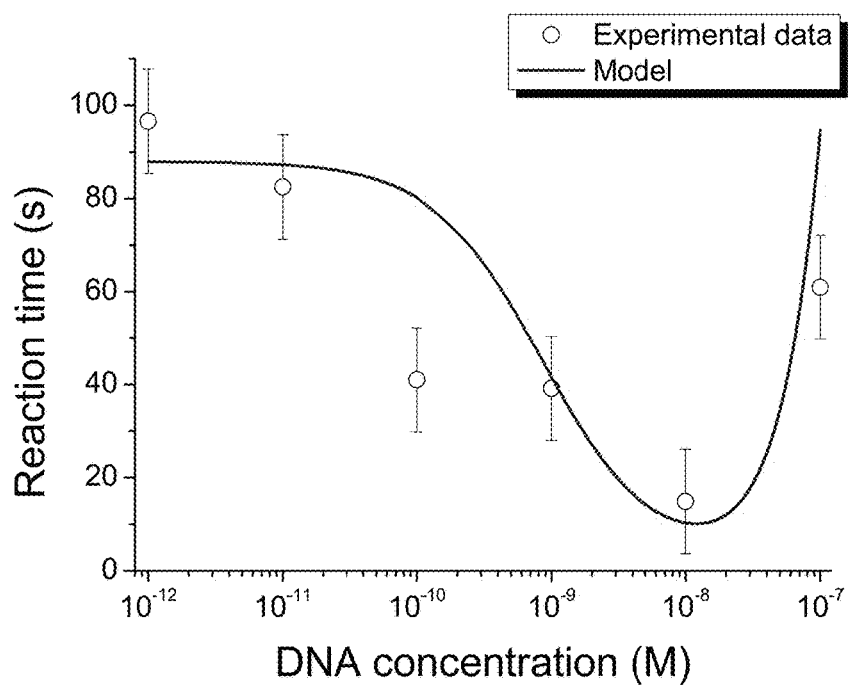
FIG. 27C. Biomolecular association speeds up as a function of DNA concentration. At optimal DNA concentration, an increase of a factor of 5 in association rate can be obtained. The blue line denotes a fit with an analytical model that describes the kinetics of both 3-dimensional, solution-based diffusion as well as 1-dimensional, DNA-based diffusion.

The structure of AVP was solved with molecular replacement. The final model refined against the diffraction data measured from crystals of the native protein contained 1799 non-hydrogen atoms, 194 residues and 253 waters and gave a crystallographic R factor of 13.5% (R$_{free}$=16.8%) for the data from 20 to 0.98 Å. An example of the high resolution of the electron density is shown in FIG. 23; residues 29-32, highly conserved among AVP genes, are depicted with the 2 F$_o$-F$_F$ map contoured at 1.5 sigma. Residues 48-53 and 97-104 could not be modeled due to undefined electron density in those regions. These two regions lie within loop regions of the AVP-pVIc structure used to initiate the molecular replacement solution. Seven residues were found whose side chains exhibited multiple conformations-Glu7, Asp26, Cys67, Arg169, Gln173, Ser176 and Ser194. The weights of the stereochemical restraints used during the refinement together with the final deviations of the geometrical parameters from ideal values are shown in Table 6.

TABLE 6

Summary of the properties of the model.
Summary of properties of the model

R$_{factor}$ = 0.1354 (F > 4σF) = 0.1238
R$_{free}$ = 0.1678 (F > 4σF) = 0.1587
Number of amino acids: 194
Number of atomic sites with dual conformers: 7
Number of atomic sites with water: 253

| Standard | σ | Deviation | Number of parameters |
|---|---|---|---|
| Distances (Å) | | | |
| Bond lengths | 0.020 | 0.029 | 1612 |
| Bond angles | 0.040 | 0.045 | 2178 |
| Chiral volumes | | | |
| Zero | 0.1 | 0.093 | 251 |
| Non-zero | 0.1 | 0.172 | 222 |

The Ramachandran plot (Ramakrishnan and Ramachandran, 1965, Stereochemical criteria for polypeptide and protein chain conformation. Biophys. J., 5, 909-933), produced by the program PROCHECK shows 93.3% of the non-proline, non-glycine residues in most favored regions, 6.1% in additional allowed regions. One residue had main-chain dihedral angles (Ψ, ψ) outside the allowed region, Lys27 (68.1, -48.7°). The average B value for the main chain atoms was 11.63 Å$^2$, and 18.43 Å$^2$ for side chain atoms. The overall B value from the Wilson plot was 8.6 Å$^2$.

Overall Fold of the Structure.

AVP has an a +P fold structure, ovoid in shape with dimensions of approximately 45×35×33 Å, FIG. 24A. The structure contains five β-strands, six α-helices, two 3-10 helices and is arranged into two domains with the active site situated at the domain interface. One domain, the a-helical domain, is composed of four α-helices and both 3-10 helices, encompassing the N-terminal 15 residues and residues 113-204. The other domain, the β-strand domain, contains five β-strands arranged in a β-sheet that is sandwiched between a long α-helix and the helical domain, encompassing residues 16-112. The molecule contains 204 amino acids, 194 of which could be mapped into the electron density. The β-sheet domain contains the two loops whose backbone positions could not be mapped due to a lack of electron density.

Comparison to AVP-pVIc.

The structure of AVP was solved by molecular replacement using as a search model the structure of the proteinase from the AVP-pVIc covalent complex (1NLN), FIG. 24B. The aligned structures of AVP and of the AVP-pVIc complex are shown in FIGS. 24C, D, with the root mean square differences between each highlighted in color and the similarities between the two colored in beige. Overall, the structures of AVP and the AVP-pVIc complex are very similar, with an r.m.s.d. for 680 backbone atoms of 0.78 Å$^2$; for 1024 atoms from all aligned residues, the r.m.s.d was 0.37 Å$^2$. The similarities and differences seem to be domain specific.

The similarities in the two structures are mostly in the a-helical domain. The backbone in the α-helical domain is practically identical between the two structures, only the last three residues at the C-terminus of the protein diverge in position between the two structures.

The major differences between the two structures are found in the β-sheet domain. The β-strands at each end of the central β-sheet are altered when compared to the AVP-pVIc structure. Strand S1 is extended one residue in AVP encompassing residues 21 through 26. Strand S5 is three residues shorter, extending from residues 106 through 109 rather than from residues 104 through 110. The region connecting strands S1 and S2 has residues that have undergone a significant backbone rearrangement, resulting in a different arrangement of their side chains, FIG. 24A. The most significant difference in structure in the β-sheet domain is in the long helix above the β-sheet, extending from residues 78 through 95 in AVP. In the AVP-pVIc structure, this region of the structure forms a helix-coil-helix motif, followed by a small coil from residues 99 through 103. There are two loops whose paths could not be completely traced in the β-sheet domain. One of these loops extends from residues 45 through 53. There is insufficient electron density to map residues 47 through 51. This loop connects strands S2 and S3. The second loop extends from residues 96 through 105. Residues 97 through 104 could not be mapped in the structure. This loop extends from the C-terminal end of the long helix to strand S5.

The Active Sites and the Amino Acid Residues Involved in Catalysis.

In the AVP-pVIc complex, the active site is located within a 25 Å long bent groove that is ~8 Å wide. Cys122 and His54, the active site nucleophile and the general base, respectively, are located in the middle of the groove. These amino acids are conserved among adenovirus serotypes. A 3.9 Å hydrogen bond is formed between atoms Sγ of Cys122 and N6 of His54. This is probably a thiolate-imidazolium ion pair, like the nucleophilic Cys-His ion pair in papain (Drenth et al., 1971, Papain, X-ray structure. Academic Press, New York), because a thiolate anion in AVP can be titrated at pH 5.0 with dithiodipyridine (Mangel et al., 1996, Characterization of three components of human adenovirus proteinase activity in vitro. J. Biol. Chem., 271, 536-543). Glu71, probably the third member of the charge-relay system (Blow et al., 1969, Role of a buried acid group in the mechanism of action of chymotrypsin. Nature, 221, 337-340) lies on the other side of the imidazole ring of His54 from Cys122. A hydrogen bond is formed between atoms Oε2 of Glu71 and Nε2 of His54. Glu71 is replaced only by Asp among adenovirus strains. The backbone nitrogen of Cys122 and side chain nitrogen of Gln115 form the presumed oxyanion hole.

In the AVP structure, the "active" site is in a similar position to its location in the structure of the AVP-pVIc complex. Comparison of the positions of the four amino acids involved in catalysis by the AVP-pVIc complex to the positions of those amino acids in AVP reveals why AVP is inactive. In AVP, three of the catalytic amino acids, Cys122, Glu71 and Gln115, occupy nearly identical positions to the ones they have in the active AVP-pVIc complex. However, the position of His54 in AVP is different than its position in the AVP-pVIc complex. The His54 N6 has moved from being 3.87 Å from the Cys122 Sγ nucleophile in the AVP-pVIc complex to being to 7.01 Å away in AVP. This is a result of the repositioning of the loop containing residues 46-54 in AVP. This movement, of 3.14 Å, puts His54 and its N6 atom at a distance and in an orientation by which it can no longer abstract the proton on Sγ. Thus a thiolate-imidazolium ion-pair cannot form that would render Cys122 nucleophilic. As a consequence, AVP cannot be catalytically active.

There is a fifth amino involved in catalysis by the AVP-pVIc complex. In the AVP-pVIc complex structure, His54 forms a cation-π interaction with Tyr84. The preferred mode for such an interaction is usually stacked offset (face-to-face with the rings in a staggered arrangement) (Samanta et al., 1999, Packing of aromatic rings against tryptophan residues in proteins. Acta Cryst. D., 55, 1421-1427). In barnase, Tyr 94 interacts more strongly with the protonated form of His18 (Loewenthal et al., 1992, Histidine-aromatic interactions in Barnase elevation of histidine $pK_a$ and contribution to protein stability. J. Mol. Biol., 224, 759-770). This aromatic-histidine interaction stabilizes the protonated form of histidine by 0.8-1 kcal mol$^{-1}$ relative to the unprotonated form, and, thereby, increases its pKa value. This function of the aromatic group would be analogous to that of the aspartic residue in the catalytic triad of the serine proteinase (Blow, 1976, Structure and mechanism of chymotrypsin. Acc. Chem. Res., 9, 145-152), i.e. to stabilize the protonated form of histidine in a transition state of a reaction in which the histidine acts as a proton acceptor. A second function of the cation-π interaction between Tyr84 and His54 may be that it prevents the imidazole ring from rotating thereby freezing its Nδ atom in a position that is optimal for the ion-pair interaction with Cys122. In AVP, Tyr84 is more than 11 Å away from its position in the AVP-pVIc complex. Thus, another reason AVP is inactive is that Try84 is too far away from His54 for a cation-π interaction to take place.

Substrate Binding Site in AVP.

In AVP, a substrate cannot bind in the active site. In the AVP-pVIc complex, the active site lies with a long deep curved groove at the domain interface that extends across one face of the structure. Near the middle, at the bend of the curve, is Cys122. A salt bridge between Glu5 and Arg48, located approximately 13 Å from the Cys122 Sγ, effectively seals one end of the groove. This salt bridge forms an end wall of the groove and forms part of a pocket deep enough to accommodate the P4 residue (Leu, Ile, or Met) of substrates containing AVP consensus cleavage sites. In the AVP structure, that salt bridge is absent. Furthermore, part of the loop containing His54 that connects β-strands S2 and S3 is repositioned. In AVP, residues 52 through 54 extend across the active site groove, effectively blocking it at Cys122. This leaves Cys122 at the base of this new wall. The repositioned portion of the His54 loop that lies across the active site groove also shortens the groove by about 11 Å. These changes render the active site unable to bind an AVP substrate.

pVIc Binding Site in AVP.

pVIc, FIG. 25B, appears to function as a strap holding together one domain containing Cys122 with the other domain containing His54 and Glu71 in a configuration for optimal catalysis, FIG. 25C. The N-terminus of pVIc (Gly1', Val2' and Gln3') binds in a pocket, the "NT-pocket," which is an invagination within the helical domain of AVP, FIG. 25A. Binding displaces a well-ordered Na atom in the "NT-pocket. That this pocket is structurally conserved between AVP, FIG. 25A and AVP-pVIc, FIG. 25C, implies that perhaps the first step in the binding of pVIc to AVP is the binding of the N-terminus of pVIc in this pocket. The binding of the next 3 amino acids of pVIc (Ser4', Leu5', and Lys6') also do not alter the structure of AVP; only surface side chain movements are necessary to accommodate these residues binding as an extended β-strand. It is at Arg7' and beyond that the binding of pVIc begins to induce significant rearrangements in AVP. The net results of these changes are formation of a disulfide bond between Cy10' of pVIc and Cys104 of AVP and the formation of a new pocket in AVP, the "CT-pocket," into which Phe11' of pVIc binds, FIG. 25C. Since in AVP, the location of Cys104 could not be defined, the extension of strand S5 and the formation of the disulfide bond between Cys104 and Cys10' can only happen as the binding of pVIc induces the formation of the "CT-pocket."

Model for the Activation of AVP by pVIc—Activation Pathways.

pVIc which exerts powerful control on the rate of catalysis by AVP, binds quite far from the active-site residues involved in catalysis; Cys104 of AVP, which forms the disulfide bond with Cys10' of pVIc, is 32 Å from Cys122, the active site nucleophile. One reason for this is that pVIc is a "molecular sled" that slides the AVP-pVIc complex along the viral DNA via one-dimensional diffusion to process the virion precursor proteins also bound to the viral DNA (Blainey et al., 2012, "Molecular sled"—11-amino acid peptide mediates one-dimensional biochemistry by sliding enzymes and substrates on DNA and Blainey et al., 2012, Viral proteinase slides along DNA to locate and process its substrates). If the active site were too close to pVIc, and, therefore, close to the DNA, it might be difficult for the active site to interact with substrate binding sites. But this then raises the questions as to how does the binding of pVIc far from the active site influence the active site residues involved in catalysis.

that this binding causes an extension of the last β-strand (S5) of the β-sheet by three amino acids-Ile105, Cys 104, and Ser110. After formation of a tight turn, the C-terminus of the long helix is extended from Ser95 to Ser99. In addition, this portion of the helix has rotated approximately 20 degrees from the long helix axis and changed its pitch by a similar amount. This is the common activation pathway, colored green FIG. 26A,B.

His54 Activation Pathway.

The extension of the helix by a full turn and its movement alter the positions of the side chains that interact with the coil connecting strands S1 and S2 (colored yellow in FIG. 26A,B) above the C-terminus of the helix. This results in repositioning of the backbone amino acids residues 26-33, Table 7, causing them to twist up to 180 degrees. Now, different regions of amino acids 26-28 are opposite some of the amino acids in the undefined loop between residues 47-52 in AVP; this change allows residues 26-28 to form hydrogen bonds with residues within the undefined loop such that it now becomes much less flexible. This rearrangement moves the backbone of His54 and enables His54 to drop down to its position optimal for catalysis.

TABLE 7

Phi and Psi angles and alignment rmsd in residues between β-strands S1 and S2 in AVP versus AVP-pVIc. RMSD values are calculated with AVP as the reference molecule. Largest deviations are between residues 28 through 32.

|  | AVP | | | AVP-pVIc | |
| --- | --- | --- | --- | --- | --- |
|  | phi | psi | rmsd (A) | phi | psi |
| Tyr25 | -128 | 148 | 0.534 | -137 | 163 |
| Asp26 | -99 | 107 | 1.488 | -89 | -172 |
| Lys27 | 68 | -49 | 1.120 | -60 | -13 |
| Arg28 | -89 | 159 | 2.595 | -85 | 9 |
| Phe29 | -72 | 164 | 2.109 | -46 | 122 |
| Pro30 | -55 | 157 | 2.907 | -66 | -30 |
| Gly31 | -57 | -43 | 3.655 | 120 | -176 |
| Phe32 | -156 | 160 | 2.889 | -98 | 131 |
| Val33 | -123 | 153 | 2.513 | -118 | 79 |
| Ser34 | -105 | 146 | 0.926 | -158 | 66 |
| Pro35 | -71 | -4 | 0.967 | -62 | -23 |
| His36 | -113 | -2 | 0.324 | -129 | 15 |

The structural changes that occur upon the binding of pVIc to AVP are localized to more than half of the β-strand domain and appear to follow a path over 62 amino acids, FIG. 26. This implies there may be an "activation" pathway in which contiguous conformation changes occur, like falling dominos. Applicants' model is: Upon the binding of pVIc to AVP, a series of structural transitions occurs in AVP beginning with the induction of the CT-pocket, FIG. 26A. There is a common pathway, green in FIG. 26B that then bifurcates into a pathway that leads to the repositioning of Tyr84, yellow in FIG. 26B, and into a pathway that leads to repositioning of His54, blue in FIG. 26B. His54 and Tyr84 are the two amino acids in AVP that must move in order for the AVP-pVIc complex to become active.

Common Activation Pathway.

The activation pathway is triggered when the three N-terminal amino acids of pVIc bind in a preformed, hydrophobic pocket, the NT-pocket, on AVP. Beginning with Leu5', the remaining amino acids of pVIc lay down upon AVP as an extended β-strand. Cys10' of pVIc forms a disulfide bond with Cys104 of AVP. The C-terminal amino acid, Phe11', binds in an induced, hydrophobic pocket. The differences in the structure of AVP and the AVP-pVIc complex indicate Tyr84 Activation Pathway.

Triggering of the common activation pathway which ends at Ser99 also initiates changes in the Tyr84 branch of the activation pathway, (colored blue in FIG. 26A,B. At Tyr88, the long helix breaks, changing into a coil which continues through Tyr84. The opening of this portion of the long helix, along with the 'tethering' of the N-terminal portion to the central strand of the beta sheet, enables the N-terminal portion of the long helix to rotate roughly 105 degrees finalizing the helix-coil-helix motif of AVP-pVIc. This movement also completes the formation of the active site groove across the domain interface. These events allow Tyr84 to move almost 11 Å so that it can now form a cation-π interaction with His54.

The structure of AVP, in comparison with the structure of the AVP-pVIc complex, revealed why AVP is inactive and provided insights into the mechanisms of activation of AVP by the binding of pVIc. In AVP and in AVP-pVIc complexes, most of the α-helical domains are almost identical in structure. The orientation of the nucleophile and the oxyanion hole are maintained, as is the region of molecule that interacts with the N-terminus of pVIc. There are, however, major differences in structure in the loops and in the β-sheet domain between the active and inactive forms of the enzymes. Loop flexibility, in particular, plays a significant role in the change from the inactive to the active state. Although pVIc binds quite far from the active site, the binding of its C-terminus into the CT-pocket and subsequent formation of a disulfide bond between pVIc Cys10' and AVP Cys104, initiates activation pathways. The change from a single long helix to a helix-coil-helix and the rearrangements of the two disordered loops result in the movement of His54 to a position in the structure where it can interact with the nucleophile, Cys122 and in the movement of Tyr84 to a position over His54 such that a cation-π interaction occurs undoubtedly adds to the nucleophilicity of the active site. The high resolution crystal structure reported here should facilitate the identification of compounds that prevent AVP from being active and therefore act as antiviral agents.

AVP.

Recombinant adenovirus proteinase (AVP) was purified from *E. coli*, as described previously (Anderson, 1993, Expression and purification of the adenovirus proteinase polypeptide and of a synthetic proteinase substrate. Protein Express. Purif., 4, 8-15 and Mangel et al., 1996). The concentration of AVP was determined using a molar absorbance coefficient at 280 nm of 26,510 calculated according to the method of Gill and von Hippel (Gill and von Hippel, 1989, Calculation of protein extinction coefficients from amino acid sequence data. Anal. Biochem., 182, 319-326).

Crystallization.

Crystals of AVP were obtained by vapor diffusion with microseeding as described previously (Baniecki et al., 2002, Adenovirus proteinase-crystallization and preliminary x-ray diffraction studies to atomic resolution. Acta Crystallogr., D58, 1462-1464). Prior to data collection, crystals were equilibrated with a cryoprotectant buffer consisting of 0.4 M sodium citrate, pH 5.6, 0.8 M sodium acetate, and 40% (v/v) glycerol. The glycerol concentration in the crystal droplets was increased in 4% increments at 5 minute intervals until the glycerol concentration reached 25%. Crystals were then placed in cryoloops and flash-frozen in the 100 K nitrogen stream. (Oxford Cryosystems, Oxford, UK).

Data Collection.

X-ray diffraction data were collected at Beamline X25 at the National Synchrotron Light Source at Brookhaven National Laboratory. The intensities were recorded using a Brandeis 4 k CCD detector (Phillips et al., 2000, Multiple CCD detector for macromolecular X-ray crystallography. J. Appl. Cryst., 33, 243-251 and Strauss et al., 1990, Large aperture CCD x-ray detector for protein crystallography using a fiberoptic taper. Proc. Soc. Photo-Opt. Instr. Eng., 1447, 12-27). The wavelength was 0.986 Å. High resolution data was collected with 60 sec exposures at a crystal to detector distance of 71.8 mm and 0.60 oscillations. The low resolution data was obtained at the same distance also with 0.60 oscillations using an attenuated beam and 10 sec exposures. The data were merged and processed with the software package HKL2000 (Otwinowski and Minor, 1997, Processing of X-ray diffraction data collected in oscillation mode. Methods Enzymol., 276, 307-326). Analysis of the data indicated the AVP crystals belonged to the $P2_1$ space group with unit cell parameters a=36.2, b=54.1, c=42.1 Å, β=100.1°.

Structure Refinement.

A clear molecular replacement solution was obtained with the starting model the coordinates of AVP from the AVP-pVIc structure (RCSB code 1NLN) (McGrath et al., 2003, Crystallographic structure at 1.6-Å resolution of the human adenovirus proteinase in a covalent complex with its 11-amino-acid peptide cofactor: insights on a new fold. Biochem. Biophys. Acta, 1648, 1-11) using the program AMoRe (Navaza and Saludijan, 1997, AMoRe: an automated molecular replacement program package. Methods Enzymol., 276, 581-594). The refinement was cross-validated by the $R_{free}$ index (Brünger, 1992, Free R value: A novel statistical quantity for assessing the accuracy of crystal structures. Nature, 355, 472-474), calculated using 5% of all reflections. The refinement was initiated using the program REFMAC (Murshudov et al., 1997, Refinement of macromolecular structures by the maximum-likelihood method. Acta Cryst., D53, 240-255). The energy function as well as X-ray terms were used as targets in the minimization procedure and the model subjected to isotropic refinement. Rigid body refinement in the resolution range of 8.0-3.0 Å was performed to compensate for any small differences in unit cell parameters. This refinement was followed by positional and overall B factor refinements with the resolution range extended to 1.5 Å. After each round of refinement, visual inspection and model corrections were made using the program Quanta (Molecular Simulations, Inc). B factors were individually refined for all non-hydrogen atoms. All reflections were used in both refinement and map calculations in all steps.

After several rounds of refinement, the diffraction data was extended to its highest resolution, 0.98 Å, and refinement continued using the program SHELXL (Sheldrick and Schneider, 1997, SHELXL: High-resolution refinement. Methods Enzymol., 277, 319-343). During the first five cycles of refinement, isotropic B factors were refined for all atoms. Later, non-hydrogen atoms were refined using anisotropic displacement parameters. At this stage, hydrogen atoms were introduced into well-ordered parts of the structure at stereochemically calculated positions. For all hydrogen atoms included in the refinement, isotropic B factors that were 20% higher than those of the parent atoms (50% higher in the case of methyl hydrogens) were applied. Manual adjustments of the model were performed with the program Quanta. The occupancies of atoms present in double conformations were refined as constrained (x) and (1-x). Water molecules were classified as either fully or half-occupied on the basis of their electron density and their distance to neighboring atoms. Their occupancies were not refined, because refinement of both occupancies and temperature factors at resolutions approaching 1 Å is generally not stable (Sevcik et al., 1996, Acta Crystallogr. Sect. D, 52, 327-344). The quality of the geometrical and stereochemical indices were continuously monitored using the program PROCHECK (Laskowski et al., 1993, PROCHECK: a program to check the stereochemical quality of protein structures. J. Appl. Cryst., 26, 283-291).

| Δ | $K_d$ | Max | Cntl | KCC | $K_m$ | $k_{cat}$ | | |
|---|---|---|---|---|---|---|---|---|
| GVQSLKRRRCF (SEQ ID NO: 12) | | | | | | | | |
| | 0.76 ± 0.27 | | | (20) | 6.36 ± 0.33 | 15.89 ± 0.25 V | (5.1) | KM |
| | | | | (20) | 12.8 | 27.7 V | | V |
| | 2.42 ± 0.79 | | | | 302 ± 0.94 | 2.52 ± 0.29 | | M |
| | 1.45 ± .544 | | | | 2.28 ± 0.0247 | 0.88 ± 0.039 | | J |

-continued

G̶VQSLKRRRCF (Residues 2-11 of SEQ ID NO: 12)
| | | | | | | | |
|---|---|---|---|---|---|---|---|
| 23.2 ± 9.1 | 23 ± 2.15 | 32 | (125) | 7.57 ± 0.053 | 20.23 ± 0.06 | (7.3) | KM |
| 2.70 ± 0.59 | | | | 3.47 ± 0.84 | 4.00 ± 0.42 | | M |

G̶V̶QSLKRRRCF (Residues 3-11 of SEQ ID NO: 12)
| | | | | | | | |
|---|---|---|---|---|---|---|---|
| 115 ± 22 | 13 ± 0.08 | 32 | (500) | 11.03 ± 0.26 | 20.4 ± 0.24 | (7.4) | KM |
| 56.4 ± 12.6 | | | | 3.07 ± 0.84 | 1.25 ± 0.08 | | M |

G̶V̶Q̶SLKRRRCF (Residues 4-11 of SEQ ID NO: 12)
| | | | | | | | |
|---|---|---|---|---|---|---|---|
| 797 ± 290 | 22 ± 4.7 | 33 | (600) | 13.3 ± 1.2 | 16.8 ± 0.8 | (5.9) | KM |
| 599 ± 49.6 | 14 ± 0.5 | 26 | | | | | KM |
| 16.5 ± 4.60 | | | | 4.52 ± 1.03 | 0.66 ± 0.04 | | M |
| 271 ± 59 | | | | | | | L |

G̶V̶Q̶S̶LKRRRCF (Residues 5-11 of SEQ ID NO: 12)
| | | | | | | | |
|---|---|---|---|---|---|---|---|
| 106 ± 60 | 11.3 ± 1.2 | 22 | (500) | 14 ± 0.89 | 18.6 ± 0.64 | (7.6) | KM |
| 28 ± 9.5 | 2.8 ± 0.5 | 26 | | | | | KM |
| 0.287 ± 0.05 | | | | >>20 µM | | | J |

G̶V̶Q̶S̶L̶KRRRCF (Residues 6-11 of SEQ ID NO: 12)
| | | | | | | | |
|---|---|---|---|---|---|---|---|
| 212.8 ± 27 | 7.7 ± 0.5 | 27 | (1000) | 17.7 ± 0.82 | 27.3 ± 0.7 | (7.6) | KM |
| 0.62 ± 0.16 | | | | >>20 | — | | J |

G̶V̶Q̶S̶L̶K̶RRRCF (Residues 7-11 of SEQ ID NO: 12)
| | | | | | | | |
|---|---|---|---|---|---|---|---|
| 111.9 ± 21.3 | 1.7 ± 0.12 | 27 | (560) | 36.6 ± 3.16 | 9.26 ± 0.57 | ( ) | KM |
| 51 ± 5.9 | | | | 11.84 ± 2 | 0.27 ± 0.02 | | J |

G̶V̶Q̶S̶L̶K̶R̶RRCF (Residues 8-11 of SEQ ID NO: 12)
| | | | | | | |
|---|---|---|---|---|---|---|
| NA (up to mM) | | 24 | ( ) | | | KM |
| 155 ± 26.6 | | | | 3.57 ± 0.49 | 0.103 ± 0.005 | J |

G̶V̶Q̶S̶L̶K̶R̶R̶RCF (Residues 9-11 of SEQ ID NO: 12)
| | | | | | | |
|---|---|---|---|---|---|---|
| NA | | 24 | ( ) | | | KM |
| 33.77 ± 1.52 | | | | 11.1 ± 1.66 | 0.083 ± 0.006 | J |

G̶V̶Q̶S̶L̶K̶R̶R̶R̶CF (Residue 11 of SEQ ID NO: 12)
| | | | | | | |
|---|---|---|---|---|---|---|
| | | | ( ) | | | KM |
| 99 & 97 | | | | ± | ± | L |

From the other end

| Δ | K$_d$ | Max | Cntl | KCC | K$_m$ | k$_{cat}$ | |
|---|---|---|---|---|---|---|---|

GVQSLKRRRC̶F̶ (Residues 1-10 of SEQ ID NO: 12)
| | | | | | | | |
|---|---|---|---|---|---|---|---|
| | | | | | | ( ) | KM |
| | 0.006 ± 0.0013 | | | | 1.48 ± 0.127 | 0.009 ± 0.0003 | J |
| | 0.30 ± 0.24 | | | | 0.97 ± 0.19 | 0.14 ± 0.02 | M |

GVQSLKRRR̶C̶F̶ (Residues 1-9 of SEQ ID NO: 12)
| | | | | | | | |
|---|---|---|---|---|---|---|---|
| | | | | | | ( ) | KM |
| | 80 ± 23.5 | | | | 7.16 ± 2.19 | 0.0092 ± 0.00042 | J |
| | 0.85 | | | | 0.74 ± 0.25 | 0.09 ± 0.01 | M |

GVQSLKRR̶R̶C̶F̶ (Residues 1-8 of SEQ ID NO: 12)
| | | | | | | | |
|---|---|---|---|---|---|---|---|
| | | | | | | ( ) | KM |
| | 273 ± 23.3 | | | | >>20 | 0.133 ± 0.046 | J |
| | 10.2 | | | | 0.82 ± 0.25 | 0.09 ± 0.01 | M |

GVQSLKR̶R̶R̶C̶F̶ (Residues 1-7 of SEQ ID NO: 12)

GVQSLK̶R̶R̶R̶C̶F̶ (Residues 1-6 of SEQ ID NO: 12)

Example 7: Speeding Up Bimolecular Association Reactions by the Use of a Molecular Sled As a proof-of-principle system to demonstrate the speeding up of bimolecular association using pVIc Applicants used biotin-streptavidin association. To observe the rate increase Applicants performed a solution-phase FRET experiment with acceptor-labelled streptavidin and donor-labelled biotin, both functionalised with a sled, in the presence/absence of DNA in the solution (FIGS. 27-30).

Compounds and materials were obtained from the sources indicated: salmon sperm DNA, Cy5-labelled streptavidin (Life Technologies); biotin-PEG (23 units)-pVIc conjugate and pVIc labelled with Cy3 at its N-terminus were synthesised by Bio-Synthesis, Inc.; biotin-PEG-maleimide MW 5000 (Nanocs); the latter was coupled to the Cys10 of Cy3-pVIc by a conventional maleimide-to-cysteine coupling in a 25 mM PBS buffer, pH 7.3.

The experiments were performed in the following sliding buffer: 60% wt. glycerol, 10 mM MES, 2 mM NaCl, 20 mM Ethanol, 50 µM EDTA. High glycerol content as well as bulky PEG linkers on molecules are used to allow the fast binding kinetics to be experimentally observable. The reactions were run in a 3 mL quartz cuvette (FP-1004, Jasco) on Jasco FP-8300 spectrofluorometer at 20° C., continuously stirred at 800 rpm. The excitation and emission wavelengths were 520 nm and 666 nm correspondingly. The reaction read-out is FRET signal detected as a function of time.

Cy5-streptavidin was functionalised with a sled by incubating it with a two-fold excess of biotin-PEG-pVIc in the sliding buffer for 20 min. The reaction mix of a final volume 3 mL contained 37.5 nM Cy5-streptavidin, 75 nM biotin-PEG-pVIc (no fluorescent label), DNA if indicated and 150 nM Cy3-pVIc-PEG-biotin, which was rapidly injected into the cuvette with a syringe after having started recording the FRET vs. time trace.

Applicants assumed the bimolecular association to follow single exponential law $I_{FRET} \propto (1-e^{-t/\tau})$ and Applicants fit the experimental data likewise. Applicants extracted reaction times τ from the fit for different DNA concentrations to find the conditions of optimum speed up. The average reaction time in the absence of DNA was found to be 90 s, while at the point of maximal speed up it was 15 s. Thus, a six-fold acceleration is achieved. The point of optimum speed up lies at such DNA concentration, that on average there are several molecules of both of the reagents per one DNA molecule.

Increasing the DNA concentration leads to a rapid increase of reaction time back to initial values for in this case there is only one molecule of each reagent per several DNA molecules, which leads to the effective separation of biotin and streptavidin by DNA.

Applicants developed a model to describe the kinetics of bimolecular reaction in the presence/absence of DNA. Within this model, negatively charged DNA molecules are considered to act as sinks for positively charged pVIc molecules. Once bound to DNA, pVIc performs a one-dimensional random walk along DNA with a binding lifetime of approximately 1 s and diffusion coefficient of $3 \leqslant 10^7$ bp$^2$/s, as determined in single-molecule experiments. Reducing the dimensionality of search helps facilitate the process of molecules encountering each other.

Example 8: A Molecular Sled Carrying Cargoes Along DNA

Some of the most successful ideas in biotechnology are inspired by nature. The millions of years biological processes have had to optimize some of the most challenging biochemical processes provide many clues on how Applicants can optimize man-made processes and systems. In this Example, Applicants propose to study the mechanism by which certain viral proteins utilize DNA as a catalyst to reduce the dimensionality of search processes and thus dramatically speed up protein-protein interactions. Applicants take the lessons learned from this system and use them to design a generic approach that enhance reaction rates in a variety of biotechnological and pharmaceutical processes, from PCR reactions to the development of antibiotics.

This Example revolves around pVIc, an 11-amino-acid peptide from the adenovirus, a virus that is responsible for up to 5% of infant upper respiratory infections in the western world (source; Center for Disease Control, U.S.A.).Before infection of a cell, a large number of proteins within a single viral particle need to be proteolytically processed by the adenovirus protease (AVP). However, the large number of protease targets within one particle (~3200) and the small number of proteases (~70) means that every single AVP protease protein need to cleave several dozens of protein targets. The tight packing of protein and DNA within the viral particle makes regular three dimensional diffusion as a mechanism for the protease to travel from one target to the other impossible. Instead, the AVP recruits the short pVIc peptide, itself a proteolytic product in early maturation, that in turn renders the protease to slide along the DNA inside the particle and thus effectively reduces the search space for the protease from a three-dimensional one into a one-dimensional one. Some of the most successful ideas in biotechnology are inspired by nature. The millions of years biological processes have had to optimize some of the most challenging biochemical processes provide many clues on how Applicants can optimize man-made processes and systems. In this Example, Applicants study the mechanism by which certain viral proteins utilize DNA as a catalyst to reduce the dimensionality of search processes and thus dramatically speed up protein-protein interactions. Applicants take the lessons learned from this system and use them to design a generic approach that enhance reaction rates in a variety of biotechnological and pharmaceutical processes, from PCR reactions to the development of antibiotics.

This Example revolves around pVIc, an 11-amino-acid peptide from the adenovirus, a virus that is responsible for up to 5% of infant upper respiratory infections in the western world (source; Center for Disease Control, U.S.A.).Before infection of a cell, a large number of proteins within a single viral particle need to be proteolytically processed by the adenovirus protease (AVP). However, the large number of protease targets within one particle (~3200) and the small number of proteases (~70) means that every single AVP protease protein need to cleave several dozens of protein targets. The tight packing of protein and DNA within the viral particle makes regular three dimensional diffusion as a mechanism for the protease to travel from one target to the other impossible. Instead, the AVP recruits the short pVIc peptide, itself a proteolytic product in early maturation, that in turn renders the protease to slide along the DNA inside the particle and thus effectively reduces the search space for the protease from a three-dimensional one into a one-dimensional one.

In the first part of the Example, Applicants describe a novel scheme to tag individual proteins with unprecedently bright and photostable fluophores. Using these new dyes and coupling strategies, Applicants label the protease and the pVIc peptide and use single-molecule imaging to directly demonstrate the role of the pVIc peptide in the adenovirus proteolytic maturation pathway. Applicants perform these experiments on linear stretched DNA (corresponding to a true one-dimensional situation), but also expand to 2-dimensional structures (using DNA origami) and three-dimensional DNA environments (tightly packed DNA in artificial viral capsids). Especially the latter two systems represent novel chemical biology tools for answering relevant questions in biology.

Subsequently, Applicants adopt the pVIc peptide as molecular building block to speed up biotechnologically relevant reactions in vitro. Firstly, Applicants use as a proof-of-principle reaction the association between biotin and streptavidin. Using FRET spectroscopy, Applicants monitor the association kinetics between pVIc-coupled biotin and pVIc-coupled streptavidin. Applicants use DNA present in the solution to allow the pVIc moieties to bind to DNA and use the DNA as a catalyst to speed up search by the biotin and streptavidin.

In a next step, Applicants develop novel molecular coupling strategies based on ternary complex formation for the fabrication of peptide-oligonucleotide conjugates. These molecular hybrids containing pVIc are used as primers in PCR reactions. Allowing the DNA primers to move along DNA rapidly allow them to arrive at hybridization sites much more rapidly than conventional three-dimensional diffusion allow them to. In this way, the overall reaction time for PCR is significantly reduced. Moreover, the reversibility of the ternary complex allows improved protocols for purification and immobilization of amplicons.

Finally, Applicants use the pVIc molecular sled in a number of in vivo applications. First, Applicants display the pVIc on the bacterial surface to speed up transformation. By allowing plasmid DNA to transiently bind to the outer membrane of E. coli, Applicants are able to increase the uptake of plasmids upon electroporation or salt treatment. Secondly, the pVIc molecular sled is presented on the inner cell surface in order to accelerate the production of membrane proteins. By positioning the plasmid at the periphery of the membrane the initial step of membrane protein biogenesis is located at the final destination of the mature protein. In this way, Applicants significantly reduce or even avoid the diffusion of the ribosome nascent chain complex. Thirdly, Applicants couple the pVIc sled to antibiotics. By using antibiotics that target DNA-bound proteins (such as gyrase inhibitors), Applicants are able to drastically decrease the time required to find gyrase proteins inside the crowded environment of the cell. An improvement in these kinetics lead to higher efficacies of this class of antibiotics and to potentially much lower dosages needed for treatment.

Applicants are proposing to understand how the adenovirus uses a short peptide (pVIc) to facilitate diffusive search of proteins along DNA and Applicants adopt this approach to speed up bimolecular association kinetics in a variety of biotechnologically relevant processes. To allow Applicants to transform this molecular building block into a widely applicable tool, Applicants need to develop a variety of chemical coupling chemistries to integrate pVIc into other molecular systems, both in vitro and in vivo.

The single molecule fluorescence studies as they are carried out in this project require the development of ultrastable water soluble dyes and conjugation strategies to allow tracking of the labelled peptides and proteins over extended period of times and extraction of quantitative kinetic data from these experiments.

Besides tagging biomacromolecules with fluorophores the pVIc peptide is chemically modified with gyrase inhibitors. These novel drug-peptide conjugates result in more efficient antibiotics to fight bacterial infection and resistance. Moreover, a completely new strategy for the preparation of difficult-to-synthesize peptide-oligonucleotide conjugates is envisaged that relies on ternary complex formation employing cucurbiturils that as host accommodate two guest molecules. These supramolecular hybrids enable the speed up of the biotechnologically important process of the polymerase chain reaction and offer further applications for the purification of PCR amplicons and their immobilization. The concept of supramolecular chemistry as tool in chemical biology is further extended by employing DNA origami with immobilized oligonucleotide-fluorophore conjugates to mimic and measure peptide sliding in crowded DNA environments. This is even taken further to 3D nanoobjects by compacting DNA within virus capsids—again making use of supramolecular interactions between nucleic acids and viral coat protein.

Several selective conjugation chemistries are developed to label peptide and DNA structures to generate efficient probe systems. By generating fusions of the molecular peptide sled with proteins located in the inner membrane Applicants direct membrane protein biosynthesis close to the location where they are incorporated and therewith significantly increase their expression levels. Finally, with displaying the peptide sliding motif at the cell surface Applicants localize DNA kinetically at the outer cell membrane so that recombinant nucleic acids can be taken up more effectively during transformation.

Applicants propose here to adopt a building block from nature, the 11-amino-acid adenovirus peptide pVIc that facilitates one-dimensional searching of proteins along DNA, and use it to speed up a variety of biotechnologically relevant reactions. Applicants' approach is highly multidisciplinary: Applicants develop and use organic chemistry as well as supramolecular chemistry tools to modify both proteins and nucleic acids with this peptide moiety and use novel single-molecule techniques to study its behavior. Single-molecule tools juxtaposed with dye chemistry and biomolecular conjugation strategies allow Applicants to throw light upon the complex multi-protein systems and to explore the new possibilities of enhancement of elaborate biotechnological systems.

DNA-protein interactions play a fundamental role in many biological processes, such as transcription, DNA repair, replication, and recombination. A fundamental challenge in many of these processes is the identification and targeting of specific, rare sites on DNA. For example, in order to control gene expression, transcription factors or repressor proteins often have to find one specific site on the DNA that is surrounded by billions of basepairs of 'wrong' DNA. Another example is the identification of small numbers of damaged bases in the genome by DNA-repair proteins.

In the search for its target site, the DNA-binding protein is facing both thermodynamic and kinetic difficulties. The thermodynamic challenge lies in recognizing and tightly binding a cognate (specific) site among the billions of other (non-specific) sequences on the DNA. The kinetic difficulty lies in finding a cognate site in mere seconds amidst the crowded cellular environment that is filled with other DNA sequences and proteins. For decades, it has been known that instead of relying only on 3-dimensional diffusion to associate with a target on DNA, many of these proteins reduce the dimensionality of this search process to speed up recognition. Every time the protein associates with the DNA, it transiently diffuses along the DNA in a one-dimensional fashion and thus drastically increases the number of sampled DNA positions per time unit. It then dissociates again from the DNA, diffuses through solution to rebind the DNA at an entirely different region and again searches a stretch by one-dimensional diffusion. This combination of three- and one-dimensional diffusion gives rise to a drastic increase in the effective bimolecular association rate constant that describes the association kinetics of the protein with its target.

In this Example, Applicants decipher a biological system in which one-dimensional diffusion of a protein along DNA is used to speed up molecular recognition processes that otherwise would have little chance of succeeding. Applicants lay out a strategy to utilize the molecular components that allow such a rate enhancement to speed up any type of reaction whose kinetics are limited by the association of two macromolecules. Applicants show that biotechnologically important reactions, such as primer annealing in PCR and the binding of antibiotics to their DNA-associated targets, can be significantly improved using such an approach.

As a basis for Applicants' work, Applicants use the recent discovery of a small peptide involved in adenovirus maturation that allows proteins to search along DNA in environments that are too crowded to allow any three-dimensional diffusion. It was shown that during the maturation of an adenovirus particle ~70 copies of the adenovirus protease (AVP) have to cleave ~3200 target proteins situated on the viral DNA in order to render virus particles infectious. The crowded environment in the 100-nm sized viral particle makes it impossible for the AVP proteins to utilize regular three-dimensional diffusion to find the large number of protease targets.

Figure 11A:
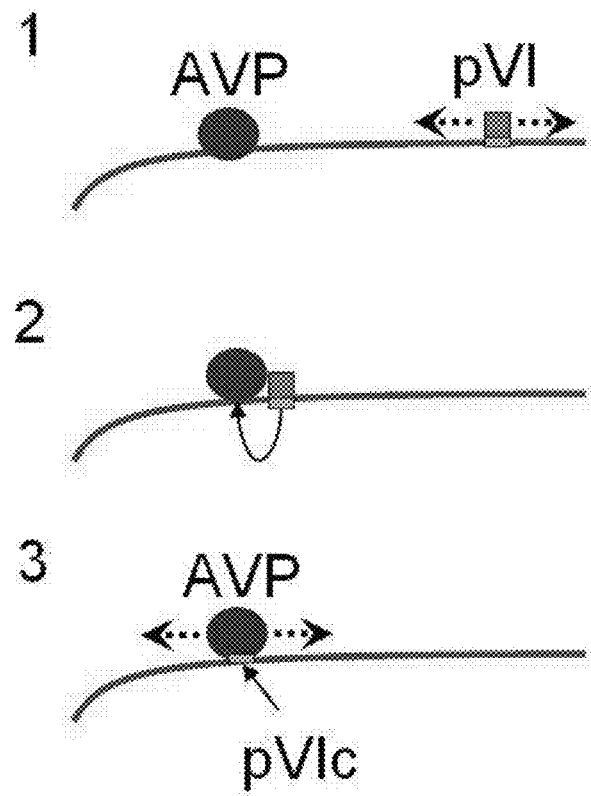
FIG. 11A. AVP is randomly distributed along the viral DNA and, as of yet, unable to move along the DNA (FIG. 11A, panel 1). The precursor of protein VI (pVI) is bound to DNA as well and diffuses one-dimensionally until it runs into AVP, an association that triggers the proteolytic cleavage of pVI at its carboxyl terminus (FIG. 11A, panel 2). This reaction liberates the 11-amino acid pVIc peptide, which binds tightly to the AVP. The resultant AVP-pVIc complex is now able to rapidly diffuse in a one-dimensional (1D) fashion along the viral DNA (FIG. 11A, panel 3). This 1D movement allows the AVP-pVIc complex to rapidly scan the viral genome to locate the large number of protease targets that are distributed along the DNA.

At the start of maturation, AVP is randomly distributed along the viral DNA and, as of yet, unable to move along the DNA (FIG. 11A, panel 1). The precursor protein VI (pVI) is bound to DNA as well and diffuses one-dimensionally until it runs into AVP, an association that triggers the proteolytic cleavage of pVI at its carboxyl terminus (FIG. 11A, panel 2). This reaction liberates the 11-amino acid pVIc peptide, which binds tightly to the AVP. The resultant AVP-pVIc complex is now able to rapidly diffuse in a one-dimensional (1D) fashion along the viral DNA (FIG. 11A, panel 3). This 1D movement allows the AVP-pVIc complex to rapidly scan the viral genome and target the large number of protease targets that are distributed along the DNA.

Applicants and others have obtained single-molecule data that directly shows the efficient and fast diffusive movement of pVIc along DNA (unpublished). In this Example, Applicants build upon these experiments and use single-molecule fluorescence imaging techniques in combination with improved fluorophores and novel conjugation protocols as chemical biology tools to visualize this unprecedented example of one dimensional biochemistry. Subsequently, Applicants utilize the molecular building blocks that allow this process to design a generic approach that allows the speed up of any type of bimolecular association between macromolecules using DNA as a catalyst for search.

Applicants combine chemical biology tools with single-molecule techniques to reconstitute the maturation reactions at three different levels, corresponding to the search mechanisms in one, two, and three dimensions. Thus, dimension by dimension, Applicants are able to relate the one-dimensional search reactions taking place on the DNA to the three-dimensional crowded DNA environment of an adenovirus particle.

Figure 11B:
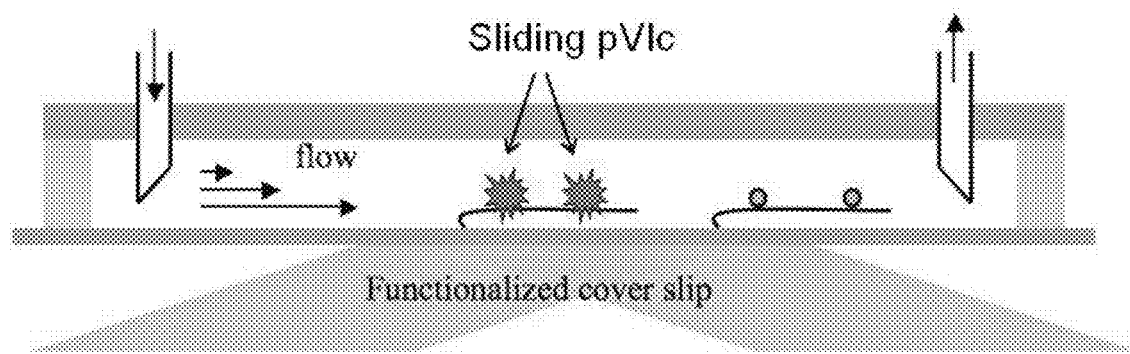
FIG. 11B. Anchoring linear fragments of DNA to the top surface of a microscope coverslip using a biotin-streptavidin interaction and stretch the DNA molecules by applying a laminar flow over the surface.

Applicants anchor linear fragments of DNA to the top surface of a microscope coverslip using a biotin-streptavidin interaction and stretch the DNA molecules by applying a laminar flow over the surface (FIG. 11B). Applicants fluorescently label the AVP and pVI proteins with dyes of different colour (using the perylene and terrylene dyes described below) and use total-internal-reflection fluorescence (TIRF) microscopy to image the fluorescence signals coming from the individual proteins moving along the DNA. Others have successfully used this approach to visualize the movement of transcription factors along individual DNA molecules.

FIG. 29 shows preliminary data Applicants have obtained visualizing the rapid one-dimensional diffusive movement of individual, fluorescently labelled pVIc peptide molecules along DNA (panel A: fluorescence trace, B: high-precision tracked trace, C: mean-square displacement versus time). From the data, it is clear that Applicants can track protein movements with a time resolution of ~50 ms and spatial resolution of ~25 nm. Building on these experiments, Applicants fluorescently label the various proteins involved in the AVP proteolytic pathway and directly visualize the kinetics of this process. In particular, Applicants label AVP with one colour and pVI with another. Thus, Applicants provide definitive data to support the hypothesis that pVIc moves along DNA, encounters immobilized AVP, which in turn cleaves of pVIc and uses it as a 'sled' to move along DNA. Applicants label pVI in two different positions: 1) at its C-terminal end (using a mutant that has only one cysteine close to the 11-a.a. C-terminal region). Using this protein, Applicants expect to see mobile, fluorescently labelled pVI that associates with the immobile AVP, after which the fluorescence of the pVI remains co-localized with the AVP in a complex that is now moving along the DNA (the AVP-pVIc complex). 2) at its N terminus (using aminereactive dyes at low pH to selectively couple to the N-terminal amine). Using the N terminally labelled pVI, Applicants expect to detect the association of pVI with AVP, upon which the pVI becomes immobile and the AVP mobile.

The combination of these experiments directly test the hypothesis that proteolytic cleavage of pVI by AVP results in a transfer of the pVIc molecular sled to AVP and thus renders AVP in a state in which it can freely diffuse along DNA. These experiments show how nature utilizes the concept of small, transferable modules to allow proteins to rapidly search along DNA.

One critical issue in observing biological entities at the single-molecule level by means of fluorescence is the label: it should be water-soluble, highly fluorescent in aqueous environment, and have a reactive group for attachment to the biomolecule, like the short sliding peptide pVIc or the adenovirus protease AVP. Moreover, the attachment should not affect the structure or function of the enzyme and its activity. Finally, an exceptional photostability of the label is needed for visualisation or tracking over a sufficient period of time. All these requirements can be met using charged rylenebisimides chromophores that have already been successfully employed in biorelated single molecule spectroscopy (SMS) experiments. For tracking of pVIc on extended DNA the corresponding amino acid sequence is synthesized by solid phase peptide synthesis (SPPS) bearing a N-terminal cysteine (Cys) to allow for specific conjugation with the thioestermodified water soluble perylenediimide derivative 1 that was successfully coupled to a derivative of the major light-harvesting complex (LHCII) (FIG. 28). For multicolour labelling of AVP, pVIc and protease targets Applicants hark back to the well known perylenes 2a and 2b as well as the new analogous terrylen derivatives 3a and 3b functionalized with amine and thiol-reactive groups, respectively (FIG. 28). The site selective incorporation of fluorophores in the proteins requires the introduction of point mutations at the surface of the protease scaffold, at the DNA sliding motif and the AVP targets. Alternatively, the protease can also be expressed with an N-terminal Cys via the well established intein technique employing fusions with the chitin binding domain for on-column release of the protein ready for N-terminal conjugation with perylene 1.

Searching in a Two-Dimensional System.

The situation described above is, however, not representative for the true biology because instead of the process taking place on a stretched piece of DNA, in reality, the process takes place in a densely packed capsid of a virus, with the DNA folded up in a complicated 3D geometry. To simulate this situation Applicants increase the complexity of the system. Following the experiments described above that rely on stretched DNA molecules (i.e., a one-dimensional system), Applicants perform similar experiments on a two dimensional DNA scaffold, namely a DNA origami, which is herein employed as a supramolecular chemical biology tool. DNA origami is defined as the principle of folding DNA into particular nanoscale shapes and patterns. A long single-stranded scaffold is folded into the desired shape and is held in place by short oligonucleotide staple-strands. The scaffold and staples self assemble into the desired shape in a single step upon mixing and labelled staple strands can be introduced at any position of the 2D structure.

Extending the 1D sliding experiment, Applicants are interested in following the diffusion behavior of the sliding peptide and the protease on such an artificial non-natural DNA architecture. The read out is done by collecting a FRET signal arising from the interaction of the fluorophores on pVIc or AVP and the array of arranged labels on the origami. Alternatively, for AVP Applicants carry out the direct visualization via AFM as well. This is done by performing sequential AFM measurements on a surface as was previously described for a 2D-DNA walker. Since in the 2D structures adjacent double helices are bridged by the staple strands, these systems differ from highly compacted double stranded (ds) DNA. To account for this difference, Applicants vary crossover densities by changing the length of the staple strands and relate this parameter to the diffusion kinetics.

Searching in a Three-Dimensional System.

To visualise DNA-protein interaction in 3D one needs to reconstitute capsids with ds DNA in them and use FRET to monitor movement of labeled pVIc/AVP-pVIc along the DNA. It is best to label pVIc with donor and DNA-immobilized protease target with acceptor dyes. The time it takes for FRET signal to appear indicates the time the pVIc-AVP needs to find its target and this rate can perhaps be modulated by changing DNA packing density, allowing Applicants to link the observed relation between packing density and search kinetics in Applicants' 'synthetic' experiment with the adenovirus data.

Since it is impossible to reconstitute the complex AV in vitro it is planned to encapsulate dsDNA with the pVIc-AVP complex and a target in simpler protein cages. As such a model scaffold the icosahedral capsid of cowpea chlorotic mottle virus (CCMV) is envisaged, which is formed by 90 homodimers of 20 kDa coat protein (CP) arranged with T=3 quasi symmetry. Previously, a general loading strategy for the incorporation of hydrophilic and hydrophobic small molecules in this CCMV envelope was developed. The key step within this procedure was that ds DNA block copolymer micelles acted as an efficient template for the formation of CCMV capsids. Within this Example Applicants incorporate ds DNA and pVIc-AVP as well as its targets within the protein shell. It is well known that CCMV CP forms 17 nm diameter tubes with dsDNA longer than 500 base pairs, which are the first study objects for single-molecule experiments of AVP working within highly confined and condensed DNA environments. Subsequently, Applicants incubate plasmid DNA with CCMV CP that was beforehand treated with gyrase. In this way supercoiling and compacting of DNA are induced to achieve spherical CCMV capsid assemblies that resemble the spherical AV more closely.

The key goal of this Example is to adapt the one-dimensional search mechanisms used by the adenovirus protease to speed up biochemical reactions that are of biotechnological interest. The small size of the moiety responsible for the efficient search of AVP along DNA (an 11-amino acid peptide), makes it an ideal candidate of a molecular building block that can be fused to any macromolecule and render that molecule able to efficiently move along DNA. The general approach is that the binding partners in any bimolecular reaction can be equipped with this molecular sled and that DNA can be used as a "search catalyst" in solution to reduce the dimensionality of search and speed up bimolecular association.

A Model System: Biotin-Streptavidin Interactions.

Applicants use the canonical biotin-streptavidin interaction as a proof-of-principle system to demonstrate the speed up of bimolecular associations by using pVIc. To observe the rate increase Applicants perform a solution-phase FRET experiment with donor-labeled streptavidin-pVIc and acceptor-labeled biotin-pVIc in the presence (and absence) of large amount of DNA in the solution. To allow the fast binding kinetics to be experimentally observable, Applicants slow the reaction down by coupling large polymer molecules such as PEG to the biotin. Biotin-PEG is going to be attached to fluorescently labelled pVIc by a conventional maleamide-to-primary amine coupling. Applicants functionalize fluorescently labelled streptavidin with pVIc by making use of the tetravalent nature of streptavidin: Applicants prepare streptavin that has been stoichiometrically linked to biotin-PEG-pVIc (no fluorescent label) such that each streptavidin has one pVIc. Using temporally resolved FRET allow Applicants to monitor whether the presence of DNA allows the pVIc moieties on both the streptavidin and biotin to speed up their search and increases their bimolecular association rates.

An Application: Speeding Up Primer Annealing in PCR Reactions.

After establishing the proof of concept with the biotin-streptavidin-pVIc system the molecular sliding mechanism is exploited for applications in biotechnology, in particular the Polymerase Chain Reaction (PCR) where it speeds up DNA hybridization. PCR has become extremely important in medical and biological laboratories for various applications including DNA cloning for sequencing, the diagnosis of hereditary diseases, the identification of genetic fingerprints (used in forensic sciences and paternity testing) and pathogen detection.

The exponential amplification of DNA can be divided into three distinct steps. The first step is the denaturation of the template, followed by primer annealing (step 2) and elongation with the polymerase. Applicants believe that the PCR process, especially the annealing step, can be speeded up significantly by preparing single stranded (ss) DNA-pVIc conjugates that act as primers in PCR. These conjugates are able to reach their position for DNA strand invasion much faster than the unfunctionalized primers. The performance of oligonucleotide (ODN)-pVIc hybrids are assessed in real-time PCR experiments with a standard molecular beacon that efficiently reports amplicon formation. Special attention is paid to how far the annealing time of primers and primer concentration can be reduced. Applicants are well aware of the fact that during the denaturation step the template gets fully or partially separated depending on the sequence composition. The presence of ssDNA not impair with the action of pVIc since binding of the oligopeptide was recently also suggested to take place on ss substrates.

Assuming duration of 30 seconds for annealing during a standard PCR protocol (30 cycles), Applicants estimate to decrease the whole PCR procedure by 7 to 10 minutes employing pVIc modified primers, which has tremendous economic potential taking into account the widespread use of this technique.

Fabrication of the peptide-ODN conjugates is not a trivial task because the protecting groups used in solid phase synthesis of ODNs and peptides are incompatible with each other and, although covalent coupling after separate synthesis can be performed, both methods are only applicable on a restricted selection of sequences and require a number of preparation and purification steps which leads to product loss and low overall yields. To overcome these synthetic limitations, Applicants present a new way of conjugating ODNs to oligopeptides. The approach is based on the formation of a ternary complex involving cucurbit[8]uril (CB[8]), which is able to strongly bind two guest molecules, an electron deficient moiety as first guest and an electron rich second guest. It is planned to terminally functionalise the ODN sequence with methyl viologen (first guest) and the peptide sequence is synthesized with a N-terminal tryptophan-glycine-glycine sequence acting as second guest. Upon addition of CB[8] both units self-assemble into a conjugate system acting as primer in PCR.

The ternary complex formation employing CB[8] does not only offer an easy synthetic protocol for conjugate formation but exhibits additional possibilities for downstream processing. Removal of peptide fragments can easily be achieved by applying different stimuli (reduction, optical switching, addition of a competitive guest) so that amplicons can be further used in cloning procedures. Another interesting feature is that amplicons containing first guest molecules can be immobilized on surfaces modified with second guests allowing implementation in PCR purification kits or for surface functionalization of DNA chips or nanoparticles.

In addition to the utilization of pVIc as a means of speeding up recognition processes in in vitro applications, this molecular sled offers a multitude of potential applications in in vivo processes. Here, Applicants describe three proof-of principle experiments that use the pVIc-DNA interaction to speed up bacterial transformation, to increase membrane protein production and to improve the action of gyrase inhibitors. These experiments are just three examples from a much wider set of possible applications. The successful implementation of any of these applications already is a significant step forward in the utilization of one-dimensional search processes in biotechnological applications.

Speeding Up Bacterial Transformation.

Bacterial transformation is a technique widely applied in molecular biology to introduce foreign plasmid DNA into bacteria. In molecular cloning the ligation of inserts into vectors is an extremely low yielding process and therefore requires high transformation efficiencies for successful gene incorporation. Moreover, in protein evolution a low transfection efficiency is a major bottleneck hampering sampling of large sequence space. The successful uptake of plasmids by transformation of competent cells is in essence determined by a kinetic barrier. Currently, standard protocols rely on having a high concentration of plasmid in the bacterial cultures while electroporation or exposure to calcium chloride transiently permeates the bacterial membrane. One possible improvement is to locally increase the plasmid concentration by allowing the DNA to bind non-specifically to DNA-binding moieties expressed on the bacterial surface.

Here, Applicants propose to display pVIc peptide on the surface of Gram negative bacteria by fusion to outer membrane proteins. Well suited targets are Int550 (C-terminal fusion), FhuA (N- and C-terminal fusion) and the AIDA-I autotransporter. Especially the latter has been shown being suited for surface exposure of passenger peptides and even a stable presentation of functional lactamase on the E. coli outer membrane was achieved. With such a pVIc presenting system the DNA is stably localized and kept in a mobile state at the cell surface. These combined features result in enhanced DNA uptake through transiently induced pores in the cell wall compared to wild type cells.

The corresponding transformation efficiency is determined by adding equal amounts of plasmid DNA containing an antibiotic resistance gene to the same number of cells. Subsequent spreading of dilution series on plates supplemented with and without the corresponding antibiotic allow calculating the transformation efficiency.

Increasing the Efficiency of Membrane Protein Production.

Instead of presenting the pVIc to the outside of the cell, displaying the sliding peptide on the inner surface of the cytoplasmic membrane offers exciting opportunities as well. Fusion of pVIc to cytoplasmic termini of inner membrane proteins like YidC (N- or C terminus), the N-terminus of FtsQ or YddG (N- and C-terminus) results in localization of plasmid or genomic DNA close to the inner cell surface. This situation enables bringing the first step of membrane protein biogenesis, the transcription, closer to the mature protein's final destination. Usually, the translation of mRNA into the membrane protein is stalled as soon as the first hydrophobic transmembrane segment emerges from the ribosome. Subsequently, this complex is transported to the membrane and transferred to the insertion pore (SecYEG). Upon this binding event translation is restarted and the protein is cotranslationally inserted into the membrane. By bringing the first step of membrane protein biogenesis close to the membrane a significant acceleration of protein production is anticipated. The overexpression of membrane proteins in contrast to soluble proteins is still a major obstacle in current biotechnological research and industry.

To prove Applicants' hypothesis Applicants overexpress standard membrane proteins like leader peptidase LepB (2 transmembrane segments) or LacY (12 transmembrane segments) in E. coli. By comparing PVIc presenting cells to the wild type the change in protein expression levels is determined.

Speeding Up Antibiotic Recognition

Another in vivo application is increasing the efficiency of antibiotics with the help of the molecular sled. For that purpose known antimicrobial agents are selected that interfere with the bacterial DNA machinery. Especially the conjugation of pVIc with DNA gyrase inhibitors leads to improved drug efficiency. DNA gyrase is an important protein involved in bacterial DNA replication, because it helps to release strain that arises from unwinding of the ds DNA by helicase. The mode of action of bacterial topoisomerase II inhibitors is the stabilization of the cleavage complexes in an open form with the generation of chromosome breaks. Thereby the bacterial DNA gyrases convert into potent cellular toxins leading to cell death. pVIc is attached to the amino group of Gemifloxacin, a gyrase inhibitor of the 4th generation. The attachment point of pVIc is chosen in such a way that it is well separated from the pharmacophore scaffold and does not interfere with drug action. Alternatively, pVIc is coupled to Norfloxacin (2nd generation inhibitor). In both conjugates the antibiotic activity is strongly increased due to the fact that the 3D diffusion of the drugs is reduced to a one dimensional search process. After the synthesis of the novel conjugate its antimicrobial activity is tested against E. coli ATCC 25922, which is a standard strain to evaluate the efficiency of antibiotics. Two methods, the Kirby-Bauer Disk Test and the determination of the Minimal Inhibitory Concentration (MIC), is employed for that purpose.

The main goal is to adopt a molecular system employed by nature to speed up search processes on DNA and to speed up biotechnologically relevant processes. This aspect of the proposed work is highly innovative and has many applications. The chemical tools to characterize this system and develop applications are innovative as well. For example, the methods described here to couple synthetic dyes to DNA and proteins are novel and represent a significant improvement with respect to the commercially available probes. As such, it impacts on how researchers use fluorescent dyes as reporters for DNA and/or protein dynamics. Also, the use of 2D DNA origami and 3D DNA-containing artificial capsids to study the effect of DNA crowding on DNA-protein interactions is novel and allows researchers to investigate DNA-protein interactions in more complex, physiologically relevant environments.

Figure 30A:
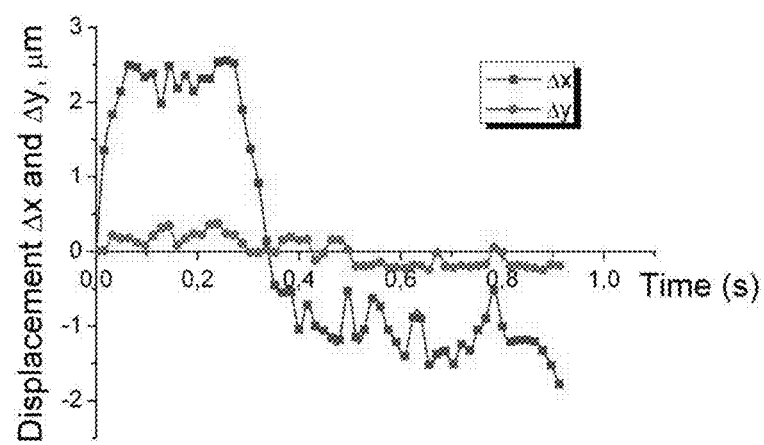
FIG. 30A. Single-molecule sliding trajectory (blue=longitudinal; red=transversal).
Figure 30B:
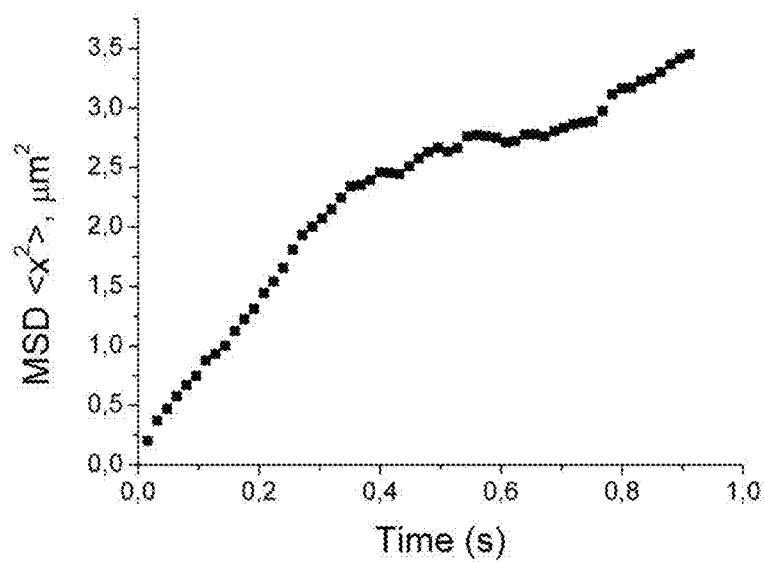
FIG. 30B. Mean-square displacement (MSD) versus time of trace in FIG. 30A. Average diffusion coefficient is $25 \times 10^6$ bp$^2$/sec.

Example 9: Single-Molecule Observation of 1-Dimensional Sliding of a 6-a.a. Long, Truncated pVIc Using single-molecule fluorescence imaging, Applicants visualized the truncated adenovirus pVIc peptide (KIRRRCF (SEQ ID NO: 5) labeled with Cy3b) sliding along flow-stretched DNA. Conditions are identical as in the above Examples, with a pH of 7.5 and a peptide concentration of 100 pM (FIG. 30).

Example 10: Functionalization of Primers with a Molecular Sled Leads to Shortening of the PCR Process Polymerase Chain Reaction (PCR) is a well-known and effective tool for the amplification of DNA targets of interest and it has found widespread applications in many fields (M. F. Sábato; M. L. Shiffman; M. R. Langley; D. S. Wilkinson; A. Ferreira-Gonzalez. J. Clin. Microbiol. 2007, 45, 2529-2536 and T. Bar; A. Stahlberg; A. Muszta; M. Kubista. Nucl. Acids Res. 2003, 31, e105). Considering its broad use, the speed up of DNA amplification to shorten the whole PCR procedure has tremendous economic potential.

Figure 31:
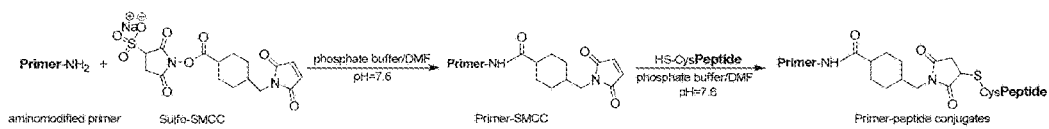
FIG. 31. Schematic of primer-peptide conjugate preparation.

Here, Applicants present a way to accelerate DNA amplification evidenced by Real-Time PCR (RT-PCR) employing primers modified with peptides. The peptide pVIc is an 11-amino acid sequence and it has been proven to slide along DNA (V. Graziano; G. Luo; P. Blainey; A. Pérez-Berná; W. McGrath; S. Jane Flint; C. Martin; X. Xie; W. Mangel. J. Biol. Chem. 2013, 288, 2068-2080 and P. Blainey; V. Graziano; A. Pérez-Berná; W. McGrath; S. Jane Flint; C. Martin; X. Xie; W. Mangel. J. Biol. Chem. 2013, 288, 2092-2102). When modifying PCR primers with this motif they are supposed to find their complementary position on the template more quickly than unmodified primers. In this Example, four peptides (W: WGGGVQSLKRRRCF (SEQ ID NO: 24), pVIc: GVQSLKRRRCF (SEQ ID NO: 12), K: KRRRCF (SEQ ID NO: 5) and S: SFRRCGLRQVK (SEQ ID NO: 10)) covalently linked to primers were studied. The first three peptides share the sequence (KRRRCF (SEQ ID NO: 5)) carrying four positive charges which are responsible for the sliding on DNA. In contrast, peptide S consists of the same amino acids as pVIc but connected in a different order. The peptide sequence S is known not to slide on DNA and is therefore used as a control. The synthesis of the primer-peptide conjugates was carried out according to literature procedures (FIG. 31) (Ching-Hsuan Tung; M. Jonathan Rudolph; Stanley Stein. Bloconjugate Chem. 1991, 2, 464-465 and Andrew W. Fraley; Benedicte Pons; Deniz Dalkara; Gerard Nullans; Jean-Paul Behr; Guy Zuber. J. Am. Chem. Soc. 2006, 128, 10763-10771). The nucleic acid-peptide hybrids were characterized by gel electrophoresis and mass spectrometry (see experimental section).

Figure 32A:
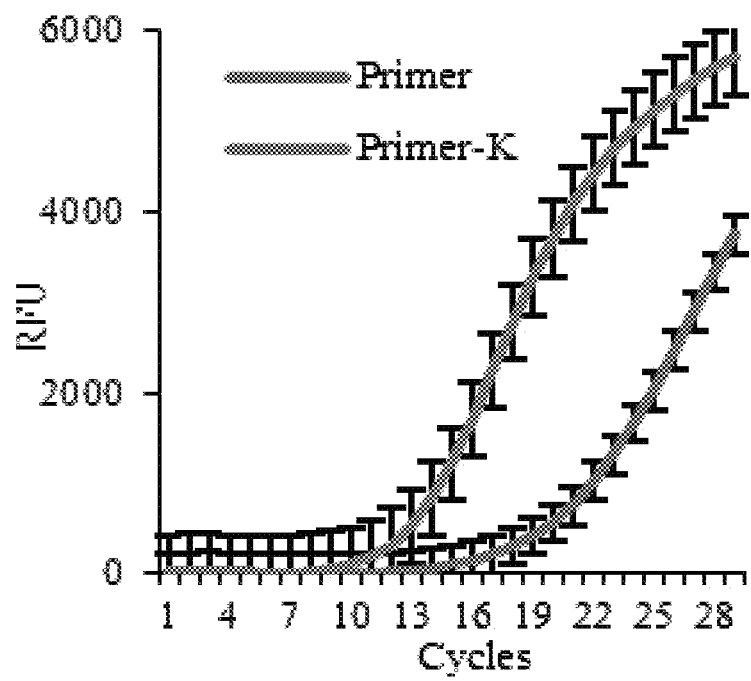
FIG. 32A-D. a-c) RT-PCR data for different primer-peptide conjugates (blue curve) compared to unmodified primers (red curve); d) comparison of sliding peptide pVIc versus non-sliding peptide S.
Figure 32B:
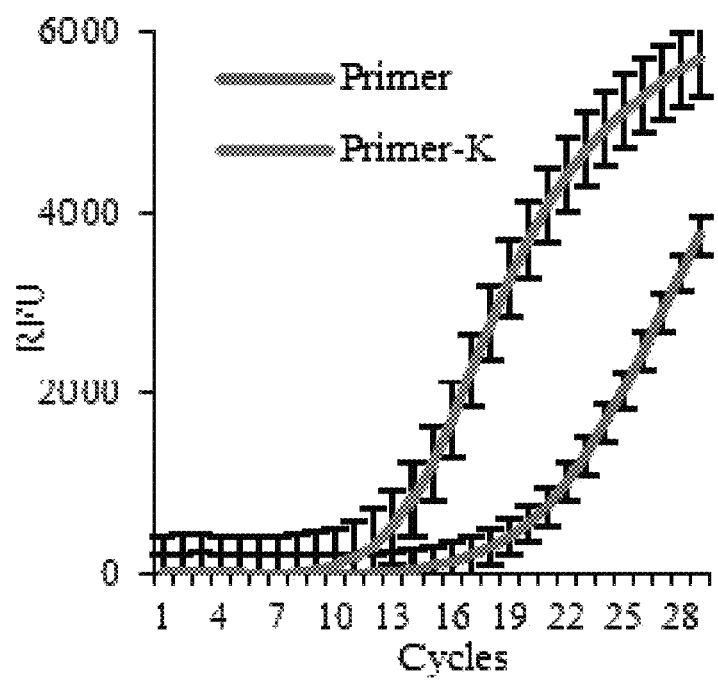
Figure 32C:
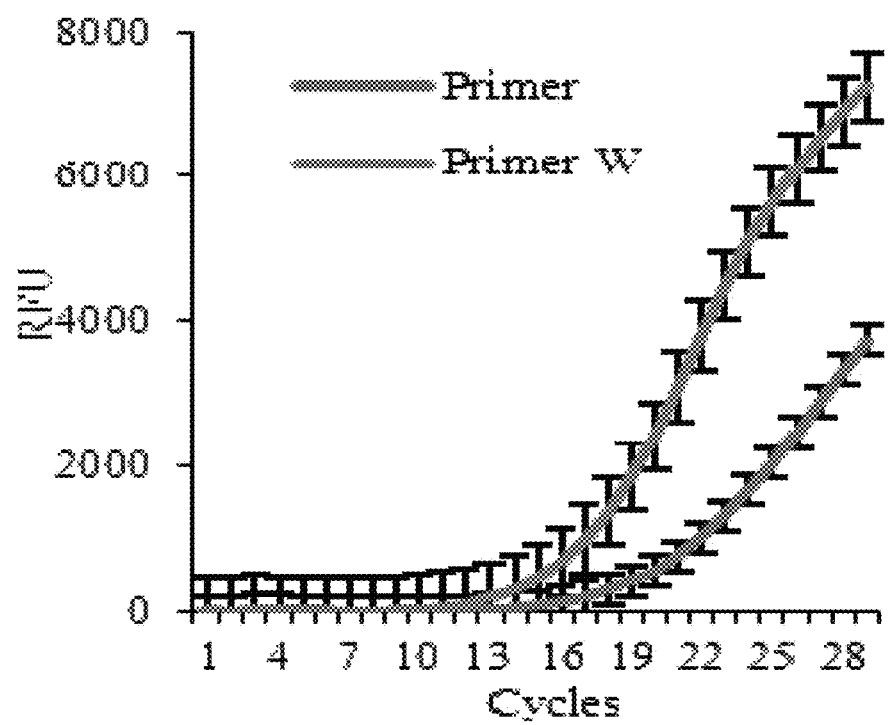
Figure 32D:
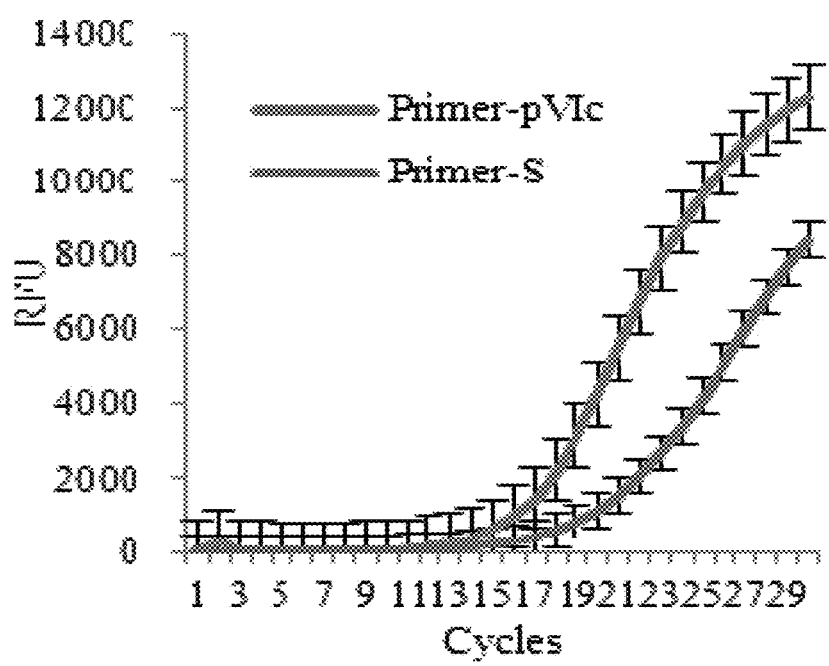

In the PCR experiments employing the primer-peptide conjugates, the length of target sequence was 816 bp on a circular template (plasmid: dsM13KO7) consisting of 8.669 bp. In every RT-PCR experiment, PCR reactions were carried out in triplicate. According to the results shown in FIG. 32, the primers modified with the peptides speed up DNA amplification. This behavior is evidenced by the rising of the fluorescence signal of the reporter dye in RT-PCR at lower cycle numbers (blue curves) compared to unmodified primers (red curve)(FIG. 32a-c). When the peptide is not able to slide along DNA larger cycle numbers are needed to achieve amplification in relation to sliding ones (compare FIG. 32d red versus blue curve). Applicants repeated several times the RT-PCR experiments and found that the accelerated DNA amplification is reproducible. For different PCR runs the procedure can be shortened by 15%-27% through the use of sliding peptide-modified primers. This technique might be a promising tool to reduce the times for PCR for certain applications.

Experimental section. The sequences for the primers are as follows: Forward primer: 5'-NH2-CTCATCGAGCATCAA-3' (SEQ ID NO: 25) and Reverse primer: 5'-NH2-ATGAGCCATATTCAA-3' (SEQ ID NO: 26).

General procedure for the synthesis of primer-peptide conjugates: The lyophilized amino modified primers were dissolved in 0.1 M sodium phosphate buffer (pH 7.6) to obtain a 1.5 mM solution of the nucleic acid component. Sulfosuccinimidyl-4-[N-maleimidomethyl]cyclohexane-1-carboxylate (Sulfo-SMCC) reagent (20 equiv) in DMF was added to the primers, and the reaction was allowed to shake at ambient temperature overnight. After incubation, the reaction mixtures were centrifuged three times using 5000 Da Mw cut-off tubes to remove excess Sulfo-SMCC and other small molecules. Thereby, the buffer solution was replaced by Milli-Q water. The remaining solution was lyophilized and used for the next coupling procedure without further treatment. The coupling yield was around 50%.

Figure 33:
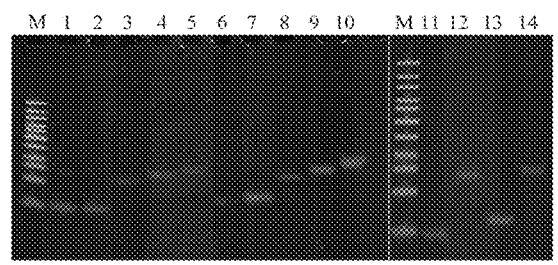
FIG. 33. Primer-peptide conjugate analysis by polyacrylamide gel electrophoresis after purification. M is a DNA ladder for reference (10-300 bp) and 1-14 lanes are different forward primer (FP) and backward primer (BP) conjugates. FP (1), FP-SMCC (2), FP-K (3), FP-pVIc (4), FP-W (5), BP (6), BP-SMCC (7), BP-K (8), BP-pVIc (9), BP-W (10), FP (11), FP-S (12), BP (13) and BP-S (14). According to gel electrophoresis results the primer-peptide conjugates were obtained in pure form. The MALDI-TOF-MS data support this statement (FIG. 34).
Figure 34G:
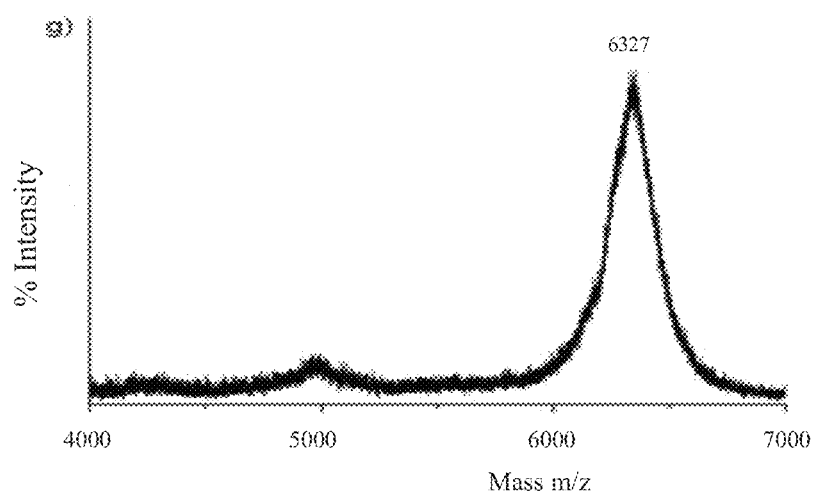

To the lyophilized primer-SMCC derivative 0.1 M sodium phosphate buffer (pH 7.6) was added to obtain a 200 µM solution. Then the dry peptides (5 equiv) were added. If the peptide did not dissolve completely DMF was added until a clear solution was visible. The reaction mixture was vortexed at room temperature overnight and the product was then purified by reversed-phase chromatography (buffer A: 0.1 M TEAT (triethylammonium acetate) containing 5% Acetonitrile; Buffer B: 0.1 M TEAT containing 65% Acetonitrile). Finally, the buffer was exchanged to Milli-Q water by centrifugation in a 5000 Da Mw cut-off tube. The products were analyzed by polyacrylamide gel electropherisis (FIG. 33) and matrix assisted laser desorption ionization time of flight mass spectrometry (MALDI-TOF-MS). For further use the conjugates were lyophilized. A coupling yield of 30-40% was achieved.

General procedure for the RT-PCR experiments: In every RT-PCR experiment, a 20 uL reaction mix contained forward and backward primers (0.5 uM), DNA template (10ng), Sybr Green I (1×), Qiagen fast cycling PCR kit (1×) and Q-solution (1×). All 20 uL reactions were performed in triplicate and run on a Bio-Rad iQ5 thermal cycler with a thermal cycling protocol of 98° C. (5 min); [98° C. (1 min), 55.6° C. (1 s), 68° C. (30 s)] 30 cycles; 68° C. (4 min).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A non-naturally occurring or engineered composition comprising:
   (a) a molecular sled comprising a core sequence of amino acids, wherein the core sequence is KKRRRCX" (SEQ ID NO: 2), or KKRRRCF (SEQ ID NO: 4), wherein X" is any amino acid;
   (b) one or more linkers comprising one or more amino acids; and
   (c) a molecular cargo linked to the one or more linkers; and
   wherein the core sequence of amino acids KKRRRCX" (SEQ ID NO: 2), or KKRRRCF (SEQ ID NO: 4) is capable of sliding on a negatively charged polymer track.

2. The composition of claim 1, further comprising a nuclear localization signal (NLS).

3. The composition of claim 1, wherein the one or more linkers are attached with a covalent bond, a non-covalent bond, or a neutrally charged ionic bond.

4. The composition of claim 1, further comprising a molecular capsule, a small molecule, a nucleic acid, a peptide, a protein or an analog or derivative thereof.

5. The composition of claim 1, wherein the molecular cargo is chemically modified with one or more gyrase inhibitors.

6. The composition of claim 1, further comprising a molecular capsule, cyclodextrin or pillararene.

7. The composition of claim 1, wherein the molecular cargo is covalently linked to the one or more linkers.

8. The composition of claim 1, wherein the negatively charged track is double stranded DNA, single stranded DNA, engineered DNA nanostructures, a nucleosome, chromatin, or other natural or engineered DNA-protein complex, RNA, a ribosome or other natural or engineered ribonucleoprotein complex, a synthetic polymer or a natural polymer, organic nanowires or surfaces, inorganic nanowires or surfaces.

9. The composition of claim 1, further comprising one or more additional sleds, linkers or cargo.

10. The composition of claim 1, further comprising a peptide nucleic acid (PNA) brake or a sled-PNA conjugate.

11. The composition of claim 4, wherein the small molecule is a drug.

12. The composition of claim 6, wherein the molecular capsule is calixarene or cucurbituril.

13. The composition of claim 8, wherein the engineered DNA nanostructure is DNA origami, the synthetic polymer is polyglutamic acid or the natural polymer is actin or tubulin.

14. The composition of claim 10, wherein the sled-PNA conjugate is a chromatin modifying factor.

* * * * *

SEQUENCE LISTING

<160> NUMBER OF SEQ ID NOS: 35

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic

```
                peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 1

Xaa Lys Arg Arg Arg Cys Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 2

Lys Lys Arg Arg Arg Cys Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 3

Xaa Lys Arg Arg Arg Cys Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Lys Arg Arg Arg Cys Phe
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Arg Arg Arg Cys Phe
1               5
```

<210> SEQ ID NO 6
<211> LENGTH: 11
<212> TYPE: PRT
<213> ORGANISM: Human immunodeficiency virus

<400> SEQUENCE: 6

Tyr Gly Arg Lys Lys Arg Arg Gln Arg Arg Arg
1               5                   10

<210> SEQ ID NO 7
<211> LENGTH: 7
<212> TYPE: PRT
<213> ORGANISM: Simian virus 40

<400> SEQUENCE: 7

Pro Lys Lys Lys Arg Lys Val
1               5

<210> SEQ ID NO 8
<211> LENGTH: 16
<212> TYPE: PRT
<213> ORGANISM: Xenopus sp.
<220> FEATURE:
<221> NAME/KEY: MOD_RES
<222> LOCATION: (3)..(12)
<223> OTHER INFORMATION: Any amino acid

<400> SEQUENCE: 8

Lys Arg Xaa Xaa Xaa Xaa Xaa Xaa Xaa Xaa Xaa Xaa Lys Lys Lys Leu
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ile Val His Arg Lys Cys Phe
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Phe Arg Arg Cys Gly Leu Arg Gln Val Lys
1               5                   10

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Lys Lys Arg Lys Arg Arg Leu Tyr Gly Arg Lys Lys Arg Arg Gln
1               5                   10                  15

Arg Arg Arg

<210> SEQ ID NO 12
<211> LENGTH: 11
<212> TYPE: PRT
<213> ORGANISM: Human adenovirus

<400> SEQUENCE: 12

Gly Val Gln Ser Leu Lys Arg Arg Arg Cys Phe
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg Gly Gly
1

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagggtctca catggaagac atcaactttg cgtctctg                                38

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaagcatcgt cggcgcttca gggattg                                            27

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
attccatatg gccttcagct ggggctcgct g                                       31

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggttggatcc ttacagaccc acgatgctgt tcag                                    34

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gacgactagg at                                                        12

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caggaaacag ctatgacc                                                  18

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Gly Pro Ser Ile Val His Arg Lys Cys Phe
1               5                   10

<210> SEQ ID NO 21
<211> LENGTH: 4
<212> TYPE: PRT
<213> ORGANISM: Unknown
<220> FEATURE:
<223> OTHER INFORMATION: Description of Unknown: pVIc conserved motif
      peptifde

<400> SEQUENCE: 21

Lys Arg Arg Arg
1

<210> SEQ ID NO 22
<211> LENGTH: 9
<212> TYPE: PRT
<213> ORGANISM: Homo sapiens

<400> SEQUENCE: 22

Thr Ser Arg His Lys Lys Leu Met Phe
1               5

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gattgcatga ttagagtgtg ctggatgtga tagtga                              36

-continued

```
<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Gly Gly Gly Val Gln Ser Leu Lys Arg Arg Arg Cys Phe
1               5                   10

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctcatcgagc atcaa                                                          15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atgagccata ttcaa                                                          15

<210> SEQ ID NO 27
<211> LENGTH: 11
<212> TYPE: PRT
<213> ORGANISM: Human adenovirus

<400> SEQUENCE: 27

Gly Val Gln Ser Leu Lys Arg Arg Arg Cys Tyr
1               5                   10

<210> SEQ ID NO 28
<211> LENGTH: 11
<212> TYPE: PRT
<213> ORGANISM: Human adenovirus

<400> SEQUENCE: 28

Gly Val Lys Ser Leu Lys Arg Arg Arg Cys Tyr
1               5                   10

<210> SEQ ID NO 29
<211> LENGTH: 11
<212> TYPE: PRT
<213> ORGANISM: Bovine adenovirus

<400> SEQUENCE: 29

Gly Val Arg Thr Val Lys Arg Arg Arg Cys Tyr
1               5                   10

<210> SEQ ID NO 30
<211> LENGTH: 11
<212> TYPE: PRT
<213> ORGANISM: Porcine adenovirus

<400> SEQUENCE: 30
```

```
Gly Val Arg Ser Val Lys Arg Arg Cys Phe
1               5                   10

<210> SEQ ID NO 31
<211> LENGTH: 11
<212> TYPE: PRT
<213> ORGANISM: Murine adenovirus

<400> SEQUENCE: 31

Gly Leu Gln Pro Ile Lys Arg Arg Arg Cys Phe
1               5                   10

<210> SEQ ID NO 32
<211> LENGTH: 11
<212> TYPE: PRT
<213> ORGANISM: Simian adenovirus

<400> SEQUENCE: 32

Gly Val Gln Ser Val Lys Arg Arg Arg Cys Tyr
1               5                   10

<210> SEQ ID NO 33
<211> LENGTH: 11
<212> TYPE: PRT
<213> ORGANISM: Fowl adenovirus

<400> SEQUENCE: 33

Gly Val Ala Val Ser Lys Arg Arg Met Cys Tyr
1               5                   10

<210> SEQ ID NO 34
<211> LENGTH: 9
<212> TYPE: PRT
<213> ORGANISM: Homo sapiens

<400> SEQUENCE: 34

Thr Ser Arg Asn Lys Lys Leu Met Phe
1               5

<210> SEQ ID NO 35
<211> LENGTH: 5
<212> TYPE: PRT
<213> ORGANISM: Human adenovirus

<400> SEQUENCE: 35

Ile Val Gly Leu Gly
1               5
```